(12) United States Patent
Miner et al.

(10) Patent No.: US 9,095,581 B2
(45) Date of Patent: Aug. 4, 2015

(54) COMBINATIONS OF MEK INHIBITORS AND RAF KINASE INHIBITORS AND USES THEREOF

(75) Inventors: Jeffrey N. Miner, San Diego, CA (US); Mark S. Chapman, San Diego, CA (US); Barry Quart, Encinitas, CA (US); Alex Adjei, Williamsville, NY (US); Chunrong Yu, Williamsville, NY (US)

(73) Assignee: Ardea Biosciences, Inc., San Diego, CA (US)

( * ) Notice: Subject to any disclaimer, the term of this patent is extended or adjusted under 35 U.S.C. 154(b) by 685 days.

(21) Appl. No.: 12/956,177

(22) Filed: Nov. 30, 2010

(65) Prior Publication Data
US 2012/0136030 A1 May 31, 2012

Related U.S. Application Data

(63) Continuation of application No. 12/671,271, filed as application No. PCT/US2008/071397 on Jul. 28, 2008, now abandoned.

(51) Int. Cl.
| A61K 31/4439 | (2006.01) |
| A61K 31/18 | (2006.01) |
| A61K 31/4412 | (2006.01) |
| A61K 45/06 | (2006.01) |

(52) U.S. Cl.
CPC ............ *A61K 31/4439* (2013.01); *A61K 31/18* (2013.01); *A61K 31/4412* (2013.01); *A61K 45/06* (2013.01)

(58) Field of Classification Search
CPC ............ A61K 31/4439; A61K 31/18; A61K 31/4412; A61K 45/06
See application file for complete search history.

(56) References Cited

U.S. PATENT DOCUMENTS

| 6,316,462 B1 | 11/2001 | Bishop et al. |
| 7,820,664 B2 | 10/2010 | Koh et al. |
| 7,897,624 B2 | 3/2011 | Yan et al. |
| 8,063,049 B2 | 11/2011 | Koh et al. |
| 2004/0171632 A1 | 9/2004 | Gowan et al. |
| 2007/0244164 A1 | 10/2007 | Yan et al. |
| 2008/0058340 A1* | 3/2008 | Maderna et al. ......... 514/252.12 |
| 2008/0255133 A1 | 10/2008 | Vernier et al. |
| 2010/0331334 A1 | 12/2010 | Koh et al. |
| 2011/0112152 A1 | 5/2011 | Yan et al. |

FOREIGN PATENT DOCUMENTS

| WO | 2004064733 A2 | 8/2004 |
| WO | 2006067446 A1 | 6/2006 |
| WO | 2007014011 A2 | 2/2007 |
| WO | 2007121481 A2 | 10/2007 |
| WO | 2008089459 A1 | 7/2008 |
| WO | 2008120004 A1 | 10/2008 |

OTHER PUBLICATIONS

Yu et al 'Inhibition of MAPK signaling enhances Sorafenib-mediated cytotoxicity in human cancer cells in vitro and in vivo' AACR Annual Meeting, Abstract 3692, Apr. 2009.*
International Search Report of PCT/US2008/071397 (Oct. 7, 2008).
Supplementary European Search Report for EP08782470 dated Oct. 26, 2010.
Kohno, M. et al., "Targeting the ERK signaling pathway in cancer therapy," Annals of Medicine, 2006, vol. 38, pp. 200-211.
Shelton, J. G. et al., "Differential effects of kinase cascade inhibitors on neoplastic and cytokine-mediated cell proliferation," Molecular Targets for Therapy (MTT), Leukemia, 2003, vol. 17, pp. 1765-1782.

* cited by examiner

Primary Examiner — Wu-Cheng Winston Shen
Assistant Examiner — Christopher R Stone
(74) Attorney, Agent, or Firm — Millen, White, Zelano & Branigan, P.C.

(57) ABSTRACT

This invention concerns combinations of inhibitors of MEK, Raf protein kinases, and other kinases including VEGFR1-3 and PDGFR-β. This invention also concerns pharmaceutical compositions comprising the compounds described herein and methods of use of the compounds and compositions described herein, including the use in the treatment and/or prevention of cancer and other hyperproliferative disorders.

14 Claims, 13 Drawing Sheets

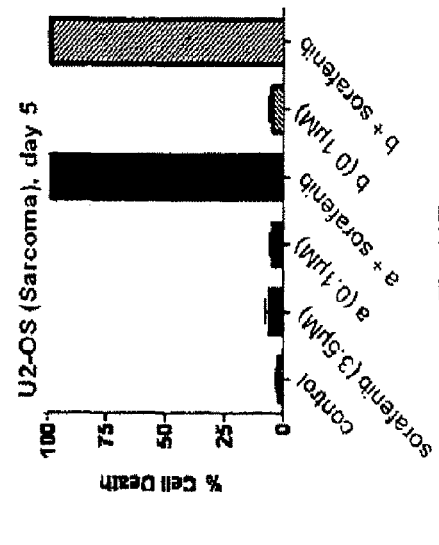
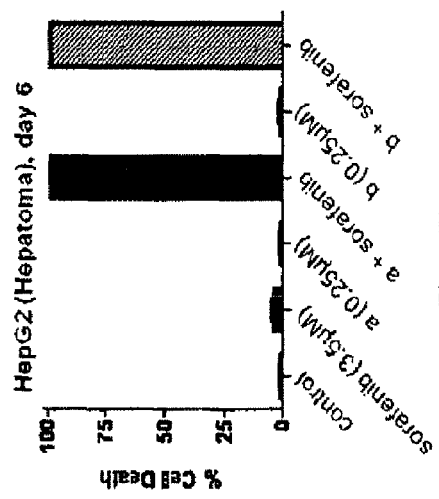
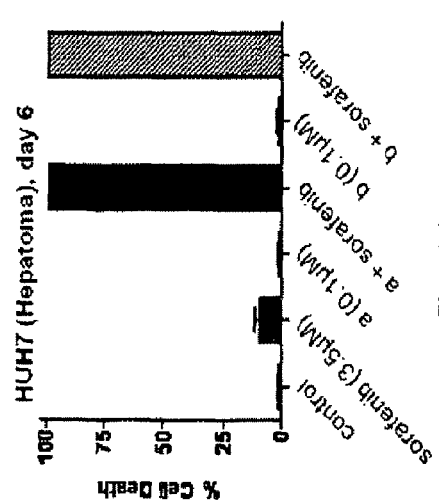
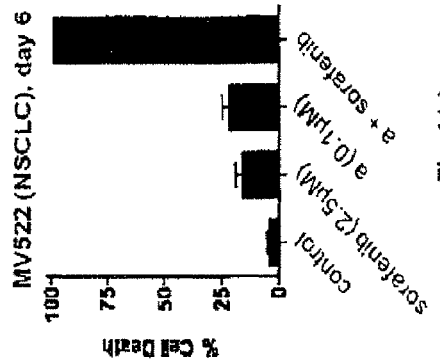
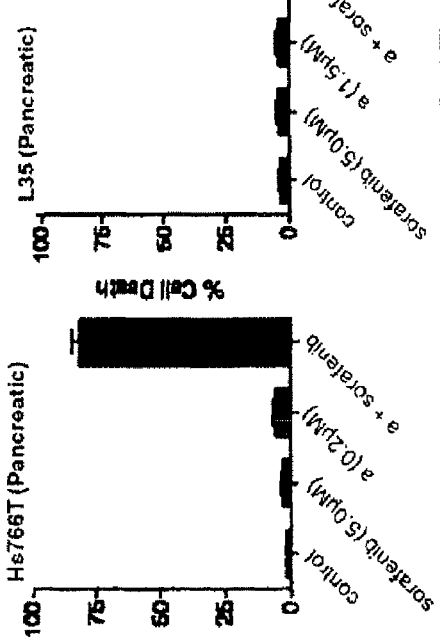
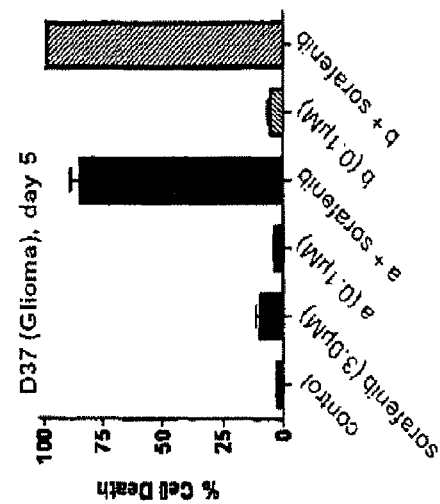

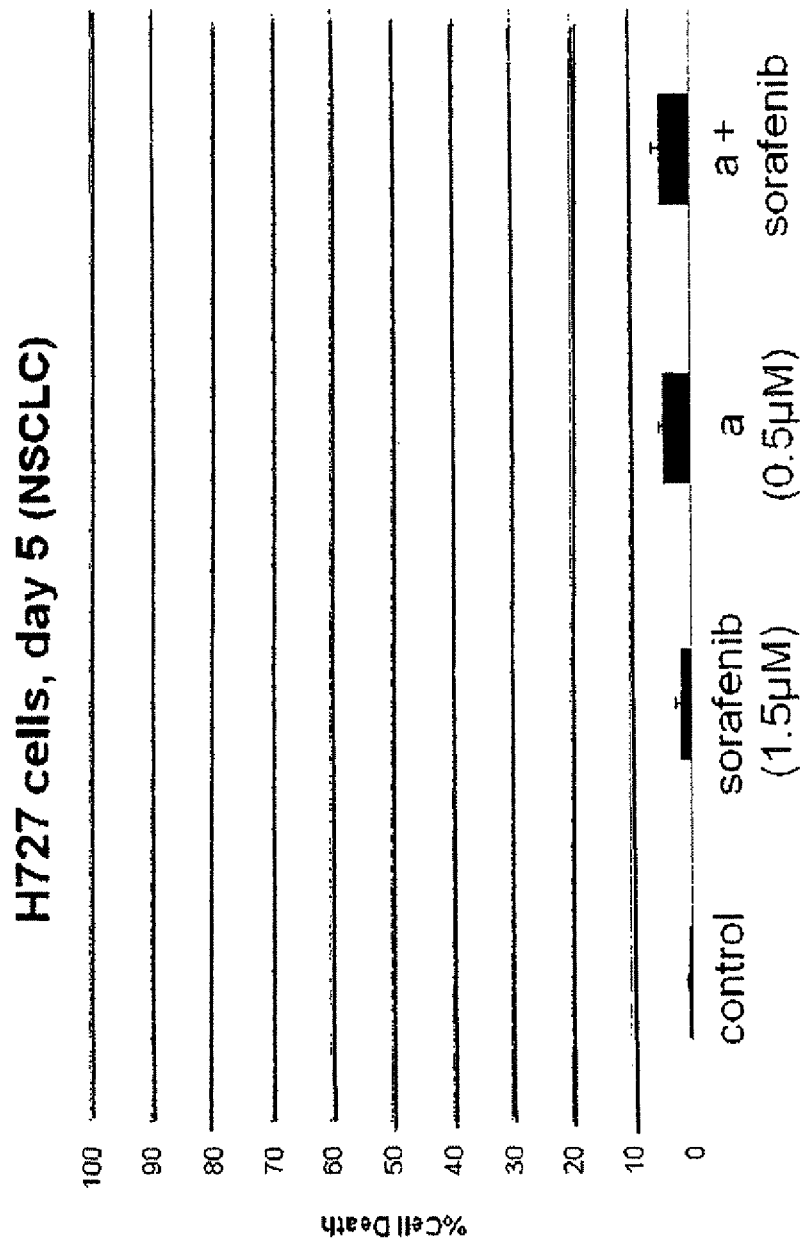

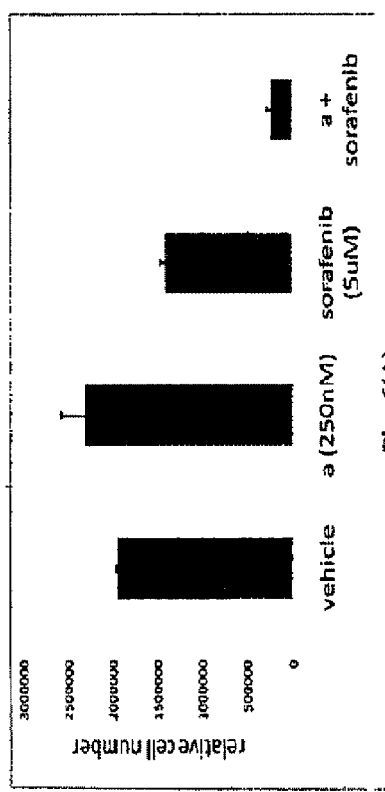
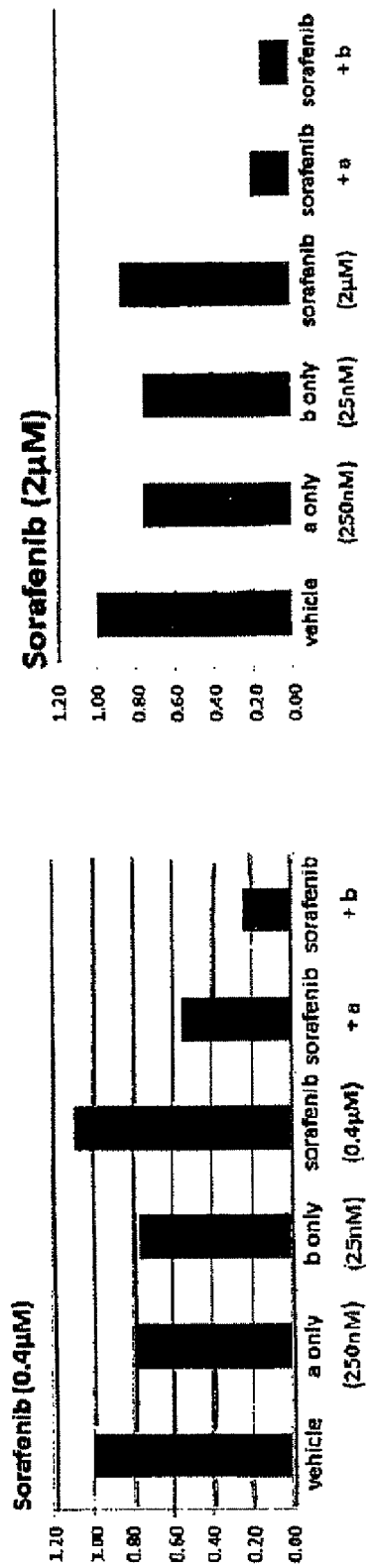
Fig. 6(A)
Fig. 6(B)
Fig. 6(C)

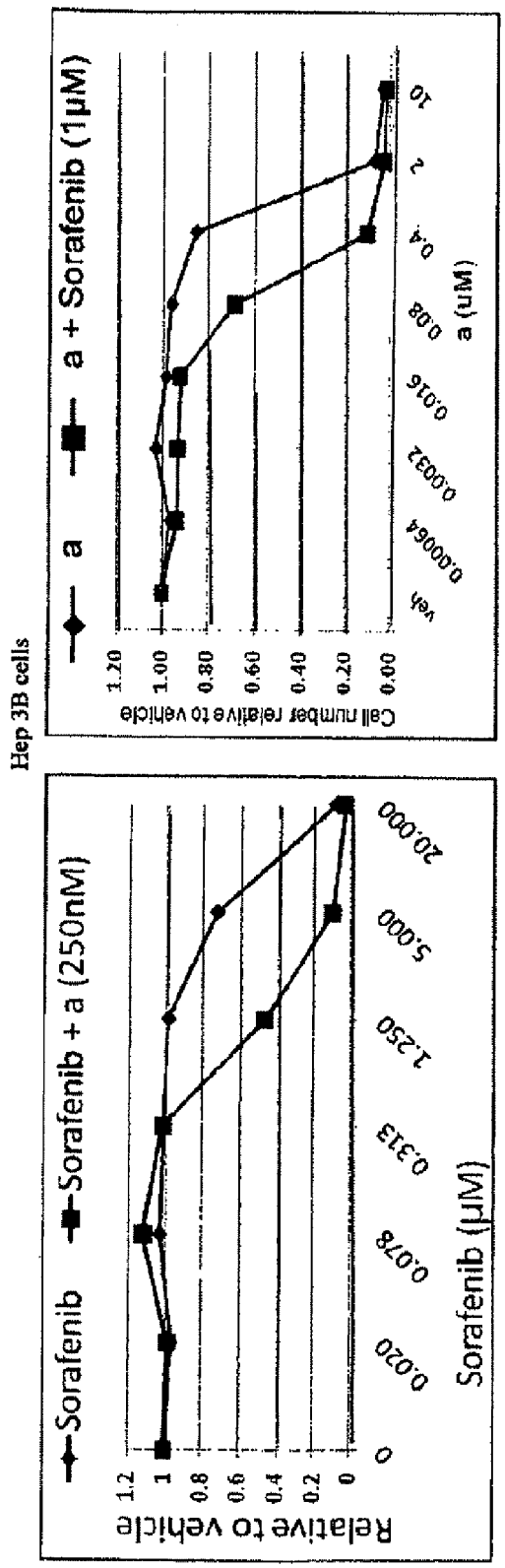
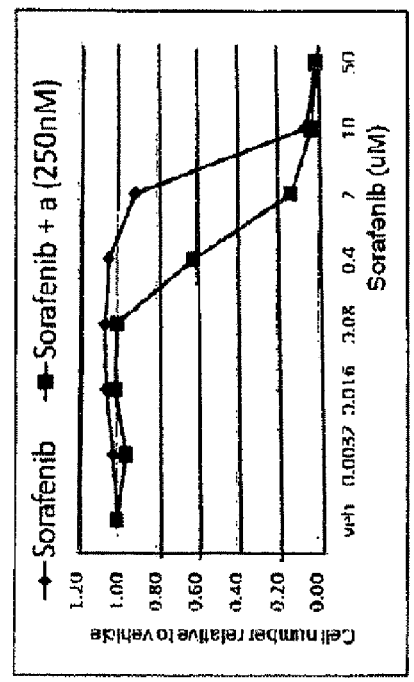
Fig. 8(A)
Fig. 8(B)
Fig. 8(C)

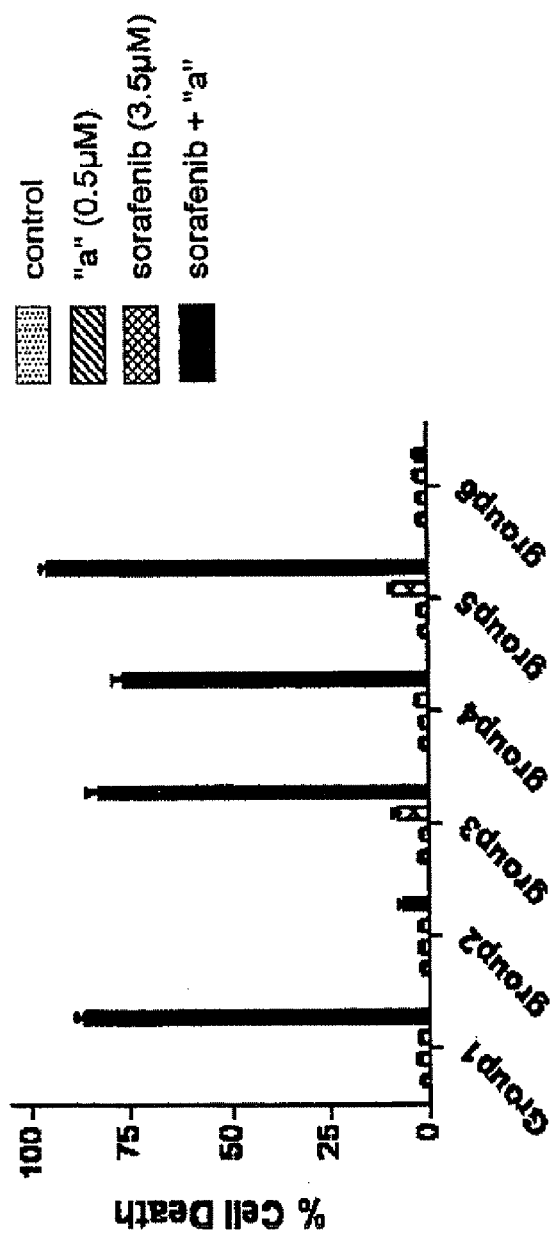

COMBINATIONS OF MEK INHIBITORS AND RAF KINASE INHIBITORS AND USES THEREOF

CROSS REFERENCE TO RELATED APPLICATIONS

This application is a continuation of U.S. application Ser. No. 12/671,271, filed Jan. 29, 2010 and claims priority to U.S. application Ser. No. 11/830,733, filed Jul. 30, 2007, which is a continuation-in-part application of International Application Ser. No PCT/US2006/028326 filed Jul. 21, 2006, which claims priority to U.S. Provisional Application Ser. No. 60/701,814, filed Jul. 21, 2005; to U.S. Provisional Application Ser. No. 60/706,719, filed Aug. 8, 2005; to U.S. Provisional Application Ser. No. 60/731,633, filed Oct. 28, 2005; and to U.S. Provisional Application Ser. No. 60/883,886, filed Jul. 28, 2006; each of which are hereby incorporated by reference in the entirety.

This application also claims priority to U.S. application Ser. No. 12/016,897 filed Jan. 18, 2008, which claims priority to U.S. Provisional Application No. 60/885,849 filed on Jan. 19, 2007; each of which is hereby incorporated by reference in the entirety.

This application also claims priority to U.S. application Ser. No. 11/737,109 filed Apr. 18, 2007, which claims priority to U.S. Provisional Application Ser. No. 60/793,129 filed Apr. 18, 2006; each of which is hereby incorporated by reference in the entirety.

FIELD OF THE INVENTION

This invention concerns synergistic combinations of inhibitors of MEK, Raf protein kinases and other kinases including VEGFR1-3 and PDGFR-β. This invention also concerns pharmaceutical compositions comprising the compounds described herein and methods of use of the compounds and compositions described herein, including the use in the treatment and/or prevention of cancer and other hyperproliferative.

BACKGROUND OF THE INVENTION

Oncogenes—genes that contribute to the production of cancers—are generally mutated forms of certain normal cellular genes ("proto-oncogenes"). Oncogenes often encode abnormal versions of signal pathway components, such as receptor tyrosine kinases, serine-threonine kinases, or downstream signaling molecules. The central downstream signaling molecules are the Ras proteins, which are anchored on the inner surfaces of cytoplasmic membranes, and which hydrolyze bound guanosine triphosphate (GTP) to guanosine diphosphate (GDP). When activated by a growth factor, growth factor receptors initiate a chain of reactions that leads to the activation of guanine nucleotide exchange activity on Ras. Ras alternates between an active "on" state with a bound GTP (hereafter "Ras.GTP") and an inactive "off state with a bound GDP. The active "on" state, Ras.GTP, binds to and activates proteins that control the growth and differentiation of cells.

For example, in the "mitogen-activated protein kinase (MAP kinase) cascade," Ras.GTP leads to the activation of a cascade of serine/threonine kinases. One of several groups of kinases known to require a Ras.GTP for their own activation is the Raf family. The Raf proteins activate "MEK1" and "MEK2," abbreviations for mitogen-activated ERK-activating kinases (where ERK is extracellular signal-regulated protein kinase, another designation for MAPK). MEK1 and MEK2 are dual-function serine/threonine and tyrosine protein kinases and are also known as MAP kinase kinases. Thus, Ras.GTP activates Raf, which activates MEK1 and MEK2, which activate MAP kinase (MAPK). Activation of MAP kinase by mitogens appears to be essential for proliferation, and constitutive activation of this kinase is sufficient to induce cellular transformation. Blockade of downstream Ras signaling, as by use of a dominant negative Raf-1 protein, can completely inhibit mitogenesis, whether induced from cell surface receptors or from oncogenic Ras mutants.

The interaction of Raf and Ras is a key regulatory step in the control of cell proliferation. To date, no substrates of MEK other than MAPK have been identified; however, recent reports indicate that MEK may also be activated by other upstream signal proteins such as MEK kinase or MEKK1 and PKC. Activated MAPK translocates and accumulates in the nucleus, where it can phosphorylate and activate transcription factors such as Elk-1 and Sapla, leading to the enhanced expression of genes such as that for c-fos.

Once activated, Raf and other kinases phosphorylate MEK on two neighboring serine residues, S218 and S222 in the case of MEK1. These phosphorylations are required for activation of MEK as a kinase. In turn, MEK phosphorylates MAP kinase on two residues separated by a single amino acid: a tyrosine, Y185 and a threonine, T183. MEK appears to associate strongly with MAP kinase prior to phosphorylating it, suggesting that phosphorylation of MAP kinase by MEK may require a prior strong interaction between the two proteins. Two factors—MEK's unusual specificity and its requirement for a strong interaction with MAP kinase prior to phosphorylation—suggest that MEK's mechanism of action may differ sufficiently from the mechanisms of other protein kinases as to allow for selective inhibitors of MEK. Possibly, such inhibitors would operate through allosteric mechanisms rather than through the more usual mechanism involving blockage of an ATP binding site.

Thus, MEK1, MEK2 and Raf are validated and accepted targets for anti-proliferative therapies, even when the oncogenic mutation does not affect MEK structure or expression. See, e.g., U.S. Patent Publications 2003/0149015 by Barrett et al. and 2004/0029898 by Boyle et al. There is a need for more effective approaches to treating cancer and antiproliferative diseases targeting the MAP kinase cascade.

SUMMARY OF THE INVENTION

In one aspect, provided herein are pharmaceutical combinations and methods of treating cancer comprising a synergistic amount of: (a) at least one MEK protein kinase inhibitor; and (b) at least one Raf protein kinase inhibitor. In some embodiments, provided are pharmaceutical combinations and methods of treating cancer wherein the administration of the combination of the MEK protein kinase inhibitor and the Raf protein kinase inhibitor to the first patient provides an increase in apoptosis level at about day 7 compared to the combined apoptosis level at about day 7 of (1) a second patient administered only the MEK protein kinase inhibitor and (2) a third patient administered only the Raf protein kinase inhibitor.

In another aspect, provided are pharmaceutical combinations and methods of treating cancer comprising a therapeutically effective amount of: (a) at least one MEK protein kinase inhibitor; and (b) at least one Raf protein kinase inhibitor, wherein an administration of the combination of the MEK protein kinase inhibitor and the Raf protein kinase inhibitor to a first patient provides an increase in apoptosis level at about day 7 compared to the combined apoptosis level by administration of either inhibitor alone. In some embodiments, contacting a first sample of cancer cells with the combination of the MEK protein kinase inhibitor and the Raf protein kinase inhibitor provides an increase in apoptosis level at day 7 compared to the combined apoptosis level at day 7 of (1) a second sample provided by contacting cancer cells of the second sample with only the MEK protein kinase inhibitor and the (2) the apoptosis level of a third sample provided by contacting cancer cells of the third sample with only the Raf protein kinase inhibitor.

In other aspects, provided herein are pharmaceutical combinations and methods of treating cancer comprising a therapeutically effective amount of (a) at least one MEK protein kinase inhibitor; and (b) at least one Raf protein kinase inhibitor, wherein an administration of the combination of the MEK protein kinase inhibitor and the Raf protein kinase inhibitor to a first patient provides a decrease in cell proliferation count at about day 7 compared to the difference in cell proliferation count by administration of either inhibitor alone. In some embodiments, the administration of the combination of the MEK protein kinase inhibitor and the Raf protein kinase inhibitor to the first patient provides a cell proliferation count at about day 7 that is less than the difference between (1) the cell proliferation count at about day 7 of a second patient administered only the MEK protein kinase inhibitor and (2) the cell proliferation count at about day 7 of a third patient administered only the Raf protein kinase inhibitor.

In one aspect, provided herein are pharmaceutical combinations and methods of treating cancer comprising a therapeutically effective amount of: (a) at least one MEK protein kinase inhibitor; and (b) at least one Raf protein kinase inhibitor, wherein contacting a first sample of cancer cells with the combination of the MEK protein kinase inhibitor and the Raf protein kinase inhibitor provides a cell proliferation count of the first sample that is less than the difference in cell proliferation count by administration of either inhibitor alone. In some embodiments, contacting a first sample of cancer cells with the combination of the MEK protein kinase inhibitor and the Raf protein kinase inhibitor provides a cell proliferation count of a first sample that is less than the difference between (1) the cell proliferation count of a second sample of cancer cells contacted with only the MEK protein kinase inhibitor and (2) the cell proliferation count of a third sample of cancer cells contacted with only the Raf protein kinase inhibitor.

In another aspect, provided herein are pharmaceutical combinations and methods of treating cancer comprising a therapeutically effective amount of: (a) at least one MEK protein kinase inhibitor; and (b) at least one Raf protein kinase inhibitor, wherein an administration of the combination of the MEK protein kinase inhibitor and the Raf protein kinase inhibitor results in a decreased side effect compared to the combined side effect of administration by either inhibitor alone. In some embodiments, the administration of the combination of the MEK protein kinase inhibitor and the Raf protein kinase inhibitor results in a lesser degree of a side effect at about day 7 of a first patient compared to the combined degree of the side effects at about day 7 of (1) a second patient administered only the MEK protein kinase inhibitor and (2) a third patient administered only the Raf protein kinase inhibitor.

In other aspects, provided herein are methods and combinations for resensitizing cancer cells to treatment in a patient having or suspected of having a cancer resistant to an anticancer agent, comprising the step of administering to the patient a therapeutically effective amount of at least one MEK protein kinase inhibitor and at least one Raf protein kinase inhibitor. In certain embodiments, the cancer is resistant to treatment of a MEK protein kinase inhibitor. In other embodiments, the cancer is resistant to treatment of a Raf protein kinase inhibitor. In still further embodiments, the resistance is acquired resistance. In other embodiments, the resistance is de novo resistance. In further or additional embodiments, the cancer is resistant to an anticancer agent. In other embodiments, the anticancer agent is selected from the group consisting of STI-571, imatinib, capecitibine (fluorouracil; OSI-774), adriamycin (ADM), gemcitabine, RTA 402, calcitriol, docetaxel, erlotinib, bevacizumab, cetuximab; oxaliplatin, dalteparin, temsirolimus, temozolomide, perifosine, or gefitinib.

In an additional aspect, provided herein are combinations and methods of treating cancer comprising a therapeutically effective amount of: (a) at least one MEK protein kinase inhibitor; and (b) at least one Raf protein kinase inhibitor, wherein the ratio of the MEK protein kinase inhibitor to the Raf protein kinase inhibitor administered to a patient is about 100:1 to about 2.5:1. In certain embodiments, the molar ratio is about 50:1 to about 5:1. In other embodiments, the molar ratio is about 45:1 to about 10:1. In further embodiments, the molar ratio is about 40:1 to about 20:1. In yet other embodiments, the molar ratio is about 30:1.

In another aspect, provided herein are combinations and methods for the treatment of cancer comprising a therapeutically effective amount of: (a) at least one MEK protein kinase inhibitor; and (b) at least one Raf protein kinase inhibitor, wherein the therapeutically effective amount of the MEK protein kinase inhibitor is lower when administered in combination with the Raf protein kinase inhibitor than when administered alone.

In one aspect, provided herein are pharmaceutical combinations and methods for treating cancer comprising a therapeutically effective amount of: (a) at least one MEK protein kinase inhibitor; and (b) at least one Raf protein kinase inhibitor, wherein an administration of the combination of the MEK protein kinase inhibitor and the Raf protein kinase inhibitor to a first patient provides: (i) an increase in the area under the serum concentration time curve (AUC) of the MEK protein kinase inhibitor of the first patient compared to the AUC of the MEK protein kinase of a second patient when only the MEK protein kinase is administered to the second patient; or (ii) an increase in the AUC of the Raf protein kinase inhibitor of the first patient compared to the AUC of the Raf protein kinase of a second patient when only the Raf protein kinase is administered to the second patient.

In another aspect, provided herein are pharmaceutical combinations and methods of treating cancer comprising a MEK protein kinase inhibitor in combination with a Raf protein kinase inhibitor, wherein the MEK protein kinase is CI-1040 (PD184352), GSK1120212, PD-0325901, PD-98059, PD-184161, PD-0318088, PD-184386, PD-171984, PD-170611, PD-177168, PD-184352, ARRY-438162, AZD6244/ARRY-886, AZD 8330, XL518, UO125, UO126, SL 327, quercetin, or a pharmaceutically acceptable salt, solvate, polymorph, ester, tautomer or prodrug thereof.

In other aspects, the MEK protein kinase inhibitor is a compound of formula A, or a pharmaceutically acceptable salt, solvate, polymorph, ester, amide, tautomer or prodrug thereof:

Formula A

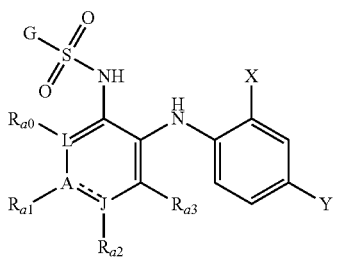

wherein

G is $G_1$, $G_2$, $R_{1a}$, $R_{1b}$, $R_{1c}$, $R_{1d}$, $R_{1e}$, $Ar_1$, $Ar_2$ or $Ar_3$;

$R_{a0}$, $R_1$ and $R_2$ are independently selected from H, halogen, cyano, cyanomethyl, nitro, difluoromethoxy, difluoromethoxy, trifluoromethyl, azido, amino, alkylamino, dialkylamino, $CO_2R_5$, $OR_5$, —O—(CO)—$R_5$, —O—C(O)—N($R_5$)$_2$, —$NR_5C(O)NR_6R_7$, —$SR_5$, $NHC(O)R_5$, —$NHSO_2R_5$, $SO_2N(R_5)_2$, C1-C6 alkyl, C1-C4 alkoxy, C3-C6 cycloalkyl, C2-C6 alkenyl, C2-C6 alkynyl, aryl, alkylaryl, arylalkyl, and heterocyclic;

each $R_5$ is selected from H, lower alkyl, substituted lower alkyl, aryl, or substituted aryl, and $NR_7R_6$; wherein each $R_6$ and $R_7$ is independently selected from hydrogen or lower alkyl; wherein said alkyl, cycloalkyl, alkenyl, aryl, alkylaryl, arylalkyl, heterocyclic and alkynyl groups are optionally substituted with 1-3 substituents selected independently from halogen, OH, CN, cyanomethyl, nitro, phenyl, difluoromethoxy, difluoromethoxy, and trifluoromethyl;

said C1-C6 alkyl and C1-C4 alkoxy groups are optionally substituted with $OCH_3$ or $OCH_2CH_3$;

$R_{a1}$ is H, $C_1$-$C_6$ alkyl, $C_3$-$C_6$ cycloalkyl, $C_2$-$C_6$ alkenyl, $C_5$-$C_6$ cycloalkenyl or $C_2$-$C_6$ alkynyl;

wherein each alkyl, cycloalkyl, alkenyl, cycloalkenyl or alkynyl group is optionally substituted with 1-3 substituents selected independently from halogen, hydroxy, $C_1$-$C_4$ alkyl, $C_1$-$C_4$ alkoxy, cyano, cyanomethyl, nitro, azido, trifluoromethyl difluoromethoxy and phenyl, and one or two ring carbon atoms of said $C_3$-$C_6$ cycloalkyl groups are optionally replaced with, independently, O, N, or S; or $R_{a1}$ is a 5 or 6-atom heterocyclic group, which group may be saturated, unsaturated, or aromatic, containing 1-5 heteroatoms selected independently from O, N, and S, which heterocyclic group is optionally substituted with 1-3 substituents selected independently from halogen, hydroxy, $C_1$-$C_4$ alkyl, $C_1$-$C_4$ alkoxy, cyano, cyanomethyl, nitro, azido, trifluoromethyl difluoromethoxy and phenyl;

$R_{a2}$ is H, halogen, F, or oxo; or $R_{a1}$ and $R_{a2}$, taken together, are -Q($R_2$)—U($R_1$)=D-

$R_{a3}$ is H, halogen, hydroxy, azido, cyano, cyanomethyl, $C_1$-$C_6$ alkyl, $C_3$-$C_6$ cycloalkyl, $C_2$-$C_6$ alkenyl, $C_5$-$C_6$ cycloalkenyl or $C_2$-$C_6$ alkynyl, wherein each alkyl, cycloalkyl, alkenyl cycloalkenyl or alkynyl group is optionally substituted with 1-3 substituents selected independently from halogen, hydroxy, $C_1$-$C_4$ alkoxy, cyano, cyanomethyl, nitro, azido, trifluoromethyl and phenyl;

═ is a single or a double bond;

X and Y are independently selected from F, I, Br, Cl, $CF_3$, C1-C3 alkyl, $C_2$-$C_3$ alkenyl, $C_2$-$C_3$ alkynyl, cyclopropyl, phenyl, pyridyl, pyrazolyl, OMe, OEt, or SMe, or Het, where Het is a 5- to 10-membered mono- or bicyclic heterocyclic group, which group is saturated, olefinic, or aromatic, containing 1-5 ring heteroatoms selected independently from N, O, and S; where all said phenyl or Het groups are optionally substituted with F, Cl, Br, I, acetyl, methyl, CN, $NO_2$, $CO_2H$, $C_1$-$C_3$ alkyl, $C_1$-$C_3$ alkoxy, $C_1$-$C_3$ alkyl-C(═O)—, $C_1$-$C_3$ alkyl-C(═S)—, $C_1$-$C_3$ alkoxy-C(═S)—, $C_1$-$C_3$ alkyl-C(═O)O—, $C_1$-$C_3$ alkyl-O—(C═O)—, $C_1$-$C_3$ alkyl-C(═O)NH—, $C_1$-$C_3$ alkyl-C(═NH)NH—, $C_1$-$C_3$ alkyl-NH—(C═O)—, di-$C_1$-$C_3$ alkyl-N—(C═O)—, $C_1$-$C_3$ alkyl-C(═O)N($C_1$-$C_3$ alkyl)-, $C_1$-$C_3$ alkyl-S(═O)$_2$NH— or trifluoromethyl;

all said methyl, ethyl, $C_1$-$C_3$ alkyl, and cyclopropyl groups of X and Y are optionally substituted with OH;

all said phenyl, pyridyl, pyrazolyl groups of Y are optionally substituted with halogen, acetyl, methyl, and trifluoromethyl; and all said methyl groups of X and Y are optionally substituted with one, two, or three F atoms;

A, D, J, L, Q, U are independently selected from C, CH, —NH, N, O, and —N($CH_3$)—;

$G_1$ is $C_1$-$C_6$ alkyl optionally substituted with one amino, $C_1$-$C_3$ alkylamino, or dialkylamino group, said dialkylamino group comprising two $C_1$-$C_4$ alkyl groups which may be identical or non-identical; or $G_1$ is a $C_3$-$C_8$ diamino alkyl group;

$G_2$ is a 5- or 6-membered ring, which is saturated, unsaturated, or aromatic, containing 1-3 ring heteroatoms selected independently from N, O, and S, optionally substituted with 1-3 substituents selected independently from F, Cl, OH, O($C_1$-$C_3$ alkyl), $OCH_3$, $OCH_2CH_3$, $CH_3C(═O)NH$, $CH_3C(═O)O$, CN, $CF_3$, and a 5-membered aromatic heterocyclic group containing 1-4 ring heteroatoms selected independently from N, O, and S;

$R_{1a}$ is methyl, cyclopropoxy or C1-C4 alkoxy; wherein the methyl is optionally substituted with OH, 1-3 fluorine atoms or 1-3 chlorine atoms;

the C1-C4 alkyl moieties of said C1-C4 alkoxy are optionally substituted with one hydroxy or methoxy group; and all C2-C4 alkyl groups within said C1-C4 alkoxy are optionally further substituted with a second OH group;

$R_{1b}$ is $CH(CH_3)$—$C_{1-3}$ alkyl or $C_3$-$C_6$ cycloalkyl, said $CH_3$, alkyl, and cycloalkyl groups optionally substituted with 1-3 substituents selected independently from F, Cl, Br, I, OH, $C_1$-$C_4$ alkoxy and CN;

$R_{1c}$ is $(CH_2)_nO_mR'$, where m is 0 or 1;

n is 0, 1, 2, or 3;

R' is C1-C6 alkyl, optionally substituted with 1-3 substituents selected independently from F, Cl, OH, $OCH_3$, $OCH_2CH_3$, and C3-C6 cycloalkyl;

$R_{1d}$ is C(A')(A")(B)— wherein

B, A', and A" are, independently, H, substituted or unsubstituted C1-6 alkyl, substituted or unsubstituted C2-6 alkenyl, or A' and A", together with the carbon atom to which they are attached, form a substituted or unsubstituted 3- to 6-member saturated ring;

$R_{1e}$ is benzyl or 2-phenyl ethyl, in which the phenyl group is optionally substituted

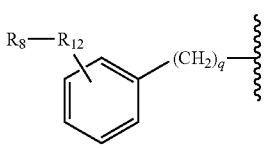

where
q is 1 or 2;
R$_8$ and R$_9$ are, independently, H, F, Cl, Br, CH$_3$, CH$_2$F, CHF$_2$, CF$_3$, OCH$_3$, OCH$_2$F, OCHF$_2$, OCF$_3$, ethyl, n-propyl, isopropyl, cyclopropyl, isobutyl, sec-butyl, tert-butyl, and methylsulfonyl;
R$_{10}$ is H, F, Cl, Br, CH$_3$, CH$_2$F, CHF$_2$, CF$_3$, OCH$_3$, OCH$_2$F, OCHF$_2$, OCF$_3$, ethyl, n-propyl, isopropyl, cyclopropyl, isobutyl, sec-butyl, tert-butyl, and methylsulfonyl, nitro, acetamido, amidinyl, cyano, carbamoyl, methylcarbamoyl, dimethylcarbamoyl, 1,3,4-oxadiazol-2-yl, 5-methyl-1,3,4-5 oxadiazolyl, 1,3,4-thiadiazolyl, 5-methyl-1,3,4-thiadiazol-1H-tetrazolyl, N-morpholinyl carbonylamino, N-morpholinylsulfonyl or N-pyrrolidinylcarbonylamino;
R$_{11}$ and R$_{12}$ are, independently, H, F, Cl, or methyl;
Ar$_1$ is

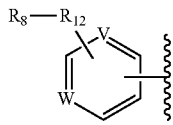

where
W and V are, independently, N, CR$_8$ or CR$_9$;
R$_8$, R$_9$ and R$_{10}$ are, independently, H, F, Cl, Br, CH$_3$, CH$_2$F, CHF$_2$, CF$_3$, OCH$_3$, OCH$_2$F, OCHF$_2$, OCF$_3$, ethyl, n-propyl, isopropyl, cyclopropyl, isobutyl, sec-butyl, tert-butyl, and methylsulfonyl, nitro, acetamido, amidinyl, cyano, carbamoyl, methylcarbamoyl, dimethylcarbamoyl, 1,3,4-oxadiazol-2-yl, 5-methyl-1,3,4-oxadiazol, 1,3,4-thiadiazol, 5-methyl-1,3,4-thiadiazol, 1H-tetrazolyl, N-morpholinylcarbonylamino, N-morpholinylsulfonyl and N-pyrrolidinylcarbonylamino;
R$_{11}$ and R$_{12}$ are, independently, H, F, Cl or methyl;
Ar$_1$ is

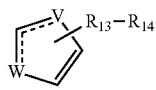

where
the dashed line represents a double bond which may be located formally either between V and the carbon between W and V, or between W and the carbon between W and V;
W is —S—, —O— or —N=, wherein
when W is —O— or —S—, V is —CH=, —CCl= or —N=; and
when W is —N=, V is CH, CCl, N or —NCH$_3$—;
R$_{13}$ and R$_{14}$ are, independently, H, methoxycarbonyl, methylcarbamoyl, acetamido, acetyl, methyl, ethyl, trifluoromethyl or halogen;

Ar$_3$ is

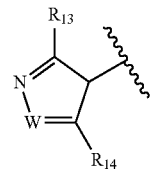

where
W is —NH—, —NCH$_3$— or —O—; and
R$_{13}$ and R$_{14}$ are, independently, H, F, Cl, or methyl.
In still further aspects, provided herein MEK protein kinase inhibitors selected from the group consisting of a compound of formula I,

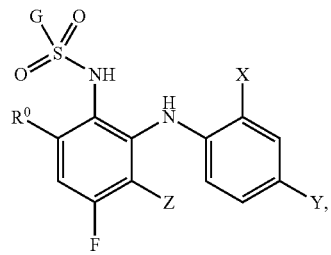

a compound of formula II,

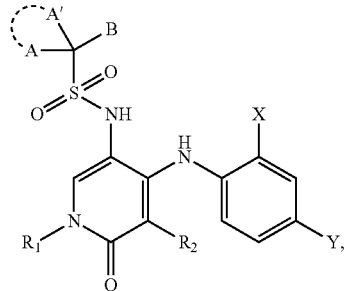

and a compound of formula III,

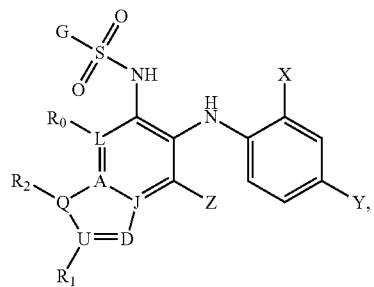

or a pharmaceutically acceptable salt, solvate, polymorph, ester, amide, tautomer or prodrug thereof.
In other aspects, provided herein are Raf protein kinase inhibitors in combination with a MEK protein kinase inhibitor. In some embodiments, the Raf protein kinase inhibitor comprises an A-Raf inhibitor, a B-Raf inhibitor, or a C-Raf inhibitor (Raf-1 inhibitor). In other embodiments, the Raf protein kinase inhibitor comprises sorafenib (Bayer) XL71

(Exelixis), SB386023, Raf 265 (Novartis), ISIS 5132 (Isis), Trapidil, GW5074, ZM336372, or quercetin (red wine extract), or a pharmaceutically acceptable salt, solvate, polymorph, ester, tautomer or prodrug thereof.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 1A shows a bar graph of the increase in apoptosis levels of the combination of 0.1 μM of compound A and 3.5 μM of sorafenib and the combination of 0.1 μM compound B and 3.5 μM of sorafenib in Hepatoma HUH7 cells at day 6.

FIG. 1B shows a bar graph of the increase in apoptosis levels of the combination of 0.25 μM of compound A and 3.5 μM sorafenib and the combination of 0.25 μM compound B and 3.5 μM sorafenib in Hepatoma HepG2 cells at day 6.

FIG. 1C shows a bar graph of the increase in apoptosis levels of the combination of 0.1 μM of compound A and 3.5 μM of sorafenib and the combination of 0.1 μM of compound B and 3.5 μM of sorafenib in Sarcoma U2-OS cells at day 5.

FIG. 1D shows a bar graph of the increase in apoptosis levels of the combination of 0.1 μM of compound A and 3.0 μM of sorafenib and the combination of 0.1 μM of compound A and 3.0 μM of sorafenib in Glioma D 37 cells at day 5.

FIG. 1E shows a bar graph of the increase in apoptosis level of the combination of 0.2 μM of compound A and 5.0 μM of sorafenib in Pancreatic Hs766T cells.

FIG. 1F shows a bar graph of the apoptosis level of the combination of 1.5 μM of compound A and 5.0 μM of sorafenib in Pancreatic L35 cells.

FIG. 1G shows a bar graph of the increase in apoptosis levels of the combination of 0.1 μM of compound A and 2.5 μM of sorafenib and the combination of 0.1 μM of AZD6244 and 2.5 μM of sorafenib in non-small cell lung cancer (NSCLC) MV522 cells at day 6.

FIG. 5 shows a bar graph at day 5 of the apoptosis level at day 4 of the combination of 0.5 μM of a compound of formula I (compound A) and 1.5 μM of sorafenib in non-small cell lung cancer (NSCLC) H727 cells.

FIG. 6A depicts a bar graph showing a decrease in cell proliferation count of Hep3B Hepatoma cells treated with 250 nM of a compound A and 5 μM of sorafenib.

FIG. 6B depicts a bar graph showing a decrease in cell proliferation count relative to vehicle in Hep3B Hepatoma cells treated with 250 nM of a compound A and 0.4 μM of sorafenib and 25 nM of compound B and 0.4 μM of sorafenib.

FIG. 6C depicts a bar graph showing a decrease in cell proliferation count relative to vehicle in Hep3B Hepatoma cells treated with 250 nM of a compound A and 2.0 μM of sorafenib and 25 nM of compound B and 2.0 μM of sorafenib.

FIG. 8A shows that sorafenib exhibits little activity in inhibiting proliferation of Hep3B cells after 3 days at doses of 5 μM and lower. The addition of a subefficacious dose of 250 nM of compound A greatly increases the inhibition of cell proliferation by sorafenib at both 5 μM and 1.25 μM.

FIG. 8B demonstrates that compound A shows little activity in inhibiting proliferation of Hep3B cells after 4 days at doses of 0.4 μM and lower. The addition of a subefficacious dose of 1 μM sorafenib greatly increases the inhibition of cell proliferation by compound A at both 0.4 μM and 0.08 μM.

FIG. 8C demonstrates that sorafenib exhibits little or no inhibition of proliferation of Hep3B cells after 4 days at doses of 2 μM and lower. The addition of a subefficacious dose of 250 nM of compound A greatly increases the inhibition of cell proliferation by sorafenib at 2 uM and 0.4 μM.

FIG. 10 shows a bar graph of the increase in apoptosis levels of HUH7 cells treated with 0.5 μM compound A and 3.5 μM sorafenib at day 4 with washing in between treatment of each agent in certain samples. The figure shows that washing the cells after 28 hours of treatment with sorafenib followed with treatment of compound A did not prevent the synergistic increase in apoptosis from taking effect despite the washing of the sorafenib. The washing of the cells in between treatment represents sequential treatment of sorafenib and compound A.

DETAILED DESCRIPTION OF THE INVENTION

Figure 2:
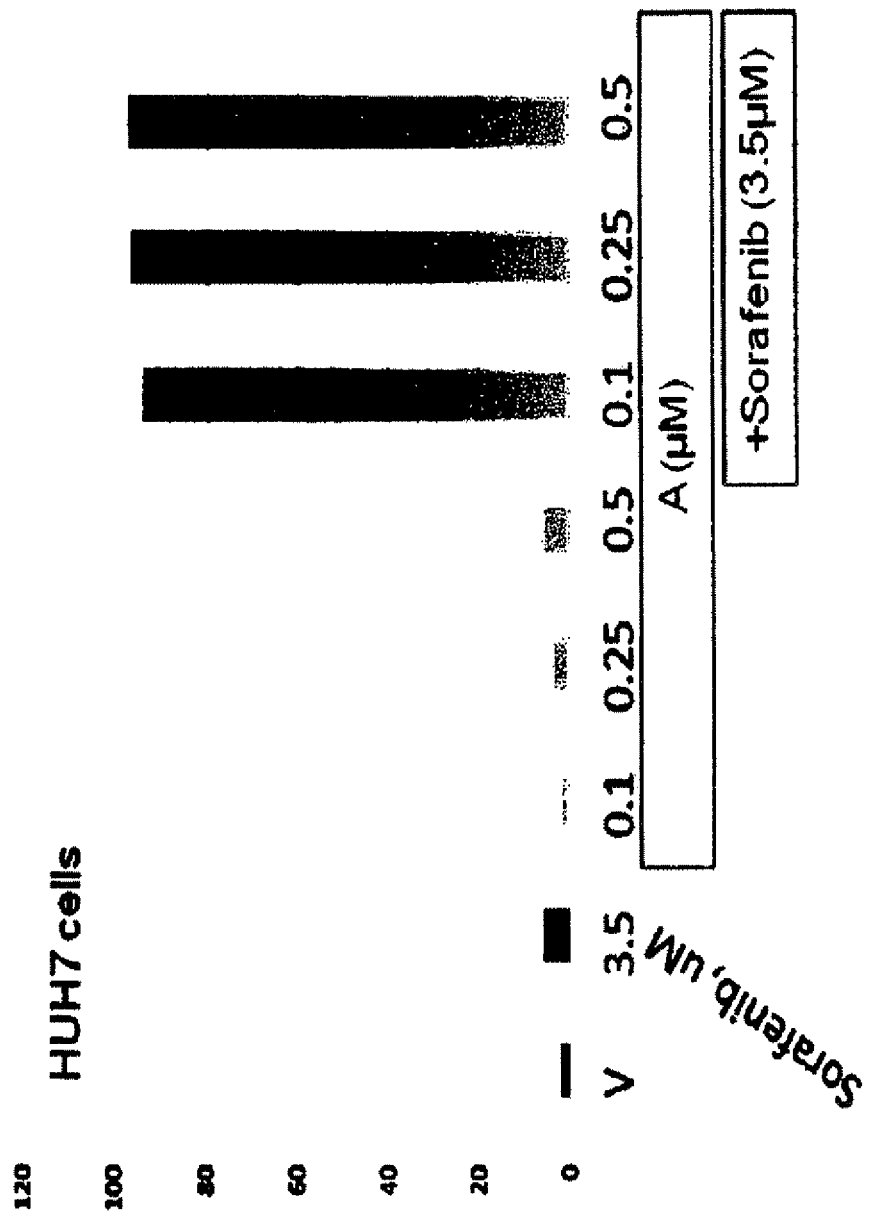
FIG. 2 shows a bar graph of the increase in apoptosis level of sorafenib resistant Hepatoma HUH7 cells to increasing concentrations of 0.1 μM, 0.25 μM, and 0.5 μM of compound A in combination with 3.5 μM sorafenib.
Figure 3:
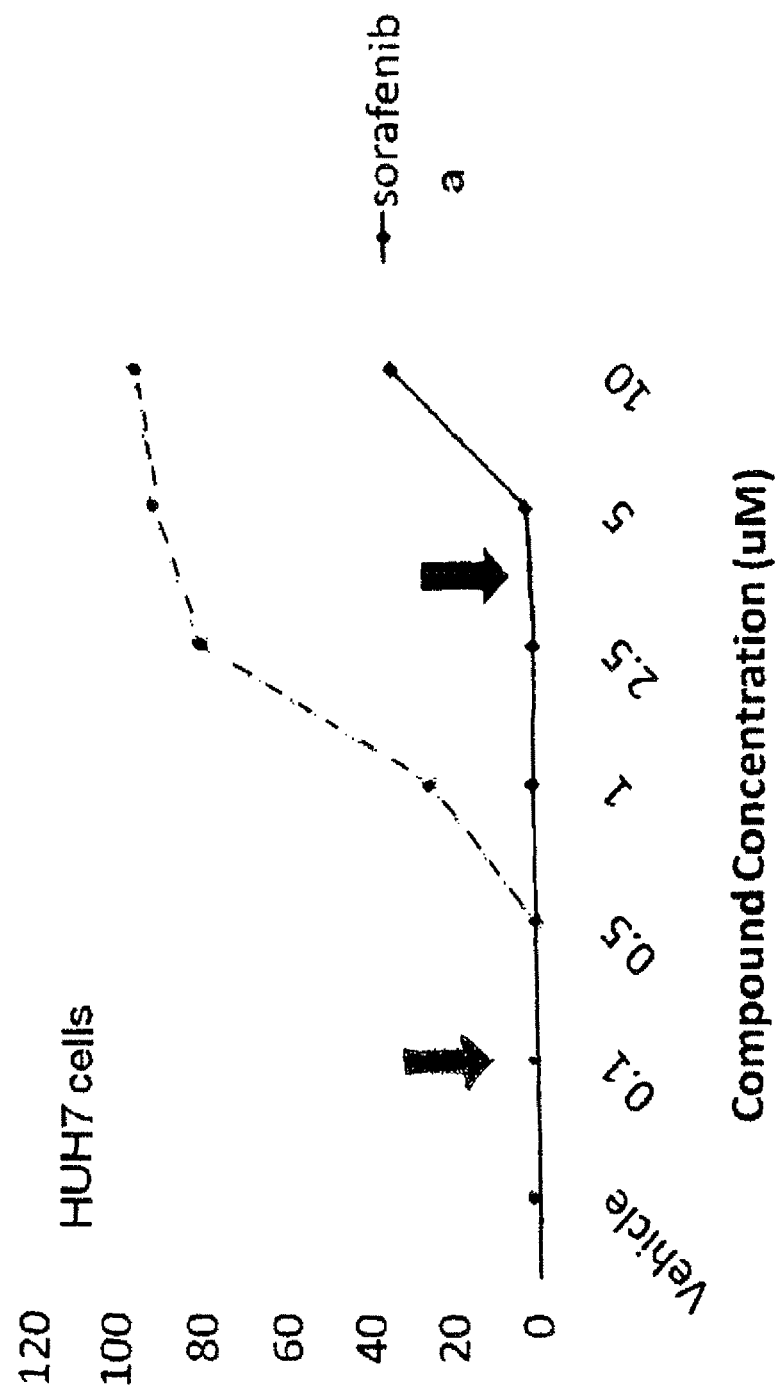
FIG. 3 shows a graph of the treatment of sorafenib resistant Hepatoma HUH7 cells with increasing concentrations of compound A.
Figure 4A:
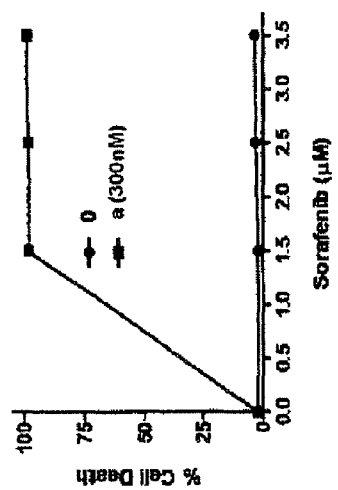
FIG. 4A shows a graph at day 4 of the increase in apoptosis level of Hep3B cell lines treated with 300 nM of compound A in combination with increasing concentrations of sorafenib.
Figure 4B:
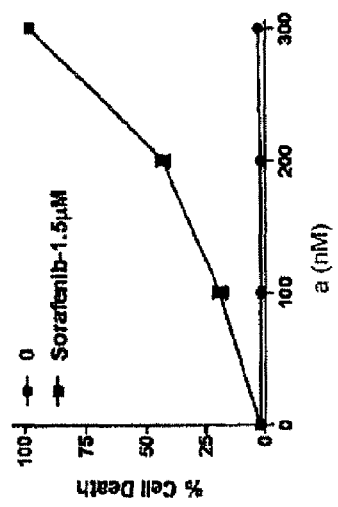
FIG. 4B shows a graph of the increase in apoptosis level at day 4 of Hep3B cell lines treated with 1. μM sorafenib in combination with increasing concentrations of a compound of formula I (compound A).
Figure 4C:
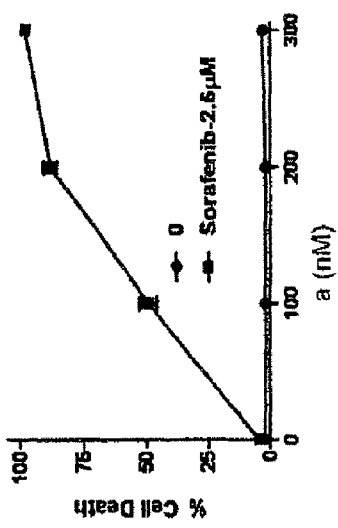
FIG. 4C shows a graph of the increase in apoptosis level at day 4 of Hep3B cell lines treated with 2.5 μM sorafenib in combination with increasing concentrations of compound A.
Figure 4D:
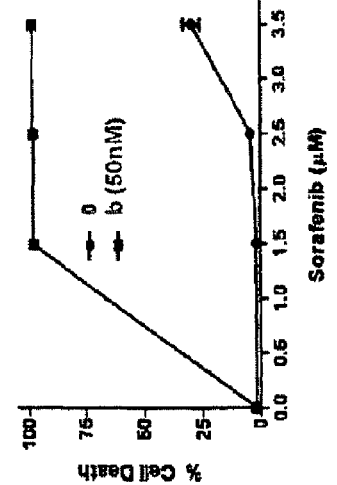
FIG. 4D provides a graph of the increase in apoptosis level at day 4 of Hep3B cells treated with 50 nM of compound B and increasing concentrations of sorafenib.
Figure 4E:
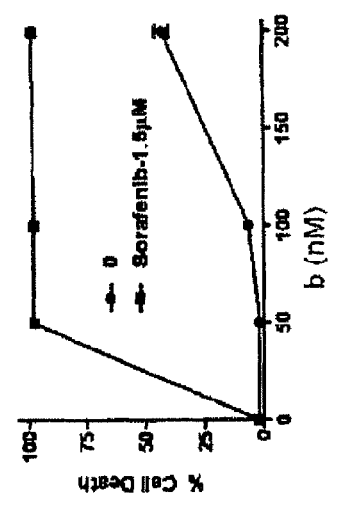
FIG. 4E provides a graph of the increase in apoptosis level at day 4 of Hep3B cells treated with 1.5 μM of compound B and increasing concentrations of sorafenib.
Figure 4F:
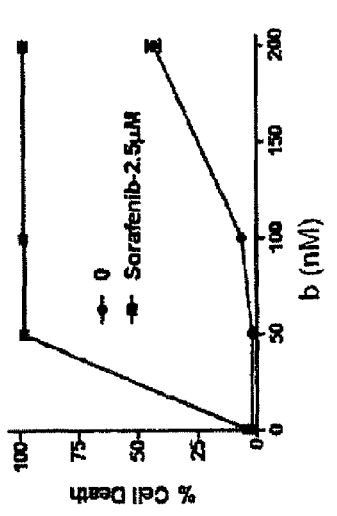
FIG. 4F provides a graph of the increase in apoptosis level at day 4 of Hep3B cells treated with 2.5 μM of compound B and increasing concentrations of sorafenib.

The section headings used herein are for organizational purposes only and are not to be construed as limiting the subject matter described. All documents, or portions of documents, cited in the application including, without limitation, patents, patent applications, articles, books, manuals, and treatises are hereby expressly incorporated by reference in their entirety for any purpose.

Certain Chemical Terminology

Unless defined otherwise, all technical and scientific terms used herein have the same meaning as is commonly understood by one of skill in the art to which the claimed subject matter belongs. All patents, patent applications, published materials referred to throughout the entire disclosure herein, unless noted otherwise, are incorporated by reference in their entirety. In the event that there is a plurality of definitions for terms herein, those in this section prevail. Where reference is made to a URL or other such identifier or address, it is understood that such identifiers can change and particular information on the internet can come and go, but equivalent information can be found by searching the internet or other appropriate reference source. Reference thereto evidences the availability and public dissemination of such information.

It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a", "an" and "the" include plural referents unless the context clearly dictates otherwise. It should also be noted that use of "or" means "and/or" unless stated otherwise. Furthermore, use of the term "including" as well as other forms, such as "include", "includes", and "included" is not limiting.

Definition of standard chemistry terms may be found in reference works, including Carey and Sundberg "Advanced Organic Chemistry 4th Ed." Vols. A (2000) and B (2001), Plenum Press, New York. Unless otherwise indicated, conventional methods of mass spectroscopy, NMR, HPLC, IR and UV/Vis spectroscopy and pharmacology, within the skill of the art are employed. Unless specific definitions are provided, the nomenclature employed in connection with, and the laboratory procedures and techniques of, analytical chemistry, synthetic organic chemistry, and medicinal and pharmaceutical chemistry described herein are those known in the art. Standard techniques can be used for chemical syntheses, chemical analyses, pharmaceutical preparation, formulation, and delivery, and treatment of patients. Reactions and purification techniques can be performed e.g., using kits of manufacturer's specifications or as commonly accomplished in the art or as described herein. The foregoing techniques and procedures can be generally performed of conventional methods well known in the art and as described in various general and more specific references that are cited and discussed throughout the present specification. Throughout the specification, groups and substituents thereof can be chosen by one skilled in the field to provide stable moieties and compounds.

Where substituent groups are specified by their conventional chemical formulas, written from left to right, they equally encompass the chemically identical substituents that would result from writing the structure from right to left. As a non-limiting example, —CH$_2$O— is equivalent to —OCH$_2$—.

Unless otherwise noted, the use of general chemical terms, such as though not limited to "alkyl," "amine," "aryl," are equivalent to their optionally substituted forms. For example, "alkyl," as used herein, includes optionally substituted alkyl.

The compounds presented herein may possess one or more stereocenters and each center may exist in the R or S configuration, or combinations thereof. Likewise, the compounds presented herein may possess one or more double bonds and each may exist in the E (trans) or Z (cis) configuration, or combinations thereof. Presentation of one particular stereoisomer, regioisomer, diastereomer, enantiomer or epimer should be understood to include all possible stereoisomers, regioisomers, diastereomers, enantiomers or epimers and mixtures thereof. Thus, the compounds presented herein include all separate configurational stereoisomeric, regioisomeric, diastereomeric, enantiomeric, and epimeric forms as well as the corresponding mixtures thereof. Presentation of one particular chemical structure or chemical name for a compound which contains one or more chiral centers, but which does not designate a particular stereochemistry, should be understood to include all possible stereoisomers, including mixtures of all possible stereoisomers, pure forms or substantially pure forms of one particular stereoisomer and pure forms or substantially pure forms of the alternate stereoisomer. Techniques for inverting or leaving unchanged a particular stereocenter, and those for resolving mixtures of stereoisomers are well known in the art and it is well within the ability of one of skill in the art to choose an appropriate method for a particular situation. See, for example, Furniss et al. (eds.), VOGEL'S ENCYCLOPEDIA OF PRACTICAL ORGANIC CHEMISTRY 5.sup.TH ED., Longman Scientific and Technical Ltd., Essex, 1991, 809-816; and Heller, Acc. Chem. Res. 1990, 23, 128.

The terms "moiety", "chemical moiety", "group" and "chemical group", as used herein refer to a specific segment or functional group of a molecule. Chemical moieties are often recognized chemical entities embedded in or appended to a molecule.

The term "bond" or "single bond" refers to a chemical bond between two atoms, or two moieties when the atoms joined by the bond are considered to be part of larger substructure.

The term "optional" or "optionally" means that the subsequently described event or circumstance may or may not occur, and that the description includes instances where said event or circumstance occurs and instances in which it does not. For example, "optionally substituted alkyl" means either "alkyl" or "substituted alkyl" as defined below. Further, an optionally substituted group may be un-substituted (e.g., —CH2CH3), fully substituted (e.g., —CF2CF3), mono-substituted (e.g., —CH2CH2F) or substituted at a level anywhere in-between fully substituted and mono-substituted (e.g., —CH2CHF2, —CH2CF3, —CF2CH3, —CFHCHF2, etc). It will be understood by those skilled in the art with respect to any group containing one or more substituents that such groups are not intended to introduce any substitution or substitution patterns (e.g., substituted alkyl includes optionally substituted cycloalkyl groups, which in turn are defined as including optionally substituted alkyl groups, potentially ad infinitum) that are sterically impractical and/or synthetically non-feasible. Thus, any substituents described should generally be understood as having a maximum molecular weight of about 1,000 daltons, and more typically, up to about 500 daltons (except in those instances where macromolecular substituents are clearly intended, e.g., polypeptides, polysaccharides, polyethylene glycols, DNA, RNA and the like).

Unless otherwise noted, the use of general chemical terms, such as though not limited to "alkyl," "amine," "aryl," are unsubstituted.

As used herein, C1-Cx includes C1-C2, C1-C3 . . . C1-Cx. By way of example only, a group designated as "C1-C4" indicates that there are one to four carbon atoms in the moiety, i.e. groups containing 1 carbon atom, 2 carbon atoms, 3 carbon atoms or 4 carbon atoms, as well as the ranges C1-C2 and C1-C3. Thus, by way of example only, "C1-C4 alkyl" indicates that there are one to four carbon atoms in the alkyl group, i.e., the alkyl group is selected from among methyl, ethyl, propyl, iso-propyl, n-butyl, iso-butyl, sec-butyl, and t-butyl. Whenever it appears herein, a numerical range such as "1 to 10" refers to each integer in the given range; e.g., "1 to 10 carbon atoms" means that the group may have 1 carbon atom, 2 carbon atoms, 3 carbon atoms, 4 carbon atoms, 5 carbon atoms, 6 carbon atoms, 7 carbon atoms, 8 carbon atoms, 9 carbon atoms, or 10 carbon atoms.

The term "A and A', together with the carbon atom to which they are attached, form a 3- to 6-member saturated ring", as used herein, refers to the following structures for compounds of formula I:

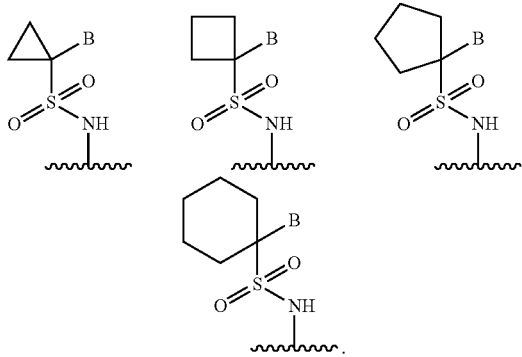

The terms "heteroatom" or "hetero" as used herein, alone or in combination, refer to an atom other than carbon or hydrogen. Heteroatoms are may be independently selected from among oxygen, nitrogen, sulfur, phosphorous, silicon, selenium and tin but are not limited to these atoms. In embodiments in which two or more heteroatoms are present, the two or more heteroatoms can be the same as each another, or some or all of the two or more heteroatoms can each be different from the others.

The term "alkyl" as used herein, alone or in combination, refers to a straight-chain or branched-chain saturated hydrocarbon monoradical having from one to about ten carbon atoms, or one to six carbon atoms. Examples include, but are not limited to methyl, ethyl, n-propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, n-butyl, isobutyl, sec-butyl, t-butyl, n-pentyl, isopentyl, neopentyl, text-amyl and hexyl, and longer alkyl groups, such as heptyl, octyl and the like. Whenever it appears herein, a numerical range such as "$C_1$-$C_6$ alkyl" or "$C_{1-6}$ alkyl", means that the alkyl group may consist of 1 carbon atom, 2 carbon atoms, 3 carbon atoms, 4 carbon atoms, 5 carbon atoms or 6 carbon atoms. In one embodiment, the "alkyl" is substituted. Unless otherwise indicated, the "alkyl" is unsubstituted.

The term "alkenyl" as used herein, alone or in combination, refers to a straight-chain or branched-chain hydrocarbon monoradical having one or more carbon-carbon double-bonds and having from two to about ten carbon atoms, or two to about six carbon atoms. The group may be in either the cis or trans conformation about the double bond(s), and should be understood to include both isomers. Examples include, but are not limited to ethenyl (—CH=CH2), 1-propenyl (—CH2CH=CH2), isopropenyl [—O(CH3)=CH2], butenyl, 1,3-butadienyl and the like. Whenever it appears herein, a numerical range such as "C2-C6 alkenyl" or "C2-6 alkenyl", means that the alkenyl group may consist of 2 carbon atoms, 3 carbon atoms, 4 carbon atoms, 5 carbon atoms or 6 carbon atoms. In one embodiment, the "alkenyl" is substituted. Unless otherwise indicated, the "alkenyl" is unsubstituted.

The term "alkynyl" as used herein, alone or in combination, refers to a straight-chain or branched-chain hydrocarbon monoradical having one or more carbon-carbon triple-bonds and having from two to about ten carbon atoms, or from two to about six carbon atoms. Examples include, but are not limited to ethynyl, 2-propynyl, 2-butynyl, 1,3-butadiynyl and the like. Whenever it appears herein, a numerical range such as "C2-C6 alkynyl" or "C2-6 alkynyl", means that the alkynyl group may consist of 2 carbon atoms, 3 carbon atoms, 4 carbon atoms, 5 carbon atoms or 6 carbon atoms. In one embodiment, the "alkynyl" is substituted. Unless otherwise indicated, the "alkynyl" is unsubstituted.

The terms "heteroalkyl", "heteroalkenyl" and "heteroalkynyl" as used herein, alone or in combination, refer to alkyl, alkenyl and alkynyl structures respectively, as described above, in which one or more of the skeletal chain carbon atoms (and any associated hydrogen atoms, as appropriate) are each independently replaced with a heteroatom (i.e. an atom other than carbon, such as though not limited to oxygen, nitrogen, sulfur, silicon, phosphorous, tin or combinations thereof), or heteroatomic group such as though not limited to —O—O—, —S—S—, —O—S—, —S—O—, —N—N—, —N=N—NH—, —P(O)$_2$—, —O—P(O)$_2$—, —P(O)$_2$—O—, —S(O)—, —S(O)$_2$—, —SnH$_2$— and the like.

The terms "haloalkyl", "haloalkenyl" and "haloalkynyl" as used herein, alone or in combination, refer to alkyl, alkenyl and alkynyl groups respectively, as defined above, in which one or more hydrogen atoms is replaced by fluorine, chlorine, bromine or iodine atoms, or combinations thereof. In some embodiments two or more hydrogen atoms may be replaced with halogen atoms that are the same as each another (e.g. difluoromethyl); in other embodiments two or more hydrogen atoms may be replaced with halogen atoms that are not all the same as each other (e.g. 1-chloro-1-fluoro-1-iodoethyl). Non-limiting examples of haloalkyl groups are fluoromethyl, chloromethyl and bromoethyl. A non-limiting example of a haloalkenyl group is bromoethenyl. A non-limiting example of a haloalkynyl group is chloroethynyl.

The term "carbon chain" as used herein, alone or in combination, refers to any alkyl, alkenyl, alkynyl, heteroalkyl, heteroalkenyl or heteroalkynyl group, which is linear, cyclic, or any combination thereof. If the chain is part of a linker and that linker comprises one or more rings as part of the core backbone, for purposes of calculating chain length, the "chain" only includes those carbon atoms that compose the bottom or top of a given ring and not both, and where the top and bottom of the ring(s) are not equivalent in length, the shorter distance shall be used in determining the chain length. If the chain contains heteroatoms as part of the backbone, those atoms are not calculated as part of the carbon chain length.

The terms "cycle", "cyclic", "ring" and "membered ring" as used herein, alone or in combination, refer to any covalently closed structure, including alicyclic, heterocyclic, aromatic, heteroaromatic and polycyclic fused or non-fused ring systems as described herein. Rings can be optionally substituted. Rings can form part of a fused ring system. The term "membered" is meant to denote the number of skeletal atoms that constitute the ring. Thus, by way of example only, cyclohexane, pyridine, pyran and pyrimidine are six-membered rings and cyclopentane, pyrrole, tetrahydrofuran and thiophene are five-membered rings.

The term "fused" as used herein, alone or in combination, refers to cyclic structures in which two or more rings share one or more bonds.

The term "cycloalkyl" as used herein, alone or in combination, refers to a saturated, hydrocarbon monoradical ring, containing from three to about fifteen ring carbon atoms or from three to about ten ring carbon atoms, though may include additional, non-ring carbon atoms as substituents (e.g. methylcyclopropyl). Whenever it appears herein, a numerical range such as "C3-C6 cycloalkyl" or "C3-6 cycloalkyl", means that the cycloalkyl group may consist of 3 carbon atoms, 4 carbon atoms, 5 carbon atoms or 6 carbon atoms, i.e., is cyclopropyl, cyclobutyl, cyclopentyl or cycloheptyl, although the present definition also covers the occurrence of the term "cycloalkyl" where no numerical range is designated. The term includes fused, non-fused, bridged and spiro radicals. A fused cycloalkyl may contain from two to four fused rings where the ring of attachment is a cycloalkyl ring, and the other individual rings may be alicyclic, heterocyclic, aromatic, heteroaromatic or any combination thereof. Examples include, but are not limited to cyclopropyl, cyclopentyl, cyclohexyl, decalinyl, and bicyclo[2.2.1]heptyl and adamantyl ring systems. Illustrative examples include, but are not limited to the following moieties:

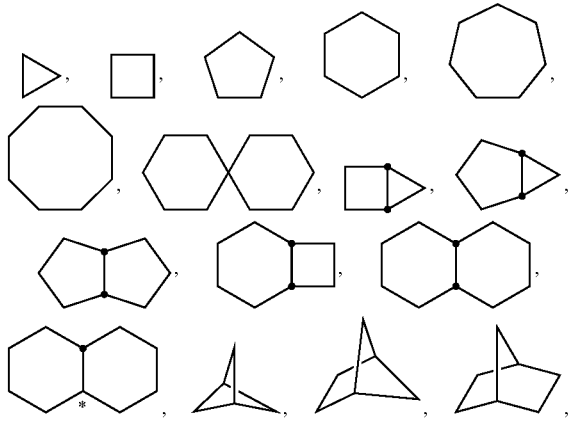

and the like.

In one embodiment, the "cycloalkyl" is substituted. Unless otherwise indicated, the "cycloalkyl" is unsubstituted.

The terms "non-aromatic heterocyclyl" and "heteroalicyclyl" as used herein, alone or in combination, refer to a saturated, partially unsaturated, or fully unsaturated nonaromatic ring monoradicals containing from three to about twenty ring atoms, where one or more of the ring atoms are an atom other than carbon, independently selected from among oxygen, nitrogen, sulfur, phosphorous, silicon, selenium and tin but are not limited to these atoms. In embodiments in which two or more heteroatoms are present in the ring, the two or more heteroatoms can be the same as each another, or some or all of the two or more heteroatoms can each be different from the others. The terms include fused, non-fused, bridged and spiro radicals. A fused non-aromatic heterocyclic radical may contain from two to four fused rings where the attaching ring is a non-aromatic heterocycle, and the other individual rings may be alicyclic, heterocyclic, aromatic, heteroaromatic or any combination thereof. Fused ring systems may be fused across a single bond or a double bond, as well as across bonds that are carbon-carbon, carbon-hetero atom or hetero atom-hetero atom. The terms also include radicals having from three to about twelve skeletal ring atoms, as well as those having from three to about ten skeletal ring atoms. Attachment of a non-aromatic heterocyclic subunit to its parent molecule can be via a heteroatom or a carbon atom. Likewise, additional substitution can be via a heteroatom or a carbon atom. As a non-limiting example, an imidazolidine non-aromatic heterocycle may be attached to a parent molecule via either of its N atoms (imidazolidin-1-yl or imidazolidin-3-yl) or any of its carbon atoms (imidazolidin-2-yl, imidazolidin-4-yl or imidazolidin-5-yl). In certain embodiments, non-aromatic heterocycles contain one or more carbonyl or thiocarbonyl groups such as, for example, oxo- and thio-containing groups. Examples include, but are not limited to pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl and quinolizinyl. Illustrative examples of heterocycloalkyl groups, also referred to as non-aromatic heterocycles, include:

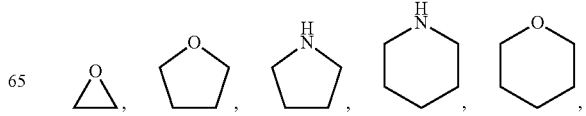

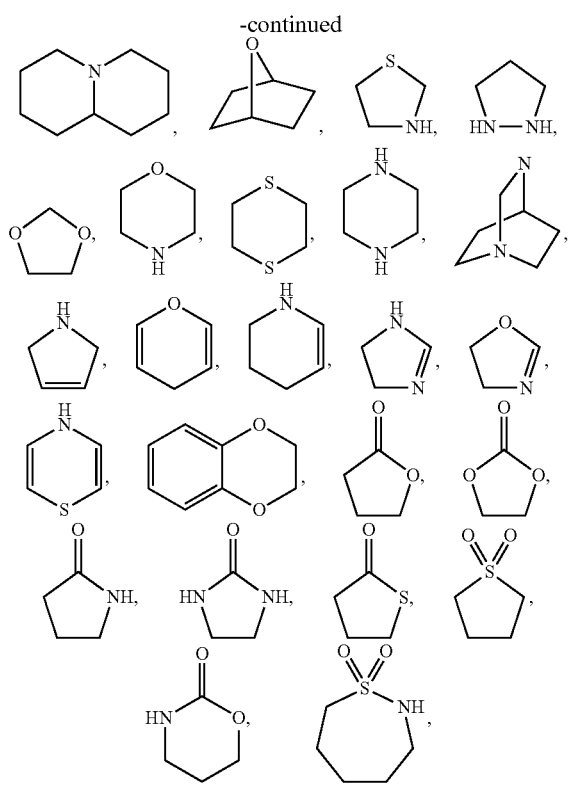

and the like.

The terms also include all ring forms of the carbohydrates, including but not limited to the monosaccharides, the disaccharides and the oligosaccharides. In one embodiment, the "non-aromatic heterocyclyl" or "heteroalicyclyl" is substituted. Unless otherwise indicated, the "non-aromatic heterocyclyl" or "heteroalicyclyl" is unsubstituted.

The term "aryl" as used herein, alone or in combination, refers to an aromatic hydrocarbon radical of six to about twenty ring carbon atoms, and includes fused and non-fused aryl rings. A fused aryl ring radical contains from two to four fused rings where the ring of attachment is an aryl ring, and the other individual rings may be alicyclic, heterocyclic, aromatic, heteroaromatic or any combination thereof. Further, the term aryl includes fused and non-fused rings containing from six to about twelve ring carbon atoms, as well as those containing from six to about ten ring carbon atoms. A non-limiting example of a single ring aryl group includes phenyl; a fused ring aryl group includes naphthyl, phenanthrenyl, anthracenyl, azulenyl; and a non-fused bi-aryl group includes biphenyl. In one embodiment, the "aryl" is substituted. Unless otherwise indicated, the "aryl" is unsubstituted.

The term "heteroaryl" as used herein, alone or in combination, refers to an aromatic monoradicals containing from about five to about twenty skeletal ring atoms, where one or more of the ring atoms is a heteroatom independently selected from among oxygen, nitrogen, sulfur, phosphorous, silicon, selenium and tin but not limited to these atoms and with the proviso that the ring of said group does not contain two adjacent O or S atoms. In embodiments in which two or more heteroatoms are present in the ring, the two or more heteroatoms can be the same as each another, or some or all of the two or more heteroatoms can each be different from the others. The term heteroaryl includes fused and non-fused heteroaryl radicals having at least one heteroatom. The term heteroaryl also includes fused and non-fused heteroaryls having from five to about twelve skeletal ring atoms, as well as those having from five to about ten skeletal ring atoms. Bonding to a heteroaryl group can be via a carbon atom or a heteroatom. Thus, as a non-limiting example, an imidazole group may be attached to a parent molecule via any of its carbon atoms (imidazol-2-yl, imidazol-4-yl or imidazol-5-yl), or its nitrogen atoms (imidazol-1-yl or imidazol-3-yl). Likewise, a heteroaryl group may be further substituted via any or all of its carbon atoms, and/or any or all of its heteroatoms. A fused heteroaryl radical may contain from two to four fused rings where the ring of attachment is a heteroaromatic ring and the other individual rings may be alicyclic, heterocyclic, aromatic, heteroaromatic or any combination thereof. A non-limiting example of a single ring heteroaryl group includes pyridyl; fused ring heteroaryl groups include benzimidazolyl, quinolinyl, acridinyl; and a non-fused bi-heteroaryl group includes bipyridinyl. Further examples of heteroaryls include, without limitation, furanyl, thienyl, oxazolyl, acridinyl, phenazinyl, benzimidazolyl, benzofuranyl, benzoxazolyl, benzothiazolyl, benzothiadiazolyl, benzothiophenyl, benzoxadiazolyl, benzotriazolyl, imidazolyl, indolyl, isoxazolyl, isoquinolinyl, indolizinyl, isothiazolyl, isoindolyloxadiazolyl, indazolyl, pyridyl, pyridazyl, pyrimidyl, pyrazinyl, pyrrolyl, pyrazinyl, pyrazolyl, purinyl, phthalazinyl, pteridinyl, quinolinyl, quinazolinyl, quinoxalinyl, triazolyl, tetrazolyl, thiazolyl, triazinyl, thiadiazolyl and the like, and their oxides, such as for example pyridyl-N-oxide. Illustrative examples of heteroaryl groups include the following moieties:

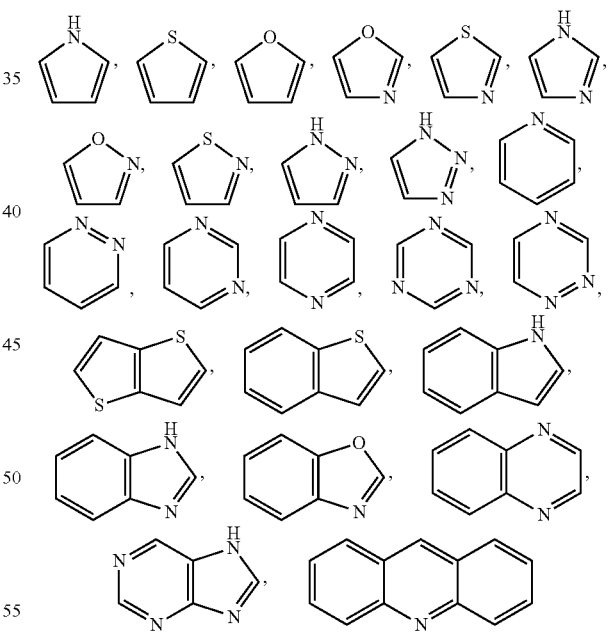

and the like.

In one embodiment, the "heteroaryl" is substituted. Unless otherwise indicated, the "heteroaryl" is unsubstituted.

The term "heterocyclyl" as used herein, alone or in combination, refers collectively to heteroalicyclyl and heteroaryl groups. Herein, whenever the number of carbon atoms in a heterocycle is indicated (e.g., C1-C6 heterocycle), at least one non-carbon atom (the heteroatom) must be present in the ring. Designations such as "C1-C6 heterocycle" refer only to the number of carbon atoms in the ring and do not refer to the total number of atoms in the ring. Designations such as "4-6 membered heterocycle" refer to the total number of atoms that are contained in the ring (i.e., a four, five, or six membered ring, in which at least one atom is a carbon atom, at least one atom is a heteroatom and the remaining two to four atoms are either carbon atoms or heterocycles). For heterocycles having two or more heteroatoms, those two or more heteroatoms can be the same or different from one another. Non-aromatic heterocyclic groups include groups having only three atoms in the ring, while aromatic heterocyclic groups must have at least five atoms in the ring. Bonding (i.e. attachment to a parent molecule or further substitution) to a heterocycle can be via a heteroatom or a carbon atom. In one embodiment, the "heterocyclyl" is substituted. Unless otherwise indicated, the "heterocycyl" is unsubstituted.

The terms "halogen", "halo" or "halide" as used herein, alone or in combination refer to fluoro, chloro, bromo and/or iodo.

The term "amino" as used herein, alone or in combination, refers to the monoradical —NH2.

The term "alkylamino" as used herein, alone or in combination, refers to the monoradical —NH(alkyl) where alkyl is as defined herein.

The term "dialkylamino" as used herein, alone or in combination, refers to the monoradical —N(alkyl)(alkyl) where each alkyl may be identical or non-identical and is as defined herein.

The term "diamino alkyl" as used herein, alone or in combination, refers to an alkyl group containing two amine groups, wherein said amine groups may be substituents on the alkyl group which may be amino, alkylamino, or dialkylamino groups, or wherein one or both of said amine groups may form part of an alkyl chain to form -alkylene-N(H or alkyl)-alkylene-N(H or alkyl or alkylene-)(H or alkyl or alkylene-).

The term "hydroxy" as used herein, alone or in combination, refers to the monoradical —OH.

The term "cyano" as used herein, alone or in combination, refers to the monoradical —CN.

The term "cyanomethyl" as used herein, alone or in combination, refers to the monoradical —CH2CN.

The term "nitro" as used herein, alone or in combination, refers to the monoradical —NO2.

The term "oxy" as used herein, alone or in combination, refers to the diradical —O—.

The term "oxo" as used herein, alone or in combination, refers to the diradical =O.

The term "carbonyl" as used herein, alone or in combination, refers to the diradical —C(=O)—, which may also be written as —C(O)—.

The terms "carboxy" or "carboxyl" as used herein, alone or in combination, refer to the moiety —C(O)OH, which may also be written as —COOH.

The term "alkoxy" as used herein, alone or in combination, refers to an alkyl ether radical, —O-alkyl, including the groups —O-aliphatic and —O-carbocyclyl, wherein the alkyl, aliphatic and carbocyclyl groups may be optionally substituted, and wherein the terms alkyl, aliphatic and carbocyclyl are as defined herein. Non-limiting examples of alkoxy radicals include methoxy, ethoxy, n-propoxy, isopropoxy, n-butoxy, iso-butoxy, sec-butoxy, tert-butoxy and the like.

The term "sulfinyl" as used herein, alone or in combination, refers to the diradical —S(=O)—.

The term "sulfonyl" as used herein, alone or in combination, refers to the diradical —S(=O)2—.

The terms "sulfonamide", "sulfonamido" and "sulfonamidyl" as used herein, alone or in combination, refer to the diradical groups —S(=O)2—NH— and —NH—S(=O)2—.

The terms "sulfamide", "sulfamido" and "sulfamidyl" as used herein, alone or in combination, refer to the diradical group —NH—S(=O)2—NH—.

The term "reactant," as used herein, refers to a nucleophile or electrophile used to create covalent linkages.

It is to be understood that in instances where two or more radicals are used in succession to define a substituent attached to a structure, the first named radical is considered to be terminal and the last named radical is considered to be attached to the structure in question. Thus, for example, the radical arylalkyl is attached to the structure in question by the alkyl group.

Certain Pharmaceutical Terminology

The term "MEK inhibitor" as used herein refers to a compound that exhibits an IC50 with respect to MEK activity, of no more than about 100 µM or not more than about 50 µM, as measured in the Mek1 kinase assay described generally herein. "IC50" is that concentration of inhibitor which reduces the activity of an enzyme (e.g., MEK) to half-maximal level. Compounds useful in certain of the combinations and methods described herein preferably exhibit an IC50 with respect to MEK of no more than about 10 µM, more preferably, no more than about 5 µM, even more preferably not more than about 1 µM, and most preferably, not more than about 200 nM, as measured in the Mek1 kinase assay described herein.

The term "Raf inhibitor" or "Raf kinase inhibitor" as used herein refers to a compound that exhibits an IC50 with respect to Raf activity, of no more than about 100 µM or not more than about 50 µM, as measured in the Raf kinase assay described generally herein. "IC50" is that concentration of inhibitor which reduces the activity of an enzyme (e.g., Raf) to half-maximal level. Compounds useful in the certain of the combinations and method described herein preferably exhibit an IC50 with respect to Raf of no more than about 10 µM, more preferably, no more than about 5 µM, even more preferably not more than about 1 µM, and most preferably, not more than about 200 nM, as measured in the Raf kinase assay described generally herein.

The term "subject", "patient" or "individual" as used herein in reference to individuals suffering from a disorder, and the like, encompasses mammals and non-mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. In one embodiment of the methods and compositions provided herein, the mammal is a human.

In some embodiments, significance may be determined statistically—in which case two measured parameters may be referred to as statistically significant. In some embodiments, statistical significance may be quantified in terms of a stated confidence interval (CI), e.g. greater than 90%, greater than 95%, greater than 98%, etc. In some embodiments, statistical significance may be quantified in terms of a p value, e.g. less than 0.5, less than 0.1, less than 0.05, etc. The person skilled in the art will recognize these expressions of significance and will know how to apply them appropriately to the specific parameters that are being compared.

The terms "treat," "treating" or "treatment," and other grammatical equivalents as used herein, include alleviating, abating or ameliorating a disease or condition symptoms, preventing additional symptoms, ameliorating or preventing the underlying metabolic causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition, and are intended to include prophylaxis. The terms further include achieving a therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. For prophylactic benefit, the compositions may be administered to a patient at risk of developing a particular disease, or to a patient reporting one or more of the physiological symptoms of a disease, even though a diagnosis of this disease may not have been made.

The terms "effective amount", "therapeutically effective amount" or "pharmaceutically effective amount" as used herein, refer to an amount of at least one agent or compound being administered that is sufficient to treat or prevent the particular disease or condition. The result can be reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in a disease. An appropriate "effective" amount in any individual case may be determined using techniques, such as a dose escalation study.

The terms "administer," "administering", "administration," and the like, as used herein, refer to the methods that may be used to enable delivery of compounds or compositions to the desired site of biological action. These methods include, but are not limited to oral routes, intraduodenal routes, parenteral injection (including intravenous, subcutaneous, intraperitoneal, intramuscular, intravascular or infusion), topical and rectal administration. Those of skill in the art are familiar with administration techniques that can be employed with the compounds and methods described herein, e.g., as discussed in Goodman and Gilman, The Pharmacological Basis of Therapeutics, current ed.; Pergamon; and Remington's, Pharmaceutical Sciences (current edition), Mack Publishing Co., Easton, Pa. In preferred embodiments, the compounds and compositions described herein are administered orally.

The term "acceptable" as used herein, with respect to a formulation, composition or ingredient, means having no persistent detrimental effect on the general health of the subject being treated.

The term "pharmaceutically acceptable" as used herein, refers to a material, such as a carrier or diluent, which does not abrogate the biological activity or properties of the compounds described herein, and is relatively nontoxic, i.e., the material may be administered to an individual without causing undesirable biological effects or interacting in a deleterious manner with any of the components of the composition in which it is contained.

The term "pharmaceutical composition," as used herein, refers to a biologically active compound, optionally mixed with at least one pharmaceutically acceptable chemical component, such as, though not limited to carriers, stabilizers, diluents, dispersing agents, suspending agents, thickening agents, and/or excipients.

The term "carrier" as used herein, refers to relatively non-toxic chemical compounds or agents that facilitate the incorporation of a compound into cells or tissues.

The term "agonist," as used herein, refers to a molecule such as a compound, a drug, an enzyme activator or a hormone modulator which enhances the activity of another molecule or the activity of a receptor site.

The term "antagonist," as used herein, refers to a molecule such as a compound, a drug, an enzyme inhibitor, or a hormone modulator, which diminishes, or prevents the action of another molecule or the activity of a receptor site.

The term "modulate," as used herein, means to interact with a target either directly or indirectly so as to alter the activity of the target, including, by way of example only, to enhance the activity of the target, to inhibit the activity of the target, to limit the activity of the target, or to extend the activity of the target.

The term "modulator," as used herein, refers to a molecule that interacts with a target either directly or indirectly. The interactions include, but are not limited to, the interactions of an agonist and an antagonist.

The term "pharmaceutically acceptable derivative or prodrug" as used herein, refers to any pharmaceutically acceptable salt, ester, salt of an ester or other derivative of a compound of formula I, which, upon administration to a recipient, is capable of providing, either directly or indirectly, a compound of this invention or a pharmaceutically active metabolite or residue thereof. Particularly favored derivatives or prodrugs are those that increase the bioavailability of the compounds of this invention when such compounds are administered to a patient (e.g., by allowing orally administered compound to be more readily absorbed into blood) or which enhance delivery of the parent compound to a biological compartment (e.g., the brain or lymphatic system).

As used herein, a "prodrug" is a compound that may be converted under physiological conditions or by solvolysis to the specified compound or to a pharmaceutically acceptable salt of such compound. Prodrugs include compounds wherein an amino acid residue, or a polypeptide chain of two or more amino acid residues, is covalently joined through an amide or ester bond to a free amino, hydroxy, or carboxylic acid group of compounds of Formulas I. The amino acid residues contemplated include but are not limited to the 20 naturally-occurring amino acids. Other suitable amino acids include 4-hydroxyproline, hydroxylysine, demosine, isodemosine, 3-methyl histidine, norvaline, β-alanine, γ-aminobutyric acid, cirtulline, homocysteine, homoserine, ornithine and methionine sulfone. Additional types of prodrugs are well known in the art.

Pharmaceutically acceptable prodrugs of the compounds described herein include, but are not limited to, esters, carbonates, thiocarbonates, N-acyl derivatives, N-acyloxyalkyl derivatives, quaternary derivatives of tertiary amines, N-Mannich bases, Schiff bases, amino acid conjugates, phosphate esters, metal salts and sulfonate esters. Various forms of prodrugs are well known in the art. See for example Design of Prodrugs, Bundgaard, A. Ed., Elseview, 1985 and Method in Enzymology, Widder, K. et al., Ed.; Academic, 1985, vol. 42, p. 309-396; Bundgaard, H. "Design and Application of Prodrugs" in A Textbook of Drug Design and Development, Krosgaard-Larsen and H. Bundgaard, Ed., 1991, Chapter 5, p. 113-191; and Bundgaard, H., Advanced Drug Delivery Review, 1992, 8, 1-38, each of which is incorporated herein by reference. The prodrugs described herein include, but are not limited to, the following groups and combinations of these groups; amine derived prodrugs:

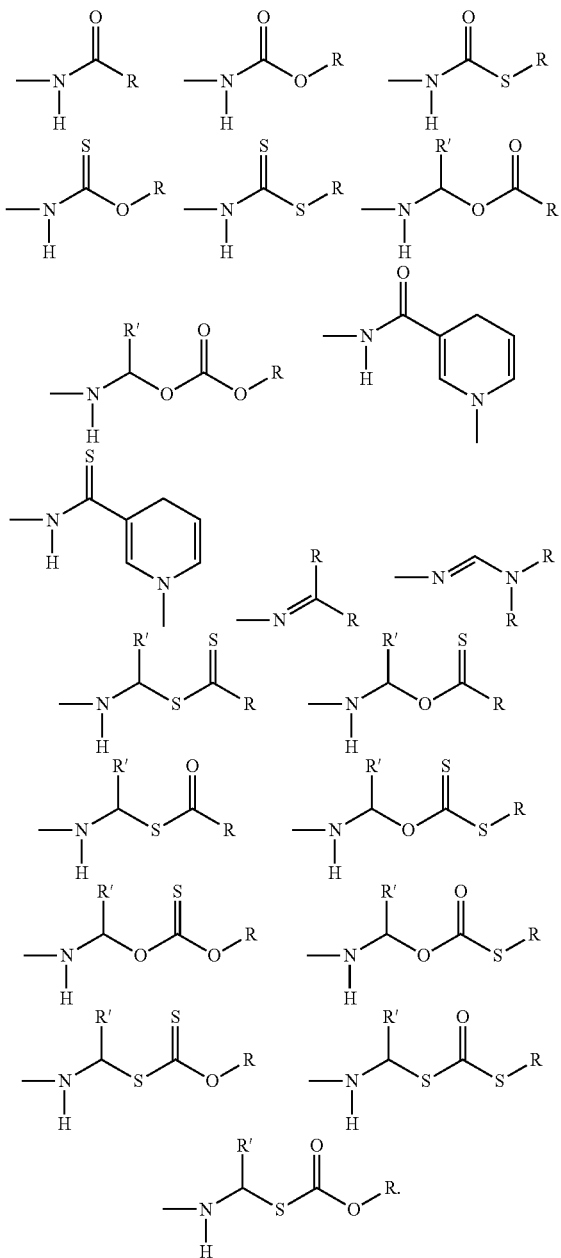

Hydroxy prodrugs include, but are not limited to acyloxyalkyl esters, alkoxycarbonyloxyalkyl esters, alkyl esters, aryl esters and disulfide containing esters.

The term "pharmaceutically acceptable salt" as used herein, includes salts that retain the biological effectiveness of the free acids and bases of the specified compound and that are not biologically or otherwise undesirable. Compounds described may possess acidic or basic groups and therefore may react with any of a number of inorganic or organic bases, and inorganic and organic acids, to form a pharmaceutically acceptable salt. Examples of pharmaceutically acceptable salts include those salts prepared by reaction of the compounds described herein with a mineral or organic acid or an inorganic base, such salts including, acetate, acrylate, adipate, alginate, aspartate, benzoate, benzenesulfonate, bisulfate, bisulfate, bromide, butyrate, butyn-1,4-dioate, camphorate, camphorsulfonate, caproate, caprylate, chlorides, chlorobenzoate, chloride, citrate, cyclopentanepropionate, decanoate, digluconate, dihydrogenphosphate, dinitrobenzoate, dodecylsulfate, ethanesulfonate, formate, fumarate, glucoheptanoate, glycerophosphate, glycolate, hemisulfate, heptanoate, hexanoate, hexyne-1,6-dioate, hydroxybenzoate, γ-hydroxybutyrate, hydrochloride, hydrobromide, hydroiodide, 2-hydroxyethanesulfonate, iodide, isobutyrate, lactate, maleate, malonate, methanesulfonate, mandelate, metaphosphate, methanesulfonate, methoxybenzoate, methylbenzoate, monohydrogenphosphate, 1-napthalenesulfonate, 2-napthalenesulfonate, nicotinate, nitrate, oxalates, palmoate, pectinate, persulfate, phenylacetates, phenylpropionates, 3-phenylpropionate, phosphate, picrate, pivalate, propionate, pyrosulfate, pyrophosphate, propiolate, propionates, phthalate, phenylbutyrate, propanesulfonate, pyrophosphates, salicylate, succinate, sulfate, sulfite, succinate, suberate, sebacate, sulfonate, tartrate, thiocyanate, tosylate undeconate and xylenesulfonate. Other acids, such as oxalic, while not in themselves pharmaceutically acceptable, may be employed in the preparation of salts useful as intermediates in obtaining the compounds of the invention and their pharmaceutically acceptable acid addition salts. (See for example Berge et al., J. Pharm. Sci. 1977, 66, 1-19.) Further, those compounds described herein which may comprise a free acid group may react with a suitable base, such as the hydroxide, carbonate or bicarbonate of a pharmaceutically acceptable metal cation, with ammonia, or with a pharmaceutically acceptable organic primary, secondary or tertiary amine. Representative alkali or alkaline earth salts include the lithium, sodium, potassium, calcium, magnesium, and aluminum salts and the like. Illustrative examples of bases include sodium hydroxide, potassium hydroxide, choline hydroxide, sodium carbonate, N+(C1-4 alkyl)4, and the like. Representative organic amines useful for the formation of base addition salts include ethylamine, diethylamine, ethylenediamine, ethanolamine, diethanolamine, piperazine and the like. It should be understood that the compounds described herein also include the quaternization of any basic nitrogen-containing groups they may contain. Water or oil-soluble or dispersible products may be obtained by such quaternization. See, for example, Berge et al., supra. These salts can be prepared in situ during the final isolation and purification of the compounds of the invention, or by separately reacting a purified compound in its free base form with a suitable organic or inorganic acid, and isolating the salt thus formed.

The terms "enhance" or "enhancing," as used herein, means to increase or prolong either in potency or duration a desired effect. Thus, in regard to enhancing the effect of therapeutic agents, the term "enhancing" refers to the ability to increase or prolong, either in potency or duration, the effect of other therapeutic agents on a system. An "enhancing-effective amount," as used herein, refers to an amount adequate to enhance the effect of another therapeutic agent in a desired system.

The terms "pharmaceutical combination", "administering an additional therapy", "administering an additional therapeutic agent" and the like, as used herein, refer to a pharmaceutical therapy resulting from the mixing or combining of more than one active ingredient and includes both fixed and non-fixed combinations of the active ingredients. The term "fixed combination" means that at least one of the compounds described herein, and at least one co-agent, are both administered to a patient simultaneously in the form of a single entity or dosage. The term "non-fixed combination" means that at least one of the compounds described herein, and at least one co-agent, are administered to a patient as separate entities either simultaneously, concurrently or sequentially with variable intervening time limits, wherein such administration provides effective levels of the two or more compounds in the body of the patient. These also apply to cocktail therapies, e.g. the administration of three or more active ingredients.

The terms "co-administration", "administered in combination with" and their grammatical equivalents or the like, as used herein, are meant to encompass administration of the selected therapeutic agents to a single patient, and are intended to include treatment regimens in which the agents are administered by the same or different route of administration or at the same or different times. In some embodiments the compounds described herein will be co-administered with other agents. These terms encompass administration of two or more agents to an animal so that both agents and/or their metabolites are present in the animal at the same time. They include simultaneous administration in separate compositions, administration at different times in separate compositions, and/or administration in a composition in which both agents are present. Thus, in some embodiments, the compounds of the invention and the other agent(s) are administered in a single composition. In some embodiments, compounds of the invention and the other agent(s) are admixed in the composition.

The term "metabolite," as used herein, refers to a derivative of a compound which is formed when the compound is metabolized.

The term "active metabolite," as used herein, refers to a biologically active derivative of a compound that is formed when the compound is metabolized.

The term "metabolized," as used herein, refers to the sum of the processes (including, but not limited to, hydrolysis reactions and reactions catalyzed by enzymes) by which a particular substance is changed by an organism. Thus, enzymes may produce specific structural alterations to a compound. For example, cytochrome P450 catalyzes a variety of oxidative and reductive reactions while uridine diphosphate glucuronyltransferases catalyze the transfer of an activated glucuronic-acid molecule to aromatic alcohols, aliphatic alcohols, carboxylic acids, amines and free sulphydryl groups. Further information on metabolism may be obtained from The Pharmacological Basis of Therapeutics, 9th Edition, McGraw-Hill (1996).

MEK Protein Kinase Inhibitors

In various embodiments, provided are pharmaceutical combinations comprising a synergistic and therapeutically effective amount of a MEK protein kinase inhibitor and Raf protein kinase inhibitor. In some embodiments, provided are methods of treating cancer comprising the administration of a synergistic and therapeutically effective amount of a pharmaceutical combination, further comprising a MEK protein kinase inhibitor and Raf protein kinase inhibitor.

In further or additional embodiments, provided are pharmaceutical combinations and methods of treating cancer comprising a MEK protein kinase inhibitor. In some embodiments, the MEK protein kinase inhibitor is CI-1040 (PD184352) (Calbiochem), which has the chemical name 2-(2-chloro-4-iodo-phenylamino)-N-cyclopropylmethoxy-3,4-difluoro-benzamide and the following structure:

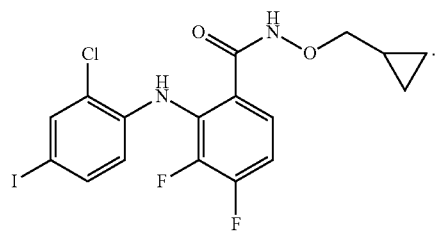 [SMILES: O=C(NOCC1CC1)c1ccc(F)c(F)c1Nc1ccc(I)cc1Cl]

In further embodiments, the MEK protein kinase inhibitor is PD-98059 (Biaffin GmbH & Co. KG; Germany), which has the chemical name 2'-Amino-3'-methoxyflavone and the following chemical structure:

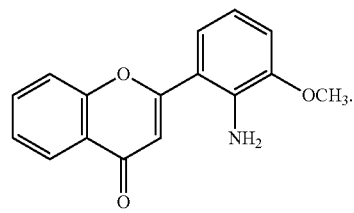 [SMILES: COc1cccc(-c2cc(=O)c3ccccc3o2)c1N]

In some embodiments, the MEK protein kinase inhibitor is UO126 (Biaffin GmbH & Co. KG; Germany), which has the chemical name 1,4-Diamino-2,3-dicyano-1,4-bis(2-aminophenylthio)-butadiene and the following chemical structure:

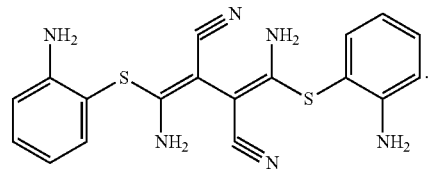 [SMILES: N#CC(=C(/N)Sc1ccccc1N)/C(C#N)=C(\N)Sc1ccccc1N]

In further embodiments, the MEK protein kinase inhibitor is SL 327 (Biaffin GmbH & Co. KG; Germany), which has the chemical name α-[Amino[(4-aminophenyl)thio]methylene]-2-(trifluoromethyl)benzeneacetonitrile and the following chemical structure:

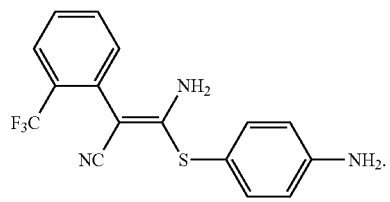 [SMILES: N#C/C(=C(/N)Sc1ccc(N)cc1)c1ccccc1C(F)(F)F]

In other embodiments, the MEK protein kinase inhibitor is the phytochemical quercetin, which has the chemical name 2-(3,4-dihydroxyphenyl)-3,5,7-trihydroxy-4H-chromen-4-one and the following chemical structure:

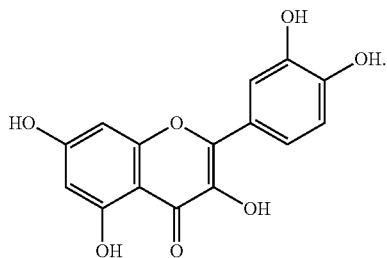 [SMILES: O=c1c(O)c(-c2ccc(O)c(O)c2)oc2cc(O)cc(O)c12]

In additional embodiments, the MEK protein kinase inhibitor is PD-184161, which has the chemical name 2-(2-Chloro-4-iodophenylamino)-N-cyclopropylmethoxy-3,4-difluoro-5-bromobenzamide.

In further or additional embodiments, the MEK protein kinase inhibitor is GSK1120212. In some embodiments, the MEK protein kinase inhibitor is PD-0325901. In further embodiments, the MEK protein kinase inhibitor is PD 0318088. In other embodiments, the MEK protein kinase inhibitor is PD-184386. In some embodiments, the MEK protein kinase inhibitor is PD-170611. In additional embodiments, the MEK protein kinase inhibitor is PD-177168. In further embodiments, the MEK protein kinase inhibitor is PD-184352. In further embodiments, the MEK protein kinase inhibitor is PD-171984. In other embodiments, the MEK protein kinase inhibitor is ARRY-438162. In some embodiments, the MEK protein kinase inhibitor is AZD6244/ARRY-886. In additional embodiments, the MEK protein kinase inhibitor is AZD 8330. In further embodiments, the MEK protein kinase inhibitor is XL518. In one embodiment, the MEK protein kinase inhibitor is UO125 (Calbiochem), which has the chemical name.

In some embodiments, the MEK protein kinase inhibitor is a combination or method comprising a compound of formula A, or a pharmaceutically acceptable salt, solvate, polymorph, ester, amide, tautomer or prodrug thereof:

Formula A

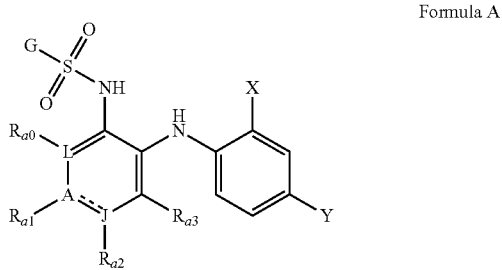

wherein

G is $G_1$, $G_2$, $R_{1a}$, $R_{1b}$, $R_{1c}$, $R_{1d}$, $R_{1e}$, $Ar_1$, $Ar_2$ or $Ar_3$;

$R_{a0}$, $R_1$ and $R_2$ are independently selected from H, halogen, cyano, cyanomethyl, nitro, difluoromethoxy, difluoromethoxy, trifluoromethyl, azido, amino, alkylamino, dialkylamino, $CO_2R_5$, $OR_5$, —O—(CO)—$R_5$, —O—C(O)—N($R_5$)$_2$, —N$R_5$C(O)N$R_6R_7$, —S$R_5$, NHC(O)$R_5$, —NHSO$_2R_5$, SO$_2$N($R_5$)$_2$, C1-C6 alkyl, C1-C4 alkoxy, C3-C6 cycloalkyl, $C_2$-$C_6$ alkenyl, $C_2$-$C_6$ alkynyl, aryl, alkylaryl, arylalkyl, and heterocyclic;

each $R_5$ is selected from H, lower alkyl, substituted lower alkyl, aryl, or substituted aryl, and N$R_7R_6$; wherein each $R_6$ and $R_7$ is independently selected from hydrogen or lower alkyl; wherein said alkyl, cycloalkyl, alkenyl, aryl, alkylaryl, arylalkyl, heterocyclic and alkynyl groups are optionally substituted with 1-3 substituents selected independently from halogen, OH, CN, cyanomethyl, nitro, phenyl, difluoromethoxy, difluoromethoxy, and trifluoromethyl;

said C1-C6 alkyl and C1-C4 alkoxy groups are optionally substituted with OCH$_3$ or OCH$_2$CH$_3$;

$R_{a1}$ is H, $C_1$-$C_6$ alkyl, $C_3$-$C_5$ cycloalkyl, $C_2$-$C_6$ alkenyl, $C_5$-$C_6$ cycloalkenyl or $C_2$-$C_6$ alkynyl;

wherein each alkyl, cycloalkyl, alkenyl, cycloalkenyl or alkynyl group is optionally substituted with 1-3 substituents selected independently from halogen, hydroxy, $C_1$-$C_4$ alkyl, $C_1$-$C_4$ alkoxy, cyano, cyanomethyl, nitro, azido, trifluoromethyl difluoromethoxy and phenyl, and one or two ring carbon atoms of said $C_3$-$C_5$ cycloalkyl groups are optionally replaced with, independently, O, N, or S; or $R_{a1}$ is a 5 or 6-atom heterocyclic group, which group may be saturated, unsaturated, or aromatic, containing 1-5 heteroatoms selected independently from O, N, and S, which heterocyclic group is optionally substituted with 1-3 substituents selected independently from halogen, hydroxy, $C_1$-$C_4$ alkyl, $C_1$-$C_4$ alkoxy, cyano, cyanomethyl, nitro, azido, trifluoromethyl difluoromethoxy and phenyl;

$R_{a2}$ is H, halogen, F, or oxo; or $R_{a1}$ and $R_{a2}$, taken together, are -Q($R_2$)—U($R_1$)=D-

$R_{a3}$ is H, halogen, hydroxy, azido, cyano, cyanomethyl, $C_1$-$C_6$ alkyl, $C_3$-$C_6$ cycloalkyl, $C_2$-$C_6$ alkenyl, $C_5$-$C_6$ cycloalkenyl or $C_2$-$C_6$ alkynyl, wherein each alkyl, cycloalkyl, alkenyl cycloalkenyl or alkynyl group is optionally substituted with 1-3 substituents selected independently from halogen, hydroxy, $C_1$-$C_4$ alkoxy, cyano, cyanomethyl, nitro, azido, trifluoromethyl and phenyl;

═ is a single or a double bond;

X and Y are independently selected from F, I, Br, Cl, CF3, C1-C3 alkyl, C2-C3 alkenyl, C2-C3 alkynyl, cyclopropyl, phenyl, pyridyl, pyrazolyl, OMe, OEt, or SMe, or Het, where Het is a 5- to 10-membered mono- or bicyclic heterocyclic group, which group is saturated, olefinic, or aromatic, containing 1-5 ring heteroatoms selected independently from N, O, and S; where all said phenyl or Het groups are optionally substituted with F, Cl, Br, I, acetyl, methyl, CN, NO$_2$, CO$_2$H, $C_1$-$C_3$ alkyl, $C_1$-$C_3$ alkoxy, $C_1$-$C_3$ alkyl-C(═O)—, $C_1$-$C_3$ alkyl-C(═S)—, $C_1$-$C_3$ alkoxy-C(═S)—, $C_1$-$C_3$ alkyl-C(═O)O—, $C_1$-$C_3$ alkyl-O—(C═O)—, $C_1$-$C_3$ alkyl-O(═O)NH—, $C_1$-$C_3$ alkyl-C(═NH)NH—, $C_1$-$C_3$ alkyl-NH—(C═O)—, di-$C_1$-$C_3$ alkyl-N—(C═O)—, $C_1$-$C_3$ alkyl-C(═O)N($C_1$-$C_3$ alkyl)-, $C_1$-$C_3$ alkyl-S(═O)$_2$NH— or trifluoromethyl;

all said methyl, ethyl, C1-C3 alkyl, and cyclopropyl groups of X and Y are optionally substituted with OH;

all said phenyl, pyridyl, pyrazolyl groups of Y are optionally substituted with halogen, acetyl, methyl, and trifluoromethyl; and all said methyl groups of X and Y are optionally substituted with one, two, or three F atoms;

A, D, J, L, Q, U are independently selected from C, CH, —NH, N, O, and —N(CH$_3$)—;

$G_1$ is $C_1$-$C_6$ alkyl optionally substituted with one amino, $C_1$-$C_3$ alkylamino, or dialkylamino group, said dialkylamino group comprising two $C_1$-$C_4$ alkyl groups which may be identical or non-identical; or $G_1$ is a $C_3$-$C_8$ diamino alkyl group;

$G_2$ is a 5- or 6-membered ring, which is saturated, unsaturated, or aromatic, containing 1-3 ring heteroatoms selected independently from N, O, and S, optionally substituted with 1-3 substituents selected independently from F, Cl, OH, O($C_1$-$C_3$ alkyl), $OCH_3$, $OCH_2CH_3$, $CH_3C(=O)NH$, $CH_3C(=O)O$, CN, $CF_3$, and a 5-membered aromatic heterocyclic group containing 1-4 ring heteroatoms selected independently from N, O, and S;

$R_{1a}$ is methyl, cyclopropoxy or C1-C4 alkoxy; wherein
the methyl is optionally substituted with OH, 1-3 fluorine atoms or 1-3 chlorine atoms;
the C1-C4 alkyl moieties of said C1-C4 alkoxy are optionally substituted with one hydroxy or methoxy group; and
all C2-C4 alkyl groups within said C1-C4 alkoxy are optionally further substituted with a second OH group;

$R_{1b}$ is $CH(CH_3)$—C1-3 alkyl or C3-C6 cycloalkyl, said $CH_3$, alkyl, and cycloalkyl groups optionally substituted with 1-3 substituents selected independently from F, Cl, Br, I, OH, C1-C4 alkoxy and CN;

$R_{1c}$ is $(CH_2)_nO_mR'$, where
m is 0 or 1;
n is 0, 1, 2, or 3;
R' is C1-C6 alkyl, optionally substituted with 1-3 substituents selected independently from F, Cl, OH, $OCH_3$, $OCH_2CH_3$, and C3-C6 cycloalkyl;

$R_{1d}$ is C(A')(A")(B)— wherein
B, A', and A" are, independently, H, substituted or unsubstituted C1-6 alkyl, substituted or unsubstituted C2-6 alkenyl, or
A' and A", together with the carbon atom to which they are attached, form a substituted or unsubstituted 3- to 6-member saturated ring;

$R_{1e}$ is benzyl or 2-phenyl ethyl, in which the phenyl group is optionally substituted

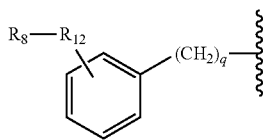

where
q is 1 or 2;
$R_8$ and $R_9$ are, independently, H, F, Cl, Br, $CH_3$, $CH_2F$, $CHF_2$, $CF_3$, $OCH_3$, $OCH_2F$, $OCHF_2$, $OCF_3$, ethyl, n-propyl, isopropyl, cyclopropyl, isobutyl, sec-butyl, tert-butyl, and methylsulfonyl;
$R_{10}$ is H, F, Cl, Br, $CH_3$, $CH_2F$, $CHF_2$, $CF_3$, $OCH_3$, $OCH_2F$, $OCHF_2$, $OCF_3$, ethyl, n-propyl, isopropyl, cyclopropyl, isobutyl, sec-butyl, tert-butyl, and methylsulfonyl, nitro, acetamido, amidinyl, cyano, carbamoyl, methylcarbamoyl, dimethylcarbamoyl, 1,3,4-oxadiazol-2-yl, 5-methyl-1,3,4-5 oxadiazolyl, 1,3,4-thiadiazolyl, 5-methyl-1,3,4-thiadiazol-1H-tetrazolyl, N-morpholinyl carbonylamino, N-morpholinylsulfonyl or N-pyrrolidinylcarbonylamino;
$R_{11}$ and $R_{12}$ are, independently, H, F, Cl, or methyl;
$Ar_1$ is

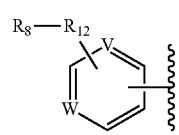

where
W and V are, independently, N, $CR_8$ or $CR_9$;

$R_8$, $R_9$ and $R_{10}$ are, independently, H, F, Cl, Br, $CH_3$, $CH_2F$, $CHF_2$, $CF_3$, $OCH_3$, $OCH_2F$, $OCHF_2$, $OCF_3$, ethyl, n-propyl, isopropyl, cyclopropyl, isobutyl, sec-butyl, tert-butyl, and methylsulfonyl, nitro, acetamido, amidinyl, cyano, carbamoyl, methylcarbamoyl, dimethylcarbamoyl, 1,3,4-oxadiazol-2-yl, 5-methyl-1,3,4-oxadiazol, 1,3,4-thiadiazol, 5-methyl-1,3,4-thiadiazol, 1H-tetrazolyl, N-morpholinylcarbonylamino, N-morpholinylsulfonyl and N-pyrrolidinylcarbonylamino;

$R_{11}$ and $R_{12}$ are, independently, H, F, Cl or methyl;

$Ar_2$ is

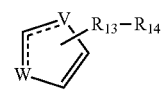

where
the dashed line represents a double bond which may be located formally either between V and the carbon between W and V, or between W and the carbon between W and V;

W is —S—, —O— or —N=, wherein
when W is —O— or —S—, V is —CH=, —CCl= or —N=; and
when W is —N=, V is CH, CCl, N or —$NCH_3$—;

$R_{13}$ and $R_{14}$ are, independently, H, methoxycarbonyl, methylcarbamoyl, acetamido, acetyl, methyl, ethyl, trifluoromethyl or halogen;

$Ar_3$ is

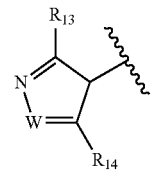

where
W is —NH—, —$NCH_3$— or —O—; and
$R_{13}$ and $R_{14}$ are, independently, H, F, Cl, or methyl.

In further or additional embodiments, provided herein is the combination or method as described herein wherein the MEK protein kinase inhibitor is selected from the group consisting of a compound of formula I,

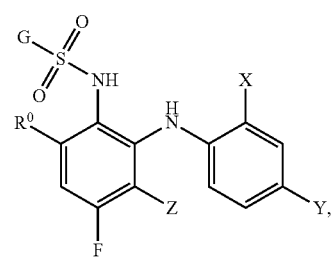

a compound of formula II,

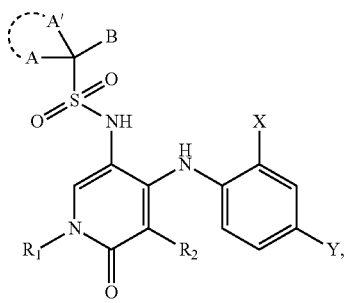

and a compound of formula III,

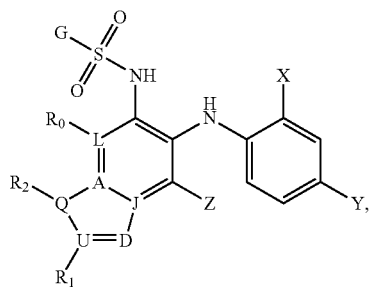

or a pharmaceutically acceptable salt, solvate, polymorph, ester, amide, tautomer or prodrug thereof.

In other embodiments, the MEK protein kinase inhibitor is a compound of formula I, or a pharmaceutically acceptable salt, solvate, polymorph, ester, amide, tautomer or prodrug thereof:

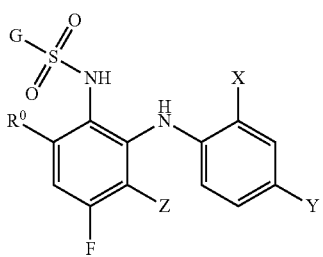

formula I wherein

Z is H or F;

X is F, Cl, $CH_3$, $CH_2OH$, $CH_2F$, $CHF_2$, or $CF_3$;

Y is I, Br, Cl, $CF_3$, $C_1$-$C_3$ alkyl, $C_2$-$C_3$ alkenyl, $C_2$-$C_3$ alkynyl, cyclopropyl, OMe, OEt, SMe, phenyl or Het, where Het is a 5- to 10-membered mono- or bicyclic heterocyclic group, which group is saturated, olefinic, or aromatic, containing 1-5 ring heteroatoms selected independently from N, O, and S; where all said phenyl or Het groups are optionally substituted with F, Cl, Br, I, acetyl, methyl, CN, $NO_2$, $CO_2H$, $C_1$-$C_3$ alkyl, $C_1$-$C_3$ alkoxy, $C_1$-$C_3$ alkyl-C(=O)—, $C_1$-$C_3$ alkyl-C(=S)—, $C_1$-$C_3$ alkoxy-C(=S)—, $C_1$-$C_3$ alkyl-C(=O)O—, $C_1$-$C_3$ alkyl-O—(C=O)—, $C_1$-$C_3$ alkyl-C(=O)NH—, $C_1$-$C_3$ alkyl-C(=NH)NH—, $C_1$-$C_3$ alkyl-NH—(C=O)—, di-$C_1$-$C_3$ alkyl-N—(C=O)—, $C_1$-$C_3$ alkyl-C(=O)N($C_1$-$C_3$ alkyl)-, $C_1$-$C_3$ alkyl-S(=O)$_2$NH— or trifluoromethyl;

all said methyl, ethyl, $C_1$-$C_3$ alkyl, and cyclopropyl groups are optionally substituted with OH;

all said methyl groups are optionally substituted with one, two, or three F atoms;

$R^0$ is H, F, Cl, Br, I, $CH_3NH$—, $(CH_3)_2N$—, $C_1$-$C_6$ alkyl, $C_1$-$C_4$ alkoxy, $C_3$-$C_6$ cycloalkyl, $C_2$-$C_6$ alkenyl, $C_2$-$C_6$ alkynyl, phenyl, monosubstituted phenyl, O($C_1$-$C_4$ alkyl), O—C(=O)($C_1$-$C_4$ alkyl) or C(=O)O($C_1$-$C_4$ alkyl); where said alkyl, alkoxy, cycloalkyl, alkenyl, alkynyl and phenyl groups are optionally substituted with 1-3 substituents selected independently from F, Cl, Br, I, OH, CN, cyanomethyl, nitro, phenyl and trifluoromethyl;

said $C_1$-$C_6$ alkyl and $C_1$-$C_4$ alkoxy groups also optionally substituted with $OCH_3$ or $OCH_2CH_3$;

G is $G_1$, $G_2$, $R_{1a}$, $R_{1b}$, $R_{1c}$, $R_{1d}$, $R_{1e}$, $Ar_1$, $Ar_2$ or $Ar_3$; where $G_1$ is $C_1$-$C_6$ alkyl optionally substituted with one amino, $C_1$-$C_3$ alkylamino, or dialkylamino group, said dialkylamino group comprising two $C_1$-$C_4$ alkyl groups which may be identical or non-identical; or $G_1$ is a $C_3$-$C_8$ diamino alkyl group;

$G_2$ is a 5- or 6-membered ring, which is saturated, unsaturated, or aromatic, containing 1-3 ring heteroatoms selected independently from N, 0, and S, optionally substituted with 1-3 substituents selected independently from F, Cl, OH, O($C_1$-$C_3$ alkyl), $OCH_3$, $OCH_2CH_3$, $CH_3C(=O)NH$, $CH_3C(=O)O$, CN, $CF_3$, and a 5-membered aromatic heterocyclic group containing 1-4 ring heteroatoms selected independently from N, O, and S;

$R_{1a}$ is methyl, optionally substituted with 1-3 fluorine atoms or 1-3 chlorine atoms, or with OH, cyclopropoxy, or $C_1$-$C_3$ alkoxy, where said cyclopropoxy group or the $C_1$-$C_3$ alkyl moieties of said $C_1$-$C_3$ alkoxy groups are optionally substituted with one hydroxy or methoxy group, and where all $C_3$-alkyl groups within said $C_1$-$C_4$ alkoxy are optionally further substituted with a second OH group;

$R_{1b}$ is $CH(CH_3)$—$C_{1-3}$ alkyl or $C_3$-$C_6$ cycloalkyl, said alkyl and cycloalkyl groups optionally substituted with 1-3 substituents selected independently from F, Cl, Br, I, OH, $OCH_3$, and CN;

$R_{1c}$ is $(CH_2)_nO_mR'$; where m is 0 or 1; and where when m is 0, n is 1 or 2;

when m is 1, n is 2 or 3;

R' is $C_1$-$C_6$ alkyl, optionally substituted with 1-3 substituents selected independently from F, Cl, OH, $OCH_3$, $OCH_2CH_3$, and $C_3$-$C_6$ cycloalkyl;

$R_{1d}$ is C(A)(A')(B)—; where

B is H or $C_{1-4}$ alkyl, optionally substituted with one or two OH groups;

A and A' are independently H or $C_{1-4}$ alkyl, optionally substituted with one or two OH groups; or A and A', together with the carbon atom to which they are attached, form a 3- to 6-member saturated ring;

$R_{1e}$ is

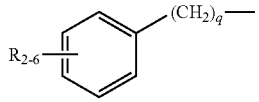

where
q is 1 or 2;
$R_2$ and $R_3$ are each independently, H, F, Cl, Br, $CH_3$, $CH_2F$, $CHF_3$, $CF_3OCH_3$, $OCH_2F$, $OCHF_2$, $OCF_3$, ethyl, n-propyl, isopropyl, cyclopropyl, isobutyl, sec-butyl, tert-butyl or methylsulfonyl;
$R_4$ is H, F, Cl, Br, $CH_3$, $CH_2F$, $CHF_2$, $CF_3OCH_3$, $OCH_2F$, $OCHF_2$, $OCF_3$, ethyl, n-propyl, isopropyl, cyclopropyl, isobutyl, sec-butyl, tert-butyl, methylsulfonyl, nitro, acetamido, amidinyl, cyano, carbamoyl, methylcarbamoyl, dimethylcarbamoyl, 1,3,4-oxadiazol-2-yl, 5-methyl-1,3,4-oxadiazol, 1,3,4-thiadiazol, 5-methyl-1,3,4-thiadiazol 1H-tetrazolyl, N-morpholyl carbonyl amino, N-morpholylsulfonyl and N-pyrrolidinylcarbonylamino;
$R_5$ is H, F, Cl or methyl;
$R_6$ is H, F, Cl or methyl;
$Ar_1$ is

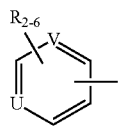

where
U and V are, independently, N, $CR_2$ or $CR_3$;
$R_2$, $R_3$ and $R_4$ are, independently, H, F, Cl, Br, $CH_3$, $CH_2F$, $CHF_2$, $CF_3OCH_3$, $OCH_2F$, $OCHF_2$, $OCF_3$, ethyl, n-propyl, isopropyl, cyclopropyl, isobutyl, sec-butyl, tert-butyl, acetamido, amidinyl, cyano, carbamoyl, methylcarbamoyl, dimethylcarbamoyl, 1,3,4-oxadiazol-2-yl, 5-methyl-1,3,4-oxadiazolyl, 1,3,4-thiadiazolyl, 5-methyl-1,3,4-thiadiazolyl, 1H-tetrazolyl, N-morpholylcarbonylamino, N-morpholylsulfonyl, N-pyrrolidinylcarbonylamino, and methylsulfonyl;
$R_5$ and are, independently, H, F, Cl or methyl;
$Ar_2$ is

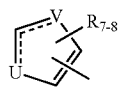

where
the dashed line represents alternative formal locations for the second ring double bond;
U is —S—, —O— or —N=, and where
when U is —O— or —S—, V is —CH=, —CCl= or —N=;
when U is —N=, V is —CH=, —CCl=, or —N=;
$R_7$ is H or methyl;
$R_8$ is H, acetamido, methyl, F or Cl;
$Ar_3$ is

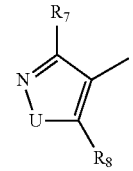

where
U is —NH—, —$NCH_3$— or —O—;
$R_7$ and $R_8$ are, independently, H, F, Cl, or methyl.

In addition to the definitions given herein for the groups G, $R^0$, X, Y and Z, additional substitutions which could be contemplated by those of skill in the chemical and pharmaceutical arts are included.

In some embodiments, the invention provides a pharmaceutical combination and method of treating cancer comprising a compound of formula I, where G is $G_1$ or $G_2$. In other embodiments, G is $G_1$. In further or additional embodiments, G is $G_2$.

In some embodiments, the invention provides a pharmaceutical combination and method of treating cancer comprising a compound of formula I, where G is $R_{1a}$, $R_{1b}$, $R_{1c}$, $R_{1d}$, $R_{1e}$, $Ar_1$, $Ar_2$ or $Ar_3$. In further or additional embodiments, G is $R_{1a}$, $R_{1b}$, $R_{1c}$, $R_{1d}$ or $R_{1e}$. In further or additional embodiments, G is $R_{1a}$. In further or additional embodiments, G is $R_{1b}$. In further or additional embodiments, G is $R_{1c}$. In further or additional embodiments, G is $R_{1d}$. In further or additional embodiments, G is $R_{1e}$. In further or additional embodiments, G is $Ar_1$, $Ar_2$ or $Ar_3$. In further or additional embodiments, G is $Ar_1$. In further or additional embodiments, G is $Ar_2$. In further or additional embodiments, G is $Ar_3$ In some embodiments provided are pharmaceutical combinations and methods of treating cancer comprising compounds of formula I, or their pharmaceutically acceptable salts. In further or additional embodiments, provided herein are compounds of formula I, or their solvates. In further or additional embodiments, provided herein are compounds of formula I or their polymorphs. In further or additional embodiments, provided herein are compounds of formula I, or their esters. In further or additional embodiments, provided herein are compounds of formula I, or their amides. In further or additional embodiments, provided herein are compounds of formula I or their tautomers. In further or additional embodiments, provided herein are compounds of formula I or their prodrugs.

In some embodiments, Z is H. In some embodiments, Z is F. In some embodiments, X is F. In some embodiments, X is Cl. In some embodiments, X is $CH_3$. In some embodiments, X is $CH_2OH$. In some embodiments, X is $CH_2F$. In some embodiments, X is $CHF_2$. In some embodiments, X is $CF_3$. In some embodiments, X is F, Cl, or $CH_3$.

In some embodiments, G is $G_1$ or $G_2$, X is F, Cl, or $C_1$-$C_3$; Y is I, Br, Cl, $CF_3$, $C_1$-$C_3$ alkyl, phenyl, pyridyl, pyrrolyl, pyrazolyl, said phenyl, pyridyl, pyrrolyl, and pyrazolyl groups optionally substituted with F, Cl, Br, I, acetyl, methyl, CN, $NO_2$, $CO_2H$, $C_1$-$C_3$ alkyl, $C_1$-$C_3$ alkoxy, $C_1$-$C_3$ alkyl-C(=O)—, $C_1$-$C_3$ alkyl-C(=S)—, $C_1$-$C_3$ alkoxy-C(=S)—, $C_1$-$C_3$ alkyl-C(=O)O—, $C_1$-$C_3$ alkyl-O—(C=O)—, $C_1$-$C_3$ alkyl-C(=O)NH—, $C_1$-$C_3$ alkyl-C(=NH)NH—, $C_1$-$C_3$ alkyl-NH—(C=O)—, di-$C_1$-$C_3$ alkyl-N—(C=O)—, $C_1$-$C_3$ alkyl-C(=O)N($C_1$-$C_3$ alkyl)-, $C_1$-$C_3$ alkyl-S(=O)$_2$NH— or trifluoromethyl; and Z is H or F. In further or additional embodiments, G is $G_1$ or $G_2$, and $R^0$ is F, Cl, $C_1$-$C_4$ alkyl or $C_1$-$C_4$ alkoxy, said $C_1$-$C_4$ alkyl group and the $C_1$-$C_4$ alkyl moiety of said $C_1$-$C_4$ alkoxy group optionally substituted with F, Cl, $OCH_3$, or $OCH_2CH_3$. In further or additional embodiments, G is $G_1$ or $G_2$, and $R^0$ is H, F, Cl, $C_1$-$C_4$ alkyl, methoxy, ethoxy, or 2-methoxy-ethoxy.

In some embodiments, $G_1$ is N-methyl-2-aminoethyl. In further or additional embodiments, $G_1$ is $(CH_3)_2N$—$CH_2CH_2$—NH—$(CH_2)_n$—, where n is 1, 2, or 3. In further or additional embodiments, $G_1$ is $(CH_3)_2N$—$CH_2CH_2$—NH—$(CH_2)_n$—, where n is 1, 2, or 3, and X is F. In further or additional embodiments, $G_1$ is $(CH_3)_2N$—$CH_2CH_2$—NH—$(CH_2)_n$—, where n is 1, 2, or 3, X is F and Z is F.

In some embodiments, $G_2$ is 1-piperidyl, 2-piperidyl, 3-piperidyl, or 4-piperidyl. In further or additional embodiments, $G_2$ is morpholyl, 1-piperazyl, or 2-piperazyl.

In some embodiments, G is $R_{1a}$, $R_{1b}$, $R_{1c}$, $R_{1d}$, $R_{1e}$, $Ar_1$, $Ar_2$ or $Ar_3$ and X is F, Cl, or $CH_3$. In further or additional embodiments, G is $R_{1a}$, $R_{1b}$, $R_{1c}$, $R_{1d}$, $R_{1e}$, $Ar_1$, $Ar_2$ or $Ar_3$, X is F, Cl, or $CH_3$ and Y is I, Br, Cl, $CF_3$, or $C_1$-$C_3$ alkyl In further or additional embodiments, G is $R_{1a}$, $R_{1b}$, $R_{1c}$, $R_{1d}$, $R_{1e}$, $Ar_1$, $Ar_2$ or $Ar_3$, X is F, Cl, or $CH_3$, Y is I, Br, Cl, $CF_3$, or $C_1$-$C_3$ alkyl and Z is H or F In further or additional embodiments, G is $R_{1a}$, $R_{1b}$, $R_{1c}$, $R_{1d}$, $R_{1e}$, $Ar_1$, $Ar_2$ or $Ar_3$ and $R^0$ is F, Cl, $C_1$-$C_4$ alkyl or $C_1$-$C_4$ alkoxy, said $C_1$-$C_4$ alkyl group and the $C_1$-$C_4$ alkyl moiety of said $C_1$-$C_4$ alkoxy group optionally substituted with F, Cl, $OCH_3$, or $OCH_2CH_3$. In further or additional embodiments, G is $R_{1a}$, $R_{1b}$, $R_{1c}$, $R_{1d}$, $R_{1e}$, $Ar_1$, $Ar_2$ or $Ar_3$ and $R^0$ is H, F, Cl, $C_1$-$C_4$ alkyl, methoxy, ethoxy, or 2-methoxy-ethoxy.

In some embodiments, G is $R_{1a}$; and Z is F. In further or additional embodiments, G is $R_{1a}$ where $R_{1a}$ is $CH_3$, $R^0$ is H; and Y is Br, I, $CF_3$, or $CH_3$. In some embodiments, G is $R_{1b}$ and Z is F. In further or additional embodiments, G is $R_{1b}$, Z is F, and $R^0$ is H, F, or $OCH_3$. In further or additional embodiments, G is $R_{1b}$, Z is F, $R^0$ is H, F, or $OCH_3$, and X is F or $CH_3$. In further or additional embodiments, G is $R_{1b}$, Z is F, $R^0$ is H, F, or $OCH_3$, X is F or $CH_3$ and Y is Br, I or $CH_3$. In further or additional embodiments, G is $R_{1b}$ where $R_{1b}$ is $C_3$-$C_6$ cycloalkyl. In further or additional embodiments, G is $R_{1b}$ where $R_{1b}$ is substituted $C_3$-$C_6$ cycloalkyl. In further or additional embodiments, G is $R_{1b}$ where $R_{1b}$ is unsubstituted $C_3$-$C_6$ cycloalkyl. In further or additional embodiments, G is $R_{1b}$ where $R_{1b}$ is unsubstituted $C_3$-$C_6$ cycloalkyl and $R^0$ is H. In further or additional embodiments, G is $R_{1b}$ where $R_{1b}$ is isopropyl or cyclopropyl.

In some embodiments, G is $R_{1c}$, and Y is I, Br, $CH_3$, or $CF_3$. In further or additional embodiments, G is $R_{1c}$, Y is I, Br, $CH_3$, or $CF_3$, and Z is F. In further or additional embodiments, G is Y is I, Br, $CH_3$, or $CF_3$, Z is F and m is zero.

In some embodiments, G is $R_{1d}$ and $R^0$ is fluoro, chloro, methyl, ethyl, propyl, isopropyl, sec-butyl, iso-butyl, tert-butyl, cyclopropyl, cyclobutyl, fluoromethyl, methoxy, fluoromethoxy, methylamino or dimethylamino. In further or additional embodiments, G is $R_{1d}$, $R^0$ is fluoro, chloro, methyl, ethyl, propyl, isopropyl, sec-butyl, iso-butyl, tert-butyl, cyclopropyl, cyclobutyl, fluoromethyl, methoxy, fluoromethoxy, methylamino or dimethylamino and X is F, Cl, $CH_3$, or mono-, di- or tri-fluoromethyl. In further or additional, G is $R_{1d}$, $R^0$ is fluoro, chloro, methyl, ethyl, propyl, isopropyl, sec-butyl, iso-butyl, tert-butyl, cyclopropyl, cyclobutyl, fluoromethyl, methoxy, fluoromethoxy, methylamino or dimethylamino, X is F, Cl, $CH_3$, or mono-, di- or tri-fluoromethyl and Y is I, Br, Cl, or mono-, di- or tri-fluoromethyl. In further or additional embodiments, G is $R_{1d}$, $R^0$ is fluoro, chloro, methyl, ethyl, propyl, isopropyl, sec-butyl, iso-butyl, tert-butyl, cyclopropyl, cyclobutyl, fluoromethyl, methoxy, fluoromethoxy, methylamino or dimethylamino, X is F, Cl, $CH_3$, or mono-, di- or tri-fluoromethyl, Y is I, Br, Cl, or mono-, di- or tri-fluoromethyl and Z is H or F. In further or additional embodiments, G is $R_{1d}$ and $R^0$ is F, Cl, methyl, ethyl, methoxy, ethoxy, or 2-methoxy-ethoxy.

In further or additional embodiments, G is $R_{1d}$, $R^0$ is F, Cl, methyl, ethyl, methoxy, ethoxy, or 2-methoxy-ethoxy and X is F, Cl, or $CH_3$. In further or additional embodiments, G is $R_{1d}$, $R^0$ is F, Cl, methyl, ethyl, methoxy, ethoxy, or 2-methoxy-ethoxy, X is F, Cl, or $CH_3$ and Y is I, Br, Cl, or mono-, di- or tri-fluoromethyl. In further or additional embodiments, G is $R_{1d}$, $R^0$ is F, Cl, methyl, ethyl, methoxy, ethoxy, or 2-methoxy-ethoxy, X is F, Cl, or $CH_3$, Y is I, Br, Cl, or mono-, di- or tri-fluoromethyl and Z is H or F. In further or additional embodiments, G is $R_{1d}$ and $R^0$ is H; X is F, Cl, $CH_3$, or mono-, di- or tri-fluoromethyl. In further or additional embodiments, G is $R_{1d}$, $R^0$ is H; X is F, Cl, $CH_3$, or mono-, di- or tri-fluoromethyl and Y is I, Br, Cl, or mono-, di- or tri-fluoromethyl. In further or additional embodiments, G is $R_{1d}$, $R^0$ is H; X is F, Cl, $CH_3$, or mono-, di- or tri-fluoromethyl, Y is I, Br, Cl, or mono-, di- or tri-fluoromethyl and Z is H or F.

In further or additional embodiments, G is $R_{1d}$ where $R_{1d}$ is C(A)(A') is $C_1$-$C_6$ cycloalkyl. In further or additional embodiments, G is $R_{1d}$ where $R_{1d}$ is C(A)(A') is $C_1$-$C_6$ cycloalkyl and B is H. In further or additional embodiments, G is $R_{1d}$ where $R_{1d}$ is C(A)(A') is $C_1$-$C_6$ cycloalkyl and B is methyl, ethyl, 2-hydroxyethyl, n-propyl, 3-hydroxypropyl, 2,3-dihydroxypropyl, 3,4-dihydroxybutyl, isopropyl, 1-methyl-2-hydroxy ethyl, n-butyl, sec-butyl, isobutyl, or 2-hydroxymethyl-3-hydroxy propyl.

In further or additional embodiments, G is $R_{1d}$ where $R_{1d}$ is C(A)(A') is $C_1$-$C_6$ cycloalkyl and B is 2,3-dihydroxypropyl or 3,4-dihydroxybutyl. In further or additional embodiments, G is $R_{1d}$ where $R_{1d}$ is C(A)(A') is $C_1$-$C_6$ cycloalkyl and B is 2,3-dihydroxypropyl or 3,4-dihydroxybutyl, in which the chiral carbon in B is in the R configuration. In further or additional embodiments, G is $R_{1d}$ where $R_{1d}$ is C(A)(A') is $C_1$-$C_6$ cycloalkyl and B is 2,3-dihydroxypropyl or 3,4-dihydroxybutyl, in which the chiral carbon in B is in the S configuration. In further or additional embodiments, G is $R_{1d}$ where $R_{1d}$ is C(A)(A') is $C_1$-$C_6$ cycloalkyl and B is methyl, optionally substituted with one OH group, or $C_2$-$C_4$ optionally substituted with one or two OH groups. In further or additional embodiments, G is $R_{1d}$ where $R_{1d}$ is C(A)(A') is $C_1$-$C_6$ cycloalkyl and $R^0$ is fluoro, chloro, methyl, ethyl, propyl, isopropyl, sec-butyl, iso-butyl, tert-butyl, cyclopropyl, cyclobutyl, fluoromethyl, methoxy, fluoromethoxy, methylamino or dimethylamino. In further or additional embodiments, G is $R_{1d}$ where $R_{1d}$ is C(A)(A') is $C_1$-$C_6$ cycloalkyl and $R^0$ is F, Cl, methyl, ethyl, methoxy, ethoxy, or 2-methoxy-ethoxy. In further or additional embodiments, G is $R_{1d}$ where $R_{1d}$ is C(A)(A') is $C_1$-$C_6$ cycloalkyl and $R^0$ is H; X is F, Cl, $CH_3$, or mono-, di- or tri-fluoromethyl.

In further or additional embodiments, the invention provides a pharmaceutical combination in a composition and methods of treating cancer comprising a compound of formula I, where G is $R_{1d}$ where $R_{1d}$ is C(A)(A') is $C_1$-$C_6$ cycloalkyl and B is 2,3-dihydroxypropyl or 3,4-dihydroxybutyl, in which the chiral carbon in B is in the R configuration, which is substantially free of the S isomer. In further or additional embodiments, the invention provides a composition comprising a compound of formula I, where G is $R_{1d}$ where $R_{1d}$ is C(A)(A') is $C_1$-$C_6$ cycloalkyl and B is 2,3-dihydroxypropyl, in which the chiral carbon in B is in the R configuration, which is substantially free of the S isomer. In further or additional embodiments, the invention provides a composition comprising a compound of formula I, where G is $R_{1d}$ where $R_{1d}$ is C(A)(A') is $C_1$-$C_6$ cycloalkyl and B is 3,4-dihydroxybutyl, in which the chiral carbon in B is in the R configuration, which is substantially free of the S isomer. In further or additional embodiments, the invention provides a composition comprising a compound of formula I, where G is $R_{1d}$ where $R_{1d}$ is C(A)(A') is $C_1$-$C_6$ cycloalkyl and 13 is 2,3-dihydroxypropyl or 3,4-dihydroxybutyl, in which the chiral carbon in B is in the S configuration, which is substantially free of the R isomer. In further or additional embodiments, the invention provides a composition comprising a compound of formula I, where G is $R_{1d}$ where $R_{1d}$ is C(A)(A') is $C_1$-$C_6$ cycloalkyl and B is 2,3-dihydroxypropyl, in which the chiral carbon in B is in the S configuration, which is substantially free of the R isomer. In further or additional embodiments, the invention provides a composition comprising a compound of formula I, where G is $R_{1d}$ where $R_{1d}$ is C(A)(A') is $C_1$-$C_6$ cycloalkyl and B is 3,4-dihydroxybutyl, in which the chiral carbon in B is in the S configuration, which is substantially free of the R isomer.

In further or additional embodiments, G is $R_{1d}$ where $R_{1d}$ is C(A)(A') is cyclopropyl. In further or additional embodiments, G is $R_{1d}$ where $R_{1d}$ is C(A)(A') is cyclopropyl and B is H. In further or additional embodiments, G is $R_{1d}$ where $R_{1d}$ is C(A)(A') is cyclopropyl and B is methyl, ethyl, 2-hydroxyethyl, n-propyl, 3-hydroxypropyl, 2,3-dihydroxypropyl, 3,4-dihydroxybutyl, isopropyl, 1-methyl-2-hydroxy ethyl, n-butyl, sec-butyl, isobutyl, or 2-hydroxymethyl-3-hydroxy propyl. In further or additional embodiments, G is $R_{1d}$ where $R_{1d}$ is C(A)(A') is cyclopropyl and B is 2,3-dihydroxypropyl or 3,4-dihydroxybutyl. In further or additional embodiments, G is $R_{1d}$ where $R_{1d}$ is C(A)(A') is cyclopropyl and B is 2,3-dihydroxypropyl or 3,4-dihydroxybutyl, in which the chiral carbon in B is in the R configuration. In further or additional embodiments, G is $R_{1d}$ where $R_{1d}$ is C(A)(A') is cyclopropyl and B is 2,3-dihydroxypropyl or 3,4-dihydroxybutyl, in which the chiral carbon in B is in the S configuration. In further or additional embodiments, G is $R_{1d}$ where $R_{1d}$ is C(A)(A') is cyclopropyl and B is methyl, optionally substituted with one OH group, or $C_2$-$C_4$ alkyl, optionally substituted with one or two OH groups. In further or additional embodiments, G is $R_{1d}$ where $R_{1d}$ is C(A)(A') is cyclopropyl and $R^0$ is fluoro, chloro, methyl, ethyl, propyl, isopropyl, sec-butyl, iso-butyl, tert-butyl, cyclopropyl, cyclobutyl, fluoromethyl, methoxy, fluoromethoxy, methylamino or dimethylamino. In further or additional embodiments, G is $R_{1d}$ where $R_{1d}$ is C(A)(A') is cyclopropyl and $R^0$ is F, Cl, methyl, ethyl, methoxy, ethoxy, or 2-methoxy-ethoxy. In further or additional embodiments, G is $R_{1d}$ where $R_{1d}$ is C(A)(A') is cyclopropyl and $R^0$ is H; X is F, Cl, $CH_3$, or mono-, di- or tri-fluoromethyl.

In further or additional embodiments, provided are pharmaceutical combinations and methods of treating cancer comprising a composition that further comprises a compound of formula I, where G is $R_{1d}$ where $R_{1d}$ is C(A)(A') is cyclopropyl and B is 2,3-dihydroxypropyl or 3,4-dihydroxybutyl, in which the chiral carbon in B is in the R configuration, which is substantially free of the S isomer. In further or additional embodiments, the invention provides a composition comprising a compound of formula I, where G is $R_{1d}$ where $R_{1d}$ is C(A)(A') is cyclopropyl and B is 2,3-dihydroxypropyl, in which the chiral carbon in B is in the R configuration, which is substantially free of the S isomer. In further or additional embodiments, the invention provides a composition comprising a compound of formula I, where G is $R_{1d}$ where $R_{1d}$ is C(A)(A') is cyclopropyl and B is 3,4-dihydroxybutyl, in which the chiral carbon in B is in the R configuration, which is substantially free of the S isomer. In further or additional embodiments, the invention provides a composition comprising a compound of formula I, where G is $R_{1d}$ where $R_{1d}$ is C(A)(A') is cyclopropyl and B is 2,3-dihydroxypropyl or 3,4-dihydroxybutyl, in which the chiral carbon in B is in the S configuration, which is substantially free of the R isomer. In further or additional embodiments, the invention provides a composition comprising a compound of formula I, where G is $R_{1d}$ where $R_{1d}$ is C(A)(A') is cyclopropyl and B is 2,3-dihydroxypropyl, in which the chiral carbon in B is in the S configuration, which is substantially free of the R isomer. In further or additional embodiments, the invention provides a composition comprising a compound of formula I, where G is $R_{1d}$ where $R_{1d}$ is C(A)(A') is cyclopropyl and B is 3,4-dihydroxybutyl, in which the chiral carbon in B is in the S configuration, which is substantially free of the R isomer.

In some embodiments, G is $R_{1e}$ and n is 1. In further or additional embodiments, G is $R_{1e}$, $R^0$ is H, $R_{4-6}$ are H, $R_2$ and $R_3$ are, independently, H, F, Cl, Br, $CH_3$, $CH_2F$, $CHF_2$, $CF_3$, $OCH_3$, $OCH_2F$, $OCHF_2$, $OCF_3$, ethyl, n-propyl, isopropyl, cyclopropyl, isobutyl, sec-butyl, tert-butyl, and methylsulfonyl, X is F and Y is I.

In some embodiments, G is $Ar_1$ where $Ar_1$ is phenyl optionally substituted with one group selected from acetamido, amidinyl, cyano, carbamoyl, methylcarbamoyl, dimethylcarbamoyl, 1,3,4-oxadiazol-2-yl, 5-methyl-1,3,4-oxadiazolyl, 1,3,4-thiadiazolyl, 5-methyl-1,3,4-thiadiazolyl, 1H-tetrazolyl, N-morpholylcarbonylamino, N-morpholylsulfonyl, N-pyrrolidinylcarbonylamino, and methylsulfonyl, optionally substituted with 1-3 substituents selected independently from F, Cl, and $CH_3$. In further or additional embodiments, G is $Ar_1$ where $Ar_1$ is phenyl optionally substituted with one group selected from acetamido, amidinyl, cyano, carbamoyl, methylcarbamoyl, dimethylcarbamoyl, 1,3,4-oxadiazol-2-yl, 5-methyl-1,3,4-oxadiazolyl, 1,3,4-thiadiazolyl, 5-methyl-1,3,4-thiadiazolyl, 1H-tetrazolyl, N-morpholylcarbonylamino, N-morpholylsulfonyl, N-pyrrolidinylcarbonylamino, and methylsulfonyl, optionally substituted with 1-3 substituents selected independently from F, Cl, and $CH_3$, $R^0$ is H, X is F, Cl, or methyl and Y is Br, I, $CF_3$, $C_1$-$C_3$ alkyl, $C_2$-$C_3$ alkenyl, $C_2$-$C_3$ alkynyl, cyclopropyl, $OCH_3$, $OCH_2CH_3$ or $SCH_3$. In some embodiments, G is $Ar_1$ where $Ar_1$ is

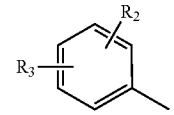

and where $R_2$ and $R_3$ are, independently, H, F, Cl, $CH_3$, $CF_3$, $OCH_3$. In further or additional embodiments, G is $Ar_1$ where $Ar_1$ is

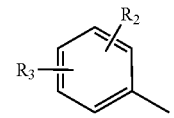

and where $R_2$ and $R_3$ are, independently, H, F, Cl, $CH_3$, $CF_3$, $OCH_3$, X is F or $CH_3$, Y is I, Br, or Cl; and Z is F. In further or additional embodiments, G is $Ar_1$ where $Ar_1$ is phenyl or mono-substituted phenyl. In further or additional embodiments, G is $Ar_1$ where $Ar_1$ is phenyl or mono-substituted phenyl, X is F or $CH_3$, Y is I, Br, or Cl, Z is F; and $R^0$ is F, methyl, ethyl, methoxy, or 2-methoxy-ethoxy. In further or additional embodiments, G is $Ar_1$ where U is N or $CR_2$ and V is N. In further or additional embodiments, G is $Ar_1$ where U is N or $CR_2$ and V is CR. In further or additional embodiments, G is $Ar_1$ where U is N or $CR_2$, V is CR, $R^0$ is H, X is F, Cl, or methyl and Y is Br, I, $CF_3$, $C_1$-$C_3$ alkyl, $C_2$-$C_3$ alkenyl, $C_2$-$C_3$ alkynyl, cyclopropyl, $OCH_3$, $OCH_2CH_3$ or $SCH_3$.

In some embodiments, G is $Ar_2$ where $Ar_2$ is

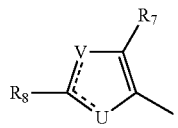

where $R_7$ is H or methyl and $R_8$ is H, acetamido, methyl, F or Cl. In further or additional embodiments, G is $Ar_2$ where $Ar_2$ is

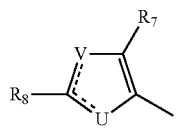

where $R_7$ is H or methyl, $R_8$ is H, acetamido, methyl, F or Cl, $R^0$ is H, X is F, Cl, or methyl, Y is Br, I, $CF_3$, $C_1$-$C_3$ alkyl, $C_2$-$C_3$ alkenyl, $C_2$-$C_3$ alkynyl, cyclopropyl, $OCH_3$, $OCH_2CH_3$ or $SCH_3$, and Z is F. In further or additional embodiments, G is $Ar_2$ where $Ar_2$ is

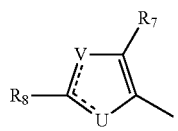

where U is S or O, V is CH=, and $R_8$ is H or $CH_3$, $R_7$ is H or methyl, $R_8$ is H, acetamido, methyl, F or Cl, $R^0$ is H, X is F, Cl, or methyl, Y is Br, I, $CF_3$, $C_1$-$C_3$ alkyl, $C_2$-$C_3$ alkenyl, $C_2$-$C_3$ alkynyl, cyclopropyl, $OCH_3$, $OCH_2CH_3$ or $SCH_3$ and Z is F. In further or additional embodiments, $R^0$ is H. In further or additional embodiments, $R^0$ is H, X is F or Cl and Y is Br, I, $CH_2CH_3$ or $SCH_3$ In some embodiments, G is $Ar_3$ where U is —O—.

In further or additional embodiments, G is $R_{1a}$, where $R_{1a}$ is defined as above. In further or additional embodiments, G is $R_{1a}$, and $R^0$ is H, where $R_{1a}$ is defined as above. In further or additional embodiments, G is $R_{1a}$ and $R^0$ is as defined above, other than H, and $R_{1a}$ is defined as above. In further or additional embodiments, G is $R_{1a}$, where $R_{1a}$ is methyl, monohalomethyl, $C_1$-$C_3$ alkoxymethyl, or cyclopropoxymethyl. In further or additional embodiments, G is $R_{1a}$, where $R_{1a}$ is methyl, monohalomethyl, $C_1$-$C_3$ alkoxymethyl, or cyclopropoxy methyl and where $R^0$ is F, Cl, $C_1$-$C_3$ alkyl, monochloro $C_1$-$C_3$ alkyl, $C_1$-$C_3$ alkoxy, trifluoro methoxy, or 2-methoxy-ethoxy.

In further or additional embodiments, G is $R_{1b}$, where $R_{1b}$ is defined as above. In further or additional embodiments, G is $R_{1b}$, and $R^0$ is H, where $R_{1b}$ is defined as above. In further or additional embodiments, G is $R_{1b}$, $R^0$ is H and Z is F, where $R_{1b}$ is defined as above. In further or additional embodiments, G is $R_{1b}$ and $R^0$ is as defined above, other than H, and $R_{1b}$ is defined as above. In further or additional embodiments, G is $R_{1b}$, where $R_{1b}$ is isopropyl, 2-butyl, 2-pentyl, cyclopropyl, cyclobutyl, cyclopentyl, or cyclohexyl, all optionally substituted with 1 or 2 substituents selected independently from F, Cl, OH, and $OCH_3$; Y is Br, I, methyl, or trifluoromethyl. In further or additional embodiments, G is $R_{1b}$, where $R_{1b}$ is isopropyl, 2-butyl, 2-pentyl, cyclopropyl, cyclobutyl, cyclopentyl, or cyclohexyl, optionally substituted with 1 or 2 substituents selected independently from F, Cl, OH, and $OCH_3$; Y is Br, I, methyl, or trifluoromethyl; and $R^0$ is F, Cl, $C_1$-$C_3$ alkyl, monochloro $C_1$-$C_3$ alkyl, $C_1$-$C_3$ alkoxy, trifluoromethoxy, or 2-methoxy-ethoxy. In further or additional embodiments, G is $R_{1b}$, where $R_{1b}$ is isopropyl, 2-butyl, 2-pentyl, cyclopropyl, cyclobutyl, cyclopentyl, or cyclohexyl, all optionally substituted with one Cl or with 1 or 2 OH groups; and Y is Br, I, methyl, or trifluoromethyl. In further or additional embodiments, G is $R_{1b}$, where $R_{1b}$ is isopropyl, 2-butyl, 2-pentyl, cyclopropyl, cyclobutyl, cyclopentyl, or cyclohexyl, all optionally substituted with one Cl or with 1 or 2 OH groups; Y is Br, I, methyl, or trifluoromethyl; and $R^0$ is F, Cl, $C_1$-$C_3$ alkyl, monochloro $C_1$-$C_3$ alkyl, $C_1$-$C_3$ alkoxy, trifluoromethoxy, or 2-methoxy-ethoxy.

In further or additional embodiments, G is $R_{1c}$, where $R_{1c}$ is defined as above. In further or additional embodiments, G is $R_{1c}$, and $R^0$ is H, where $R_{1c}$ is defined as above. In further or additional embodiments, G is $R_{1c}$ and $R^0$ is as defined above, other than H, and $R_{1c}$ is defined as above. In further or additional embodiments, G is $R_{1c}$, and $R^0$ is H, where $R_{1c}$ is $(CH_2)_nO_mR'$, where m is 0 or 1, n is 2 or 3 when m is 1, and n is 1 or 2 when m is 0, and R' is $C_1$-$C_6$ alkyl, optionally substituted with 1-3 substituents selected independently from F, Cl, OH, $OCH_3$, $OCH_2CH_3$, and $C_3$-$C_6$ cycloalkyl. In another more specific subgeneric embodiment, m is zero, n is 1 or 2, and R' is $C_1$-$C_4$ alkyl, optionally substituted as described above. In another more specific subgeneric embodiment, m is 1, n is 2 or 3, and R' is $C_1$-$C_4$ alkyl, optionally substituted as described above. In a still more specific subgeneric embodiment, m is zero, n is 1 or 2, and R' is $C_1$-$C_4$ alkyl, optionally substituted with 1-3 groups selected from OH, $OCH_3$, Cl, and cyclopropyl.

In further or additional embodiments, G is $R_{1d}$, where $R_{1d}$ is defined as above. In further or additional embodiments, G is $R_{1d}$, and $R^0$ is H, where $R_{1d}$ is defined as above. In further or additional embodiments, G is $R_{1d}$ and $R^0$ is as defined above, other than H, and $R_{1d}$ is defined as above. In further or additional embodiments, G is $R_{1d}$, and $R^0$ is H, where $R_{1d}$ is C(A)(A')(B)— where B, A, and A' are, independently, H or $C_{1-4}$ alkyl, optionally substituted with one or two OH groups or halogen atoms, or A and A¹, together with the carbon atom to which they are attached, form a 3- to 6-member saturated ring, said ring optionally containing one or two heteroatoms selected, independently, from O, N, and S and optionally substituted with one or two groups selected independently from methyl, ethyl, fluoro, chloro, bromo and iodo.

In further or additional embodiments, G is $R_{1e}$, where $R_{1e}$ is defined as above. In further or additional embodiments, G is $R_{1e}$, and $R^0$ is H, where $R_{1e}$ is defined as above. In further or additional embodiments, G is $R_{1e}$ and $R^0$ is as defined above, other than H, and $R_{1e}$ is defined as above.

In further or additional embodiments, G is $Ar_1$, where $Ar_1$ is defined as above. In further or additional embodiments, G is $Ar_1$, and $R^0$ is H, where $Ar_1$ is defined as above. In further or additional embodiments, G is $Ar_1$ and $R^0$ is as defined above, other than H, and $Ar_1$ is defined as above.

In further or additional embodiments, G is $Ar_2$, where $Ar_2$ is defined as above. In further or additional embodiments, G is $Ar_2$, and $R^0$ is H, where $Ar_2$ defined as above. In further or additional embodiments, G is $Ar_2$ and $R^0$ is as defined above, other than H, and $Ar_2$ is defined as above.

In further or additional embodiments, X is F, Cl, or $CH_3$; Y is I, Br, Cl, $CF_3$ or $C_1$-$C_3$ alkyl, and Z is H or F. In further or additional embodiments, X is F, Cl, or $CH_3$: Y is I, Br, Cl, $CF_3$, or $C_1$-$C_3$ alkyl, Z is H or F, and $R^0$ is halogen, $C_1$-$C_6$ alkyl, monohalo $C_1$-$C_6$ alkyl, $C_3$-$C_6$ cycloalkyl, $C_2$-$C_6$ alkenyl, $C_2$-$C_6$ alkynyl, phenyl, monosubstituted phenyl, $OR_3$, O—C(=O)$R_4$, or C(=O)$OR_5$. In further or additional embodiments, X is F, Cl, or $CH_3$: Y is I, Br, Cl, $CF_3$, or $C_1$-$C_3$ alkyl, Z is H or F, and $R^0$ is furyl, thienyl, thiazolyl, isothiazolyl, oxazolyl, isoxazolyl, pyrrolyl, or pyrazolyl. In further or additional embodiments, X is F, Cl, or $CH_3$: Y is I, Br, Cl, $CF_3$, or $C_1$-$C_3$ alkyl, Z is H or F, and $R^0$ is F, Cl, $C_1$-$C_4$ alkyl, $C_1$-$C_3$ alkoxy, trifluoromethoxy, or 2-methoxy-ethoxy.

In another more specific subgeneric embodiment, $R_{1d}$ is cycloalkyl or 1-alkyl-cycloalkyl, in which the 1-alkyl group is optionally substituted with one or two OH groups or with one or two halogen atoms.

In another more specific subgeneric embodiment, $R^0$ is halogen, $C_1$-$C_5$ alkyl, monohalo $C_1$-$C_6$ alkyl, $C_3$-$C_6$ cycloalkyl, $C_2$-$C_6$ alkenyl, $C_2$-$C_6$ alkynyl, phenyl, monosubstituted phenyl, $OR_3$, O—C(=O)$R_4$, or C(=O)$OR_5$; and $R_{1d}$ is cycloalkyl or 1-alkyl-cycloalkyl, in which the 1-alkyl group is optionally substituted with one or two OH groups or with one or two halogen atoms.

In another more specific subgeneric embodiment, $R^0$ is furyl, thienyl, thiazolyl, isothiazolyl, oxazolyl, isoxazolyl, pyrrolyl, or pyrazolyl; and $R_{1d}$ is cycloalkyl or 1-alkyl-cycloalkyl, in which the 1-alkyl group is optionally substituted with one or two OH groups or one or two halogen atoms.

In another more specific subgeneric embodiment, $R_{1d}$ is cycloalkyl or 1-alkyl-cycloalkyl, in which the 1-alkyl group is optionally substituted with one or two OH groups, and where Y is Br, I, methyl, or trifluoromethyl. In another more specific subgeneric embodiment, $R_{1d}$ is cycloalkyl or 1-alkyl-cycloalkyl, in which the 1-alkyl group is optionally substituted with one or two fluorine or chlorine atoms, and where Y is Br, I, methyl, or trifluoromethyl. In another more specific subgeneric embodiment, $R_{1d}$ is cycloalkyl or (1-alley 1)-cycloalkyl, in which the I-alkyl group is optionally substituted with one or two OH groups, and where $R^{0\prime}$ is F, Cl, $C_1$-$C_3$ alkyl, monochloro $C_1$-$C_3$ alkyl, $C_1$-$C_3$ alkoxy, trifluoromethoxy, or 2-methoxy-ethoxy. In another more specific subgeneric embodiment, $R_{1d}$ is tetrahydrofuryl, tetrahydrothienyl, pyrrolidyl, piperidyl, piperazinyl, or morpholyl, each optionally substituted as described above, and where Y is Br, I, methyl, or trifluoromethyl. In another more specific subgeneric embodiment, $R_{1d}$ is oxazolidinyl, thiazolidinyl, isoxazolidinyl, isothiazolidinyl, tetrahydrofuryl, tetrahydrothienyl, pyrrolidyl, piperidyl, piperazinyl, or morpholyl, each optionally substituted as described above, and where Y is Br, I, methyl, or trifluoromethyl. In another more specific subgeneric embodiment, $R_{1d}$ is cyclopropyl or 1-alkyl-cyclopropyl, in which the 1-alkyl group is optionally substituted with one or two OH groups, and where $R^{0\prime}$ is F, Cl, methyl, ethyl, chloromethyl, $C_1$-$C_2$ alkoxy, trifluoromethoxy, or 2-methoxy-ethoxy. In an even more specific embodiment, $R_{1d}$ is 1-(monohydroxyalkyl)cycloalkyl. In another more specific embodiment, $R_{1d}$ is 1-(monohydroxyalkyl)cycloalkyl, where $R^{0\prime}$ is F, Cl, methyl, ethyl, chloromethyl, $C_1$-$C_2$ alkoxy, trifluoromethoxy, or 2-methoxy-ethoxy. In an even more specific embodiment, $R_{1d}$ is 1-(dihydroxyalkyl)cycloalkyl. In another more specific embodiment, $R_{1d}$ is 1-(dihydroxyalkyl)cycloalkyl, where $R^{0\prime}$ is F, Cl, methyl, ethyl, chloromethyl, $C_1$-$C_2$ alkoxy, trifluoromethoxy, or 2-methoxy-ethoxy.

In a more specific subgeneric embodiment U is $CR_2$ and V is N. In another more specific, subgeneric embodiment, U and V are both N. In a more specific, subgeneric embodiment, U is $CR_2$ and V is $CR_3$.

In a still more specific subgeneric embodiment, this invention provides a compound of formula I, where G is $Ar_1$ and $Ar_1$ is phenyl or monosubstituted phenyl, $R^0$ is F, methyl, ethyl, $C_1$-$C_3$ alkoxy, trifluoromethoxy, or 2-methoxy-ethoxy; X is F, Cl, or $CH_3$; Y is I; and Z is F. In another subgeneric embodiment, this invention provides a compound of formula I, where G is $Ar_1$, where $Ar_1$ is phenyl or monosubstituted phenyl, $R^0$ is halogen, $C_1$-$C_6$ alkyl, $C_3$-$C_6$ cycloalkyl, $C_2$-$C_6$ alkenyl, $C_2$-$C_6$ alkynyl, all such alkyl, cycloalkyl, alkenyl, and alkynyl groups optionally substituted with 1-3 substituents selected independently from halogen, OH, CN, cyanomethyl, nitro, phenyl, and trifluoromethyl; or $R^0$ is phenyl, $OR_3$, furyl, thienyl, thiazolyl, isothiazolyl, oxazolyl, isoxazolyl, pyrrolyl, or pyrazolyl. In a more specific subgeneric embodiment, this invention provides a compound of formula I, where A is $Ar_1$, where $Ar_1$ is phenyl or monosubstituted phenyl, $R^0$ is F, Cl, $C_1$-$C_3$ alkyl, $C_1$-$C_3$ alkoxy, 2-methoxyethoxy, $C_2$-$C_3$ alkenyl, $C_2$-$C_3$ alkynyl, trifluoromethyl, phenyl, furyl, or thienyl, thiazolyl, isothiazolyl, oxazolyl, isoxazolyl, pyrrolyl, or pyrazolyl; X is F, Cl, or methyl; Y is I, Br, Cl, $CF_3$, or $C_1$-$C_3$ alkyl; and Z is F.

In another still more specific subgeneric embodiment, this invention provides a compound of formula I, where G is $Ar_1$, where $Ar_1$ is phenyl or monosubstituted phenyl, $R^0$ is H; X is F, Cl, or $CH_3$; Y is Br or I; and Z is F.

In another subgeneric embodiment his invention provides a compound of formula I, where G is $Ar_2$, where $Ar_2$ is 2-thienyl, 2-furyl, 3-thienyl, 3-furyl, 2-pyrrolyl, or 3-pyrrolyl, all optionally substituted with methoxycarbonyl, methylcarbamoyl, acetamido, acetyl, methyl, ethyl, trifluoromethyl, or halogen. In a more specific subgeneric embodiment his invention provides a compound of formula I, where G is $Ar_2$, where $Ar_2$ is 2-thienyl, 2-furyl, 3-thienyl, 3-furyl, 2-pyrrolyl, or 3-pyrrolyl, all optionally substituted with methoxycarbonyl, methylcarbamoyl, acetamido, acetyl, methyl, ethyl, trifluoromethyl, or halogen; $R^0$ is other than H; X is F, Cl, or $CH_3$: Y is I, Br, Cl, $CF_3$, or $C_1$-$C_3$ alkyl, and Z is H or F. In another subgeneric embodiment this invention provides a compound of formula I, where G is $Ar_2$, where $Ar_2$ is 2-thienyl, 2-furyl, 3-thienyl, 3-furyl, 2-pyrrolyl, or 3-pyrrolyl, all optionally substituted with methoxycarbonyl, methylcarbamoyl, acetamido, acetyl, methyl, ethyl, trifluoromethyl, or halogen; $R^0$ is F, Cl, $C_1$-$C_3$ alkyl, monochloro $C_1$-$C_3$ alkyl, $C_1$-$C_3$ alkoxy, trifluoromethoxy, methyloxy-methoxy, or 2-methoxy-ethoxy; X is F, Cl, or $CH_3$; Y is I, Br, Cl, $CF_3$, or $C_1$-$C_3$ alkyl, and Z is H or F. In another subgeneric embodiment his invention provides a compound of formula I, where G is $Ar_2$, where $Ar_2$ is 2-thienyl, 2-furyl, 3-thienyl, 3-furyl, 2-pyrrolyl, or 3-pyrrolyl, all optionally substituted with methoxycarbonyl, methylcarbamoyl, acetamido, acetyl, methyl, ethyl, trifluoromethyl, or halogen; $R^0$ is H; X is F, Cl, or $CH_3$: Y is I, Br, Cl, $CF_3$, or $C_1$-$C_3$ alkyl, and Z is H or F. In another subgeneric embodiment his invention provides a compound of formula I, where G is $Ar_2$, where $Ar_2$ is thiazolyl, isothiazolyl, oxazolyl, isoxazolyl, pyrrolyl, or pyrazolyl, all optionally substituted with methoxycarbonyl, methylcarbamoyl, acetamido, acetyl, methyl, ethyl, trifluoromethyl, or halogen; $R^0$ is H or methoxy; X is F, Cl, or $CH_3$: Y is I, Br, Cl, $CF_3$, or $C_1$-$C_3$ alkyl, and Z is H or F.

In some embodiments, the provided are pharmaceutical combinations and methods of treating cancer comprising a compound of formula (I), or a pharmaceutical salt thereof, that is selected from:

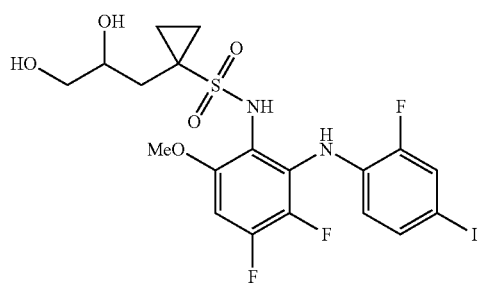

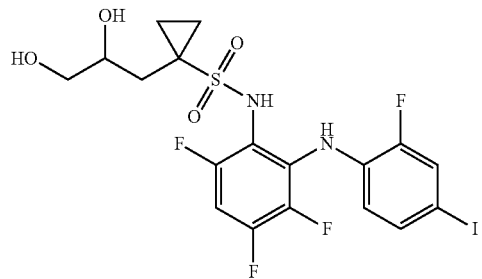 [SMILES: O=S(=O)(Nc1c(F)cc(F)c(F)c1Nc1ccc(I)cc1F)C1(CC(O)CO)CC1]

In some embodiments, provided are pharmaceutical combinations and methods of treating cancer comprising a compound of formula I, or a pharmaceutical salt thereof, selected from:

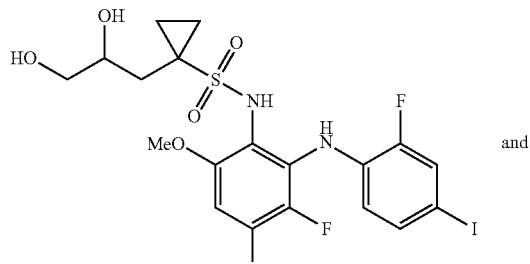

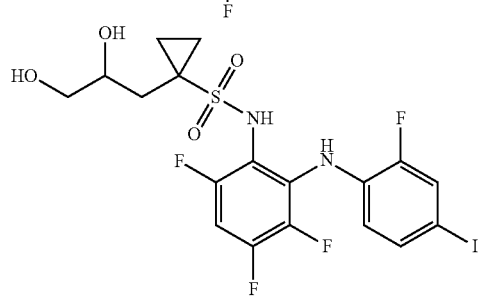

where the 2-OH carbon is in the R configuration.

In some embodiments, provided are pharmaceutical combinations and methods of treating cancer comprising a compound of formula I, or a pharmaceutical salt thereof, selected from:

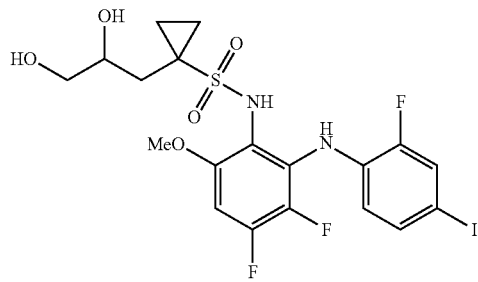

and

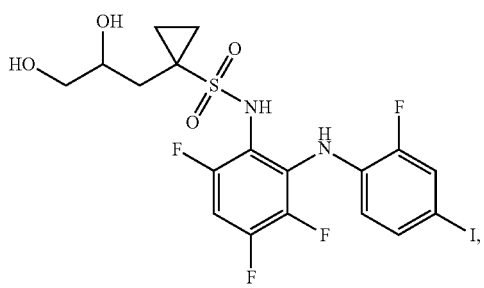

where the 2-OH carbon is in the S configuration.

In further or additional embodiments, provided are pharmaceutical combinations and methods of treating cancer comprising a compound of formula (I), or a pharmaceutical salt thereof, is

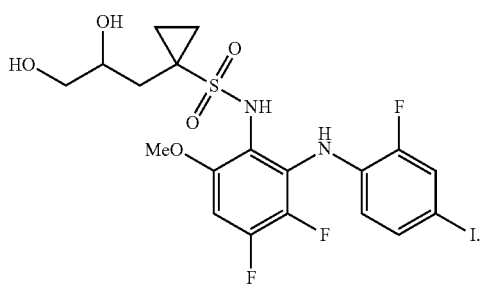

In further or additional embodiments, provided are pharmaceutical combinations and methods of treating cancer comprising the compound of formula (I), or a pharmaceutical salt thereof, is

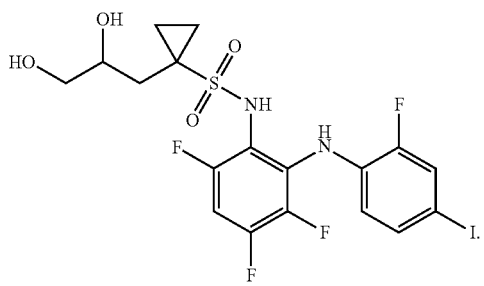 [SMILES: O=S(=O)(Nc1c(F)cc(F)c(F)c1Nc1ccc(I)cc1F)C1(CC(O)CO)CC1]

In some embodiments, provided are pharmaceutical compositions and methods of treating cancer comprising a compound of formula I, selected from those shown below, where the 2-OH carbon is in the R configuration, substantially free of the S-isomer:

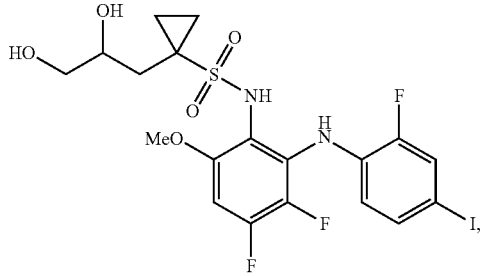 [SMILES: COc1cc(F)c(F)c(Nc2ccc(I)cc2F)c1NS(=O)(=O)C1(CC(O)CO)CC1]

-continued

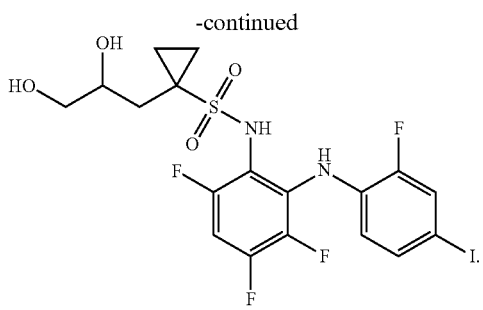

In some embodiments, provided are pharmaceutical compositions and methods of treating cancer comprising a compound of formula I, selected from those shown below, where the 2-OH carbon is in the S configuration, substantially free of the R-isomer:

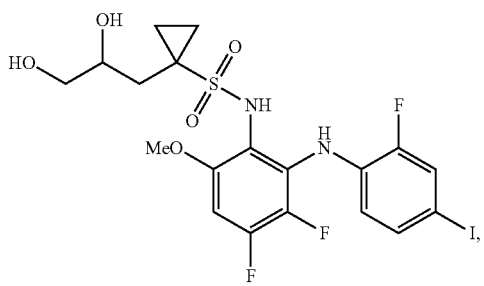

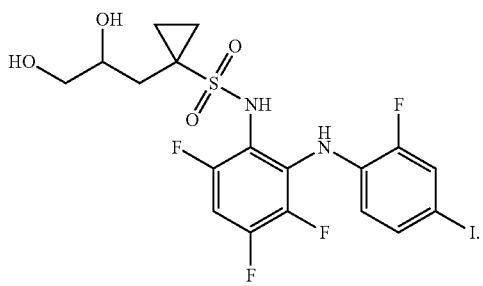 [SMILES: O=S(=O)(Nc1c(F)cc(F)c(F)c1Nc1ccc(I)cc1F)C1(CC(O)CO)CC1]

In some embodiments, this invention provides a pharmaceutical combination and method of treating cancer comprising a compound of formula I, where Y is phenyl, pyridyl, or pyrazolyl. In another subgeneric embodiment, this invention provides a compound of formula I, where Y is substituted phenyl, pyridyl, or pyrazolyl. In yet another subgeneric embodiment, this invention provides a compound of formula I, where Y is Br or I. In one subgeneric embodiment, this invention provides a compound of formula I, where G is 1-piperidyl, 2-piperidyl, 3-piperidyl, or 4-piperidyl. In another subgeneric embodiment, this invention provides a compound of formula I, where G is 1-piperazyl or 2-piperazyl. In another subgeneric embodiment, this invention provides a compound of formula I, where G is morpholyl. In another subgeneric embodiment, this invention provides a compound of formula I, where G is N-methyl-2-aminoethyl. In one subgeneric embodiment, this invention provides a compound of formula I, where G is N-methyl-3-amino-n-propyl. In another subgeneric embodiment, this invention provides a compound of formula I, where G is $(CH_3)_2N-CH_2CH_2-NH-(CH_2)_n-$, where n is 1, 2, or 3. In another subgeneric embodiment, this invention provides a compound of formula I, where G is $(CH_3CH_2)_2N-CH_2CH_2-NH-(CH_2)_n-$, where n is 1 or 2. In a more specific subgeneric embodiment, this invention provides a compound of formula I, where G is 1-piperidyl, 2-piperidyl, 3-piperidyl, or 4-piperidyl; $R^o$ is H, halo, or methoxy; X is F; and Y is I. In another more specific subgeneric embodiment, this invention provides a compound of formula I, where G is 1-piperazyl or 2-piperazyl; $R^o$ is H, halo, or methoxy; X is F; and Y is I In another more specific subgeneric embodiment, this invention provides a compound of formula I, where G is morpholyl; $R^o$ is H, halo, or methoxy; X is F; and Y is I. In another more specific subgeneric embodiment, this invention provides a compound of formula I, where G is N-methyl-2-aminoethyl; $R^o$ is H, halo, or methoxy; X is F; and Y is I In another more specific subgeneric embodiment, this invention provides a compound of formula I, where G is N-methyl-3-amino-n-propyl; $R^o$ is H, halo, or methoxy; X is F; and Y is I. In another more specific subgeneric embodiment, this invention provides a compound of formula I, where G is $(CH_3)_2N-CH_2CH_2-NH-(CH_2)_n-$, where n is 1, 2, or 3; $R^o$ is H, halo, or methoxy; X is F; and Y is I. In another more specific subgeneric embodiment, this invention provides a compound of formula I, where G is $(CH_3CH_2)_2N-CH_2CH_2-NH-(CH_2)_n-$, where n is 1 or 2; $R^o$ is H, halo, or methoxy; X is F; and Y is I.

In some embodiments, the provided are pharmaceutical compositions and methods of treating cancer comprising a compound of formula I or a pharmaceutically acceptable salt, solvate, polymorph, ester, amide, tautomer or prodrug thereof. In some embodiments the pharmaceutical composition further comprises at least one pharmaceutically acceptable carrier.

In some embodiments, provided are pharmaceutical compositions and methods of treating cancer comprising a compound selected from:

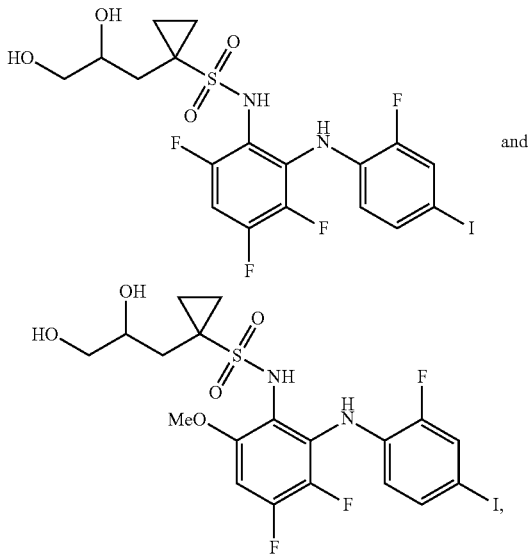

or a pharmaceutically acceptable salt, solvate, polymorph, ester, amide, tautomer or prodrug thereof. In some embodiments, "compound A" is:

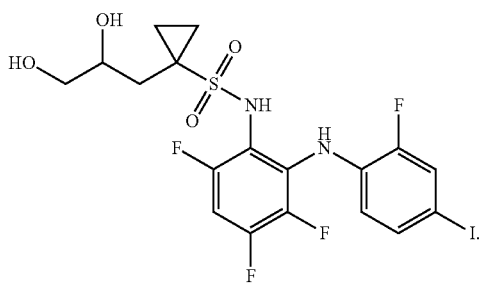

In other embodiments, "compound A" is

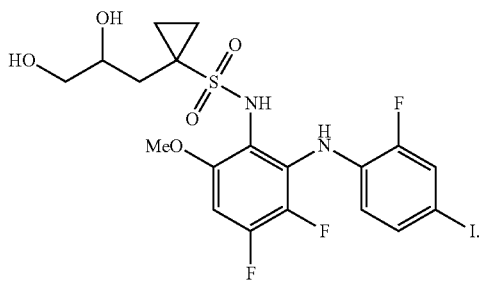

In some embodiments, "compound A" is selected from the group consisting of

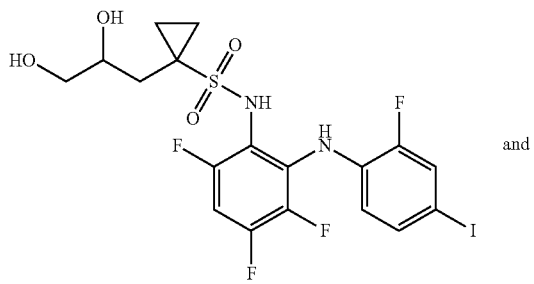

and

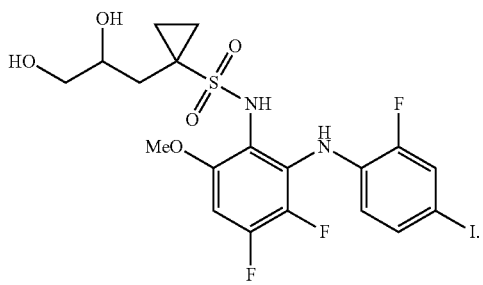 [SMILES: COc1cc(F)c(F)c(Nc2ccc(I)cc2F)c1NS(=O)(=O)C1(CC(O)CO)CC1]

In some embodiments, the pharmaceutical composition further comprises at least one pharmaceutically acceptable carrier. In some embodiments, the compound is in the R configuration. In some embodiments, the compound is in the R configuration, substantially free of the S-isomer. In some embodiments, the compound is in the S configuration. In some embodiments, the compound is in the S configuration, substantially free of the R-isomer. In some embodiments, the compound is:

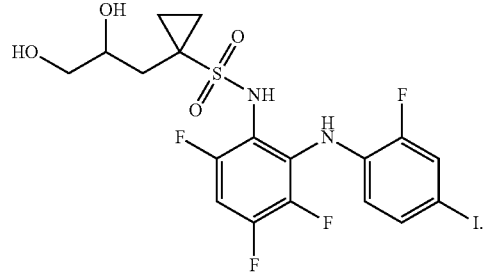

In some embodiments, the compound is:

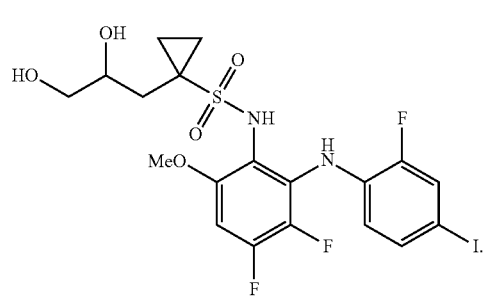

Additional non-limiting examples of pharmaceutical combinations and methods of treating cancer comprising compounds falling within formula I, including methods of synthesizing such compounds, with and without the use of protecting groups, as well as isomers, labeled compounds, pharmaceutically acceptable salts, solvates, polymorphs, prodrugs, and other derivatives are provided for in International Application Ser. No. PCT/US2006/028326, filed on Jul. 21, 2006, and U.S. application Ser. No. 11/830,733, filed Jul. 30, 2007, each of which are hereby incorporated by reference in their entirety for all purposes.

In some embodiments, provided herein are pharmaceutical combinations and methods of treating cancer comprising a MEK protein kinase inhibitor, wherein the MEK protein kinase inhibitor is a compound of formula II, or a pharmaceutically acceptable salt, solvate, polymorph, ester, amide, tautomer or prodrug thereof:

formula II

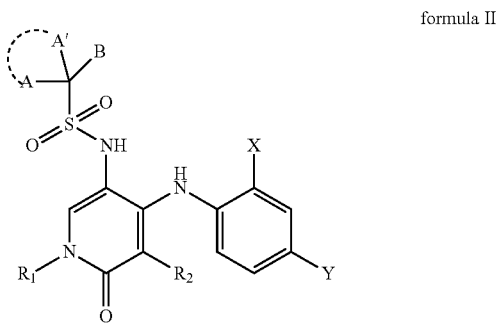

wherein
B is H, $C_1$-$C_6$ alkyl or $C_2$-$C_6$ alkenyl;
    wherein said $C_1$-$C_5$ alkyl is optionally substituted with one or two groups selected independently from hydroxy, alkoxy, oxy, amine and substituted amine;
A and A' are each independently H, $C_1$-$C_6$ alkyl, or $C_2$-$C_6$ alkenyl;

wherein each $C_1$-$C_6$ alkyl is optionally substituted with one or two groups selected independently from hydroxy, alkoxy, oxy, amine and substituted amine; or A and A' together with the carbon atom to which they are attached, form a cyclopropyl, cyclobutyl, or cyclopentyl group, wherein each cyclopropyl, cyclobutyl, or cyclopentyl group is optionally substituted with one or two groups selected independently from methyl, hydroxy, and halogen;

X and Y are each independently halogen, methyl, $SCH_3$ or trifluoromethyl;

$R_1$ is H, $C_1$-$C_6$ alkyl, $C_3$-$C_6$ cycloalkyl, $C_2$-$C_6$ alkenyl, $C_5$-$C_6$ cycloalkenyl or $C_2$-$C_6$ alkynyl;
  wherein each alkyl, cycloalkyl, alkenyl, cycloalkenyl or alkynyl group is optionally substituted with 1-3 substituents selected independently from halogen, hydroxy, alkyl, $C_1$-$C_4$ alkoxy, cyano, cyanomethyl, nitro, azido, trifluoromethyl difluoromethoxy and phenyl, and
  one or two ring carbon atoms of said $C_3$-$C_6$ cycloalkyl groups are optionally replaced with, independently, O, N, or S; or $R_1$ is a 5 or 6-atom heterocyclic group, which group may be saturated, unsaturated, or aromatic, containing 1-5 heteroatoms selected independently from O, N, and S, which heterocyclic group is optionally substituted with 1-3 substituents selected independently from halogen, hydroxy, $C_1$-$C_4$ alkyl, alkoxy, cyano, cyanomethyl, nitro, azido, trifluoromethyl difluoromethoxy and phenyl; and $R_2$ is H, halogen, hydroxy, azido, cyano, cyanomethyl, $C_1$-$C_6$ alkyl, $C_3$-$C_6$ cycloalkyl, $C_2$-$C_6$ alkenyl, $C_5$-$C_6$ cycloalkenyl or $C_2$-$C_6$ alkynyl, wherein each alkyl, cycloalkyl, alkenyl cycloalkenyl or alkynyl group is optionally substituted with 1-3 substituents selected independently from halogen, hydroxy, $C_1$-$C_4$ alkoxy, cyano, cyanomethyl, nitro, azido, trifluoromethyl and phenyl.

In one subgeneric embodiment, provided herein are pharmaceutical combinations and methods of treating cancer comprising at least one MEK protein kinase inhibitor and at least one Raf protein kinase inhibitor, wherein the MEK protein kinase inhibitor further comprises a compound of formula II, where X and Y are both halogen. In another subgeneric embodiment, the provided herein are combinations and methods of treating comprising a compound of formula II, where X is halogen and Y is $CH_3$, $CH_2F$, $CHF_2$, or $CF_3$. In a more specific subgeneric embodiment, the provided are combinations and methods of treating cancer comprising a compound of formula II where X is F and Y is Br or I. In another subgeneric embodiment, provided herein are combinations and methods of treating cancer comprising a compound of formula II, where X and Y are both halogen. In another subgeneric embodiment, the invention provides a compound of formula II, where X is $CH_3$, $CH_2F$, $CHF_2$, or $CF_3$, and Y is halogen. In another subgeneric embodiment, the invention provides a compound of formula II, where X and Y are halogen and $R_1$ is $C_1$-$C_6$ alkyl, optionally substituted as described above. In another subgeneric embodiment, the invention provides a compound of formula II, where X, Y, and $R_2$ are halogen and $R_1$ is $C_1$-$C_6$ alkyl, optionally substituted as described above. In another subgeneric embodiment, the invention provides a compound of formula II, where X and Y are halogen, $R_2$ is H, and $R_1$ is $C_1$-$C_6$ alkyl, optionally substituted as described above.

In a more specific subgeneric embodiment, provided herein are pharmaceutical combinations and methods of treating cancer comprising a compound of formula II, where X, Y, and $R_2$ are halogen, $R_1$ is $C_1$-$C_6$ alkyl, C(A)A' is cyclopropyl, and B is H or $C_1$-$C_6$ alkyl, where cyclopropyl and $C_1$-$C_6$ alkyl are optionally substituted as described above.

In another more specific subgeneric embodiment, provided herein are pharmaceutical combinations and methods of treating cancer comprising a compound of formula II, where X and Y are halogen, $R_2$ is H or methyl, $R_1$ is $C_1$-$C_6$ alkyl, C(A)A' is cyclopropyl, and 13 is H or $C_1$-$C_6$ alkyl, where cyclopropyl and $C_1$-$C_6$ alkyl are optionally substituted as described above.

In a more specific subgeneric embodiment, provided herein are pharmaceutical combinations and methods of treating cancer comprising a compound of formula II, where X, Y, and $R_2$ are halogen, $R_1$ is $C_1$-$C_6$ alkyl, C(A)A' is cyclobutyl, and B is H or $C_1$-$C_6$ alkyl, where $C_1$-$C_6$ alkyl is optionally substituted as described above.

In another more specific subgeneric embodiment, provided herein are pharmaceutical combinations and methods of treating cancer comprising a compound of formula II, where X and Y are halogen, $R_2$ is H, $R_1$ is $C_1$-$C_6$ alkyl, C(A)A' is cyclobutyl, and B is H or $C_1$-$C_6$ alkyl, where cyclobutyl and $C_1$-$C_6$ alkyl are optionally substituted as described above.

In a more specific subgeneric embodiment, provided herein are pharmaceutical combinations and methods of treating cancer comprising a compound of formula II, where X, Y, and $R_2$ are halogen, $R_1$ is $C_2$-$C_6$ alkenyl, C(A)A' is cyclopropyl, and B is H or $C_1$-$C_6$ alkyl, where $C_1$-$C_6$ alkyl is optionally substituted as described above.

In another more specific subgeneric embodiment, provided are pharmaceutical combinations and methods of treatment of cancer comprising a compound of formula II, where X and Y are halogen, $R_2$ is H or methyl, $R_1$ is furyl, pyrrolyl, or thienyl, C(A)A' is cyclopropyl, and B is H or $C_1$-$C_6$ alkyl, where cyclopropyl and $C_1$-$C_6$ alkyl are optionally substituted as described above.

In a more specific subgeneric embodiment, provided herein are pharmaceutical combinations and methods of treating cancer comprising a compound of formula II, where X, Y, and $R_2$ are halogen, $R_1$ is $C_1$-$C_6$ alkyl, C(A)A' is cyclopentyl, and B is H or $C_1$-$C_6$ alkyl, where cyclobutyl and $C_1$-$C_6$ alkyl are optionally substituted as described above.

In another more specific subgeneric embodiment, provided herein are pharmaceutical combinations and methods of treating cancer comprising a compound of formula II, where X and Y are halogen, $R_2$ is H or methyl, $R_1$ is $C_1$-$C_6$ alkyl, C(A)A' is cyclobutyl, and B is H or $C_1$-$C_6$ alkyl, where cyclobutyl and $C_1$-$C_6$ alkyl are optionally substituted as described above.

In another subgeneric embodiment, provided are pharmaceutical combinations and methods of treating cancer comprising a compound of formula II, where X and Y are halogen, $R_2$ is halogen, C(A)A' is cyclobutyl, B is dihydroxy-$C_1$-$C_6$ alkyl and $R_1$ is $C_1$-$C_6$ alkyl, which cyclobutyl and $C_1$-$C_6$ alkyl are optionally substituted as described above.

In a more specific subgeneric embodiment, provided are pharmaceutical combinations and methods of treating cancer comprising at least one MEK protein kinase inhibitor and at least one Raf protein kinase inhibitor, wherein the MEK protein kinase inhibitor further comprises a compound of formula II, where X and Y are halogen, $R_2$ is halogen, C(A)A' is cyclobutyl, B is dihydroxy-$C_1$-$C_4$ alkyl and $R_1$ is $C_1$-$C_4$ alkyl, which cyclobutyl and $C_1$-$C_4$ alkyl are optionally substituted as described above.

In another subgeneric embodiment, provided herein are pharmaceutical combinations and methods of treating cancer comprising a compound of formula II, where X and Y are halogen, $R_2$ is halogen, C(A)A' is cyclopropyl, B is dihydroxy-$C_1$-$C_6$ alkyl and $R_1$ is $C_1$-$C_6$ alkyl, optionally substituted with fluoromethyl, difluoromethyl or trifluoromethyl.

In another more specific subgeneric embodiment, provided are pharmaceutical combinations and methods of treating cancer comprising a compound of formula II, where X and Y are halogen, $R_2$ is halogen, C(A)A' is cyclopropyl, B is dihydroxy-$C_1$-$C_4$ alkyl and $R_1$ is $C_1$-$C_4$ alkyl, optionally substituted with fluoromethyl, difluoromethyl, or trifluoromethyl.

In another subgeneric embodiment, provided are pharmaceutical combinations and methods of treating cancer comprising a compound of formula II, where X and Y are halogen, $R_2$ is halogen, C(A)A' is cyclopropyl, B is monohydroxy-$C_1$-$C_6$ alkyl and $R_1$ is $C_1$-$C_6$ alkyl, which alkyl and cyclopropyl groups are optionally substituted as described above.

In another subgeneric embodiment, provided herein are pharmaceutical combinations and methods of treating cancer comprising a MEK protein kinase inhibitor and Raf protein kinase inhibitor and methods of treating disease, particularly cancer, comprising the administration of a MEK protein kinase inhibitor and Raf protein kinase inhibitor, wherein the combination and the method further comprises a compound of formula II, where X and Y are halogen, $R_2$ is halogen, C(A)A' is cyclopropyl, B is monohydroxy-$C_1$-$C_6$ alkyl, and $R_1$ is $C_1$-$C_6$ alkyl, which alkyl and cyclopropyl groups are optionally substituted as described above.

In another subgeneric embodiment, provided herein are pharmaceutical combinations and methods of treating cancer comprising a compound of formula II, where X and Y are halogen, $R_2$ is halogen, C(A)A' is cyclopropyl, B is monohydroxy-$C_1$-$C_6$ alkyl and $R_1$ is $C_1$-$C_4$ alkyl, which alkyl and cyclopropyl groups are optionally substituted as described above.

In another subgeneric embodiment, provided herein are pharmaceutical combinations and methods of treating cancer comprising a compound of formula II, where X is $CF_3$, $CHF_2$, $CH_2F$, or F; Y is halogen; $R_2$ is halogen; C(A)A' is cyclopropyl; B is H or dihydroxy-$C_1$-$C_6$ alkyl; and $R_1$ is $C_1$-$C_6$ alkyl, all alkyl groups optionally substituted as described above.

In another subgeneric embodiment, provided herein are pharmaceutical combinations and methods of treating cancer comprising a compound of formula II, where X and Y are halogen, $R_2$ is halogen, C(A)A' is cyclopropyl, B is dihydroxy-$C_1$-$C_6$ alkyl and $R_1$ is $C_1$-$C_4$ alkyl, all alkyl groups optionally substituted as described above.

In certain embodiments, provided herein are pharmaceutical combinations and methods of treatment of cancer comprising a compound of formula II, wherein X and Y are both halogen. In further or additional embodiments, provided herein are pharmaceutical combinations and methods of treating cancer comprising a compound of formula II, X is F. In further or additional embodiments, the pharmaceutical combinations and methods of treating cancer as described herein further comprise a compound of formula II, Y is Br or I. In further or additional embodiments of the compound of formula II, Y is Br. In further or additional embodiments of the compound of formula II, Y is I. In further or additional embodiments of the combinations and methods of treating cancer, the compound of formula II, X is F and Y is Br. In further or additional embodiments of the compound of formula II, X is F and Y is I. In further or additional embodiments, provided are pharmaceutical combinations and methods of treating cancer comprising a compound of formula II, one of X and Y is methyl, $SCH_3$ or trifluoromethyl. In further or additional embodiments of the compound of formula II, X and Y are independently methyl, $SCH_3$ or trifluoromethyl.

In further or additional embodiments, provided herein are pharmaceutical combinations and methods of treatment comprising the compound of formula II, wherein A and A' together with the carbon atom to which they are attached, form a cyclopropyl group. In further or additional embodiments, provided herein are pharmaceutical combinations and methods of treatment comprising the compound of formula II, A and A' together with the carbon atom to which they are attached form a cyclobutyl group. In further or additional embodiments, provided herein are pharmaceutical combinations and methods of treatment of cancer comprising the compound of formula II, wherein A and A' together with the carbon atom to which they are attached form a cyclopentyl group. In further or additional embodiments, provided herein are pharmaceutical combinations and methods of treatment of cancer comprising the compound of formula II, wherein A and A' together with the carbon atom to which they are attached form a cyclopropyl, cyclobutyl, or cyclopentyl group wherein each cyclopropyl, cyclobutyl, or cyclopentyl group is optionally substituted with one or two groups selected independently from methyl, hydroxy, and halogen.

In further or additional embodiments of the combinations and methods, the combinations and methods further comprise the compound of formula II, wherein $R_1$ is H, $C_1$-$C_6$ alkyl, or $C_3$-$C_6$ cycloalkyl. In further or additional embodiments of the compound of formula II, $R_1$ is H. In further or additional embodiments of the compound of formula II, $R_1$ is $C_1$-$C_5$ alkyl. In certain embodiments, provided herein are pharmaceutical combinations and methods of treatment comprising the compound of formula II, wherein $R_1$ is $C_1$-$C_6$ alkyl optionally substituted with 1-3 substituents selected independently from halogen, hydroxy, alkyl, alkoxy, cyano, cyanomethyl, nitro, azido, trifluoromethyl difluoromethoxy and phenyl. In further or additional embodiments of the combinations and methods of treatment, the combinations and methods further comprise the compound of formula II, wherein $R_1$ is $C_3$-$C_6$ cycloalkyl. In further or additional embodiments of the compound of formula II, $R_1$ is $C_3$-$C_6$ cycloalkyl optionally substituted with 1-3 substituents selected independently from halogen, hydroxy, $C_1$-$C_4$ alkyl, alkoxy, cyano, cyanomethyl, nitro, azido, trifluoromethyl difluoromethoxy and phenyl.

In further or additional embodiments of the combinations and methods, provided is a compound of formula II, wherein $R_1$ is $C_3$-$C_6$ cycloalkyl, wherein one ring carbon atom is replaced with O, N, or S. In further or additional embodiments of the combinations and methods of treatment, provided is a compound of formula II, $R_1$ is $C_3$-$C_6$ cycloalkyl, wherein one ring carbon atom is replaced with O, N, or S optionally substituted with 1-3 substituents selected independently from halogen, hydroxy, $C_1$-$C_4$ alkyl, $C_1$-$C_4$ alkoxy, cyano, cyanomethyl, nitro, azido, trifluoromethyl difluoromethoxy and phenyl. In further or additional embodiments of the pharmaceutical combinations and methods of treating cancer, provided is a compound of formula II, $R_1$ is $C_3$-$C_6$ cycloalkyl, wherein two ring carbon atoms are replaced with O, N, or S. In further or additional embodiments of the combinations and methods, provided is a compound of formula II wherein $R_1$ is $C_3$-$C_6$ cycloalkyl, wherein two ring carbon atoms are replaced with O, N, or S optionally substituted with 1-3 substituents selected independently from halogen, hydroxy, alkyl, $C_1$-$C_4$ alkoxy, cyano, cyanomethyl, nitro, azido, trifluoromethyl difluoromethoxy and phenyl.

In certain embodiments, provided herein are pharmaceutical combinations and methods of treatment comprising a compound of formula II, wherein $R_2$ is H, halogen, or $C_1$-$C_3$ alkyl. In further or additional embodiments of the combinations and methods, provided herein is a compound of formula II wherein $R_2$ is H. In further or additional embodiments of the combinations and methods, a compound of formula II has $R_2$ as a halogen. In further or additional embodiments of the combinations and methods, provided are compounds of formula II, $R_2$ is $C_1$-$C_3$ alkyl. In further or additional embodiments, the combinations and methods further comprise the compound of formula II, wherein $R_1$ is a 5-atom heterocyclic group, which group may be saturated, unsaturated, or aromatic, containing 1-4 heteroatoms selected independently from O, N, and S. In further or additional embodiments, the combinations and methods further comprise the compound of formula II, $R_1$ is a 6-atom heterocyclic group, which group may be saturated, unsaturated, or aromatic, containing 1-5 heteroatoms selected independently from O, N, and S. In certain embodiments of the combinations and methods of treatment, provided is the compound of formula II wherein $R_1$ is furyl, imidazolyl, imidazolinyl, imidazolidinyl, dihydrofuryl, tetrahydrofuryl, pyrrolyl, pyrrolidinyl, pyrrolinyl, morpholyl, piperidinyl, pyridyl, or thienyl. In further or additional embodiments of the combinations and methods, provided is a compound of formula II wherein A and A' together with the carbon atom to which they are attached, form a cyclopropyl, cyclobutyl, or cyclopentyl group wherein each cyclopropyl, cyclobutyl, or cyclopentyl group is optionally substituted with one or two groups selected independently from methyl, hydroxy, and halogen and $R_1$ is a 5-atom heterocyclic group, which group may be saturated, unsaturated, or aromatic, containing 1-4 heteroatoms selected independently from O, N, and S. In certain embodiments, the combinations and methods provide the compound of formula II, wherein A and A' together with the carbon atom to which they are attached, form a cyclopropyl, cyclobutyl, or cyclopentyl group wherein each cyclopropyl, cyclobutyl, or cyclopentyl group is optionally substituted with one or two groups selected independently from methyl, hydroxy, and halogen and $R_1$ is a 6-atom heterocyclic group, which group may be saturated, unsaturated, or aromatic, containing 1-5 heteroatoms selected independently from O, N, and S. In some embodiments, provided are pharmaceutical combinations and methods of treating cancer comprising the compound of formula II, wherein A and A' together with the carbon atom to which they are attached, form a cyclopropyl, cyclobutyl, or cyclopentyl group wherein each cyclopropyl, cyclobutyl, or cyclopentyl group is optionally substituted with one or two groups selected independently from methyl, hydroxy, and halogen and $R_1$ is furyl, imidazolyl, imidazolinyl, imidazolidinyl, dihydrofuryl, tetrahydrofuryl, pyrrolyl, pyrrolidinyl, pyrrolinyl, morpholyl, piperidinyl, pyridyl, or thienyl. In some embodiments, provided herein are combinations and methods of the compound of formula II, wherein $R_1$ is $C_2$-$C_6$ alkenyl or $C_2$-$C_6$ alkynyl, optionally substituted with 1-3 substituents selected independently from halogen, hydroxy, $C_1$-$C_4$ alkyl, $C_1$-$C_4$ alkoxy, cyano, cyanomethyl, nitro, azido, trifluoromethyl difluoromethoxy and phenyl. In certain embodiments, provided are combinations and methods of treating cancer wherein the compound of formula II further comprises A and A' together with the carbon atom to which they are attached, form a cyclopropyl, cyclobutyl, or cyclopentyl group wherein each cyclopropyl, cyclobutyl, or cyclopentyl group is optionally substituted with one or two groups selected independently from methyl, hydroxy, and halogen and $R_1$ is $C_2$-$C_6$ alkenyl or $C_2$-$C_6$ alkynyl, optionally substituted with 1-3 substituents selected independently from halogen, hydroxy, $C_1$-$C_4$ alkyl, $C_1$-$C_4$ alkoxy, cyano, cyanomethyl, nitro, azido, trifluoromethyl difluoromethoxy and phenyl. In alternative embodiments of the combinations and methods provided herein, the combinations and methods further comprise a compound of formula II and B is unsubstituted $C_1$-$C_6$ alkyl. In additional embodiments of the pharmaceutical combinations and methods of treatment, provided is the compound of formula II, wherein B is $C_1$-$C_6$ alkyl, substituted with one hydroxy, alkoxy, oxy, amine or substituted amine group. In further embodiments of the combinations and methods provided herein, the combinations and methods further comprises the compound of formula II and the compound of formula II further comprises B, wherein B is $C_1$-$C_6$ alkyl, substituted with one hydroxy group. In further or additional embodiments of the combinations and methods of treatment, provided is the compound of formula II, wherein B is $C_1$-$C_6$ alkyl, substituted with one alkoxy group. In further or additional embodiments of the combinations or methods of treating cancer, provided is the compound of formula II, wherein B is $C_1$-$C_6$ alkyl, substituted with one oxy group. In certain embodiments of the combinations and methods of treatment, provided is the compound of formula II, B is $C_1$-$C_6$ alkyl, substituted with one amine or substituted amine group. In certain embodiments of the pharmaceutical combinations and methods of treatment, provided are compounds of formula II, 13 is $C_1$-$C_6$ alkyl, substituted with two hydroxy groups. In further or additional embodiments of the combinations and methods of treatment, the combinations and methods of treatment provide for the compound of formula II, wherein B is unsubstituted $C_2$-$C_6$ alkenyl. In further or additional embodiments of the compound of formula II, B is $C_2$-$C_6$ alkenyl, substituted with one hydroxy group. In further or additional embodiments of the pharmaceutical combinations and methods of treatment, provided is the compound of formula II, wherein B is $C_2$-$C_6$ alkenyl, substituted with two hydroxy groups.

In further or additional embodiments of the pharmaceutical combinations and methods of treatment provided are compounds of formula II, wherein A and A' together with the carbon atom to which they are attached, form a cyclopropyl, cyclobutyl, or cyclopentyl group wherein each cyclopropyl, cyclobutyl, or cyclopentyl group is optionally substituted with one or two groups selected independently from methyl, hydroxy, and B is unsubstituted $C_1$-$C_6$ alkyl.

In further or additional embodiments of the pharmaceutical combinations and methods of treating cancer, the combinations and methods of treatment provide for a compound of formula II, A and A' together with the carbon atom to which they are attached, form a cyclopropyl, cyclobutyl, or cyclopentyl group wherein each cyclopropyl, cyclobutyl, or cyclopentyl group is optionally substituted with one or two groups selected independently from methyl, hydroxy, and B is $C_1$-$C_5$ alkyl, substituted with one hydroxy group.

In further or additional embodiments of the pharmaceutical combinations and methods of treating cancer, provided is the compound of formula II, A and A' together with the carbon atom to which they are attached, form a cyclopropyl, cyclobutyl, or cyclopentyl group wherein each cyclopropyl, cyclobutyl, or cyclopentyl group is optionally substituted with one or two groups selected independently from methyl, hydroxy, and B is $C_1$-$C_6$ alkyl, substituted with two hydroxy groups.

In further or additional embodiments of the pharmaceutical combinations and methods of treatment, provided is a compound of formula II, A and A' are each independently H, $C_1$-$C_6$ alkyl or $C_2$-$C_6$ alkenyl, wherein each $C_1$-$C_6$ alkyl is independently optionally substituted with one or two hydroxy groups, and each $C_2$-$C_6$ alkenyl is independently optionally substituted with one or two hydroxy groups.

In some embodiments, the pharmaceutical combinations and methods of treatment provide a compound of formula II is selected from the following:

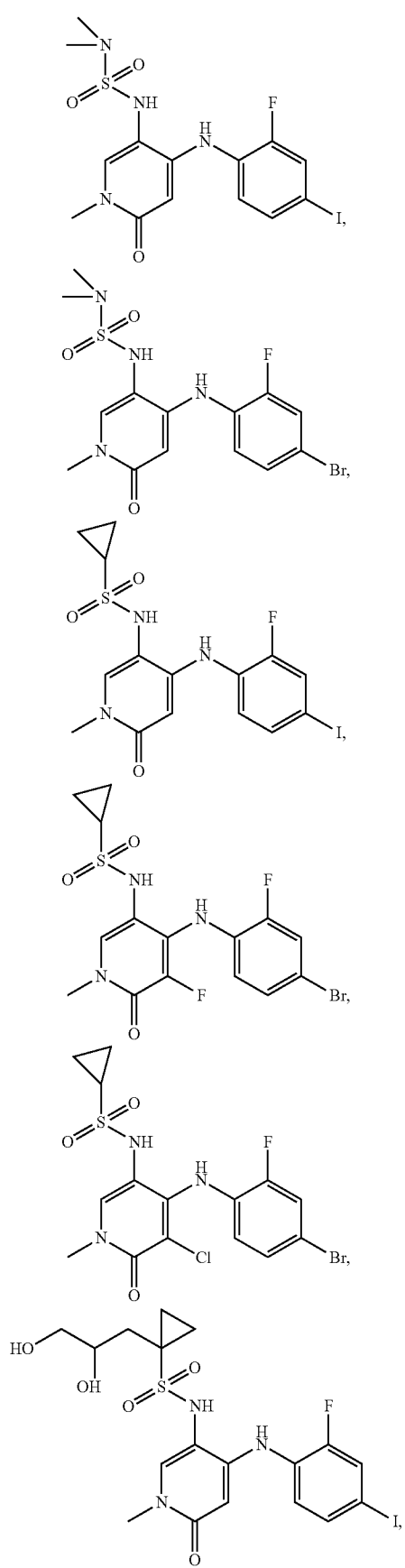
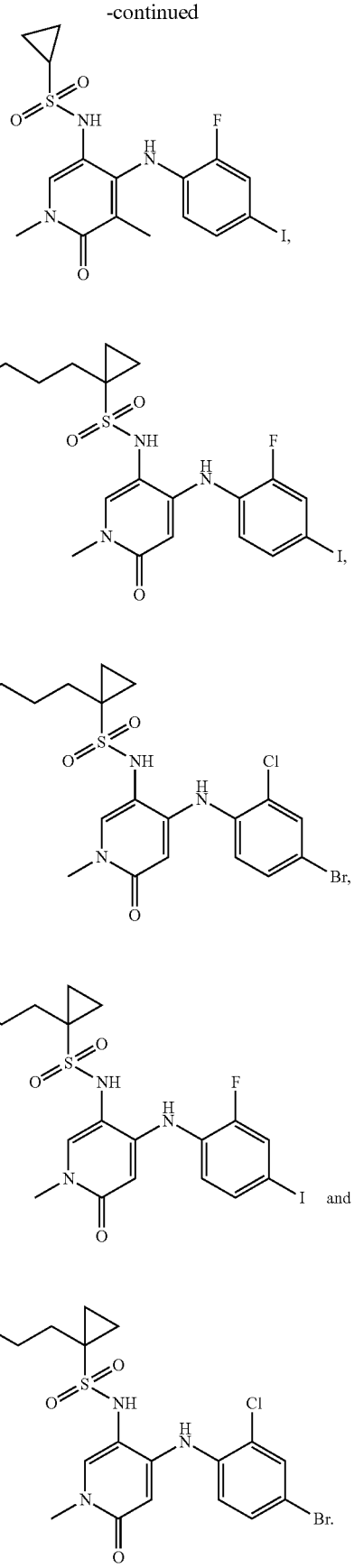

In some embodiments, "compound 13" is

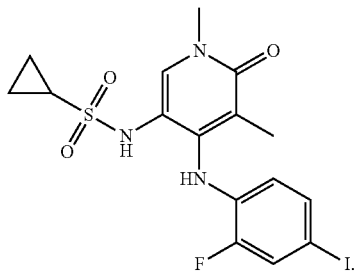 [SMILES: Cc1c(Nc2ccc(I)cc2F)c(NS(=O)(=O)C2CC2)cn(C)c1=O]

Additional non-limiting examples of compounds falling within formula II, including methods of synthesizing such compounds, with and without the use of protecting groups, as well as isomers, labeled compounds, pharmaceutically acceptable salts, solvates, polymorphs, prodrugs, and other derivatives are provided for in U.S. application Ser. No. 11/737,109, filed on Apr. 18, 2007, which is hereby incorporated by reference in its entirety for all purposes.

In another aspect, provided are combinations, compositions, and methods of treatment comprising a MEK protein kinase inhibitor and a Raf protein kinase inhibitor, wherein the ME protein kinase inhibitor further comprises a compound of formula III:

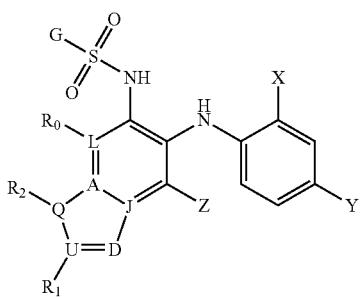

formula III wherein

G is $R_{1a}$, $R_{1b}$, $R_{1c}$, $R_{1d}$, $R_{1e}$, $Ar_1$, $Ar_2$ or $Ar_3$;

$R_0$, $R_1$ and $R_2$ are independently selected from H, halogen, cyano, cyanomethyl, nitro, difluoromethoxy, difluoromethoxy, trifluoromethyl, azido, $CO_2R_5$, $OR_5$, —O—(CO)—$R_5$, —O—C(O)—N($R_5$)$_2$, —N$R_5$C(O)N$R_6R_7$, —S$R_5$, NHC(O)$R_5$, —NHSO$_2R_5$, SO$_2$N($R_5$)$_2$, C1-C6 alkyl, C1-C4 alkoxy, C3-C6 cycloalkyl, C2-C6 alkenyl, C2-C6 alkynyl, aryl, alkylaryl, arylalkyl, and heterocyclic;

wherein said alkyl, cycloalkyl, alkenyl, aryl, alkylaryl, arylalkyl, heterocyclic and alkynyl groups are optionally substituted with 1-3 substituents selected independently from halogen, OH, CN, cyanomethyl, nitro, phenyl, difluoromethoxy, difluoromethoxy, and trifluoromethyl;

said C1-C6 alkyl and C1-C4 alkoxy groups are optionally substituted with OCH$_3$ or OCH$_2$CH$_3$;

each $R_5$ is selected from H, lower alkyl, substituted lower alkyl, aryl, or substituted aryl, and N$R_7R_6$; wherein each $R_6$ and $R_7$ is independently selected from hydrogen or lower alkyl;

X is F, Cl or methyl;

Y is I, Br, Cl, CF$_3$, C1-C3 alkyl, C2-C3 alkenyl, C2-C3 alkynyl, cyclopropyl, phenyl, pyridyl, pyrazolyl, OMe, OEt, or SMe, wherein all said methyl, ethyl, C1-C3 alkyl, and cyclopropyl groups of X and Y are optionally substituted with OH;

all said phenyl, pyridyl, pyrazolyl groups of Y are optionally substituted with halogen, acetyl, methyl, and trifluoromethyl; and all said methyl groups of X and Y are optionally substituted with one, two, or three F atoms;

Z is H, methyl, Cl or F; and

A, D, J, L, Q, U are independently selected from —CH, —NH, N, O, and —N(CH$_3$)—;

and wherein $R_{1a}$ is methyl, cyclopropoxy or C1-C4 alkoxy; wherein the methyl is optionally substituted with OH, 1-3 fluorine atoms or 1-3 chlorine atoms;

the C1-C4 alkyl moieties of said C1-C4 alkoxy are optionally substituted with one hydroxy or methoxy group; and all C2-C4 alkyl groups within said C1-C4 alkoxy are optionally further substituted with a second OH group;

$R_{1b}$ is CH(CH$_3$)—C1-3 alkyl or C3-C6 cycloalkyl, said CH$_3$, alkyl, and cycloalkyl groups optionally substituted with 1-3 substituents selected independently from F, Cl, Br, I, OH, C1-C4 alkoxy and CN.

$R_{1c}$ is (CH$_2$)$_n$O$_m$R', where m is 0 or 1; wherein when m is 1, n is 2 or 3, and when m is 0, n is 1 or 2;

R' is C1-C6 alkyl, optionally substituted with 1-3 substituents selected independently from F, Cl, OH, OCH$_3$, OCH$_2$CH3, and C3-C$_6$ cycloalkyl;

$R_{1d}$ is C(A')(A")(B)— wherein

B, A', and A" are, independently, H or C1-4 alkyl, optionally substituted with one or two OH groups or halogen atoms, or A' and A", together with the carbon atom to which they are attached, form a 3- to 6-member saturated ring, said ring optionally containing one or two heteroatoms selected, independently, from O, N, and S and optionally substituted with one or two groups selected independently from methyl, ethyl, and halo;

$R_{1e}$ is benzyl or 2-phenyl ethyl, in which the phenyl group is optionally substituted

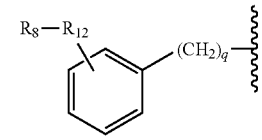

where q is 1 or 2;

$R_8$ and $R_9$ are, independently, H, F, Cl, Br, CH$_3$, CH$_2$F, CHF$_2$, CF$_3$, OCH$_3$, OCH$_2$F, OCHF$_2$, OCF$_3$, ethyl, n-propyl, isopropyl, cyclopropyl, isobutyl, sec-butyl, tert-butyl, and methylsulfonyl;

$R_{10}$ is H, F, Cl, Br, CH$_3$, CH$_2$F, CHF$_2$, CF$_3$, OCH$_3$, OCH$_2$F, OCHF$_2$, OCF$_3$, ethyl, n-propyl, isopropyl, cyclopropyl, isobutyl, sec-butyl, tert-butyl, and methylsulfonyl, nitro, acetamido, amidinyl, cyano, carbamoyl, methylcarbamoyl, dimethylcarbamoyl, 1,3,4-oxadiazol-2-yl, 5-methyl-1,3,4-5 oxadiazolyl, 1,3,4-thiadiazolyl, 5-methyl-1,3,4-thiadiazol-1H-tetrazoyl, N-morpholinyl carbonylamino, N-morpholinylsulfonyl or N-pyrrolidinylcarbonylamino;

$R_{11}$ and $R_{12}$ are, independently, H, F, Cl, or methyl;

$Ar_1$ is

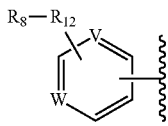

where
W and V are, independently, N, $CR_1$ or $CR_2$;
$R_8$, $R_9$ and $R_{10}$ are, independently, H, F, Cl, Br, $CH_3$, $CH_2F$, $CHF_2$, $CF_3$, $OCH_3$, $OCH_2F$, $OCHF_2$, $OCF_3$, ethyl, n-propyl, isopropyl, cyclopropyl, isobutyl, sec-butyl, tea-butyl, and methylsulfonyl, and $R_{10}$ may also be nitro, acetamido, amidinyl, cyano, carbamoyl, methylcarbamoyl, dimethylcarbamoyl, 1,3,4-oxadiazol-2-yl, 5-methyl-1,3,4-oxadiazol, 1,3,4-thiadiazol, 5-methyl-1,3,4-thiadiazol 1H-tetrazolyl, N-morpholinylcarbonylamino, N-morpholinylsulfonyl and N-pyrrolidinylcarbonylamino;
$R_{11}$ and $R_{12}$ are, independently, H, F, Cl or methyl;
$Ar_2$ is

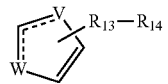

where
the dashed line represents a double bond which may be located formally either between V and the carbon between W and V, or between W and the carbon between W and V;
W is —S—, —O— or —N═, wherein
 when W is —O— or —S—, V is —CH═, —CCl═ or —N═; and
 when W is —N═, V is CH═ or —$NCH_3$—;
$R_{13}$ and $R_{14}$ are, independently, H, methoxycarbonyl, methylcarbamoyl, acetamido, acetyl, methyl, ethyl, trifluoromethyl or halogen;
$Ar_3$ is

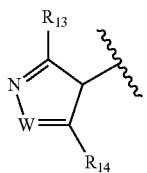

where
W is —NH—, —$NCH_3$— or —O—; and
$R_{13}$ and $R_{14}$ are, independently, H, F, Cl, or methyl.

In further or additional embodiments of the MEK protein kinase inhibitor comprising a compound of formula III, X is F, Cl, or $CH_3$; Y is I, Br, Cl, $CF_3$, or C1-C3 alkyl; and Z is H or F. In other embodiments, $R_o$ is F, Cl, $C_1$-$C_4$ alkyl or C1-C4 alkoxy, said C1-C4 alkyl group and the C1-C4 alkyl moiety of said C1-C4 alkoxy group optionally substituted with F, Cl, $OCH_3$, or $OCH_3CH_2$.

In certain embodiments of the MEK protein kinase inhibitor comprising a compound of formula III, $R_o$ is H, F, Cl, C1-C4 alkyl, methoxy, ethoxy, or 2-methoxy-ethoxy. In additional embodiments, G is $R_{1a}$ and Z is F. In other embodiments where the MEK protein kinase inhibitor is a compound of formula III, G is $CH_3$; $R_o$ is H; and Y is Br, I, $CF_3$, or $CH_3$. In further embodiments, G is $R_{1b}$. In still further embodiments, G is $R_{1b}$ and Z is F. In further or additional embodiments, $R_a$ is H; F, or $OCH_3$; X is F or $CH_3$, and Y is Br, I, or $CH_3$.

In other embodiments where the MEK protein kinase inhibitor is a compound of formula III, G is unsubstituted C3-C6 cycloalkyl. In still further embodiments, where $R_o$ is H. In further or additional embodiments, G is isopropyl or cyclopropyl. In still further embodiments, G is $R_{1c}$. In some embodiments where the MEK protein kinase inhibitor is a compound of formula III, G is $R_{1c}$; Y is I, Br, $CH_3$, or $CF_3$; and Z is F. In some embodiments, m is zero. In other embodiments, G is $R_{1d}$.

In some embodiments where the MEK protein kinase inhibitor is a compound of formula III, $R_o$ is fluoro, chloro, methyl, ethyl, propyl, isopropyl, sec-butyl, iso-butyl-tert-butyl, cyclopropyl, cyclobutyl, fluoromethyl, methoxy, fluoromethoxy, methylamino or dimethylamino; X is F, Cl, $CH_3$, or mono-, di- or trifluoromethyl; Y is I, Br, Cl, or mono-, di- or tri-fluoromethyl; and Z is H or F. In further or additional embodiments, $R_o$ is F, Cl, methyl, ethyl, methoxy, ethoxy, or 2-methoxy-ethoxy; X is F, Cl, or $CH_3$; Y is I, Br, Cl, or mono-, di- or tri-fluoromethyl; and Z is H or F. In still further embodiments, $R_o$ is H; X is F, Cl, $CH_3$, or mono-, di- or trifluoromethyl; Y is I, Br, Cl, or mono-, di- or tri-fluoromethyl; and Z is H or F.

In some embodiments where the MEK protein kinase inhibitor is a compound of formula III, C(A')(A") is C1-C6 cycloalkyl. In further or additional embodiments, B is H. In other embodiments, C(A')(A") is cyclopropyl. In further or additional embodiments, B is methyl, optionally substituted with one OH group, or C2-C4 alkyl, optionally substituted with one or two OH groups.

In some embodiments where the MEK protein kinase inhibitor is a compound of formula III, C(A')(A") is cyclopropyl. In other embodiments, B is methyl, ethyl, 2-hydroxyethyl, n-propyl, 3-5 hydroxypropyl, 2,3-dihydroxypropyl, 3,4-dihydroxybutyl, isopropyl, 1-methyl-2-hydroxyethyl, n-butyl, sec-butyl, isobutyl, or 2-hydroxymethyl-3-hydroxy propyl. In other embodiments, B is 2,3-dihydroxypropyl or 3,4-dihydroxybutyl. In further embodiments, chiral carbon in B is in the R configuration. In some of these embodiments, the chiral carbon in B is substantially free of the S isomer. In other embodiments, where G is $R_{1e}$. In some embodiments, q is 1.

In some embodiments where the MEK protein kinase inhibitor is a compound of formula III, $R_o$ is H; $R_{8-10}$ are H; $R_{11}$ and $R_{12}$ are, independently, H, F, Cl, Br, $CH_3$, $CH_2F$, $CHF_2$, $CF_3$, $OCH_3$, $OCH_2F$, $OCHF_2$, $OCF_3$, ethyl, n-propyl, isopropyl, cyclopropyl, isobutyl, sec-butyl, tert-butyl, and methylsulfonyl; X is F; and Y is I. In other embodiments, G is $Ar_1$. In further embodiments, G is phenyl, optionally substituted with one group selected from acetamido, amidinyl, cyano, carbamoyl, methylcarbamoyl, dimethylcarbamoyl, 1,3,4-oxadiazol-2-yl, 5-methyl-1,3,4-oxadiazolyl, 1,3,4-thiadiazolyl, 5-methyl-1,3,4-thiadiazolyl, 1H-tetrazolyl, N-morpholylcarbonylamino, N-morpholylsulfonyl, N-pyrrolidinylcarbonylamino, and methylsulfonyl; optionally substituted with 1-3 substituents selected independently from F, Cl, and $CH_3$; $R_o$ is H; X is F, Cl, or methyl; and Y is Br, I, $CF_3$, C1-C3 alkyl, $C_2$-$C_3$ alkenyl, $C_2$-$C_3$ alkynyl, cyclopropyl, $OCH_3$, $OCH_2CH_3$ or $SCH_3$.

In other embodiments where the MEK protein kinase inhibitor is a compound of formula III, G is

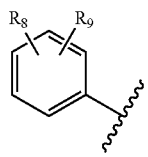

where $R_8$ and $R_9$ are, independently, H, F, Cl, $CH_3$, $CF_3$, $OCF_3$; X is F or $CH_3$; Y is I, Br, or Cl; and Z is F. In other embodiments, G is phenyl or mono-substituted phenyl; X is F or $CH_3$; Y is I, Br, or Cl; Z is F; and $R_o$ is F, methyl, ethyl, methoxy, or 2-methoxy-ethoxy. In some embodiments, W is N or $CR_2$ and V is N. In other embodiments, $R_o$ is 14, W is N or $CR_2$; V is $CR_3$; X is F, Cl, or methyl; and Y is Br, I, $CF_3$, C1-C3 alkyl, C2-C3 alkenyl, C2-C3 alkynyl, cyclopropyl, $OCH_3$, $OCH_2CH_3$ or $SCH_3$. In some embodiments G is $Ar_2$.

In some embodiments where the MEK protein kinase inhibitor is a compound of formula III, G is

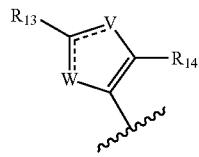

where $R_{14}$ is H or methyl, $R_{13}$ is H, acetamido, methyl, F or Cl; $R_0$ is H; X is F, Cl, or methyl; Y is Br, I, $CF_3$, C1-C3 alkyl, C2-C3 alkenyl, C2-C3 alkynyl, cyclopropyl, $OCH_3$, $OCH_2CH_3$ or $SCH_3$; and Z is F. In other embodiments, W is S or O; V is CH=; and $R_8$ is H or $CH_3$. In further or additional embodiments, $R_o$ is H. In some embodiments, X is F or Cl; and Y is Br, I, $CH_2CH_3$ or $SCH_3$. In additional embodiments, G is $Ar_3$. In other embodiments, W is O.

In some embodiments where the MEK protein kinase inhibitor is a compound of formula III, L, J, U and A are C, and Q and D are N; or L, J, Q and A are C; U is N; and D is O; or L, J, U and Q are C; and A and D are N; or L, I, Q and A are C; D is N; and U is O; or L, J, and Q are C; and A, U and D are N; or L, A, U and Q are C; and J and D are N; or A, J, and U are C; and L, Q and D are N; or Q, J, and U are C; and L, A and D are N; or Q, J, and A are C; and L, U and D are N; or Q, J, A, and U are C; and L and D are —N—; or Q, J, and A are C; U is NH, and L is N.

In further or additional embodiments where the MEK protein kinase inhibitor is a compound of formula III, the compound is selected from the group of compounds consisting of:

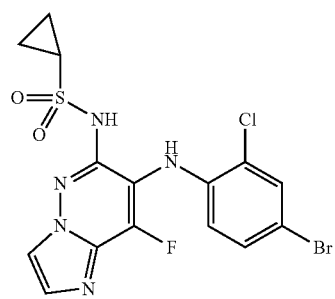

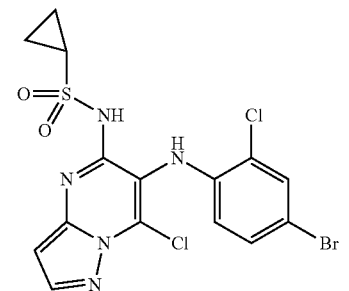

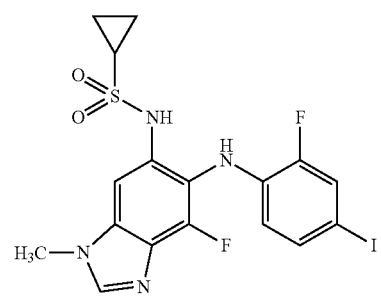

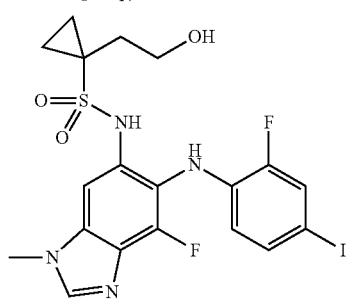

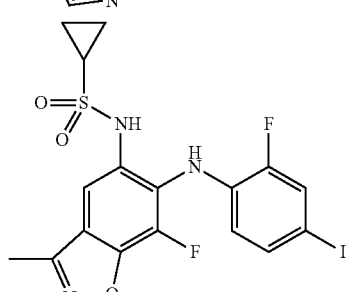

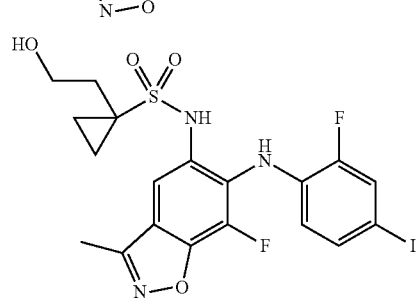

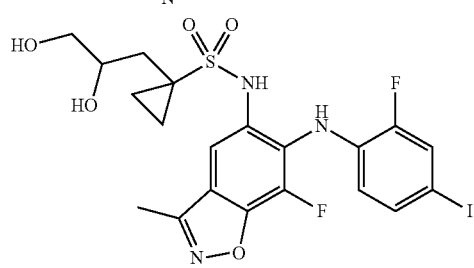

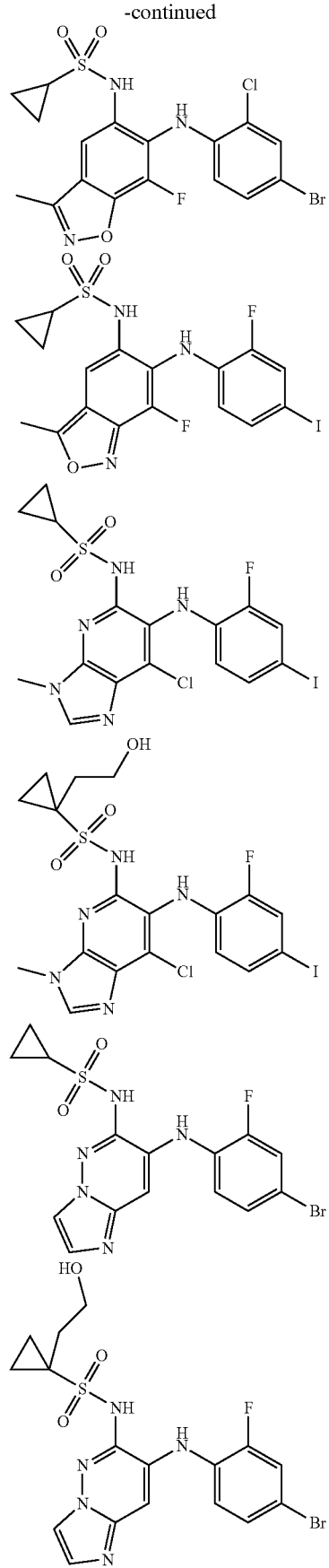
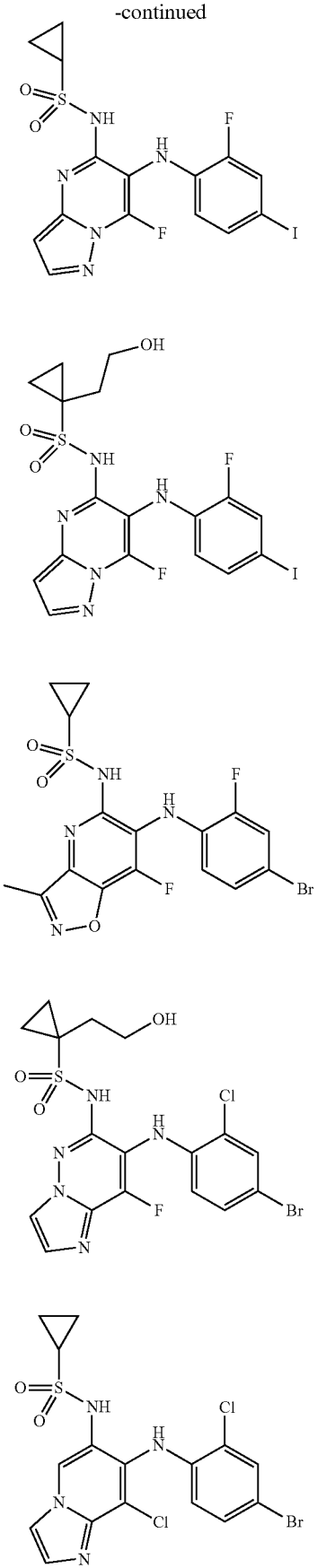

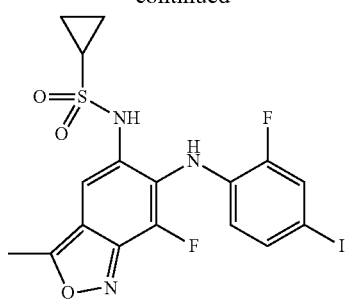
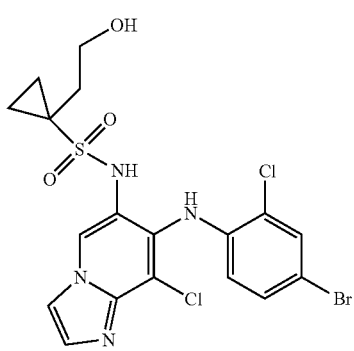
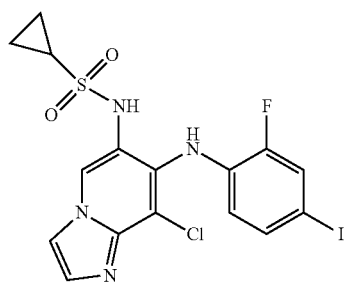
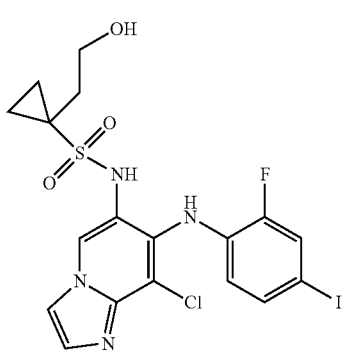
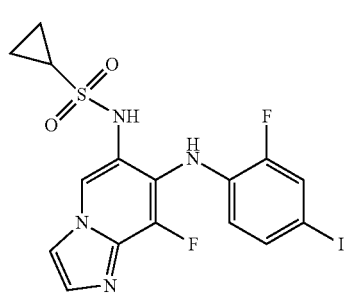
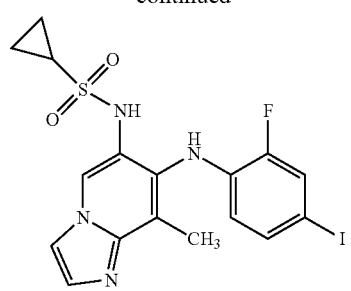
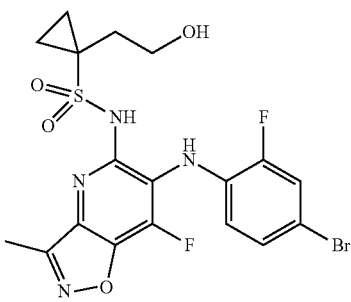
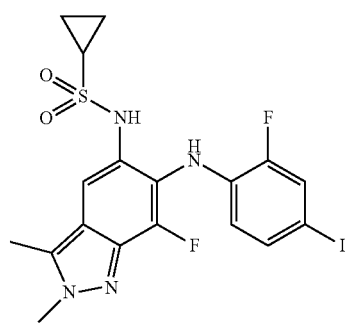
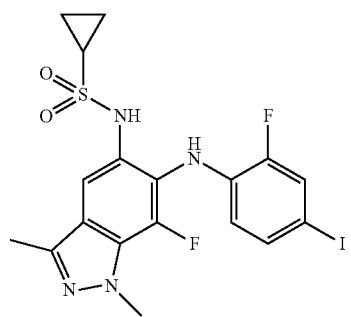
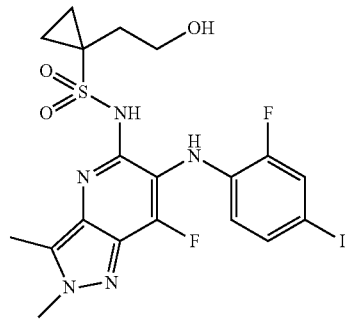

-continued
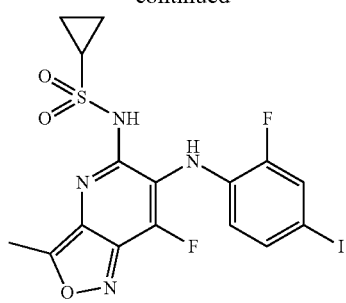
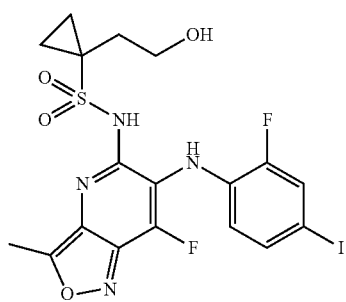
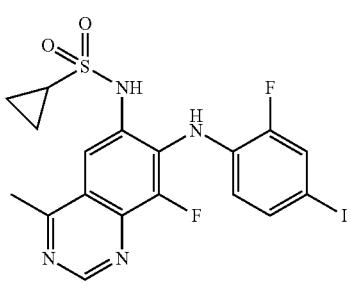
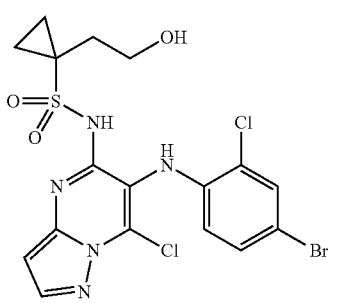
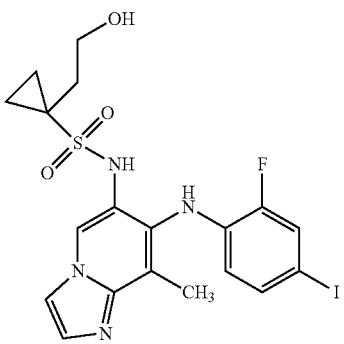
-continued
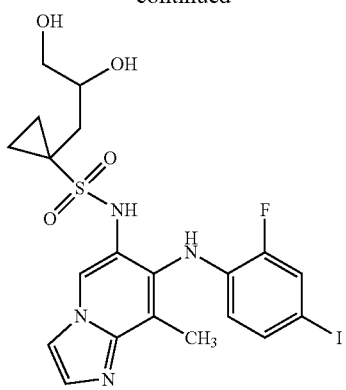
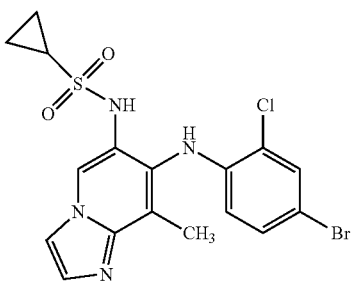
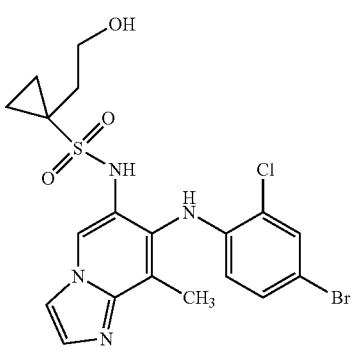
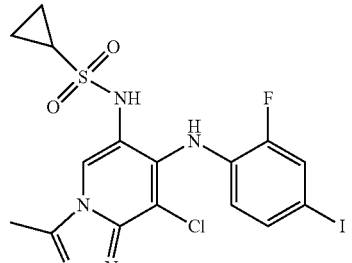
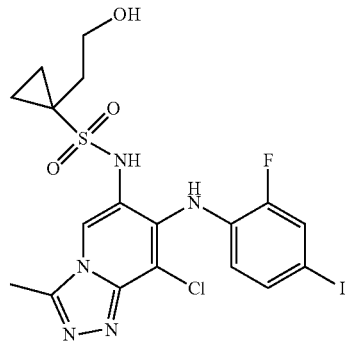

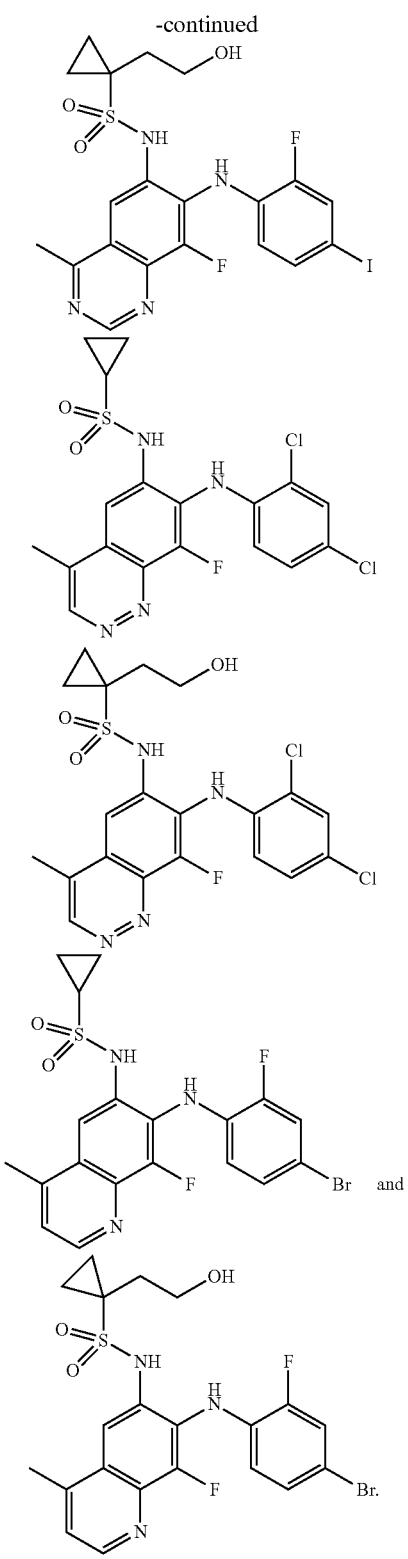

and subsequently the ERK kinase. Depending on the cellular context, this pathway mediates diverse biological functions such as cell growth, survival and differentiation predominantly through the regulation of transcription, metabolism and cytoskeletal rearrangements.

Provided herein are pharmaceutical combinations and methods for the treatment of cancer comprising a synergsitic and therapeutically effective amount of a MEK protein kinase inhibitor and Raf protein kinase inhibitor. Also provided herein are inhibitors of other kinases including VEGFR 1-3 and PDGFR-β.

In one aspect, provided are inhibitors of the Raf protein kinase. In further embodiments, the Raf protein kinase inhibitor comprises an A-Raf inhibitor, a B-Raf inhibitor, or a C-Raf inhibitor (Raf-1 inhibitor). In further embodiments, the Raf protein kinase inhibitor comprises a B-Raf inhibitor. In some embodiments, the B-Raf inhibitor is sorafenib (Nexavar®, BAY43-9006, Bayer), XL71 (Exelixis), or Raf 265 (Novartis), a pharmaceutically acceptable salt, solvate, polymorph, ester, tautomer or prodrug thereof.

In further embodiments, the Raf protein kinase inhibitor comprises a C-Raf protein kinase inhibitor. In some embodiments, the C-Raf protein kinase inhibitor is sorafenib (Nexavar®, BAY43-9006, Bayer), XL71 (Exelixis), Raf 265 (Novartis), GW5074, ZM336372, or the phytochemical quercetin, or a pharmaceutically acceptable salt, solvate, polymorph, ester, tautomer or prodrug thereof. In other embodiments, the Raf protein kinase inhibitor comprises an antisense oligonucleotide. In some embodiments, the antisense oligonucleotide is ISIS 5132.

In embodiments where the B-Raf inhibitor is Raf 265 (Novartis), it has the chemical name -methyl-5-(2-(5-(trifluoromethyl)-1H-imidazol-2-yl)pyridin-4-yloxy)-N-(4-(trifluoromethyl)phenyl)-1H-benzo[d]imidazol-2-amine and the following chemical structure:

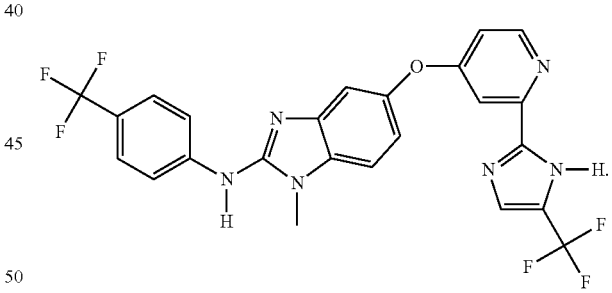

In embodiments where the B-Raf protein kinase inhibitor is sorafenib (Bayer), it has the chemical name 4-[4-[[4-chloro-3-(trifluoromethyl)phenyl]carbamoylamino]phenoxy]-N-methyl-pyridine-2-carboxamide and the following chemical structure:

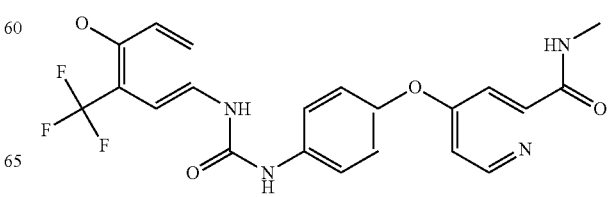

Raf Protein Kinase Inhibitors

There are three Raf isoforms in humans: A-Raf, B-Raf, and C-Raf. These serine/threonine protein kinases are components of a conserved signaling pathway downstream of the membrane-bound small G protein RAS, which is activated by growth factors, hormones, and cytokines. RAS stimulates Raf activation, which then leads to activation of the MEK kinase Pharmaceutical Combinations of MEK Inhibitors and Raf Inhibitors Provided herein are pharmaceutical combinations and methods of treating cancer comprising a synergistic and/or therapeutically effective amount of at least one MEK protein kinase inhibitor and at least one Raf protein kinase inhibitor. In some embodiments the cancer is pancreatic cancer. Upon reading the instant specification, one of skill in the art would recognize that any MEK and Raf Inhibitor would be useful in the combinations and methods described herein.

In particular embodiments, the MEK inhibitor useful in the combination is a MEK inhibitor described above. In some embodiments the MEK inhibitor useful in the combination is a compound of Formula I. In some embodiments, the MEK inhibitor useful in the combination is a compound of Formula II.

In certain embodiments the MEK protein kinase inhibitor comprises a compound selected from:

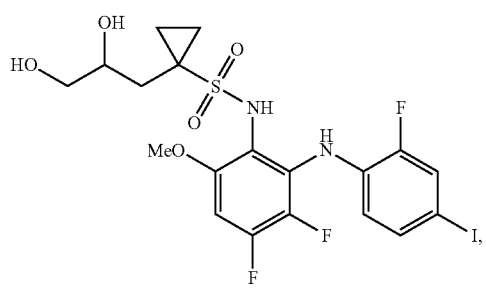

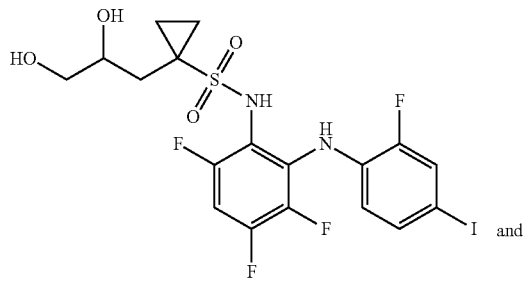

and

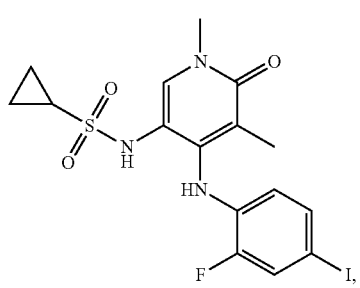

or a pharmaceutically acceptable salt, solvate, polymorph, ester, tautomer or prodrug thereof. In some embodiments, the MEK protein kinase inhibitor is

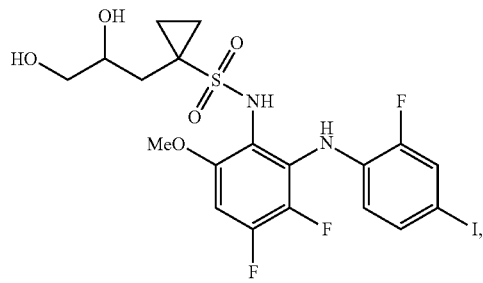 [SMILES: COc1cc(F)c(F)c(Nc2ccc(I)cc2F)c1NS(=O)(=O)C1(CC(O)CO)CC1]

or a pharmaceutically acceptable salt, solvate, polymorph, ester, tautomer or prodrug thereof. In other embodiments, the MEK protein kinase inhibitor is

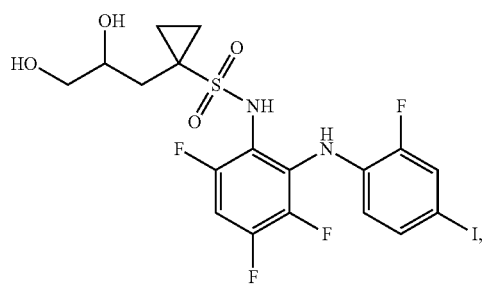

or a pharmaceutically acceptable salt, solvate, polymorph, ester, tautomer or prodrug thereof. In additional embodiments, the MEK protein kinase inhibitor is

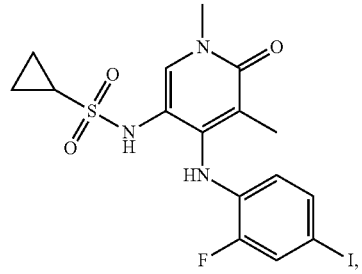 [SMILES: Cc1c(Nc2ccc(I)cc2F)c(NS(=O)(=O)C2CC2)cn(C)c1=O]

or a pharmaceutically acceptable salt, solvate, polymorph, ester, tautomer or prodrug thereof.

In further embodiments, the MEK protein kinase inhibitor is a compound of formula I and the Raf protein kinase inhibitor is sorafenib. In further embodiments, the MEK protein kinase inhibitor is a compound of formula II and the Raf protein kinase inhibitor is sorafenib. In further embodiments, the MEK protein kinase inhibitor is

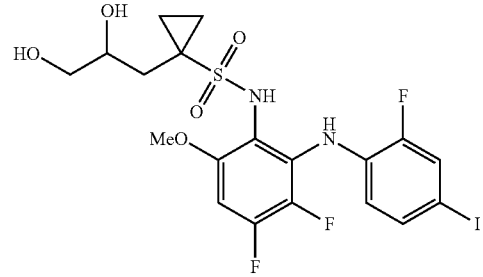 [SMILES: COc1cc(F)c(F)c(Nc2ccc(I)cc2F)c1NS(=O)(=O)C1(CC(O)CO)CC1]

and the Raf protein kinase inhibitor is sorafenib. In additional embodiments, the MEK protein kinase inhibitor is

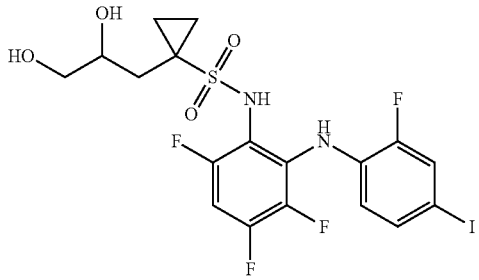

and the Raf protein kinase inhibitor is sorafenib. In further embodiments, the MEK protein kinase inhibitor is

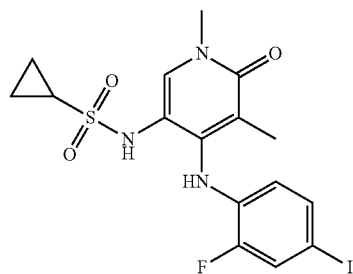 [SMILES: Cc1c(Nc2ccc(I)cc2F)c(NS(=O)(=O)C2CC2)cn(C)c1=O]

and the Raf protein kinase inhibitor is sorafenib.

Exemplary Effects of the Pharmaceutical Combination of MK Inhibitors and Raf Inhibitors Synergistic Apoptotic Effect In Vivo Synergistic Apoptotic Effect In another aspect, provided are pharmaceutical combinations and methods of treating cancer comprising a therapeutically effective amount of a MEK protein kinase inhibitor and a Raf protein kinase inhibitor, wherein an administration of the combination of the MEK protein kinase inhibitor and the Raf protein kinase inhibitor to a first patient provides an increase in apoptosis level at about day 7 compared to the combined apoptosis level at about day 7 of (1) a second patient administered only the MEK protein kinase inhibitor and (2) a third patient administered only the Raf protein kinase inhibitor. In further embodiments, the apoptosis levels are measured with an in vivo apoptosis assay, e.g. using the protocol according to Example 2 herein. Furthermore, International Application Ser. No. PCT/GB2005/00440, filed on Nov. 16, 2005 provides a method for determining apoptosis levels in vivo, and is hereby incorporated by reference in its entirety. Other in vivo methods for determining apoptotic effect are known by those of skill in the art.

In further or additional embodiments of the combinations and methods described herein, an increased apoptosis level at about day 1, about day 2, about day 3, at about day 4, about 5, about 6, about day 7, about day 8, about 9, or about 10 is measured in a first patient administered the combination of the MEK protein kinase inhibitor and Raf protein kinase inhibitor in vivo and provides about a 20%, about a 30%, about a 40%, about a 50%, about a 60%, about a 75%, about a 80%, about a 90%, about a 100%, about a 125%, about a 150%, about a 175%, about a 200%, about a 225%, about a 250%, about a 275%, about a 300%, about a 325%, about a 350%, about a 375%, about a 400%, about a 425%, about a 450%, about a 475%, about a 500%, or about a 1000% increase in apoptosis compared to the combined apoptosis levels of the second and third patients, wherein the second patient is administered only the MEK protein kinase inhibitor and wherein the third patient is administered only the Raf protein kinase inhibitor, wherein the apoptosis levels of the first, second and third patient is measured on the same day, or on about the dame day. In further or additional embodiments, an increased apoptosis level at about day 11, about day 12, about day 13, about day 14, about day 15, about day 16, about day 17, about day 18, about day 19, about day 20, about day 21, about day 22, about day 23, about day 24, about day 25, about day 26, about day 27, or about day 28 is measured in a first patient in vivo and provides about a 20%, about a 30%, about a 40%, about a 50%, about a 60%, about a 75%, about a 80%, about a 90%, about a 100%, about a 125%, about a 150%, about a 175%, about a 200%, about a 225%, about a 250%, about a 275%, about a 300%, about a 325%, about a 350%, about a 375%, about a 400%, about a 425%, about a 450%, about a 475%, about a 500%, or about a 1000% increase in apoptosis compared to the combined apoptosis levels of the second and third patients measured on the same day, or on about the dame day. In still further embodiments, a "third patient" includes more than one animal or more than one human.

In further embodiments, a first patient includes more than one animal, or more than one human. In other embodiments, a second patient includes more than one animal, or more than one human. Yet in other embodiments, the third patient includes more than one animal or more than one patient.

In some embodiments, the first patient and second patient comprises the same animal or human patient. In other embodiments, the first patient and the second patient comprise the same animals or human patients. In other embodiments, the first patient and the second patient comprises a different animal or human patient. In other embodiments, the first patient and the second patient comprise different animals or different human patients.

In certain embodiments, the first patient and the second patient comprises the same animal or human patient or a different animal or human patient. In other embodiments, the first patient and the third patient comprise the same animals or human patients. In further or additional embodiments, the first patient and the third patient comprises the same animal or human patient. In other embodiments, the first patient and the third patient comprises a different animal or human patient. In other embodiments, the first patient and the second patient comprise different animals or different human patients.

In further or additional embodiments, the second patient and the third patient comprises the same animal or human patient. In other embodiments, the second patient and the third patient comprises a different animal or human patient. In other embodiments, the second patient and the third patient comprise the same animals or human patients. In other embodiments, the second patient and third patient comprise different animals or human patients. In certain embodiments, the second patient and the third patient comprises the same animal or human patient or a different animal or human patient.

In some embodiments, each of the first patient, the second patient, and the third patient comprises the same animal or human patient. In other embodiments, each of the first patient, the second patient and the third patient comprises a different animal or human patient. In some embodiments, each of the first patient, the second patient, and the third patient comprise the same animals or human patients. In other embodiments, each of the first patient, the second patient and the third patient comprise different animals or human patients.

In some embodiments of the pharmaceutical combinations and methods of treating cancer described herein, the number of first patients administered the combination of the MEK protein kinase inhibitor and the Raf protein kinase inhibitor, the number of second patients administered the MEK protein kinase inhibitor and the number of third patients administered the Raf protein kinase inhibitor are each a large enough sample to determine whether or not a difference between the groups is significant. In some embodiments, synergy is significant if there is about a 20%, about a 30%, about a 40%, about a 50%, about a 60%, about a 75%, about a 80%, about a 90%, about a 100%, about a 125%, about a 150%, about a 175%, about a 200%, about a 225%, about a 250%, about a 275%, about a 300%, about a 325%, about a 350%, about a 375%, about a 400%, about a 425%, about a 450%, about a 475%, about a 500%, or about a 1000% increase in apoptosis.

In some embodiments, significance may be determined statistically—in which case two measured parameters may be referred to as statistically significant. In some embodiments, statistical significance may be quantified in terms of a stated confidence interval (CI), e.g. greater than 90%, greater than 95%, greater than 98%, etc. In some embodiments, statistical significance may be quantified in terms of a p value, e.g. less than 0.5, less than 0.1, less than 0.05, etc. The person skilled in the art will recognize these expressions of significance and will know how to apply them appropriately to the specific parameters that are being compared.

In Vitro Synergistic Apoptotic Effect

In another aspect, provided herein are pharmaceutical combinations and methods of treating cancer comprising a therapeutically effective amount of a MEK protein kinase inhibitor and a Raf protein kinase inhibitor. In some embodiments, contacting a first sample of cancer cells with the combination of the MEK protein kinase inhibitor and the Raf protein kinase inhibitor provides an increase in apoptosis level compared to the combined apoptosis levels of (1) a second sample provided by contacting cancer cells of the second sample with only the MEK protein kinase inhibitor and (2) a third sample provided by contacting cancer cells of the third sample with only the Raf protein kinase inhibitor. In further or additional embodiments, the cells of the first, second and third samples are analyzed with an in vitro apoptosis assay, e.g. using the protocol according to Example 1. Other in vitro apoptosis assays are known to the skilled artisan.

In further embodiments of the combinations and methods as described herein, the first, second and third samples are each analyzed about 24 hours, about 48 hours, or about 72 hours after treatment. In other embodiments, the first, second, and third samples are each analyzed about 4 days, about 5 days, about 6 days, or about 7 days after treatment. In some embodiments, the first, second, and third samples are each analyzed on the same day, or about the day as each other. In other embodiments, the first, second, and third samples are each analyzed within about 1, about 2, or about 3 days of each other.

In some embodiments of the pharmaceutical combinations and methods of treating cancer, the apoptosis level of the first sample is measured and provides about a 20%, about a 30%, about a 40%, about a 50%, about a 60%, about a 75%, about a 80%, about a 90%, about a 100%, about a 125%, about a 150%, about a 175%, about a 200%, about a 225%, about a 250%, about a 275%, about a 300%, about a 325%, about a 350%, about a 375%, about a 400%, about a 425%, about a 450%, about a 475%, about a 500%, or about a 1000% increase in apoptosis compared to the combined apoptosis levels of the second and third samples measured on the same day, or on about the dame day.

In further embodiments, a first sample includes cells from one or more cell lines or from one or more patients and may include cells from the same or different cell lines or patients as the second and third samples. In some embodiments, a first sample includes cells from one or more cell lines. In other embodiments, the first sample includes cells from one cell line. In some embodiments, the cells from the first sample include cells from the same cell line or patient as the second and third samples. In other embodiments, the cells of the first sample include cells from a different cell line or a different patient as the second and third samples. In other embodiments, a second sample includes cells from one or more cell line or from one or more patients.

In some embodiments, the cells from the second sample include cells from the same cell line or patient as the first and third samples. In some embodiments, a second sample includes cells from one or more cell lines. In other embodiments, the second sample includes cells from one cell line. In other embodiments, the cells of the second sample include cells from a different cell line or from a different patient as the first and third samples. In other embodiments, a second sample includes cells from one or more cell lines or from one or more patients.

In some embodiments, the cells from the third sample include cells from the same cell line or patient as the first and second samples. In other embodiments, the cells of the third sample include cells from a different cell line or from a different patient as the first and second samples. In other embodiments, a third sample includes cells from one or more cell lines or from one or more patients.

In further or additional embodiments of the pharmaceutical combinations and methods of treating cancer, the number of cancer cells in the first sample contacted with the combination of the MEK protein kinase inhibitor and the Raf protein kinase inhibitor, the number of cancer cells in the second sample contacted with only the MEK protein kinase inhibitor and the number of cancer cells in the third sample contacted with only the Raf protein kinase inhibitor are each a large enough sample to determine whether or not a difference between the groups is significant.

In some embodiments, synergy is significant if there is about a 20%, about a 30%, about a 40%, about a 50%, about a 60%, about a 75%, about a 80%, about a 90%, about a 100%, about a 125%, about a 150%, about a 175%, about a 200%, about a 225%, about a 250%, about a 275%, about a 300%, about a 325%, about a 350%, about a 375%, about a 400%, about a 425%, about a 450%, about a 475%, about a 500%, or about a 1000% increase in apoptosis. In some embodiments, significance may be determined statistically—in which case two measured parameters may be referred to as statistically significant. In some embodiments, statistical significance may be quantified in terms of a stated confidence interval (CI), e.g. greater than 90%, greater than 95%, greater than 98%, etc. In some embodiments, statistical significance may be quantified in terms of a p value, e.g. less than 0.5, less than 0.1, less than 0.05, etc. The person skilled in the art will recognize these expressions of significance and will know how to apply them appropriately to the specific parameters that are being compared.

Synergistic Decrease in Cell Proliferation

In Vivo Synergistic Decrease in Cell Proliferation

In another aspect, provided are pharmaceutical combinations and methods of treating cancer comprising a therapeutically effective amount of a MEK protein kinase inhibitor and a Raf protein kinase inhibitor. In further or additional embodiments, an administration of the combination of the MEK protein kinase inhibitor and the Raf protein kinase inhibitor to a first patient at day 7 provides a cell proliferation count that is less than the difference between (1) the cell proliferation count at about day 7 of a second patient administered only the MEK protein kinase inhibitor and (2) the cell proliferation count at about day 7 of a third patient administered only the Raf protein kinase inhibitor. In further embodiments, the apoptosis levels are measured with an in vivo cell proliferation assay, e.g. using the protocol according to Example 6 herein. Other in vivo cell proliferation assays are known to the skilled artisan.

In further embodiments of the pharmaceutical combinations and methods of treating cancer as described herein, the cell proliferation count of the first patient administered the combination of the MEK protein kinase inhibitor and the Raf protein kinase inhibitor at about day 1, about day 2, about day 3, at about day 4, about 5, about 6, about day 7, about day 8, about day 9, or about day 10 is about 20%, about a 30%, about a 40%, about a 50%, about a 60%, about a 75%, about a 80%, about a 90%, about a 100%, about a 125%, about a 150%, about a 175%, about a 200%, about a 225%, about a 250%, about a 275%, about a 300%, about a 325%, about a 350%, about a 375%, about a 400%, about a 425%, about a 450%, about a 475%, about a 500%, or about a 1000% less than the difference between (1) the cell proliferation count of the second sample contacted with only the MEK protein kinase inhibitor measured on the same day, or about the same day as the first sample, and (2) the cell proliferation count of the third sample contacted with only the Raf protein kinase inhibitor measured on the same day, or about the same day as the first sample and second samples.

In other embodiments of the pharmaceutical combinations and methods of treating cancer as described herein, the cell proliferation count of the first patient administered the combination of the MEK protein kinase inhibitor and the Raf protein kinase inhibitor at about day 11, about day 12, about day 13, about day 14, about day 15, about day 16, about day 17, about day 18, about day 19, about day 20, about day 21, about day 22, about day 23, about day 24, about day 25, about day 26, about day 27, or about day 28 is about 20%, about a 30%, about a 40%, about a 50%, about a 60%, about a 75%, about a 80%, about a 90%, about a 100%, about a 125%, about a 150%, about a 175%, about a 200%, about a 225%, about a 250%, about a 275%, about a 300%, about a 325%, about a 350%, about a 375%, about a 400%, about a 425%, about a 450%, about a 475%, about a 500%, or about a 1000% less than the difference between (1) the cell proliferation count of the second sample contacted with only the MEK protein kinase inhibitor measured on the same day, or about the same day as the first sample, and (2) the cell proliferation count of the third sample contacted with only the Raf protein kinase inhibitor measured on the same day, or about the same day as the first sample and second samples.

In further embodiments, a first patient includes more than one animal, or more than one human. In other embodiments, a second patient includes more than one animal, or more than one human. Yet in other embodiments, the third patient includes more than one animal or more than one patient.

In some embodiments, the first patient and second patient comprises the same animal or human patient. In other embodiments, the first patient and the second patient comprise the same animals or human patients. In other embodiments, the first patient and the second patient comprises a different animal or human patient. In other embodiments, the first patient and the second patient comprise different animals or different human patients.

In certain embodiments, the first patient and the second patient comprises the same animal or human patient or a different animal or human patient. In other embodiments, the first patient and the third patient comprise the same animals or human patients. In further or additional embodiments, the first patient and the third patient comprises the same animal or human patient. In other embodiments, the first patient and the third patient comprises a different animal or human patient. In other embodiments, the first patient and the second patient comprise different animals or different human patients.

In further or additional embodiments, the second patient and the third patient comprises the same animal or human patient. In other embodiments, the second patient and the third patient comprises a different animal or human patient. In other embodiments, the second patient and the third patient comprise the same animals or human patients. In other embodiments, the second patient and third patient comprise different animals or human patients. In certain embodiments, the second patient and the third patient comprises the same animal or human patient or a different animal or human patient.

In some embodiments, each of the first patient, the second patient, and the third patient comprises the same animal or human patient. In other embodiments, each of the first patient, the second patient and the third patient comprises a different animal or human patient. In some embodiments, each of the first patient, the second patient, and the third patient comprise the same animals or human patients. In other embodiments, each of the first patient, the second patient and the third patient comprise different animals or human patients.

In some embodiments of the pharmaceutical combinations and methods of treatment provided herein, the number of first patients administered the combination of the MEK protein kinase inhibitor and the Raf protein kinase inhibitor, the number of second patients administered the MEK protein kinase inhibitor and the number of third patients administered the Raf protein kinase inhibitor are each a large enough sample to determine whether or not a difference between the groups is significant.

In certain embodiments, synergy is significant there is about 20%, about a 30%, about a 40%, about a 50%, about a 60%, about a 75%, about a 80%, about a 90%, about a 100%, about a 125%, about a 150%, about a 175%, about a 200%, about a 225%, about a 250%, about a 275%, about a 300%, about a 325%, about a 350%, about a 375%, about a 400%, about a 425%, about a 450%, about a 475%, about a 500%, or about a 1000% decrease in cell proliferation count. In other embodiments, significance may be determined statistically—in which case two measured parameters may be referred to as statistically significant. In some embodiments, statistical significance may be quantified in terms of a stated confidence interval (CI), e.g. greater than 90%, greater than 95%, greater than 98%, etc. In some embodiments, statistical significance may be quantified in terms of a p value, e.g. less than 0.5, less than 0.1, less than 0.05, etc. The person skilled in the art will recognize these expressions of significance and will know how to apply them appropriately to the specific parameters that are being compared.

In Vitro Synergistic Decrease in Cell Proliferation

In another aspect, provided herein are pharmaceutical combinations for the treatment of cancer comprising a therapeutically effective amount of a MEK protein kinase inhibitor and a Raf protein kinase inhibitor. In some embodiments, contacting a first sample of cancer cells with the combination of the MEK protein kinase inhibitor and the Raf protein kinase inhibitor provides a cell proliferation count of a first sample that is less than the difference between (1) the cell proliferation count of a second sample of cancer cells contacted with only the MEK protein kinase inhibitor and (2) the cell proliferation count of a third sample of cancer cells contacted with only the Raf protein kinase inhibitor.

In further or additional embodiments of the combinations and methods described herein, the cells of the first, second and third samples are analyzed with an in vitro cell proliferation assay, e.g. using the protocol according to Examples 3 and 4. Other in vitro cell proliferation assays than those disclosed herein are known to the skilled artisan. In further embodiments, the first, second and third samples are each analyzed about 24 hours, about 48 hours, or about 72 hours after treatment. In other embodiments, the first, second, and third samples are each analyzed about 4 days, about 5 days, about 6 days, or about 7 days after treatment. In some embodiments, the first, second, and third samples are each analyzed on the same day, or about the day as each other. In other embodiments, the first, second, and third samples are each analyzed within about 1, about 2, or about 3 days of each other.

In some embodiments of the combinations and methods described herein, the cell proliferation count of the first sample contacted with the combination of the MEK protein kinase inhibitor and the Raf protein kinase inhibitor is about 20%, about a 30%, about a 40%, about a 50%, about a 60%, about a 75%, about a 80%, about a 90%, about a 100%, about a 125%, about a 150%, about a 175%, about a 200%, about a 225%, about a 250%, about a 275%, about a 300%, about a 325%, about a 350%, about a 375%, about a 400%, about a 425%, about a 450%, about a 475%, about a 500%, or about a 1000% less than the difference between the (1) cell proliferation count of the second sample contacted only with a MEK protein kinase inhibitor and the (2) cell proliferation count of the third sample contacted only with a Raf protein kinase inhibitor.

In further embodiments, a first sample includes cells from one or more cell lines or from one or more patients and may include cells from the same or different cell lines or patients as the second and third samples. In some embodiments, a first sample includes cells from one or more cell lines. In other embodiments, the first sample includes cells from one cell line. In some embodiments, the cells from the first sample include cells from the same cell line or patient as the second and third samples. In other embodiments, the cells of the first sample include cells from a different cell line or a different patient as the second and third samples. In other embodiments, a second sample includes cells from one or more cell line or from one or more patients.

In some embodiments, the cells from the second sample include cells from the same cell line or patient as the first and third samples. In some embodiments, a second sample includes cells from one or more cell lines. In other embodiments, the second sample includes cells from one cell line. In other embodiments, the cells of the second sample include cells from a different cell line or from a different patient as the first and third samples. In other embodiments, a second sample includes cells from one or more cell lines or from one or more patients.

In some embodiments, the cells from the third sample include cells from the same cell line or patient as the first and second samples. In other embodiments, the cells of the third sample include cells from a different cell line or from a different patient as the first and second samples. In other embodiments, a third sample includes cells from one or more cell lines or from one or more patients.

In further or additional embodiments, the number of cancer cells in the first sample contacted with the combination of the MEK protein kinase inhibitor and the Raf protein kinase inhibitor, the number of cancer cells in the second sample contacted with only the MEK protein kinase inhibitor and the number of cancer cells in the third sample contacted with only the Raf protein kinase inhibitor are each a large enough sample to determine whether or not a difference between the groups is significant.

In certain embodiments, synergy is significant there is about 20%, about a 30%, about a 40%, about a 50%, about a 60%, about a 75%, about a 80%, about a 90%, about a 100%, about a 125%, about a 150%, about a 175%, about a 200%, about a 225%, about a 250%, about a 275%, about a 300%, about a 325%, about a 350%, about a 375%, about a 400%, about a 425%, about a 450%, about a 475%, about a 500%, or about a 1000% decrease in cell proliferation count. In some embodiments, significance may be determined statistically—in which case two measured parameters may be referred to as statistically significant. In some embodiments, statistical significance may be quantified in terms of a stated confidence interval (CI), e.g. greater than 90%, greater than 95%, greater than 98%, etc. In some embodiments, statistical significance may be quantified in terms of a p value, e.g. less than 0.5, less than 0.1, less than 0.05, etc. The person skilled in the art will recognize these expressions of significance and will know how to apply them appropriately to the specific parameters that are being compared.

Decrease in Toxicity

In another aspect, provided are pharmaceutical combinations and methods of treating cancer comprising a synergistic combination of a MEK protein kinase inhibitor and a Raf protein kinase inhibitor that has reduced toxicity. In further or additional embodiments, an administration of the combination of the MEK protein kinase inhibitor and the Raf protein kinase inhibitor at about day 1, about day 2, about day 3, about day 4, about day 5, about day 6, about day 7, about day 8, about day 9, about day 10, about day 11, about day 12, about day 13, about day 14, about day 21, or about day 28 results in a lesser degree of an adverse side effect of a first patient compared to the degree of the adverse side effect on the same day, or about the same day, of a second patient administered only the MEK protein kinase inhibitor combined with the degree of the adverse side effect on the about the same day, or about the same day, of a third patient administered only the Raf protein kinase inhibitor.

In some embodiments of the combinations and methods of treating cancer, the adverse side effect comprises a gastrointestinal or skin complication. In further embodiments, the adverse side effect is a gastrointestinal complication. In other embodiments, the adverse side effect is a skin complication. In other embodiments, the adverse side effect is cardiac ischemia, hemorrhage, diarrhea, hypertension, hand and-foot skin irritation, gastrointestinal perforation, wound healing complications, teratogenicity and embryofetal toxicity.

In further embodiments, a first patient includes more than one animal, or more than one human. In other embodiments, a second patient includes more than one animal, or more than one human. Yet in other embodiments, the third patient includes more than one animal or more than one patient.

In some embodiments, the first patient and second patient comprises the same animal or human patient. In other embodiments, the first patient and the second patient comprise the same animals or human patients. In other embodiments, the first patient and the second patient comprises a different animal or human patient. In other embodiments, the first patient and the second patient comprise different animals or different human patients.

In certain embodiments, the first patient and the second patient comprises the same animal or human patient or a different animal or human patient. In other embodiments, the first patient and the third patient comprise the same animals or human patients. In further or additional embodiments, the first patient and the third patient comprises the same animal or human patient. In other embodiments, the first patient and the third patient comprises a different animal or human patient. In other embodiments, the first patient and the second patient comprise different animals or different human patients.

In further or additional embodiments, the second patient and the third patient comprises the same animal or human patient. In other embodiments, the second patient and the third patient comprises a different animal or human patient. In other embodiments, the second patient and the third patient comprise the same animals or human patients. In other embodiments, the second patient and third patient comprise different animals or human patients. In certain embodiments, the second patient and the third patient comprises the same animal or human patient or a different animal or human patient.

In some embodiments, each of the first patient, the second patient, and the third patient comprises the same animal or human patient. In other embodiments, each of the first patient, the second patient and the third patient comprises a different animal or human patient. In some embodiments, each of the first patient, the second patient, and the third patient comprise the same animals or human patients. In other embodiments, each of the first patient, the second patient and the third patient comprise different animals or human patients.

A person of ordinary skill in the art, e.g. a trained physician, upon reading this specification is able to objectively determine degrees of adverse side effects based on diagnostic or analytical measurements of a patient including the patient's compliance with a treatment regimen or other objective indicia of a patient's response to prescribed treatment. In some embodiments, the lesser degree of adverse side effect of the first patient is by a factor of about 2, about 3, about 4, about 5, about 6, about 7, about 8, about 9, or about 10. In some embodiments, a "first patient" includes more than one animal, or more than human. In other embodiments, a "second patient" includes more than one animal, or more than one human. In still further embodiments, a "third patient" includes more than one animal or more than one human. In further embodiments, the number of first patients administered the combination of the MEK protein kinase inhibitor and the Raf protein kinase inhibitor, the number of second patients administered the MEK protein kinase inhibitor and the number of third patients administered the Raf protein kinase inhibitor are each a large enough sample to determine whether or not a difference between the groups is significant. In some embodiments, significance may be determined statistically—in which case two measured parameters may be referred to as statistically significant. In some embodiments, statistical significance may be quantified in terms of a stated confidence interval (CI), e.g. greater than 90%, greater than 95%, greater than 98%, etc. In some embodiments, statistical significance may be quantified in terms of a p value, e.g. less than 0.5, less than 0.1, less than 0.05, etc. The person skilled in the art will recognize these expressions of significance and will know how to apply them appropriately to the specific parameters that are being compared.

Resensitizing Cancer Cells

In another aspect of the methods of treating cancer provided herein, provided are pharmaceutical combinations and methods for resensitizing cancer cells to treatment in a patient having or suspected of having a cancer resistant to an anticancer agent, comprising the step of administering to the patient a therapeutically effective amount of a MEK protein kinase inhibitor and a Raf protein kinase inhibitor. In some embodiments, the cancer is resistant to treatment of a MEK protein kinase inhibitor. In further embodiments, the cancer is resistant to a MEK protein kinase inhibitor, wherein the MEK protein kinase inhibitor is CI-1040 (PD184352), GSK1120212, PD-0325901, PD-98059, PD-184161, PD-0318088, PD-184386, PD-171984, PD-170611, PD-177168, PD-184352, ARRY-438162, AZD6244/ARRY-886, AZD 8330, XL518, UO125, UO126, SL 327, quercetin, or a pharmaceutically acceptable salt, solvate, polymorph, ester, tautomer or prodrug thereof. In other embodiments, the cancer is resistant to a MEK protein kinase inhibitor, wherein the MEK protein kinase inhibitor is a compound of formula I. In further embodiments, the MEK protein kinase inhibitor is selected from the group consisting of

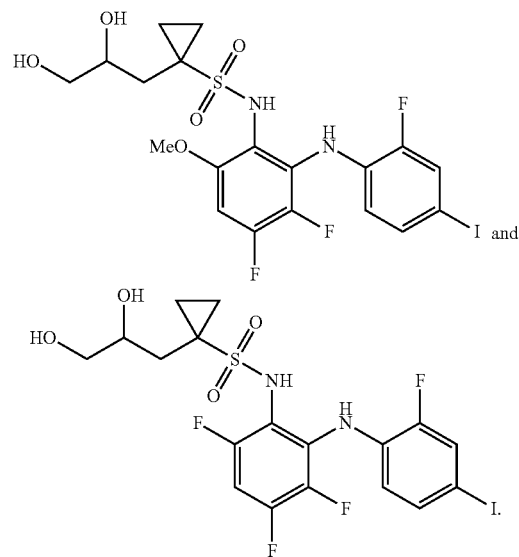

In some embodiments, provided are pharmaceutical combinations and methods for resensitizing cancer cells to treatment in a patient having or suspected of having a cancer resistant to an anticancer agent, comprising the step of administering to the patient a therapeutically effective amount of a MEK protein kinase inhibitor and a Raf protein kinase inhibitor. In some embodiments, the cancer is resistant to treatment of a Raf protein kinase inhibitor. In further embodiments, the cancer is resistant to a Raf protein kinase inhibitor and the Raf protein kinase inhibitor comprises an A-Raf inhibitor, a B-Raf inhibitor, or a C-Raf inhibitor. In further embodiments, the cancer is resistant to a Raf protein kinase inhibitor, and the Raf protein kinase inhibitor comprises a B-Raf inhibitor. In further embodiments, the cancer is resistant to a Raf protein kinase inhibitor, and the Raf protein kinase inhibitor is sorafenib or XL71, or both.

In further embodiments, the cancer is resistant to a Raf protein kinase inhibitor, and the Raf protein kinase inhibitor is a C-Raf protein kinase inhibitor. In further embodiments, the C-Raf protein kinase inhibitor is sorafenib (Bayer), XL71 (Exelixis), GW5074, ZM336372, or a pharmaceutically acceptable salt, solvate, polymorph, ester, tautomer or prodrug thereof. In further embodiments, the cancer is resistant to an antisense oligonucleotide. In further or additional embodiments, the cancer is resistant to ISIS 5132 (Isis).

In some embodiments, the cancer is resistant to an anticancer agent other than a MEK protein kinase inhibitor. In other embodiments, the cancer is resistant to an anticancer agent other than a Raf protein kinase inhibitor. In further embodiments, the cancer is resistant to a MEK protein kinase inhibitor and/or a Raf protein kinase inhibitor and is also resistant to an additional anticancer agent.

In some embodiments, the cancer is resistant to an anticancer agent. In further embodiments, the cancer is resistant to STI-571, imatinib, capecitibine (fluorouracil; OSI-774), adriamycin (ADM), gemcitabine, RTA 402, calcitriol, docetaxel, erlotinib, bevacizumab, cetuximab; oxaliplatin, dalteparin, temsirolimus, temozolomide, perifosine, or gefitinib.

In further or additional embodiments, provided are pharmaceutical combinations and methods for resensitizing cancer cells to treatment in a patient having or suspected of having a cancer resistant to an anticancer agent, comprising the step of administering to the patient a therapeutically effective amount of a MEK protein kinase inhibitor and a Raf protein kinase inhibitor. In certain embodiments, the resistance is acquired resistance. In other embodiments, the resistance is de novo resistance. In further embodiments, the resistance is acquired and de novo resistance.

In further or additional embodiments, the resistant cancer is pancreatic, melanoma, colon, lung, or stomach cancer. In further embodiments, the resistant cancer is pancreatic. In additional embodiments, the resistant cancer is stomach.

In alternative embodiments, provided are pharmaceutical combinations and methods for resensitizing cancer cells to treatment in a patient having or suspected of having a cancer resistant to an anticancer agent, comprising the step of administering to the patient a therapeutically effective amount of a MEK protein kinase inhibitor and a Raf protein kinase inhibitor. In further embodiments, the MEK protein kinase inhibitor and a Raf protein kinase inhibitor are administered in a fixed combination. In other embodiments, the MEK protein kinase inhibitor and a Raf protein kinase inhibitor is administered in a non-fixed combination.

Pharmacokinetics

In another aspect, provided herein are pharmaceutical combinations for the treatment of cancer comprising a therapeutically effective amount of a MEK protein kinase inhibitor and a Raf protein kinase inhibitor, wherein the combination provides for particular pharmacokinetic properties. In some embodiments, an administration of the combination of the MEK protein kinase inhibitor and the Raf protein kinase inhibitor to a first patient provides: (i) an increase in the area under the serum concentration time curve (AUC) of the MEK protein kinase inhibitor of the first patient compared to the AUC of the MEK protein kinase of a second patient when only the MEK protein kinase is administered to the second patient; or (ii) an increase in the AUC of the Raf protein kinase inhibitor of the first patient compared to the AUC of the Raf protein kinase of a second patient when only the Raf protein kinase is administered to the second patient.

In some embodiments, provided are a MEK protein kinase inhibitor that, upon administration to a subject, provides a $C_{max}$ between about 0.01 μg/ml to about 1.0 μg/ml on day 1. In other embodiments, upon administration to subject, the MEK protein kinase inhibitor reaches a $C_{max}$ between about 0.01 μg/ml to about 0.81 μg/ml on day 1. In certain embodiments, upon administration to a subject, the MEK protein kinase inhibitor reaches a $C_{max}$ between about 0.03 μg/ml to about 0.5 μg/ml on day 1. In further or additional embodiments, upon administration to a group of 10 subjects, the compound reaches a mean $C_{max}$ between about 0.01 μg/ml to about 1.0 μg/ml on day 1. In additional embodiments, upon administration to a subject, the MEK protein kinase inhibitor reaches a mean $C_{max}$ between about 0.01 μg/ml to about 0.8 μg/ml on day 1. In still further embodiments, upon administration to a group of 10 subjects, the MEK protein kinase inhibitor reaches a mean $C_{max}$ between about 0.03 μg/ml to about 0.5 μg/ml on day 1. In some embodiments the MEK inhibitor is a Compound A. In some embodiments, the MEK inhibitor is Compound B.

In other embodiments, provided herein are pharmaceutical combinations and methods of treating cancer where upon administration to a patient, the MEK protein kinase inhibitor has an AUC between about 0.1 μg hr/mL to about 5.0 μg hr/mL. In some embodiments, the MEK protein kinase inhibitor upon administration to a patient provides an AUC between about 0.1 μg hr/mL to about 4.0 μg hr/mL. In other embodiments, upon administration to a patient, the MEK protein kinase inhibitor has an AUC between about 0.5 μg hr/mL to about 3.0 μg hr/mL. In still further embodiments, upon administration to a patient, the MEK protein kinase inhibitor has a mean AUC between about 0.1 μg hr/mL to about 5.0 μg hr/mL. In further or additional embodiments, upon administration to a patient, the MEK protein kinase inhibitor has a mean AUC between about 0.1 μg hr/mL to about 4.0 μg hr/mL. In additional embodiments, upon administration to a patient, the MEK protein kinase inhibitor has a mean AUC between about 0.5 μg hr/mL to about 3.0 μg hr/mL. In some embodiments the MEK inhibitor is a Compound A. In some embodiments, the MEK inhibitor is Compound B.

In other embodiments, provided herein are pharmaceutical combinations and methods of treating cancer where upon administration to a patient, the MEK protein kinase inhibitor has a $T_{max}$ between 0.5 and 5.0 hours. In some embodiments, the MEK protein kinase inhibitor has a $T_{max}$ between 1.0 and 3.0 hours. In additional embodiments, the MEK protein kinase inhibitor has a $T_{max}$ between 1.0 and 2.5 hours. In additional embodiments, the MEK protein kinase inhibitor has a mean $T_{max}$ between 0.5 and 5.0 hours. In other embodiments, the MEK protein kinase inhibitor has a has a mean $T_{max}$ between 1.0 and 3.0 hours. In still further embodiments, the MEK protein kinase inhibitor has a mean $T_{max}$ between 1.0 and 2.5 hours. In some embodiments the MEK inhibitor is a Compound A. In some embodiments, the MEK inhibitor is Compound B.

In other embodiments, upon administration to a subject in combination with a Raf protein kinase inhibitor, the MEK protein kinase inhibitor provides an enhanced pharmacokinetic parameter compared to the combined pharmcokinetic parameter of the administration of the MEK protein kinase inhibitor alone and the Raf protein kinase inhibitor alone, as provided in a similar manner herein with respect to apoptosis and cell proliferation, among other examples. In some embodiments, the increased pharmcokinetic parameter is an increased AUC, a decreased $C_{max}$, an increased $C_{max}$, an increased $T_{max}$, or even a decreased $T_{max}$. In some embodiments, the increased parameter is an increased AUC. In some embodiments, the increased parameter is an increased $C_{max}$. In some embodiments, the increased parameter is a decreased $C_{max}$. In some embodiments, the increased parameter is an increased $T_{max}$. In some embodiments, the increased parameter is a decreased $T_{max}$. In some embodiments, the increased parameter is the maintenance of trough levels of MEK protein kinase inhibitor and/or Raf protein kinase inhibitor. In some embodiments the MEK inhibitor is a Compound A. In some embodiments, the MEK inhibitor is Compound B.

Selectivity of the MEK Protein Kinase Inhibitor

In another aspect, provided are pharmaceutical combinations and methods of treating cancer comprising the administration of a selective MEK protein kinase inhibitor. In some embodiments, the combinations and methods provide for a MEK protein kinase inhibitor with a binding affinity or binding constant for the MEK1 and/or MEK2 substrate of about 50 to about 500 times greater than its binding affinity or binding constant for any other enzyme. In further or additional embodiments, provided are MEK protein kinase inhibitors with a binding affinity or binding constant for the MEK1 and/or MEK2 enzyme that is about 60 to about 250 times greater than its binding affinity or binding constant for any other enzyme. In further or additional embodiments, provided are MEK protein kinase inhibitors with a binding affinity or binding constant for the MEK1 and/or MEK2 substrate that is about 80 to about 125 times greater than its binding affinity or binding constant for any other enzyme. In certain embodiments, provided are MEK protein kinase inhibitors with a binding affinity or binding constant for the MEK1 and/or MEK2 substrate that is about 100 times greater than its binding affinity or binding constant for any other enzyme. In some such embodiments, the other enzyme is a protein kinase.

In other embodiments, the MEK protein kinase inhibitor provides about 50% to about 100% inhibition of the MEK1 and/or MEK2 enzyme. In other embodiments, the MEK protein kinase inhibitor provides for about 60% to about 95% inhibition of the MEK1 or MEK2 enzyme. In some embodiments, the MEK protein kinase inhibitor provides for about 70% to about 90% inhibition. In certain embodiments, the percent inhibition is 50%, 55%, 60%, 65%, 70%, 75%, 80%, 85%, 90%, 95% or 100%.

In other embodiments, the MEK protein kinase inhibitor provides for greater selectivity for the MEK1 and MEK2 substrates compared to PD-325901 by a factor of about 10, about 20, about 30, about 40, about 50, about 60, about 70, about 80, about 80, about 100, about 110, about 120. In other embodiments, the MEK protein kinase inhibitor inhibits MEK1 and/or MEK2, but does not inhibit any other protein kinase inhibitor by more than about 60%, about 50%, about 40%, about 30%, about 20%, or more than about 10%. In other embodiments, the MEK protein kinase inhibitor does not inhibit the SRC or Ron protein kinases by more than about 5%, about 10%, about 15%, about 20%, about 25%, about 30%, about 35%, or about 40%. See, e.g., Example 12.

Pharmaceutical Compositions of MEK Inhibitors and Raf Inhibitors

Described herein are pharmaceutical compositions. In some embodiments, the pharmaceutical compositions comprise an effective and/or synergistic amount of a MEK protein kinase inhibitor and a Raf protein kinase inhibitor. In some embodiments, the MEK protein kinase inhibitor is a compound of formula A, formula I, formula II and/or formula III. In other embodiments, the Raf protein kinase inhibitor is sorafenib, or a pharmaceutically acceptable salt, solvate, polymorph, ester, amide, tautomer, prodrug, hydrate, or derivative thereof. In some embodiments, the MEK protein kinase inhibitor and the Raf protein kinase inhibitor further comprise at least one pharmaceutically acceptable carrier. In some embodiments the pharmaceutical compositions are for the treatment of disorders. In some embodiments the pharmaceutical compositions are for the treatment of disorders in a mammal. In some embodiments the pharmaceutical compositions are for the treatment of disorders in a human.

In further aspects, the present invention is directed to a pharmaceutical composition comprising a MEK protein kinase inhibitor and a Raf protein kinase inhibitor, wherein the MEK protein kinase inhibitor is a compound of formula A, formula I, formula II and/or formula III. In other embodiments, the composition comprises sorafenib. In some embodiments, the pharmaceutical compositions further comprise a pharmaceutically acceptable carrier. Such compositions may contain adjuvants, excipients, and preservatives, agents for delaying absorption, fillers, binders, adsorbents, buffers, disintegrating agents, solubilizing agents, other carriers, and other inert ingredients. Methods of formulation of such compositions are well-known in the art.

In some embodiments, the pharmaceutical composition is in a form suitable for oral administration. In further or additional embodiments, the pharmaceutical composition is in the form of a tablet, capsule, pill, powder, sustained release formulation, solution, suspension, for parenteral injection as a sterile solution, suspension or emulsion, for topical administration as an ointment or cream or for rectal administration as a suppository. In further or additional embodiments, the pharmaceutical composition is in unit dosage forms suitable for single administration of precise dosages.

In further or additional embodiments, the amount of MEK protein kinase inhibitor and/or Raf protein kinase inhibitor in combination in the range of about 0.001 to about 1000 mg/kg body weight/day. In further or additional embodiments the amount of MEK protein kinase inhibitor and/or Raf protein kinase inhibitor in combination is in the range of about 0.5 to about 50 mg/kg/day. In further or additional embodiments the amount of MEK protein kinase inhibitor and/or Raf protein kinase inhibitor in combination is about 0.001 to about 7 g/day. In further or additional embodiments the amount of MEK protein kinase inhibitor and/or Raf protein kinase inhibitor in combination is about 0.002 to about 6 g/day. In further or additional embodiments the amount of MEK protein kinase inhibitor and/or Raf protein kinase inhibitor in combination is about 0.005 to about 5 g/day. In further or additional embodiments the amount of MEK protein kinase inhibitor and/or Raf protein kinase inhibitor in combination is about 0.01 to about 5 g/day. In further or additional embodiments the amount of MEK protein kinase inhibitor and/or Raf protein kinase inhibitor in combination is about 0.02 to about 5 g/day. In further or additional embodiments the amount of MEK protein kinase inhibitor and/or Raf protein kinase inhibitor in combination is about 0.05 to about 2.5 g/day. In further or additional embodiments the amount of MEK protein kinase inhibitor and/or Raf protein kinase inhibitor in combination is about 0.1 to about 1 g/day. In further or additional embodiments, dosage levels below the lower limit of the aforesaid range may be more than adequate. In further or additional embodiments, dosage levels above the upper limit of the aforesaid range may be required. In further or additional embodiments the MEK protein kinase inhibitor and/or Raf protein kinase inhibitor in combination is administered in a single dose, once daily.

In some embodiments the MEK inhibitor and Raf inhibitor are administered on different timing regimens. For example, in some embodiments, the MEK inhibitor is administered once a day and the Raf inhibitor is administered twice a day. In other embodiments, the MEK inhibitor is administered twice a day and the Raf inhibitor is administered once a day. In some embodiments, the MEK inhibitor and Raf inhibitor are both administered once a day. In yet other embodiments, the MEK inhibitor and Raf inhibitor are administered twice a day.

In further or additional embodiments the MEK protein kinase inhibitor and Raf protein kinase inhibitor in combination is administered three times per day. In further or additional embodiments the MEK protein kinase inhibitor and Raf protein kinase inhibitor in combination is administered four times per day. In further or additional embodiments the MEK protein kinase inhibitor and Raf protein kinase inhibitor in combination is administered more than four times per day.

In some embodiments, the pharmaceutical composition is for administration to a mammal. In further or additional embodiments, the mammal is human. In further or additional embodiments, the pharmaceutical composition further comprises a pharmaceutical carrier, excipient and/or adjuvant.

In further or additional embodiments, the pharmaceutical composition further comprises at least one additional therapeutic agent. In further or additional embodiments, the therapeutic agent is selected from the group of cytotoxic agents, anti-angiogenesis agents and anti-neoplastic agents. In further or additional embodiments, the anti-neoplastic agent is selected from the group of consisting of alkylating agents, anti-metabolites, epidophyllotoxins; antineoplastic enzymes, topoisomerase inhibitors, procarbazines, mitoxantrones, platinum coordination complexes, biological response modifiers and growth inhibitors, hormonal/anti-hormonal therapeutic agents, and haematopoietic growth factors. In further or additional embodiments, the therapeutic agent is taxol, bortezomib or both. In further or additional embodiments, the pharmaceutical composition is administered in combination with an additional therapy. In further or additional embodiments, the additional therapy is radiation therapy, chemotherapy, surgery or any combination thereof.

Methods of Use

In other aspects, the present invention is directed to a method for achieving an effect in a patient comprising the administration, of an effective amount of MEK protein kinase inhibitor and Raf protein kinase inhibitor to a patient, wherein the effect is selected from the group consisting of inhibition of various cancers. In some embodiments, the effect is inhibition of various cancers.

In some embodiments, the combination of the MEK protein kinase inhibitor and Raf protein kinase inhibitor is administered with an additional therapy. In further or additional embodiments, the additional therapy is radiation therapy, chemotherapy, or surgery or any combination thereof. In further or additional embodiments, the combination is administered with at least one additional therapeutic agent.

In further or additional embodiments the amount of MEK protein kinase inhibitor and/or Raf protein kinase inhibitor in combination in the range of about 0.001 to about 1000 mg/kg body weight/day. In further or additional embodiments the amount of MEK protein kinase inhibitor and/or Raf protein kinase inhibitor in combination is in the range of about 0.5 to about 50 mg/kg/day. In further or additional embodiments the amount of MEK protein kinase inhibitor and/or Raf protein kinase inhibitor in combination is about 0.001 to about 7 g/day. In further or additional embodiments the amount of MEK protein kinase inhibitor and/or Raf protein kinase inhibitor in combination is about 0.002 to about 6 g/day. In further or additional embodiments the amount of MEK protein kinase inhibitor and/or Raf protein kinase inhibitor in combination is about 0.005 to about 5 g/day. In further or additional embodiments the amount of MEK protein kinase inhibitor and/or Raf protein kinase inhibitor in combination is about 0.01 to about 5 g/day. In further or additional embodiments the amount of MEK protein kinase inhibitor and/or Raf protein kinase inhibitor in combination is about 0.02 to about 5 g/day. In further or additional embodiments the amount of MEK protein kinase inhibitor and/or Raf protein kinase inhibitor in combination is about 0.05 to about 2.5 g/day. In further or additional embodiments the amount of MEK protein kinase inhibitor and/or Raf protein kinase inhibitor in combination is about 0.1 to about 1 g/day. In further or additional embodiments, dosage levels below the lower limit of the aforesaid range may be more than adequate.

In some embodiments the MEK inhibitor and Raf inhibitor are administered on different timing regimens. For example, in some embodiments, the MEK inhibitor is administered once a day and the Raf inhibitor is administered twice a day. In other embodiments, the MEK inhibitor is administered twice a day and the Raf inhibitor is administered once a day. In some embodiments, the MEK inhibitor and Raf inhibitor are both administered once a day. In yet other embodiments, the MEK inhibitor and Raf inhibitor are administered twice a day. In further or additional embodiments the MEK protein kinase inhibitor and/or Raf protein kinase inhibitor is administered in a single dose, once daily. In further or additional embodiments the MEK protein kinase inhibitor and/or Raf protein kinase inhibitor is administered in multiple doses, more than once per day. In further or additional embodiments the MEK protein kinase inhibitor and/or Raf protein kinase inhibitor is administered twice daily. In further or additional embodiments the MEK protein kinase inhibitor and/or Raf protein kinase inhibitor is administered three times per day. In further or additional embodiments MEK protein kinase inhibitor and/or Raf protein kinase inhibitor is administered four times per day. In further or additional embodiments the MEK protein kinase inhibitor and/or Raf protein kinase inhibitor is administered more than four times per day.

In some aspects, the present invention is directed to a method of treating a disease in an individual suffering from said disease comprising administering to said individual an effective amount of a combination comprising a MEK protein kinase inhibitor and/or Raf protein kinase inhibitor.

In other aspects, the present invention is directed to a method of treating a disorder in a mammal, comprising administering to said mammal a therapeutically effective amount a combination comprising a MEK protein kinase inhibitor and/or Raf protein kinase inhibitor.

In other aspects, the present invention is directed to a method of treating a disorder in a human, comprising administering to said mammal a therapeutically effective amount of a combination comprising a MEK protein kinase inhibitor and/or a Raf protein kinase inhibitor.

MEK Modulated Disease and Disorders

Also described herein are methods of modulating MEK activity by contacting MEK with a therapeutically effective amount of a combination comprising a MEK protein kinase inhibitor and/or Raf protein kinase inhibitor sufficient to modulate the activity of MEK. Modulate can be inhibiting or activating MEK activity. In some embodiments, the invention provides methods of inhibiting MEK activity by contacting MEK with an amount of a therapeutically effective and/or synergistic amount of a combination comprising a MEK protein kinase inhibitor and/or Raf protein kinase inhibitor sufficient to inhibit the activity of MEK. In some embodiments, the invention provides methods of inhibiting MEK activity in a solution by contacting said solution with a therapeutically effective amount of a combination comprising a MEK protein kinase inhibitor and/or Raf protein kinase inhibitor sufficient to inhibit the activity of MEK in said solution. In some embodiments, the invention provides methods of inhibiting MEK activity in a cell by contacting said cell with a therapeutically effective amount of a combination comprising a MEK protein kinase inhibitor and/or Raf protein kinase inhibitor sufficient to inhibit the activity of MEK in said cell. In some embodiments, the invention provides methods of inhibiting MEK activity in a tissue by contacting said tissue with a therapeutically effective amount of a combination comprising a MEK protein kinase inhibitor and/or Raf protein kinase inhibitor sufficient to inhibit the activity of MEK in said tissue. In some embodiments, the invention provides methods of inhibiting MEK activity in an organism by contacting said organism with a therapeutically effective amount of a combination comprising a MEK protein kinase inhibitor and/or Raf protein kinase inhibitor sufficient to inhibit the activity of MEK in said organism. In some embodiments, the invention provides methods of inhibiting MEK activity in an animal by contacting said animal with an amount of a therapeutically effective amount of a combination comprising a MEK protein kinase inhibitor and/or Raf protein kinase inhibitor sufficient to inhibit the activity of MEK in said animal. In some embodiments, the invention provides methods of inhibiting MEK activity in a mammal by contacting said mammal with a therapeutically effective amount of a combination comprising a MEK protein kinase inhibitor and/or Raf protein kinase inhibitor sufficient to inhibit the activity of MEK in said mammal. In some embodiments, the invention provides methods of inhibiting MEK activity in a human by contacting said human with a therapeutically effective amount of a combination comprising a MEK protein kinase inhibitor and/or Raf protein kinase inhibitor sufficient to inhibit the activity of MEK in said human.

The combinations described herein may modulate the activity of MEK enzymes; and, as such, are useful for treating diseases or conditions in which aberrant MEK enzyme activity contributes to the pathology and/or symptoms of a disease or condition. In some aspects, the present invention is directed to a method of treating a disorder or condition which is modulated by the MEK cascade in a mammal, including a human, comprising administering to said mammal an amount of the combination comprising a MEK protein kinase inhibitor and/or Raf protein kinase inhibitor, effective to modulate said cascade. With the teachings provided herein, the appropriate dosage for a particular patient can be determined, according to known methods, by those skilled in the art.

In other aspects, the present invention is directed to a method for inhibiting a MEK enzyme. In some embodiments, the method comprises contacting said MEK enzyme with an amount of a combination comprising MEK protein kinase inhibitor and/or Raf protein kinase inhibitor, sufficient to inhibit said enzyme, wherein said enzyme is inhibited. In further or additional embodiments the enzyme is at least about 1% inhibited. In further or additional embodiments the enzyme is at least about 2% inhibited. In further or additional embodiments the enzyme is at least about 3% inhibited. In further or additional embodiments the enzyme is at least about 4% inhibited. In further or additional embodiments the enzyme is at least about 5% inhibited. In further or additional embodiments the enzyme is at least about 10% inhibited. In further or additional embodiments the enzyme is at least about 20% inhibited. In further or additional embodiments the enzyme is at least about 25% inhibited. In further or additional embodiments the enzyme is at least about 30% inhibited. In further or additional embodiments the enzyme is at least about 40% inhibited. In further or additional embodiments the enzyme is at least about 50% inhibited. In further or additional embodiments the enzyme is at least about 60% inhibited. In further or additional embodiments the enzyme is at least about 70% inhibited. In further or additional embodiments the enzyme is at least about 75% inhibited. In further or additional embodiments the enzyme is at least about 80% inhibited. In further or additional embodiments the enzyme is at least about 90% inhibited. In further or additional embodiments the enzyme is essentially completely inhibited. In further or additional embodiments the MEK enzyme is MEK kinase. In further or additional embodiments the MEK enzyme is MEK1. In further or additional embodiments the MEK enzyme is MEK2. In further or additional embodiments the contacting occurs within a cell. In further or additional embodiments the cell is a mammalian cell.

In further or additional aspects, the present invention is directed to a method of treatment of a MEK mediated disorder in an individual suffering from said disorder comprising administering to said individual an effective amount of a combination comprising a MEK protein kinase inhibitor and/or Raf protein kinase inhibitor. In some embodiments, the combination administered orally, intraduodenally, parenterally (including intravenous, subcutaneous, intramuscular, intravascular or by infusion), topically or rectally, or a mixture thereof. In some embodiments, the pharmaceutical combination is in a form suitable for oral administration. In further or additional embodiments, the pharmaceutical composition is in the form of a tablet, capsule, pill, powder, sustained release formulations, solution, suspension, for parenteral injection as a sterile solution, suspension or emulsion, for topical administration as an ointment or cream or for rectal administration as a suppository. In further or additional embodiments, the pharmaceutical composition is in unit dosage forms suitable for single administration of precise dosages. In further or additional embodiments, the pharmaceutical composition further comprises a pharmaceutical carrier, excipient and/or adjuvant.

In further or additional embodiments the amount of MEK protein kinase inhibitor and/or Raf protein kinase inhibitor in combination in the range of about 0.001 to about 1000 mg/kg body weight/day. In further or additional embodiments the amount of MEK protein kinase inhibitor and/or Raf protein kinase inhibitor in combination is in the range of about 0.5 to about 50 mg/kg/day. In further or additional embodiments the amount of MEK protein kinase inhibitor and/or Raf protein kinase inhibitor in combination is about 0.001 to about 7 g/day. In further or additional embodiments the amount of MEK protein kinase inhibitor and/or Raf protein kinase inhibitor in combination is about 0.002 to about 6 g/day. In further or additional embodiments the amount of MEK protein kinase inhibitor and/or Raf protein kinase inhibitor in combination is about 0.005 to about 5 g/day. In further or additional embodiments the amount of MEK protein kinase inhibitor and/or Raf protein kinase inhibitor in combination is about 0.01 to about 5 g/day. In further or additional embodiments the amount of MEK protein kinase inhibitor and/or Raf protein kinase inhibitor in combination is about 0.02 to about 5 g/day. In further or additional embodiments the amount of MEK protein kinase inhibitor and/or Raf protein kinase inhibitor in combination is about 0.05 to about 2.5 g/day. In further or additional embodiments the amount of MEK protein kinase inhibitor and/or Raf protein kinase inhibitor in combination is about 0.1 to about 1 g/day. In further or additional embodiments, dosage levels below the lower limit of the aforesaid range may be more than adequate.

In some embodiments the MEK inhibitor and Raf inhibitor are administered on different timing regimens. For example, in some embodiments, the MEK inhibitor is administered once a day and the Raf inhibitor is administered twice a day. In other embodiments, the MEK inhibitor is administered twice a day and the Raf inhibitor is administered once a day. In some embodiments, the MEK inhibitor and Raf inhibitor are both administered once a day. In yet other embodiments, the MEK inhibitor and Raf inhibitor are administered twice a day. In further or additional embodiments the MEK protein kinase inhibitor and/or Raf protein kinase inhibitor is administered in a single dose, once daily. In further or additional embodiments the MEK protein kinase inhibitor and/or Raf protein kinase inhibitor is administered in multiple doses, more than once per day. In further or additional embodiments the MEK protein kinase inhibitor and/or Raf protein kinase inhibitor is administered twice daily. In further or additional embodiments the MEK protein kinase inhibitor and/or Raf protein kinase inhibitor is administered three times per day. In further or additional embodiments MEK protein kinase inhibitor and/or Raf protein kinase inhibitor is administered four times per day. In further or additional embodiments the MEK protein kinase inhibitor and/or Raf protein kinase inhibitor is administered more than four times per day.

In some embodiments, the combination is administered with an additional therapy. In further or additional embodiments, the additional therapy is radiation therapy, chemotherapy, surgery or any combination thereof. In further or additional embodiments, the combination is administered with at least one additional therapeutic agent. In further or additional embodiments, the therapeutic agent is selected from the group of cytotoxic agents, anti-angiogenesis agents and anti-neoplastic agents. In further or additional embodiments, the anti-neoplastic agent is selected from the group of consisting of alkylating agents, anti-metabolites, epidophyllotoxins; antineoplastic enzymes, topoisomerase inhibitors, procarbazines, mitoxantrones, platinum coordination complexes, biological response modifiers and growth inhibitors, hormonal/anti-hormonal therapeutic agents, and haematopoietic growth factors. In further or additional embodiments, the therapeutic agent is selected from taxol, bortezomib or both.

In some embodiments, the MEK mediated disorder is a hyperproliferative disease. In further or additional embodiments, the MEK mediated disorder is selected from the group consisting of tumors, leukemias, neoplasms, cancers, carcinomas and malignant disease. In further or additional embodiments, the cancer is brain cancer, breast cancer, lung cancer, ovarian cancer, pancreatic cancer, stomach cancer, prostate cancer, renal cancer, colorectal cancer or leukemia. In further or additional embodiments, the fibrogenetic disorder is scleroderma, polymyositis, systemic lupus, rheumatoid arthritis, liver cirrhosis, keloid formation, interstitial nephritis or pulmonary fibrosis.

Cancer

In other aspects, the present invention is directed to a method for the treatment, prevention or prophylaxis of cancer in an individual comprising administering to said individual an effective amount of a compound of formula formula II, or a pharmaceutically acceptable salt, solvate, polymorph, ester, amide, tautomer or prodrug thereof. In some embodiments, the compound or pharmaceutically acceptable salt, solvate, polymorph, ester, amide, tautomer or prodrug thereof is administered as a component of a composition that further comprises a pharmaceutically acceptable carrier or vehicle. In further or additional embodiments, the cancer is brain cancer, breast cancer, lung cancer, ovarian cancer, pancreatic cancer, stomach cancer, prostate cancer, renal cancer, colorectal cancer or leukemia. In further or additional embodiments, the fibrogenetic disorder is scleroderma, polymyositis, systemic lupus, rheumatoid arthritis, liver cirrhosis, keloid formation, interstitial nephritis or pulmonary fibrosis. In further or additional embodiments, the cancer is brain cancer, breast cancer, lung cancer, ovarian cancer, pancreatic cancer, stomach cancer, prostate cancer, renal cancer, colorectal cancer or leukemia. In further or additional embodiments, the cancer is brain cancer or adrenocortical carcinoma. In further or additional embodiments, the cancer is breast cancer. In further or additional embodiments, the cancer is ovarian cancer. In further or additional embodiments, the cancer is pancreatic cancer. In further or additional embodiments, the cancer is stomach cancer. In further or additional embodiments, the cancer is prostate cancer. In further or additional embodiments, the cancer is renal cancer. In further or additional embodiments, the cancer is colorectal cancer. In further or additional embodiments, the cancer is myeloid leukemia. In further or additional embodiments, the cancer is glioblastoma. In further or additional embodiments, the cancer is follicular lymphoma. In further or additional embodiments, the cancer is pre-B acute leukemia. In further or additional embodiments, the cancer is chronic lymphocytic B-leukemia. In further or additional embodiments, the cancer is mesothelioma. In further or additional embodiments, the cancer is small cell line cancer.

In some embodiments, the combination is administered in combination with an additional therapy. In further or additional embodiments, the additional therapy is radiation therapy, chemotherapy, surgery or any combination thereof. In further or additional embodiments, the combination is administered in combination with at least one additional therapeutic agent. In further or additional embodiments, the therapeutic agent is selected from the group of cytotoxic agents, anti-angiogenesis agents and anti-neoplastic agents. In further or additional embodiments, the anti-neoplastic agent is selected from the group of consisting of alkylating agents, anti-metabolites, epidophyllotoxins; antineoplastic enzymes, topoisomerase inhibitors, procarbazines, mitoxantrones, platinum coordination complexes, biological response modifiers and growth inhibitors, hormonal/anti-hormonal therapeutic agents, and haematopoietic growth factors. In further or additional embodiments, the therapeutic agent is selected from taxol, bortezornib or both.

In further or additional embodiments the amount of MEK protein kinase inhibitor and/or Raf protein kinase inhibitor in combination in the range of about 0.001 to about 1000 mg/kg body weight/day. In further or additional embodiments the amount of MEK protein kinase inhibitor and/or Raf protein kinase inhibitor in combination is in the range of about 0.5 to about 50 mg/kg/day. In further or additional embodiments the amount of MEK protein kinase inhibitor and/or Raf protein kinase inhibitor in combination is about 0.001 to about 7 g/day. In further or additional embodiments the amount of MEK protein kinase inhibitor and/or Raf protein kinase inhibitor in combination is about 0.002 to about 6 g/day. In further or additional embodiments the amount of MEK protein kinase inhibitor and/or Raf protein kinase inhibitor in combination is about 0.005 to about 5 g/day. In further or additional embodiments the amount of MEK protein kinase inhibitor and/or Raf protein kinase inhibitor in combination is about 0.01 to about 5 g/day. In further or additional embodiments the amount of MEK protein kinase inhibitor and/or Raf protein kinase inhibitor in combination is about 0.02 to about 5 g/day. In further or additional embodiments the amount of MEK protein kinase inhibitor and/or Raf protein kinase inhibitor in combination is about 0.05 to about 2.5 g/day. In further or additional embodiments the amount of MEK protein kinase inhibitor and/or Raf protein kinase inhibitor in combination is about 0.1 to about 1 g/day. In further or additional embodiments, dosage levels below the lower limit of the aforesaid range may be more than adequate.

In some embodiments, the composition is administered orally, intraduodenally, parenterally (including intravenous, subcutaneous, intramuscular, intravascular or by infusion), topically or rectally.

In some embodiments the MEK inhibitor and Raf inhibitor are administered on different timing regimens. For example, in some embodiments, the MEK inhibitor is administered once a day and the Raf inhibitor is administered twice a day. In other embodiments, the MEK inhibitor is administered twice a day and the Raf inhibitor is administered once a day. In some embodiments, the MEK inhibitor and Raf inhibitor are both administered once a day. In yet other embodiments, the MEK inhibitor and Raf inhibitor are administered twice a day. In further or additional embodiments the MEK protein kinase inhibitor and/or Raf protein kinase inhibitor is administered in a single dose, once daily. In further or additional embodiments the MEK protein kinase inhibitor and/or Raf protein kinase inhibitor is administered in multiple doses, more than once per day. In further or additional embodiments the MEK protein kinase inhibitor and/or Raf protein kinase inhibitor is administered twice daily. In further or additional embodiments the MEK protein kinase inhibitor and/or Raf protein kinase inhibitor is administered three times per day. In further or additional embodiments MEK protein kinase inhibitor and/or Raf protein kinase inhibitor is administered four times per day. In further or additional embodiments the MEK protein kinase inhibitor and/or Raf protein kinase inhibitor is administered more than four times per day.

Abnormal Cell Growth

Also described herein are compounds, pharmaceutical compositions and methods for inhibiting abnormal cell growth. In some embodiments, the abnormal cell growth occurs in a mammal. Methods for inhibiting abnormal cell growth comprise administering an effective amount of a MEK protein kinase inhibitor and/or Raf protein kinase inhibitor, wherein abnormal cell growth is inhibited. Methods for inhibiting abnormal cell growth in a mammal comprise administering to the mammal an amount of a MEK protein kinase inhibitor and/or Raf protein kinase inhibitor, wherein the amounts of the compound, or salt, is effective in inhibiting abnormal cell growth in the mammal.

In some embodiments, the methods comprise administering an effective amount of a MEK protein kinase inhibitor and/or Raf protein kinase inhibitor, in combination with an amount of a chemotherapeutic, wherein the amounts of the combination and the chemotherapeutic are together effective in inhibiting abnormal cell growth. Many chemotherapeutics are presently known in the art and can be used in combination. In some embodiments, the chemotherapeutic is selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, anti-hormones, angiogenesis inhibitors, and anti-androgens.

Also described are methods for inhibiting abnormal cell growth in a mammal comprising administering to the mammal an amount of a MEK protein kinase inhibitor and/or Raf protein kinase inhibitor in combination with radiation therapy, wherein the amounts of the MEK protein kinase inhibitor and/or Raf protein kinase inhibitor in combination with the radiation therapy effective in inhibiting abnormal cell growth or treating the hyperproliferative disorder in the mammal. Techniques for administering radiation therapy are known in the art, and these techniques can be used in the combination therapy described herein.

The invention also relates to a method of and to a pharmaceutical composition of inhibiting abnormal cell growth in a mammal which comprises an amount of a MEK protein kinase inhibitor and/or Raf protein kinase inhibitor, and an amount of one or more substances selected from anti-angiogenesis agents, signal transduction inhibitors, and antiproliferative agents.

Anti-angiogenesis agents, such as MMP-2 (matrix-metalloprotienase 2) inhibitors, MMP-9 (matrix-metalloprotienase 9) inhibitors, and COX-11 (cyclooxygenase 11) inhibitors, can be used in conjunction with a compound of the present invention and pharmaceutical compositions described herein. Examples of useful COX-II inhibitors include CELEBREX™ (alecoxib), valdecoxib, and rofecoxib. Examples of useful matrix metalloproteinase inhibitors are described in WO 96/33172 (published Oct. 24, 1996), WO 96/27583 (published Mar. 7, 1996), European Patent Application No. 97304971.1 (filed Jul. 8, 1997), European Patent Application No. 99308617.2 (filed Oct. 29, 1999), WO 98/07697 (published Feb. 26, 1998), WO 98/03516 (published Jan. 29, 1998), WO 98/34918 (published Aug. 13, 1998), WO 98/34915 (published Aug. 13, 1998), WO 98/33768 (published Aug. 6, 1998), WO 98/30566 (published Jul. 16, 1998), European Patent Publication 606,046 (published Jul. 13, 1994), European Patent Publication 931, 788 (published Jul. 28, 1999), WO 90/05719 (published May 31, 1990), WO 99/52910 (published Oct. 21, 1999), WO 99/52889 (published Oct. 21, 1999), WO 99/29667 (published Jun. 17, 1999), PCT International Application No. PCT/IB98/01113 (filed Jul. 21, 1998), European Patent Application No. 99302232.1 (filed Mar. 25, 1999), Great Britain Patent Application No. 9912961.1 (filed Jun. 3, 1999), U.S. Provisional Application No. 60/148,464 (filed Aug. 12, 1999), U.S. Pat. No. 5,863,949 (issued Jan. 26, 1999), U.S. Pat. No. 5,861,510 (issued Jan. 19, 1999), and European Patent Publication 780, 386 (published Jun. 25, 1997), all of which are incorporated herein in their entireties by reference. Some MMP-2 and MMP-9 inhibitors have little or no activity inhibiting MMP-1, while some selectively inhibit MMP-2 and/or AMP-9 relative to the other matrix-metalloproteinases (i.e., MAP-1, MMP-3, MMP-4, MMP-5, MMP-6, MMP-7, MMP-8, MMP-10, MMP-11, MMP-12, and MMP-13). Some specific examples of MMP inhibitors useful in the present invention are AG-3340, RO 32-3555, and RS 13-0830.

In other aspects, the present invention is directed to a method for degrading, inhibiting the growth of or killing a cancer cell comprising contacting said cell with an amount of a MEK protein kinase inhibitor and/or Raf protein kinase inhibitor effective to degrade, inhibit the growth of or to kill said cell. In some embodiments, the cancer cells comprise brain, breast, lung, ovarian, pancreatic, stomach, prostate, renal, or colorectal cancer cells.

In further or additional embodiments, the combination is administered with at least one therapeutic agent. In further or additional embodiments, the therapeutic agent is taxol, bortezomib or both. In further or additional embodiments, the therapeutic agent is selected from the group consisting of cytotoxic agents, anti-angiogenesis agents and anti-neoplastic agents. In further or additional embodiments, the anti-neoplastic agents selected from the group of consisting of alkylating agents, anti-metabolites, epidphyllotoxins; antineoplastic enzymes, topoisomerase inhibitors, procarbazines, mitoxantrones, platinum coordination complexes, biological response modifiers and growth inhibitors, hormonal/anti-hormonal therapeutic agents, and haematopoietic growth factors.

In some embodiments, the cancer cells are degraded. In further or additional embodiments, 1% of the cancer cells are degraded. In further or additional embodiments, 2% of the cancer cells are degraded. In further or additional embodiments, 3% of the cancer cells are degraded. In further or additional embodiments, 4% of the cancer cells are degraded. In further or additional embodiments, 5% of the cancer cells are degraded. In further or additional embodiments, 10% of the cancer cells are degraded. In further or additional embodiments, 20% of the cancer cells are degraded. In further or additional embodiments, 25% of the cancer cells are degraded. In further or additional embodiments, 30% of the cancer cells are degraded. In further or additional embodiments, 40% of the cancer cells are degraded. In further or additional embodiments, 50% of the cancer cells are degraded. In further or additional embodiments, 60% of the cancer cells are degraded. In further or additional embodiments, 70% of the cancer cells are degraded. In further or additional embodiments, 75% of the cancer cells are degraded. In further or additional embodiments, 80% of the cancer cells are degraded. In further or additional embodiments, 90% of the cancer cells are degraded. In further or additional embodiments, 100% of the cancer cells are degraded. In further or additional embodiments, essentially all of the cancer cells are degraded.

In some embodiments, the cancer cells are killed. In further or additional embodiments, 1% of the cancer cells are killed. In further or additional embodiments, 2% of the cancer cells are killed. In further or additional embodiments, 3% of the cancer cells are killed. In further or additional embodiments, 4% of the cancer cells are killed. In further or additional embodiments, 5% of the cancer cells are killed. In further or additional embodiments, 10% of the cancer cells are killed. In further or additional embodiments, 20% of the cancer cells are killed. In further or additional embodiments, 25% of the cancer cells are killed. In further or additional embodiments, 30% of the cancer cells are killed. In further or additional embodiments, 40% of the cancer cells are killed. In further or additional embodiments, 50% of the cancer cells are killed. In further or additional embodiments, 60% of the cancer cells are killed. In further or additional embodiments, 70% of the cancer cells are killed. In further or additional embodiments, 75% of the cancer cells are killed. In further or additional embodiments, 80% of the cancer cells are killed. In further or additional embodiments, 90% of the cancer cells are killed. In further or additional embodiments, 100% of the cancer cells are killed. In further or additional embodiments, essentially all of the cancer cells are killed.

In further or additional embodiments, the growth of the cancer cells is inhibited. In further or additional embodiments, the growth of the cancer cells is about 1% inhibited. In further or additional embodiments, the growth of the cancer cells is about 2% inhibited. In further or additional embodiments, the growth of the cancer cells is about 3% inhibited. In further or additional embodiments, the growth of the cancer cells is about 4% inhibited. In further or additional embodiments, the growth of the cancer cells is about 5% inhibited. In further or additional embodiments, the growth of the cancer cells is about 10% inhibited. In further or additional embodiments, the growth of the cancer cells is about 20% inhibited. In further or additional embodiments, the growth of the cancer cells is about 25% inhibited. In further or additional embodiments, the growth of the cancer cells is about 30% inhibited. In further or additional embodiments, the growth of the cancer cells is about 40% inhibited. In further or additional embodiments, the growth of the cancer cells is about 50% inhibited. In further or additional embodiments, the growth of the cancer cells is about 60% inhibited. In further or additional embodiments, the growth of the cancer cells is about 70% inhibited. In further or additional embodiments, the growth of the cancer cells is about 75% inhibited. In further or additional embodiments, the growth of the cancer cells is about 80% inhibited. In further or additional embodiments, the growth of the cancer cells is about 90% inhibited. In further or additional embodiments, the growth of the cancer cells is about 100% inhibited.

Many chemotherapeutics are presently known in the art and can be used in combination with the compounds and compositions of the invention. In some embodiments, the chemotherapeutic is selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, anti-hormones, angiogenesis inhibitors, and anti-androgens.

Treatment of a Hyperproliferative Disorder

In other aspects, the present invention is directed to a method of treating a hyperproliferative disorder in a mammal, including a human, comprising administering to said mammal a therapeutically effective amount of a MEK protein kinase inhibitor and/or Raf protein kinase inhibitor.

In other aspects, the present invention is directed to a method for the treatment, prevention or prophylaxis of a proliferative disease in an individual comprising administering to said individual an effective amount of a MEK protein kinase inhibitor and/or Raf protein kinase inhibitor. In some embodiments, the MEK protein kinase inhibitor and/or Raf protein kinase inhibitor is administered as a component of a composition that further comprises a pharmaceutically acceptable carrier or vehicle. In some embodiments, the proliferative disease is cancer, psoriasis, restenosis, autoimmune disease, or atherosclerosis. In further or additional embodiments, the proliferative disease is a hyperproliferative disease. In further or additional embodiments, the proliferative disease is selected from the group consisting of tumors, leukemias, neoplasms, cancers, carcinomas and malignant disease. In further or additional embodiments, the cancer is brain cancer, breast cancer, lung cancer, liver cancer, ovarian cancer, pancreatic cancer, stomach cancer, prostate cancer, renal cancer, colorectal cancer or leukemia. In further or additional embodiments, the fibrogenetic disorder is scleroderma, polymyositis, systemic lupus, rheumatoid arthritis, liver cirrhosis, keloid formation, interstitial nephritis or pulmonary fibrosis. In further or additional embodiments, the cancer is brain cancer, breast cancer, lung cancer, ovarian cancer, pancreatic cancer, stomach cancer, prostate cancer, renal cancer, colorectal cancer or leukemia. In further or additional embodiments, the cancer is brain cancer or adrenocortical carcinoma. In further or additional embodiments, the cancer is breast cancer. In further or additional embodiments, the cancer is ovarian cancer. In further or additional embodiments, the cancer is pancreatic cancer. In further or additional embodiments, the cancer is stomach cancer. In further or additional embodiments, the cancer is prostate cancer. In further or additional embodiments, the cancer is renal cancer. In further or additional embodiments, the cancer is colorectal cancer. In further or additional embodiments, the cancer is myeloid leukemia. In further or additional embodiments, the cancer is glioblastoma. In further or additional embodiments, the cancer is follicular lymphoma. In further or additional embodiments, the cancer is pre-B acute leukemia. In further or additional embodiments, the cancer is chronic lymphocytic B-leukemia. In further or additional embodiments, the cancer is mesothelioma. In further or additional embodiments, the cancer is small cell line cancer.

In some embodiments, the combination is administered in combination with an additional therapy. In further or additional embodiments, the additional therapy is radiation therapy, chemotherapy, surgery or any combination thereof.

In further or additional embodiments, the combination is administered in combination with at least one therapeutic agent. In further or additional embodiments, the therapeutic agent is selected from the group of cytotoxic agents, anti-angiogenesis agents and anti-neoplastic agents. In further or additional embodiments, the anti-neoplastic agent is selected from the group of consisting of alkylating agents, anti-metabolites, epidophyllotoxins; antineoplastic enzymes, topoisomerase inhibitors, procarbazines, mitoxantrones, platinum coordination complexes, biological response modifiers and growth inhibitors, hormonal/anti-hormonal therapeutic agents, and haematopoietic growth factors. In further or additional embodiments, the therapeutic agent is selected from taxol, bortezomib or both.

In further or additional embodiments the amount of MEK protein kinase inhibitor and/or Raf protein kinase inhibitor in combination in the range of about 0.001 to about 1000 mg/kg body weight/day. In further or additional embodiments the amount of MEK protein kinase inhibitor and/or Raf protein kinase inhibitor in combination is in the range of about 0.5 to about 50 mg/kg/day. In further or additional embodiments the amount of MEK protein kinase inhibitor and/or Raf protein kinase inhibitor in combination is about 0.001 to about 7 g/day. In further or additional embodiments the amount of MEK protein kinase inhibitor and/or Raf protein kinase inhibitor in combination is about 0.002 to about 6 g/day. In further or additional embodiments the amount of MEK protein kinase inhibitor and/or Raf protein kinase inhibitor in combination is about 0.005 to about 5 g/day. In further or additional embodiments the amount of MEK protein kinase inhibitor and/or Raf protein kinase inhibitor in combination is about 0.01 to about 5 g/day. In further or additional embodiments the amount of MEK protein kinase inhibitor and/or Raf protein kinase inhibitor in combination is about 0.02 to about 5 g/day. In further or additional embodiments the amount of MEK protein kinase inhibitor and/or Raf protein kinase inhibitor in combination is about 0.05 to about 2.5 g/day. In further or additional embodiments the amount of MEK protein kinase inhibitor and/or Raf protein kinase inhibitor in combination is about 0.1 to about 1 g/day. In further or additional embodiments, dosage levels below the lower limit of the aforesaid range may be more than adequate.

In some embodiments the MEK inhibitor and Raf inhibitor are administered on different timing regimens. For example, in some embodiments, the MEK inhibitor is administered once a day and the Raf inhibitor is administered twice a day. In other embodiments, the MEK inhibitor is administered twice a day and the Raf inhibitor is administered once a day. In some embodiments, the MEK inhibitor and Raf inhibitor are both administered once a day. In yet other embodiments, the MEK inhibitor and Raf inhibitor are administered twice a day. In further or additional embodiments the MEK protein kinase inhibitor and/or Raf protein kinase inhibitor is administered in a single dose, once daily. In further or additional embodiments the MEK protein kinase inhibitor and/or Raf protein kinase inhibitor is administered in multiple doses, more than once per day. In further or additional embodiments the MEK protein kinase inhibitor and/or Raf protein kinase inhibitor is administered twice daily. In further or additional embodiments the MEK protein kinase inhibitor and/or Raf protein kinase inhibitor is administered three times per day. In further or additional embodiments MEK protein kinase inhibitor and/or Raf protein kinase inhibitor is administered four times per day. In further or additional embodiments the MEK protein kinase inhibitor and/or Raf protein kinase inhibitor is administered more than four times per day.

Tumor Size/Tumor Load/Tumor Burden

In other aspects, the present invention is directed to a method of reducing the size of a tumor, inhibiting tumor size increase, reducing tumor proliferation or preventing tumor proliferation in an individual, comprising administering to said individual an effective amount of a MEK protein kinase inhibitor and/or Raf protein kinase inhibitor. In some embodiments, combination is administered as a component of a composition that further comprises a pharmaceutically acceptable carrier or vehicle. In some embodiments, the size of a tumor is reduced. In further or additional embodiments, the size of a tumor is reduced by at least 1%. In further or additional embodiments, the size of a tumor is reduced by at least 2%. In further or additional embodiments, the size of a tumor is reduced by at least 3%. In further or additional embodiments, the size of a tumor is reduced by at least 4%. In further or additional embodiments, the size of a tumor is reduced by at least 5%. In further or additional embodiments, the size of a tumor is reduced by at least 10%. In further or additional embodiments, the size of a tumor is reduced by at least 20%. In further or additional embodiments, the size of a tumor is reduced by at least 25%. In further or additional embodiments, the size of a tumor is reduced by at least 30%. In further or additional embodiments, the size of a tumor is reduced by at least 40%. In further or additional embodiments, the size of a tumor is reduced by at least 50%. In further or additional embodiments, the size of a tumor is reduced by at least 60%. In further or additional embodiments, the size of a tumor is reduced by at least 70%. In further or additional embodiments, the size of a tumor is reduced by at least 75%. In further or additional embodiments, the size of a tumor is reduced by at least 80%. In further or additional embodiments, the size of a tumor is reduced by at least 85%. In further or additional embodiments, the size of a tumor is reduced by at least 90%. In further or additional embodiments, the size of a tumor is reduced by at least 95%. In further or additional embodiments, the tumor is eradicated. In some embodiments, the size of a tumor does not increase.

In some embodiments, tumor proliferation is reduced. In some embodiments, tumor proliferation is reduced by at least 1%. In some embodiments, tumor proliferation is reduced by at least 2%. In some embodiments, tumor proliferation is reduced by at least 3%. In some embodiments, tumor proliferation is reduced by at least 4%. In some embodiments, tumor proliferation is reduced by at least 5%. In some embodiments, tumor proliferation is reduced by at least 10%. In some embodiments, tumor proliferation is reduced by at least 20%. In some embodiments, tumor proliferation is reduced by at least 25%. In some embodiments, tumor proliferation is reduced by at least 30%. In some embodiments, tumor proliferation is reduced by at least 40%. In some embodiments, tumor proliferation is reduced by at least 50%. In some embodiments, tumor proliferation is reduced by at least 60%. In some embodiments, tumor proliferation is reduced by at least 70%. In some embodiments, tumor proliferation is reduced by at least 75%. In some embodiments, tumor proliferation is reduced by at least 75%. In some embodiments, tumor proliferation is reduced by at least 80%. In some embodiments, tumor proliferation is reduced by at least 90%. In some embodiments, tumor proliferation is reduced by at least 95%. In some embodiments, tumor proliferation is prevented.

In some embodiments, the combination is administered in combination with an additional therapy. In further or additional embodiments, the additional therapy is radiation therapy, chemotherapy, surgery or any combination thereof.

In further or additional embodiments, the combination is administered in combination with at least one therapeutic agent. In further or additional embodiments, the therapeutic agent is selected from the group of cytotoxic agents, anti-angiogenesis agents and anti-neoplastic agents. In further or additional embodiments, the anti-neoplastic agent is selected from the group of consisting of alkylating agents, anti-metabolites, epidophyllotoxins; antineoplastic enzymes, topoisomerase inhibitors, procarbazines, mitoxantrones, platinum coordination complexes, biological response modifiers and growth inhibitors, hormonal/anti-hormonal therapeutic agents, and haematopoietic growth factors. In further or additional embodiments, the therapeutic agent is selected from taxol, bortezomib or both.

In some embodiments, the composition comprising a MEK protein kinase inhibitor and Raf protein kinase inhibitor is administered orally, intraduodenally, parenterally (including intravenous, subcutaneous, intramuscular, intravascular or by infusion), topically or rectally. In further or additional embodiments the amount of compound of formula A, formula I, formula II and/or formula III is in the range of about 0.001 to about 1000 mg/kg body weight/day. In further or additional embodiments the amount of compound of formula A, formula I, formula II and/or formula III is in the range of about 0.5 to about 50 mg/kg/day. In further or additional embodiments the amount of compound of formula A, formula I, formula II and/or formula III is about 0.001 to about 7 g/day. In further or additional embodiments the amount of compound of formula A, formula I, formula II and/or formula III is about 0.01 to about 7 g/day. In further or additional embodiments the amount of compound of formula A, formula I, formula II and/or formula III is about 0.02 to about 5 g/day. In further or additional embodiments the amount of compound of formula A, formula I, formula II and/or formula III is about 0.05 to about 2.5 g/day. In further or additional embodiments the amount of compound of formula A, formula I, formula II and/or formula III is about 0.1 to about 1 g/day. In further or additional embodiments, dosage levels below the lower limit of the aforesaid range may be more than adequate. In further or additional embodiments, dosage levels above the upper limit of the aforesaid range may be required.

In some embodiments the MEK inhibitor and Raf inhibitor are administered on different timing regimens. For example, in some embodiments, the MEK inhibitor is administered once a day and the Raf inhibitor is administered twice a day. In other embodiments, the MEK inhibitor is administered twice a day and the Raf inhibitor is administered once a day. In some embodiments, the MEK inhibitor and Raf inhibitor are both administered once a day. In yet other embodiments, the MEK inhibitor and Raf inhibitor are administered twice a day. In further or additional embodiments the MEK protein kinase inhibitor and/or Raf protein kinase inhibitor is administered in a single dose, once daily. In further or additional embodiments the MEK protein kinase inhibitor and/or Raf protein kinase inhibitor is administered in multiple doses, more than once per day. In further or additional embodiments the MEK protein kinase inhibitor and/or Raf protein kinase inhibitor is administered twice daily. In further or additional embodiments the MEK protein kinase inhibitor and/or Raf protein kinase inhibitor is administered three times per day. In further or additional embodiments MEK protein kinase inhibitor and/or Raf protein kinase inhibitor is administered four times per day. In further or additional embodiments the MEK protein kinase inhibitor and/or Raf protein kinase inhibitor is administered more than four times per day.

Modes of Administration

Described herein are MEK protein kinase inhibitor and Raf protein kinase inhibitor combinations. Also described are pharmaceutical compositions comprising a MEK protein kinase and Raf protein kinase inhibitor. The difference between a "combination" and a "composition" as used herein is that the MEK inhibitor and Raf inhibitor may be in different dosage forms in the "combination," but are in the same dosage form in the "composition." The compounds and compositions described herein may be administered either alone or in combination with pharmaceutically acceptable carriers, excipients or diluents, in a pharmaceutical composition, according to standard pharmaceutical practice.

Administration of the compounds and compositions described herein can be effected by any method that enables delivery of the compounds to the site of action. These methods include oral routes, intraduodenal routes, parenteral injection (including intravenous, subcutaneous, intraperitoneal, intramuscular, intravascular or infusion), topical, and rectal administration. For example, compounds described herein can be administered locally to the area in need of treatment. This may be achieved by, for example, but not limited to, local infusion during surgery, topical application, e.g., cream, ointment, injection, catheter, or implant, said implant made, e.g., out of a porous, non-porous, or gelatinous material, including membranes, such as sialastic membranes, or fibers. The administration can also be by direct injection at the site (or former site) of a tumor or neoplastic or preneoplastic tissue. Those of ordinary skill in the art are familiar with formulation and administration techniques that can be employed with the compounds and methods of the invention, e.g., as discussed in Goodman and Gilman, The Pharmacological Basis of Therapeutics, current ed.; Pergamon; and Remington's, Pharmaceutical Sciences (current edition), Mack Publishing Co., Easton, Pa.

The formulations include those suitable for oral, parenteral (including subcutaneous, intradermal, intramuscular, intravenous, intraarticular, and intramedullary), intraperitoneal, transmucosal, transdermal, rectal and topical (including dermal, buccal, sublingual and intraocular) administration although the most suitable route may depend upon for example the condition and disorder of the recipient. The formulations may conveniently be presented in unit dosage form and may be prepared by any of the methods well known in the art of pharmacy. All methods include the step of bringing into association a compound of the subject invention or a pharmaceutically acceptable salt, solvate, polymorph, ester, amide, tautomer, prodrug, hydrate, or derivative thereof ("active ingredient") with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation.

Formulations suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

Pharmaceutical preparations which are useful for oral administration include tablets, push-fit capsules made of gelatin, as well as soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with an inert liquid diluent. The tablets may optionally be coated or scored and may be formulated so as to provide slow or controlled release of the active ingredient therein. All formulations for oral administration should be in dosages suitable for such administration. The push-fit capsules or tablets can contain the active ingredient; in admixture with a filler such as microcrystalline cellulose, silicified microcrystalline cellulose, pregelatinized starch, lactose, dicalcium phosphate, or compressible sugar; a binder such as hypromellose, povidone or starch paste; a disintegrant such as croscarmellose sodium, crospovidone or sodium starch glycolate; a surfactant such as sodium lauryl sulfate and/or lubricants and processing aides such as talc, magnesium stearate, stearic acid or colloidal silicon dioxide and, optionally, stabilizers. In soft capsules, the active compounds may be dissolved or suspended in suitable liquids, such as fatty oils, liquid paraffin, or liquid polyethylene glycols. In addition, stabilizers may be added. Dragee cores are provided with suitable coatings. For this purpose, concentrated sugar solutions are useful, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or Dragee coatings for identification or to characterize different combinations of active compound doses Timing of Administration Fixed Combinations In another aspect of the present invention, provided are combinations, compositions and methods of treatment comprising at least one MEK protein kinase inhibitor and at least one Raf protein kinase inhibitor. In some embodiments, the MEK protein kinase inhibitor and Raf protein kinase inhibitor comprise a fixed combination. In other embodiments the term "fixed combination" means that at least one of the compounds described herein, and at least one co-agent, are both administered to a patient simultaneously in the form of a single entity or dosage.

Non-Fixed Combinations

In other embodiments, provided are at least one MEK protein kinase inhibitor and at least one Raf protein kinase inhibitor in a non-fixed combination. The term "non-fixed combination" means that at least one of the compounds described herein, and at least one co-agent, are administered to a patient as separate entities either simultaneously, concurrently or sequentially with variable intervening time limits, wherein such administration provides effective levels of the two or more compounds in the body of the patient. These also apply to cocktail therapies, e.g. the administration of three or more active ingredients. In further or additional embodiments of the non-fixed combination, the MEK protein kinase inhibitor and the Raf protein kinase inhibitor are administered simultaneously or concurrently in separate dosage forms.

In some embodiments, the degree of synergsitic effect in the provided combinations when administered to a patient as provided herein is measured by apoptosis levels, cell proliferation, toxicity, pharmacokinetics, dosing, resensitization, or as otherwise described herein or as understood by the skilled artisan. In further or additional embodiments, the degree of synergy in a patient is dependent on the order of administration of the MEK protein kinase inhibitor and Raf protein kinase inhibitor. In some of these embodiments, the degree of synergy is greater when the MEK protein kinase inhibitor is administered prior to the Raf protein kinase inhibitor. Yet in further embodiments, the degree of synergsitic effect in a patient is not dependent on the order of administration of the MEK protein kinase inhibitor or Raf protein kinase inhibitor.

In some embodiments, the MEK protein kinase inhibitor is administered before the Raf protein kinase inhibitor. In some of these embodiments, the MEK protein kinase inhibitor is administered to a patient about 1 second to about 1 month prior to the administration of the Raf protein kinase inhibitor. In some of these embodiments, the MEK protein kinase inhibitor is administered to a patient about 1 second to about two weeks prior to the administration of the Raf protein kinase inhibitor. In some of these embodiments, the MEK protein kinase inhibitor is administered to a patient about 1 second to about 7 days prior to the administration of the Raf protein kinase inhibitor. In some of these embodiments, the MEK protein kinase inhibitor is administered to a patient about 1 second to about 72 hours prior to the administration of the Raf protein kinase inhibitor. In further or additional embodiments, the MEK protein kinase inhibitor is administered to a patient about 15 seconds to about 48 hours prior to the administration of the Raf protein kinase inhibitor. In some embodiments, the MEK protein kinase inhibitor is administered about 30 seconds to about 24 hours prior to the administration of the Raf protein kinase inhibitor to the patient. In other embodiments, the MEK protein kinase inhibitor is administered about 1 minute to about 8 hours prior to the administration of the Raf protein kinase inhibitor. In further or additional embodiments, the MEK protein kinase inhibitor is administered about 5 minutes to about 4 hours prior to the administration of the Raf protein kinase inhibitor. In additional embodiments, the MEK protein kinase inhibitor is administered about 10 minutes to about 1 hours prior to the administration of the Raf protein kinase inhibitor. In other embodiments, the MEK protein kinase inhibitor is administered about 1 second, about 5 seconds, about 15 seconds, about 20 seconds, about 30 seconds, about 1 minute, about 5 minutes, about 15 minutes, about 30 minutes, about 1 hours, about 2 hours, about 4 hours, about 8 hours, about 12 hours, about 24 hours, about 48 hours, about 72 hours, about 1 week, about 2 weeks, about 3 weeks, or about 1 month prior to the administration of the Raf protein kinase to the patient.

In some embodiments, the Raf protein kinase inhibitor is administered before the MEK protein kinase inhibitor. In some of these embodiments, the Raf protein kinase inhibitor is administered to a patient about 1 second to about 1 month prior to the administration of the MEK protein kinase inhibitor. In some of these embodiments, the Raf protein kinase inhibitor is administered to a patient about 1 second to about two weeks prior to the administration of the MEK protein kinase inhibitor. In some of these embodiments, the Raf protein kinase inhibitor is administered to a patient about 1 second to about 7 days prior to the administration of the MEK protein kinase inhibitor. In some of these embodiments, the Raf protein kinase inhibitor is administered to a patient about 1 second to about 72 hours prior to the administration of the MEK protein kinase inhibitor. In further or additional embodiments, the Raf protein kinase inhibitor is administered to a patient about 15 seconds to about 48 hours prior to the administration of the MEK protein kinase inhibitor. In some embodiments, the Raf protein kinase inhibitor is administered about 30 seconds to about 24 hours prior to the administration of the MEK protein kinase inhibitor to the patient. In other embodiments, the Raf protein kinase inhibitor is administered about 1 minute to about 8 hours prior to the administration of the MEK protein kinase inhibitor. In further or additional embodiments, the Raf protein kinase inhibitor is administered about 5 minutes to about 4 hours prior to the administration of the MEK protein kinase inhibitor. In additional embodiments, the Raf protein kinase inhibitor is administered about 10 minutes to about 1 hours prior to the administration of the MEK protein kinase inhibitor. In other embodiments, the Raf protein kinase inhibitor is administered about 1 second, about 5 seconds, about 15 seconds, about 20 seconds, about 30 seconds, about 1 minute, about 5 minutes, about 15 minutes, about 30 minutes, about 1 hours, about 2 hours, about 4 hours, about 8 hours, about 12 hours, about 24 hours, about 48 hours, about 72 hours, about 1 week, about 2 weeks, about 3 weeks, or about 1 month prior to the administration of the MEK protein kinase to the patient.

Formulations

Pharmaceutical preparations may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. The formulations may be presented in unit-dose or multi-dose containers, for example sealed ampoules and vials, and may be stored in powder form or in a freeze-dried (lyophilized) condition requiring only the addition of the sterile liquid carrier, for example, saline or sterile pyrogen-free water, immediately prior to use. Extemporaneous injection solutions and suspensions may be prepared from sterile powders, granules and tablets of the kind previously described.

Formulations for parenteral administration include aqueous and non-aqueous (oily) sterile injection solutions of the active compounds which may contain antioxidants, buffers, bacteriostats and solutes which render the formulation isotonic with the blood of the intended recipient; and aqueous and non-aqueous sterile suspensions which may include suspending agents and thickening agents. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Pharmaceutical preparations may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

For buccal or sublingual administration, the compositions may take the form of tablets, lozenges, pastilles, or gels formulated in conventional manner. Such compositions may comprise the active ingredient in a flavored basis such as sucrose and acacia or tragacanth.

Pharmaceutical preparations may also be formulated in rectal compositions such as suppositories or retention enemas, e.g., containing conventional suppository bases such as cocoa butter, polyethylene glycol, or other glycerides.

Pharmaceutical preparations may be administered topically, that is by non-systemic administration. This includes the application of a compound of the present invention externally to the epidermis or the buccal cavity and the instillation of such a compound into the ear, eye and nose, such that the compound does not significantly enter the blood stream. In contrast, systemic administration refers to oral, intravenous, intraperitoneal and intramuscular administration.

Pharmaceutical preparations suitable for topical administration include liquid or semi-liquid preparations suitable for penetration through the skin to the site of inflammation such as gels, liniments, lotions, creams, ointments or pastes, and drops suitable for administration to the eye, ear or nose. The active ingredient may comprise, for topical administration, from 0.001% to 10% w/w, for instance from 1% to 2% by weight of the formulation. It may however comprise as much as 10% w/w or may comprise less than 5% w/w, or from 0.1% to 1% w/w of the formulation.

Pharmaceutical preparations for administration by inhalation are conveniently delivered from an insufflator, nebulizer pressurized packs or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Alternatively, for administration by inhalation or insufflation, pharmaceutical preparations may take the form of a dry powder composition, for example a powder mix of the compound and a suitable powder base such as lactose or starch. The powder composition may be presented in unit dosage form, in for example, capsules, cartridges, gelatin or blister packs from which the powder may be administered with the aid of an inhalator or insufflator.

It should be understood that in addition to the ingredients particularly mentioned above, the compounds and compositions described herein may include other agents conventional in the art having regard to the type of formulation in question, for example those suitable for oral administration may include flavoring agents.

The compounds or compositions described herein can be delivered in a vesicle, e.g., a liposome (see, for example, Langer, Science 1990, 249, 1527-1533; Treat et al., Liposomes in the Therapy of Infectious Disease and Cancer, Lopez-Bernstein and Fidler, Ed., Liss, N.Y., pp. 353-365, 1989). The compounds and pharmaceutical compositions described herein can also be delivered in a controlled release system. In one embodiment, a pump may be used (see, Sefton, 1987, CRC Crit. Ref. Biomed. Eng. 14:201; Buchwald et al. Surgery, 1980 88, 507; Saudek et al. N. Engl. J. Med. 1989, 321, (574). Additionally, a controlled release system can be placed in proximity of the therapeutic target. (See, Goodson, Medical Applications of Controlled Release, 1984, Vol. 2, pp. 115-138). The pharmaceutical compositions described herein can also contain the active ingredient in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions, and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents; fillers such as microcrystalline cellulose, silicified microcrystalline cellulose, pregelatinized starch, lactose, dicalcium phosphate, or compressible sugar; binders such as hypromellose, povidone or starch paste; disintegrants such as croscarmellose sodium, crospovidone or sodium starch glycolate; a surfactant such as sodium lauryl sulfate and/or lubricants and processing aides such as talc, sodium croscarmellose, corn starch, or alginic acid; binding agents, for example starch, gelatin, polyvinyl-pyrrolidone or acacia, and lubricating agents, for example magnesium stearate, stearic acid or colloidal silicon dioxide and, optionally, talc. The tablets may be un-coated or coated by known techniques to mask the taste of the drug or delay disintegration and absorption in the gastrointestinal tract and thereby provide a sustained action over a longer period. For example, a water soluble taste masking material such as hydroxypropylmethyl-cellulose or hydroxypropylcellulose, or a time delay material such as ethyl cellulose, or cellulose acetate butyrate may be employed as appropriate. Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water soluble carrier such as polyethyleneglycol or an oil medium, for example peanut oil, liquid paraffin, or olive oil. The capsule and tablet dosage forms may be prepared by various processing techniques including dry blending and wet granulation techniques. In the dry blending method of manufacture the drug substance may be incorporated into the dosage form by dry blending with the excipients followed by encapsulation into a capsule shell or compression into a tablet form. The dry blending operation may be approached in a stepwise manner and include screening steps between the blending steps to facilitate formation of a uniform blend. In the wet granulation method of manufacture the drug substance may be added to the dry excipients and mixed prior to the addition of the binder solution or the drug substance may be dissolved and added as a solution as part of granulation. In the wet granulation technique the surfactant, if used, may be added to the dry excipients or added to the binder solution and incorporated in a solution form. Capsule dosage forms may also be manufactured by dissolving the drug substance in a material that can be filled into and is compatible with hard gelatin capsule shells that can be subsequently banded and sealed. Capsule and tablet dosage forms may also be produced by dissolving the drug substance in a material such a molten form of a high molecular weight polyethylene glycol and cooling to a solid form, milling and incorporating this material into conventional capsule and tablet manufacturing processes.

Aqueous suspensions contain the active material in admixture with excipients suitable for the manufacture of aqueous suspensions. Such excipients are suspending agents, for example sodium carboxymethylcellulose, methylcellulose, hydroxypropylmethyl-cellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as butylated hydroxyanisol or alpha-tocopherol.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present. These compositions may be preserved by the addition of an anti-oxidant such as ascorbic acid.

Pharmaceutical compositions may also be in the form of an oil-in-water emulsions. The oily phase may be a vegetable oil, for example olive oil or arachis oil, or a mineral oil, for example liquid paraffin or mixtures of these. Suitable emulsifying agents may be naturally-occurring phosphatides, for example soy bean lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening agents, flavoring agents, preservatives and antioxidants.

Syrups and elixirs may be formulated with sweetening agents, for example glycerol, propylene glycol, sorbitol or sucrose. Such formulations may also contain a demulcent, a preservative, flavoring and coloring agents and antioxidant.

Pharmaceutical compositions may be in the form of a sterile injectable aqueous solution. Among the acceptable vehicles and solvents that may be employed are water, Ringer's solution and isotonic sodium chloride solution. The sterile injectable preparation may also be a sterile injectable oil-in-water microemulsion where the active ingredient is dissolved in the oily phase. For example, the active ingredient may be first dissolved in a mixture of soybean oil and lecithin. The oil solution then introduced into a water and glycerol mixture and processed to form a microemulsion. The injectable solutions or microemulsions may be introduced into a patient's blood-stream by local bolus injection. Alternatively, it may be advantageous to administer the solution or microemulsion in such a way as to maintain a constant circulating concentration of the instant compound. In order to maintain such a constant concentration, a continuous intravenous delivery device may be utilized. An example of such a device is the Deltec CADD-PLUS™ model 5400 intravenous pump. The pharmaceutical compositions may be in the form of a sterile injectable aqueous or oleagenous suspension for intramuscular and subcutaneous administration. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Pharmaceutical compositions may also be administered in the form of suppositories for rectal administration of the drug. These compositions can be prepared by mixing the inhibitors with a suitable non-irritating excipient which is solid at ordinary temperatures but liquid at the rectal temperature and will therefore melt in the rectum to release the drug. Such materials include cocoa butter, glycerinated gelatin, hydrogenated vegetable oils, mixtures of polyethylene glycols of various molecular weights and fatty acid esters of polyethylene glycol.

For topical use, creams, ointments, jellies, solutions or suspensions, etc., containing a compound or composition of the invention are useful for topical administration. As used herein, topical application can include mouth washes and gargles.

Pharmaceutical compositions may be administered in intranasal form via topical use of suitable intranasal vehicles and delivery devices, or via transdermal routes, using those forms of transdermal skin patches well known to those of ordinary skill in the art.

The formulations may conveniently be presented in unit dosage form and may be prepared by any of the methods well known in the art of pharmacy. All methods include the step of bringing into association a compound of the subject invention or a pharmaceutically acceptable salt, ester, prodrug or solvate thereof ("active ingredient") with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation. Methods of preparing various pharmaceutical compositions with a specific amount of active compound are known, or will be apparent, to those skilled in this art. To be administered in the form of transdermal delivery, the dosage form will, of course, be continuous rather than intermittent throughout the dosage regimen.

Doses
Dosage Amounts of MEK Inhibitors And Raf Inhibitors

The amount of pharmaceutical combination of MEK protein kinase inhibitor and Raf protein kinase inhibitor administered will firstly be dependent on the mammal being treated. In the instances where pharmaceutical compositions are administered to a human subject, the daily dosage will normally be determined by the prescribing physician with the dosage generally varying according to the age, sex, diet, weight, general health and response of the individual patient, the severity of the patient's symptoms, the precise indication or condition being treated, the severity of the indication or condition being treated, time of administration, route of administration, the disposition of the composition, rate of excretion, drug combination, and the discretion of the prescribing physician. Also, the route of administration may vary depending on the condition and its severity. The pharmaceutical composition may be in unit dosage form. In such form, the preparation is subdivided into unit doses containing appropriate quantities of the active component, e.g., an effective amount to achieve the desired purpose. Determination of the proper dosage for a particular situation is within the skill of the art. Generally, treatment is initiated with smaller dosages which are less than the optimum dose of the compound. Thereafter, the dosage is increased by small amounts until the optimum effect under the circumstances is reached. For convenience, the total daily dosage may be divided and administered in portions during the day if desired. The amount and frequency of administration of the compounds described herein, and if applicable other therapeutic agents and/or therapies, will be regulated according to the judgment of the attending clinician (physician) considering such factors as described above. Thus the amount of pharmaceutical composition to be administered may vary widely. Administration may occur in an amount of between about 0.001 mg/kg of body weight to about 100 mg/kg of body weight per day (administered in single or divided doses), or at least about 0.1 mg/kg of body weight per day. A particular therapeutic dosage can include, e.g., from about 0.01 mg to about 7000 mg of compound, or, e.g., from about 0.05 mg to about 2500 mg. The quantity of active compound in a unit dose of preparation may be varied or adjusted from about 0.1 mg to 1000 mg, from about 1 mg to 300 mg, or 10 mg to 200 mg, according to the particular application. In some instances, dosage levels below the lower limit of the aforesaid range may be more than adequate, while in other cases still larger doses may be employed without causing any harmful side effect, e.g. by dividing such larger doses into several small doses for administration throughout the day. The amount administered will vary depending on the particular IC50 value of the compound used. In combinational applications in which the compound is not the sole therapy, it may be possible to administer lesser amounts of compound and still have therapeutic or prophylactic effect.

In another aspect, provided herein are pharmaceutical combinations and methods of treating cancer comprising a therapeutically effective amount of a MEK protein kinase inhibitor and a Raf protein kinase inhibitor, wherein the combination allows for particular dosing.

In some embodiments of the combinations and methods provided herein, the molar ratio of the MEK protein kinase inhibitor to the Raf protein kinase inhibitor administered to a patient is about 100:1 to about 2.5:1. In other embodiments, the molar ratio of the MEK protein kinase inhibitor to the Raf protein kinase inhibitor administered to a patient is about 50:1 to about 5:1. In other embodiments, the molar ratio of the MEK protein kinase inhibitor to the Raf protein kinase inhibitor administered to a patient is about 45:1 to about 10:1. In other embodiments, the molar ratio of the MEK protein kinase inhibitor to the Raf protein kinase inhibitor administered to a patient is about 40:1 to about 20:1. In other embodiments, the molar ratio of the MEK protein kinase inhibitor to the Raf protein kinase inhibitor administered to a patient is about 30:1.

Dosage Amounts of MEK Protein Kinase Inhibitors of Formula I

In some embodiments of the combinations and methods provided herein, provided are MEK protein kinase inhibitors further comprising a compound of formula I, wherein the compound of formula I is present in an amount of about 0.1 mg to about 200 mg. In other embodiments, the MEK protein kinase inhibitor comprises a compound of formula I and is present in an amount of about 0.2 mg to about 100 mg. In other embodiments, the MEK protein kinase inhibitor comprises a compound of formula I and is present in an amount of about 0.3 mg to about 90 mg. In other embodiments, the MEK protein kinase inhibitor comprises a compound of formula I and is present in an amount of about 0.4 mg to about 80 mg.

In other embodiments, the MEK protein kinase inhibitor comprises a compound of formula I and is present in an amount of about 0.5 mg to about 70 mg. In other embodiments, the MEK protein kinase inhibitor comprises a compound of formula I and is present in an amount of about 0.4 mg to about 80 mg. In other embodiments, the MEK protein kinase inhibitor comprises a compound of formula I and is present in an amount of about 0.5 mg to about 70 mg. In other embodiments, the MEK protein kinase inhibitor comprises a compound of formula I and is present in an amount of about 1 mg to about 60 mg. In other embodiments, the MEK protein kinase inhibitor comprises a compound of formula I and is present in an amount of about 1.5 mg to about 50 mg. In other embodiments, the MEK protein kinase inhibitor comprises a compound of formula I and is present in an amount of about 2 mg to about 45 mg. In other embodiments, the MEK protein kinase inhibitor comprises a compound of formula I and is present in an amount of about 2.5 mg to about 40 mg. In further embodiments, MEK protein kinase inhibitor further comprising the compound of formula I present in the dosage amounts provided herein is selected from the group consisting of:

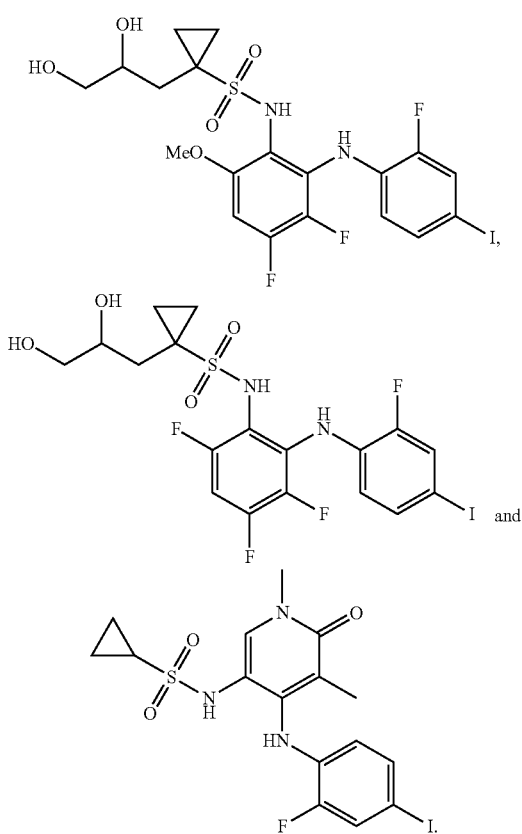

In some embodiments of the combinations and methods provided herein, provided are MEK protein kinase inhibitors further comprising a compound of formula I, wherein the compound of formula I is present in an amount of about 0.1 mg, about 0.2 mg, about 0.25 mg, about 0.3 mg, about 0.4 mg, about 0.5 mg, about 0.6 mg, about 0.7 mg, about 0.8 mg, about 0.9 mg, about 1 mg, about 1.5 mg, about 2 mg, about 2.5 mg, about 3 mg, about 3.5 mg, about 4.0 mg, about 4.5 mg, about 5 mg, about 5.5 mg, about 6 mg, about 6.5 mg, about 7 mg, about 7.5 mg, about 8 mg, about 8.5 mg, about 9 mg, about 9.5 mg, about 10 mg, about 10.5 mg, about 11 mg, about 11.5 mg, about 12 mg, about 12.5 mg, and/or about 13 mg, about 14 mg, or about 15 mg. In further embodiments, the compound of formula I present in the dosage amounts provided herein is selected from the group consisting of:

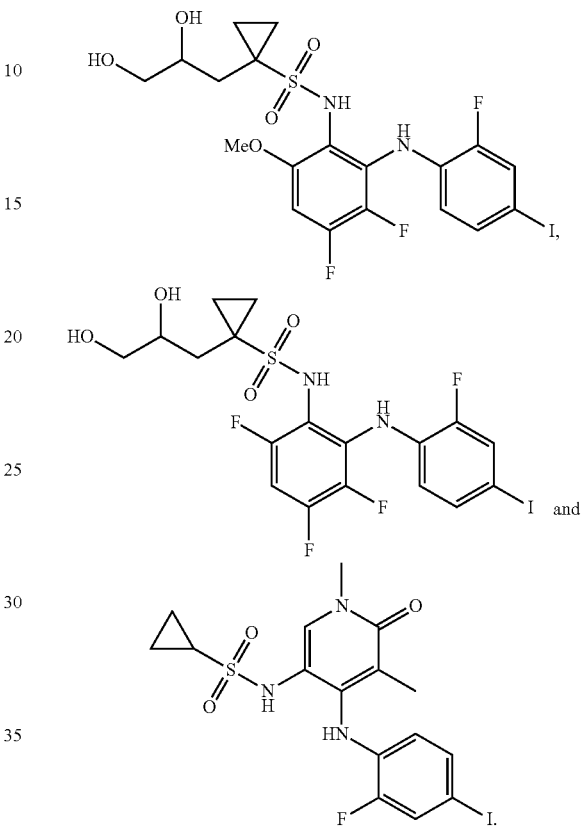

In some embodiments of the combinations and methods provided herein, provided are MEK protein kinase inhibitors further comprising a compound of formula I, wherein the compound of formula I is present in an amount of about 15 mg, about 20 mg, about 25 mg, about 30 mg, about 35 mg, about 40 mg, about 45 mg, about 50 mg, about 55 mg, about 60 mg, about 65 mg, about 75 mg, about 80 mg, about 85 mg, about 90 mg, about 95 mg, about 100 mg, about 110 mg, about 120 mg, about 125 mg, about 130 mg, about 140 mg, about 150 mg, about 160 mg, about 170 mg, about 175 mg, about 180 mg, about 190 mg, or about 200 mg. In further embodiments, the compound of formula I present in the dosage amounts provided herein is selected from the group consisting of:

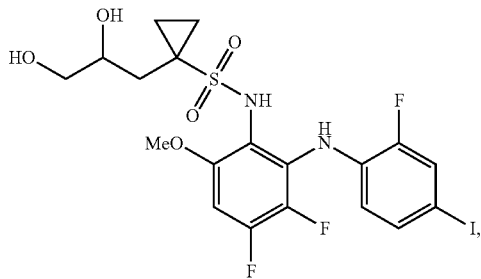

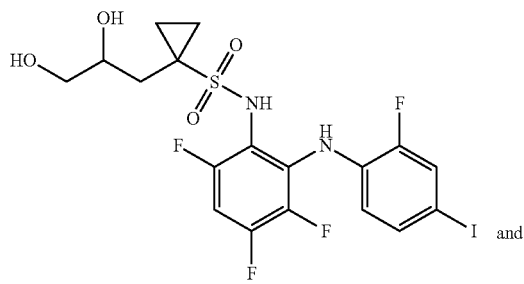

and

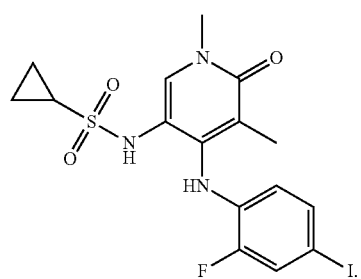

Dosage Amounts of MEK Protein Kinase Inhibitors of Formula II

In another aspect, the combinations and methods described herein provide for MEK protein kinase inhibitors further comprising a compound of formula II, wherein the compound of formula II is present in an amount of about 0.1 mg to about 200 mg. In other embodiments, the MEK protein kinase inhibitor comprises a compound of formula I and is present in an amount of about 0.2 mg to about 100 mg. In other embodiments, the MEK protein kinase inhibitor comprises a compound of formula II and is present in an amount of about 0.3 mg to about 90 mg. In other embodiments, the MEK protein kinase inhibitor comprises a compound of formula II and is present in an amount of about 0.4 mg to about 80 mg. In other embodiments, the MEK protein kinase inhibitor comprises a compound of formula II and is present in an amount of about 0.5 mg to about 70 mg. In other embodiments, the MEK protein kinase inhibitor comprises a compound of formula II and is present in an amount of about 0.4 mg to about 80 mg. In other embodiments, the MEK protein kinase inhibitor comprises a compound of formula II and is present in an amount of about 0.5 mg to about 70 mg. In other embodiments, the MEK protein kinase inhibitor comprises a compound of formula II and is present in an amount of about 1 mg to about 60 mg. In other embodiments, the MEK protein kinase inhibitor comprises a compound of formula II and is present in an amount of about 1.5 mg to about 50 mg. In other embodiments, the MEK protein kinase inhibitor comprises a compound of formula II and is present in an amount of about 2 mg to about 45 mg. In other embodiments, the MEK protein kinase inhibitor comprises a compound of formula I and is present in an amount of about 2.5 mg to about 40 mg.

In some embodiments of the combinations and methods provided herein, provided are MEK protein kinase inhibitors further comprising a compound of formula II, wherein the compound of formula II is present in an amount of about 0.1 mg, about 0.2 mg, about 0.25 mg, about 0.3 mg, about 0.4 mg, about 0.5 mg, about 0.6 mg, about 0.7 mg, about 0.8 mg, about 0.9 mg, about 1 mg, about 1.5 mg, about 2 mg, about 2.5 mg, about 3 mg, about 3.5 mg, about 4.0 mg, about 4.5 mg, about 5 mg, about 5.5 mg, about 6 mg, about 6.5 mg, about 7 mg, about 7.5 mg, about 8 mg, about 8.5 mg, about 9 mg, about 9.5 mg, about 10 mg, about 10.5 mg, about 11 mg, about 11.5 mg, about 12 mg, about 12.5 mg, and/or about 13 mg, about 14 mg, or about 15 mg.

In some embodiments of the combinations and methods provided herein, provided are MEK protein kinase inhibitors further comprising a compound of formula II, wherein the compound of formula II is present in an amount of about 15 mg, about 20 mg, about 25 mg, about 30 mg, about 35 mg, about 40 mg, about 45 mg, about 50 mg, about 55 mg, about 60 mg, about 65 mg, about 75 mg, about 80 mg, about 85 mg, about 90 mg, about 95 mg, about 100 mg, about 110 mg, about 120 mg, about 125 mg, about 130 mg, about 140 mg, about 150 mg, about 160 mg, about 170 mg, about 175 mg, about 180 mg, about 190 mg, or about 200 mg.

Dosage Amounts of Sorafenib

In another aspect, the combinations and methods described herein provide Raf protein kinase inhibitors wherein the Raf protein kinase inhibitor is sorafenib (Bayer). In some embodiments, the sorafenib is present in an amount of about 10 mg to about 1,000 mg. In further or additional embodiments, the sorafenib is present in an amount of about 20 mg to about 900 mg. In further embodiments, the sorafenib is present in an amount of about 20 mg to about 900 mg. In still further embodiments, the sorafenib is present in an amount of about 30 mg to about 850 mg. In certain embodiments, the sorafenib is present in an amount of about 40 mg to about 800 mg. In still further embodiments, the sorafenib is present in an amount of about 50 mg to about 750 mg. In other embodiments, the sorafenib is present in an amount of about 75 mg to about 700 mg, about 100 mg to about 650 mg, about 150 mg to about 600 mg, about 200 mg to about 500 mg, about 300 mg to about 400 mg.

In further or additional embodiments of the pharmaceutical combinations and methods described herein, the Raf protein kinase inhibitor is sorafenib and is present in an amount of about 10 mg, about 20 mg, about 30 mg, about 40 mg, about 50 mg, about 60 mg, about 70 mg, about 80 mg, about 90 mg, about 100 mg, about 125 mg, about 150 mg, about 200 mg, about 250 mg, about 300 mg, about 350 mg, about 400 mg, about 450 mg, about 500 mg, about 600 mg, about 700 mg, about 750 mg, about 800 mg, about 850 mg, about 900 mg, about 950 mg, or about 1000 mg.

Exemplary Combinations of MEK Inhibitors and Raf Inhibitors

Provided herein are a series of non-limiting examples of exemplary dosage amounts of specific MEK protein kinase inhibitors in combination with Raf protein kinase inhibitors. Upon reading the specification, the person or ordinary skill would understand that any of the dosage amounts disclosed herein and any of the combinations of MEK protein kinase inhibitor and Raf protein kinase inhibitor could be utilized to practice the invention.

In some embodiments, provided are pharmaceutical combinations and methods of treating cancer comprising dosage amount of a MEK protein kinase inhibitor and a dosage amount of a Raf protein kinase inhibitor. In some embodiments, the MEK protein kinase inhibitor is a compound selected from the group consisting of:

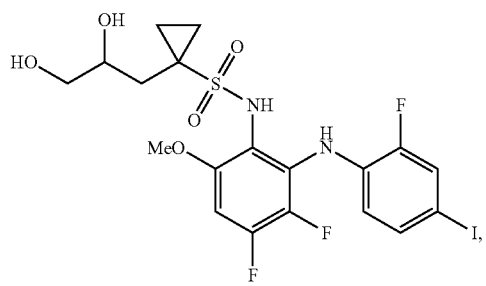

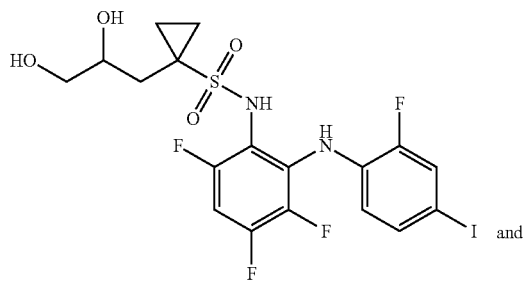

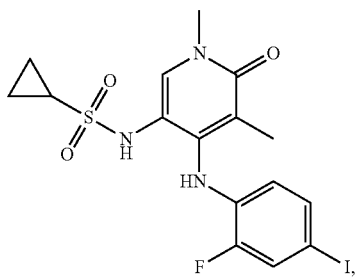

or a pharmaceutically acceptable salt, solvate, polymorph, ester, tautomer or prodrug thereof and is present in an amount of about 0.1 mg to about 200 mg and the Raf protein kinase inhibitor is a sorafenib and is present in an amount of about 10 mg to about 1000 mg. In further or additional embodiments, the MEK protein kinase inhibitor is a compound selected from the group consisting of:

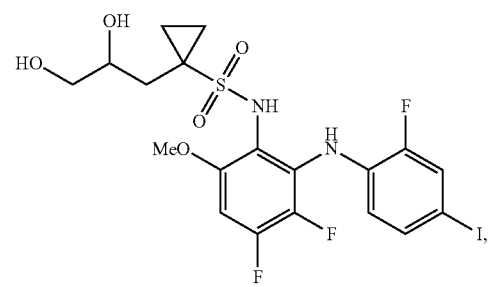

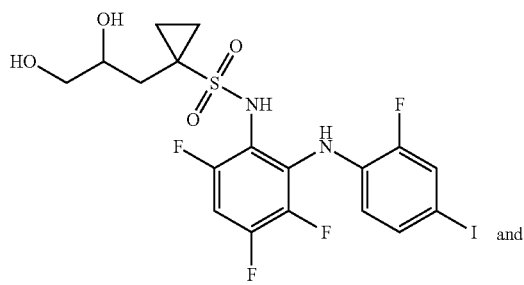

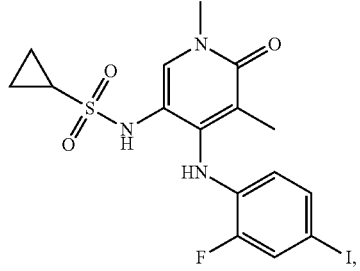

or a pharmaceutically acceptable salt, solvate, polymorph, ester, tautomer or prodrug thereof and is present in an amount of about 0.5 mg to about 100 mg and the Raf protein kinase inhibitor is a sorafenib and is present in an amount of about 50 mg to about 700 mg.

In some embodiments, the sorafenib is present in a dosage amount described herein, and the MEK protein kinase inhibitor is a compound of formula A, formula I, formula II and/or formula III in a dosage amount described herein. In further or additional embodiments, the MEK protein kinase inhibitor is a compound selected from the group consisting of:

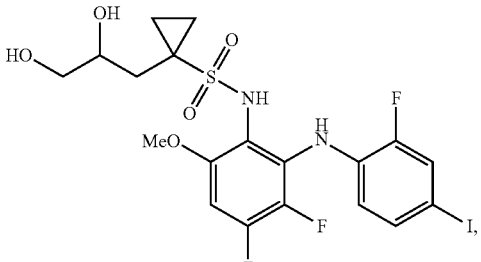

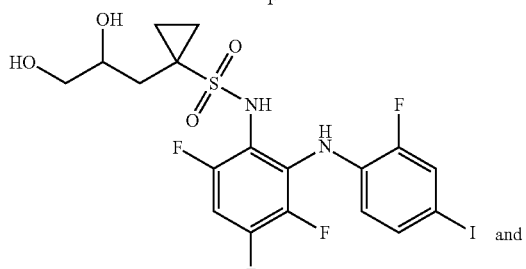

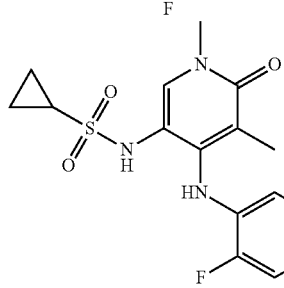

or a pharmaceutically acceptable salt, solvate, polymorph, ester, tautomer or prodrug thereof and is present in an amount of about 2 mg to about 20 mg and the Raf protein kinase inhibitor is a sorafenib and is present in an amount of about 100 mg to about 600 mg. In further or additional embodiments, the MEK protein kinase inhibitor is a compound selected from the group consisting of:

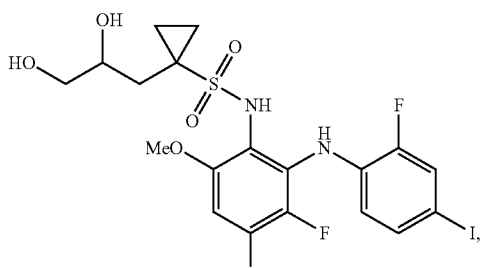

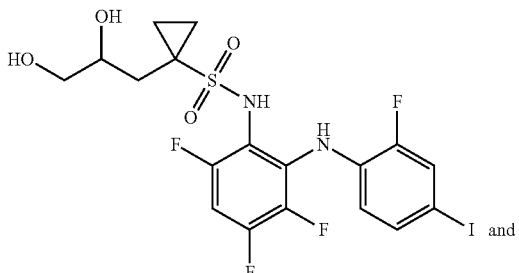

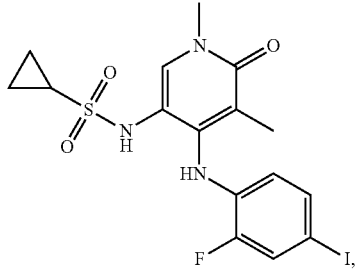

or a pharmaceutically acceptable salt, solvate, polymorph, ester, tautomer or prodrug thereof and is present in an amount of about 2 mg to about 3 mg and the Raf protein kinase inhibitor is a sorafenib and is present in an amount of about 100 mg. In other embodiments, the MEK protein kinase inhibitor is a compound selected from the group consisting of:

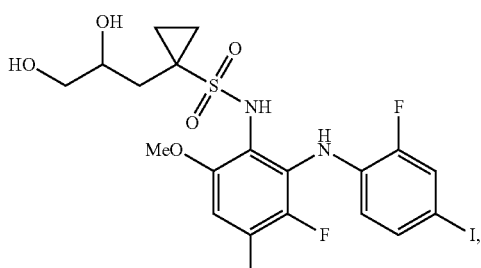

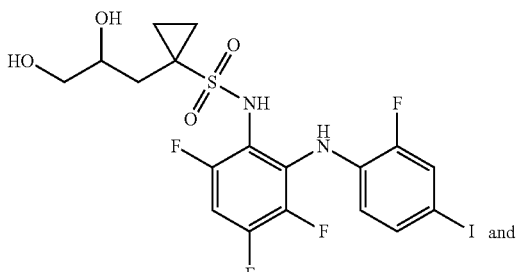

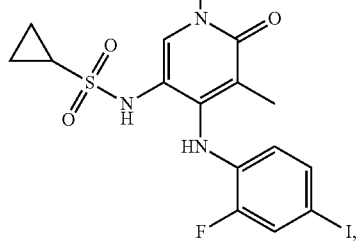

or a pharmaceutically acceptable salt, solvate, polymorph, ester, tautomer or prodrug thereof and is present in an amount of about 4 mg to about 6 mg and the Raf protein kinase inhibitor is a sorafenib and is present in an amount of about 200 mg. In additional embodiments, the MEK protein kinase inhibitor is a compound selected from the group consisting of:

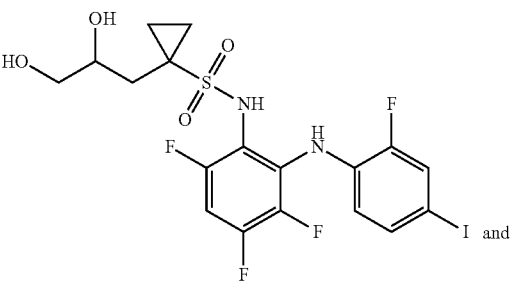

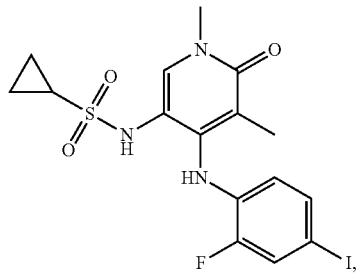

or a pharmaceutically acceptable salt, solvate, polymorph, ester, tautomer or prodrug thereof and is present in an amount of about 7 mg to about 10 mg and the Raf protein kinase inhibitor is a sorafenib and is present in an amount of about 300 mg. In additional embodiments, the MEK protein kinase inhibitor is a compound selected from the group consisting of:

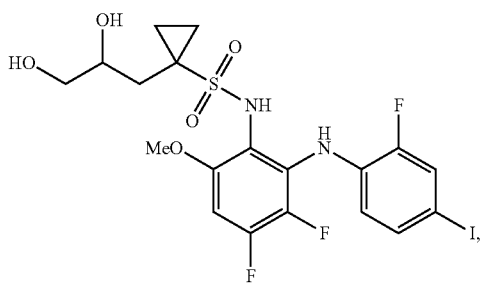

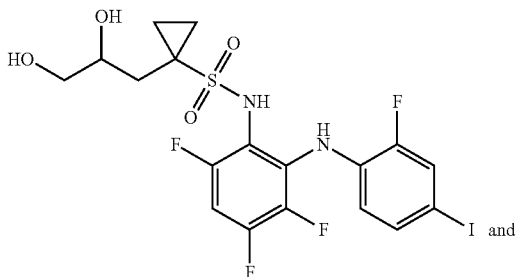

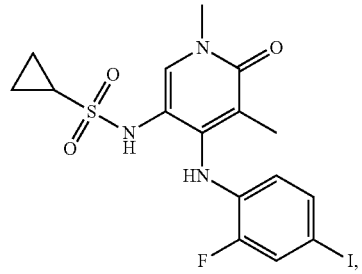

or a pharmaceutically acceptable salt, solvate, polymorph, ester, tautomer or prodrug thereof and is present in an amount of about 10 mg to about 12 mg and the Raf protein kinase inhibitor is a sorafenib and is present in an amount of about 400 mg. In some embodiments, the MEK protein kinase inhibitor is a compound selected from the group consisting of:

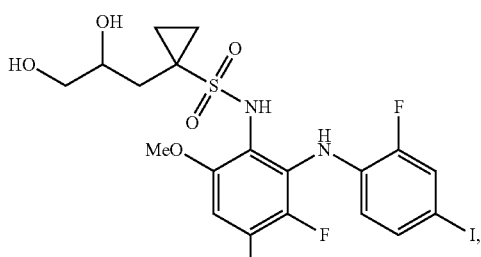

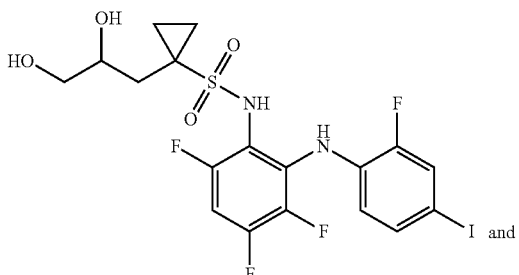

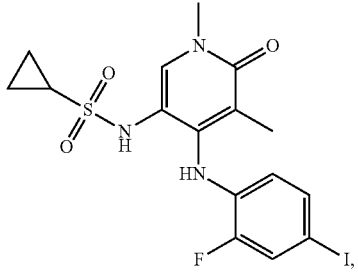

or a pharmaceutically acceptable salt, solvate, polymorph, ester, tautomer or prodrug thereof and is present in an amount of about 13 mg to about 16 mg and the Raf protein kinase inhibitor is a sorafenib and is present in an amount of about 500 mg. In certain embodiments, the MEK protein kinase inhibitor is a compound selected from the group consisting of:

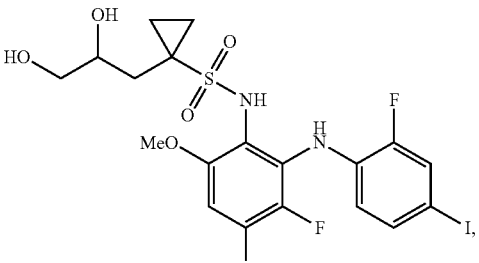

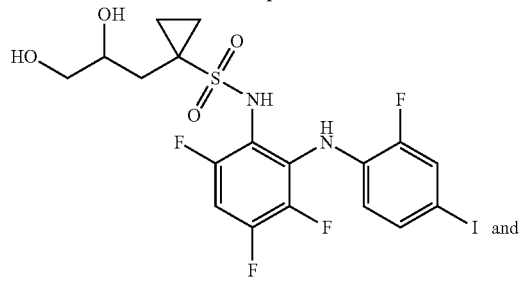

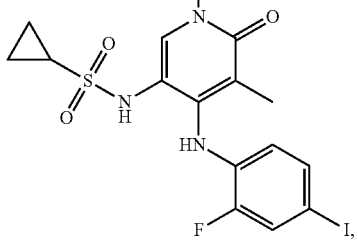

or a pharmaceutically acceptable salt, solvate, polymorph, ester, tautomer or prodrug thereof and is present in an amount of about 16 mg to about 20 mg and the Raf protein kinase inhibitor is a sorafenib and is present in an amount of about 600 mg.

Lower Dosage Amounts of MEK Inhibitors and Raf Inhibitors

In some embodiments, the therapeutically effective amount of the MEK protein kinase inhibitor is lower when administered in combination with the Raf protein kinase inhibitor than when administered alone. In some of these embodiments, the therapeutically effective amount of the MEK protein kinase inhibitor is about 10-50% lower. In some of these embodiments, the therapeutically effective amount of the MEK protein kinase inhibitor is about 50-100% lower. In some of these embodiments, the therapeutically effective amount of the MEK protein kinase inhibitor is about 100-200% lower. In some of these embodiments, the therapeutically effective amount of the MEK protein kinase inhibitor is about 200-300% lower. In some of these embodiments, the therapeutically effective amount of the MEK protein kinase inhibitor is about 300-400% lower. In some of these embodiments, the therapeutically effective amount of the MEK protein kinase inhibitor is about 400-500% lower.

In some embodiments, the therapeutically effective amount of the Raf protein kinase inhibitor is lower when administered in combination with the MEK protein kinase inhibitor than when administered alone. In some of these embodiments, the therapeutically effective amount of the Raf protein kinase inhibitor is about 10-50% lower. In some of these embodiments, the therapeutically effective amount of the Raf protein kinase inhibitor is about 50-100% lower. In some of these embodiments, the therapeutically effective amount of the Raf protein kinase inhibitor is about 100-200% lower. In some of these embodiments, the therapeutically effective amount of the Raf protein kinase inhibitor is about 200-300% lower. In some of these embodiments, the therapeutically effective amount of the Raf protein kinase inhibitor is about 300-400% lower. In some of these embodiments, the therapeutically effective amount of the Raf protein kinase inhibitor is about 400-500% lower.

Dosage Forms

The pharmaceutical composition may, for example, be in a form suitable for oral administration as a tablet, capsule, pill, powder, sustained release formulations, solution, suspension, for parenteral injection as a sterile solution, suspension or emulsion, for topical administration as an ointment or cream or for rectal administration as a suppository. The pharmaceutical composition may be in unit dosage forms suitable for single administration of precise dosages. The pharmaceutical composition will include a conventional pharmaceutical carrier or excipient and a compound according to the invention as an active ingredient. In addition, it may include other medicinal or pharmaceutical agents, carriers, adjuvants, etc.

Exemplary parenteral administration forms include solutions or suspensions of active compounds in sterile aqueous solutions, for example, aqueous propylene glycol or dextrose solutions. Such dosage forms can be suitably buffered, if desired.

Suitable pharmaceutical carriers include inert diluents or fillers, water and various organic solvents. The pharmaceutical compositions may, if desired, contain additional ingredients such as flavorings, binders, excipients and the like. Thus for oral administration, tablets containing various excipients, such as citric acid may be employed together with various disintegrants such as starch, alginic acid and certain complex silicates and with binding agents such as sucrose, gelatin and acacia. Additionally, lubricating agents such as magnesium stearate, sodium lauryl sulfate and talc are often useful for tableting purposes. Solid compositions of a similar type may also be employed in soft and hard filled gelatin capsules, including lactose or milk sugar and high molecular weight polyethylene glycols. When aqueous suspensions or elixirs are desired for oral administration the active compound therein may be combined with various sweetening or flavoring agents, coloring matters or dyes and, if desired, emulsifying agents or suspending agents, together with diluents such as water, ethanol, propylene glycol, glycerin, or combinations thereof.

Methods of preparing various pharmaceutical compositions with a specific amount of active compound are known, or will be apparent, to those skilled in this art. For examples, see Remington's Pharmaceutical Sciences, Mack Publishing Company, Ester, Pa., 18th Edition (1990).

Additional Therapies

The combinations comprising a MEK protein kinase inhibitor and a Raf protein kinase inhibitor described herein may be administered as a sole therapy. The MEK protein kinase inhibitor and Raf protein kinase inhibitor combinations and compounds described herein or a pharmaceutically acceptable salt, solvate, polymorph, ester, amide, tautomer, prodrug, hydrate, or derivative thereof may also be administered in combination with another therapy or therapies.

By way of example only, if one of the side effects experienced by a patient upon receiving one of the compounds described herein is hypertension, then it may be appropriate to administer an anti-hypertensive agent in combination with the compound. Or, by way of example only, the therapeutic effectiveness of one of the compounds described herein may be enhanced by administration of an adjuvant (i.e., by itself the adjuvant may only have minimal therapeutic benefit, but in combination with another therapeutic agent, the overall therapeutic benefit to the patient is enhanced). Or, by way of example only, the benefit experienced by a patient may be increased by administering one of the compounds described herein with another therapeutic agent (which also includes a therapeutic regimen) that also has therapeutic benefit. By way of example only, in a treatment for diabetes involving administration of one of the compounds described herein, increased therapeutic benefit may result by also providing the patient with another therapeutic agent for diabetes. In any case, regardless of the disease, disorder or condition being treated, the overall benefit experienced by the patient may simply be additive of the two therapeutic agents or the patient may experience a synergistic benefit.

Other therapies include, but are not limited to administration of other therapeutic agents, radiation therapy or both. In the instances where the compounds described herein are administered with other therapeutic agents, the compounds described herein need not be administered in the same pharmaceutical composition as other therapeutic agents, and may, because of different physical and chemical characteristics, be administered by a different route. For example, the compounds/compositions may be administered orally to generate and maintain good blood levels thereof, while the other therapeutic agent may be administered intravenously. The determination of the mode of administration and the advisability of administration, where possible, in the same pharmaceutical composition, is well within the knowledge of the skilled clinician. The initial administration can be made according to established protocols known in the art, and then, based upon the observed effects, the dosage, modes of administration and times of administration can be modified by the skilled clinician. The particular choice of compound (and where appropriate, other therapeutic agent and/or radiation) will depend upon the diagnosis of the attending physicians and their judgment of the condition of the patient and the appropriate treatment protocol. Other therapeutic agents may include chemotherapeutic agents, such as anti-tumor substances, for example those selected from, mitotic inhibitors, for example vinblastine; alkylating agents, for example cis-platin, carboplatin and cyclophosphamide; anti-metabolites, for example 5-fluorouracil, cytosine arabinside and hydroxyurea, or, for example, an anti-metabolite disclosed in European Patent Application No. 239362 such as N-(5-[N-(3,4-dihydro-2-methyl-4-oxoquinazolin-6-ylmethyl)-N-methylamino]-2-thenyl)-L-glutamic acid; growth factor inhibitors; cell cycle inhibitors; intercalating antibiotics, for example adriamycin and bleomycin; enzymes, for example, interferon; and anti-hormones, for example anti-estrogens such as Nolvadex™ (tamoxifen) or, for example anti-androgens such as Casodex™ (4'-cyano-3-(4-fluorophenylsulphonyl)-2-hydroxy-2-methyl-3'-(trifluoromethyl)propionanilide). Such conjoint treatment may be achieved by way of the simultaneous, sequential or separate dosing of the individual components of treatment.

The combinations comprising a MEK protein kinase inhibitor and a Raf protein kinase inhibitor described herein, and compositions described herein (and where appropriate chemotherapeutic agent and/or radiation) may be administered concurrently (e.g., simultaneously, essentially simultaneously or within the same treatment protocol) or sequentially, depending upon the nature of the disease, the condition of the patient, and the actual choice of chemotherapeutic agent and/or radiation to be administered in conjunction (i.e., within a single treatment protocol) with the compound/composition.

The combinations comprising a MEK protein kinase inhibitor and a Raf protein kinase inhibitor described herein in certain applications and uses, e.g. in the form of a pharmaceutically acceptable composition, further comprise a chemotherapeutic agent and/or radiation which need not be administered simultaneously or essentially simultaneously, and the initial order of administration of the combination and the chemotherapeutic agent and/or radiation, may not be important. Thus, the combinations described herein may be administered first followed by the administration of the chemotherapeutic agent and/or radiation; or the chemotherapeutic agent and/or radiation may be administered first followed by the administration of the compounds/compositions of the invention. This alternate administration may be repeated during a single treatment protocol. The determination of the order of administration, and the number of repetitions of administration of each therapeutic agent during a treatment protocol, is well within the knowledge of the skilled physician after evaluation of the disease being treated and the condition of the patient. For example, the chemotherapeutic agent and/or radiation may be administered first, especially if it is a cytotoxic agent, and then the treatment continued with the administration of the pharmaceutical combinations described herein followed, where determined advantageous, by the administration of the chemotherapeutic agent and/or radiation, and so on until the treatment protocol is complete. Thus, in accordance with experience and knowledge, the practicing physician can modify each protocol for the administration of the combination for treatment according to the individual patient's needs, as the treatment proceeds. The attending clinician, in judging whether treatment is effective at the dosage administered, will consider the general well-being of the patient as well as more definite signs such as relief of disease-related symptoms, inhibition of tumor growth, actual shrinkage of the tumor, or inhibition of metastasis. Size of the tumor can be measured by standard methods such as radiological studies, e.g., CAT or MRI scan, and successive measurements can be used to judge whether or not growth of the tumor has been retarded or even reversed. Relief of disease-related symptoms such as pain, and improvement in overall condition can also be used to help judge effectiveness of treatment.

Specific, non-limiting examples of possible therapies administered with the pharmaceutical combinations described herein include use of the compounds of the invention with agents found in the following pharmacotherapeutic classifications as indicated below. These lists should not be construed to be closed, but should instead serve as illustrative examples common to the relevant therapeutic area at present. Moreover, combination regimens may include a variety of routes of administration and should include oral, intravenous, intraocular, subcutaneous, dermal, and inhaled topical.

For the treatment of oncologic diseases, proliferative disorders, and cancers, compounds according to the present invention may be administered with an agent selected from the group comprising: aromatase inhibitors, antiestrogen, anti-androgen, corticosteroids, gonadorelin agonists, topoisomerase 1 and 2 inhibitors, microtubule active agents, alkylating agents, nitrosoureas, antineoplastic antimetabolites, platinum containing compounds, lipid or protein kinase targeting agents, IMiDs, protein or lipid phosphatase targeting agents, anti-angiogenic agents, Akt inhibitors, IGF-I inhibitors, FGF3 modulators, mTOR inhibitors, Smac mimetics, HDAC inhibitors, agents that induce cell differentiation, bradykinin 1 receptor antagonists, angiotensin II antagonists, cyclooxygenase inhibitors, heparanase inhibitors, lymphokine inhibitors, cytokine inhibitors, IKK inhibitors, P38MAPK inhibitors, ARRY-797, HSP90 inhibitors, multlikinase inhibitors, bisphosphanates, rapamycin derivatives, anti-apoptotic pathway inhibitors, apoptotic pathway agonists, PPAR agonists, RAR agonists, inhibitors of Ras isoforms, telomerase inhibitors, protease inhibitors, metalloproteinase inhibitors, aminopeptidase inhibitors, SHIP activators-AQX-MN100, Humax-CD20 (ofatumumab), CD20 antagonists, IL2-diptheria toxin fusions.

For the treatment of oncologic diseases, proliferative disorders, and cancers, compounds according to the present invention may be administered with an agent selected from the group comprising: dacarbazine (DTIC), actinomycins C2, C3, D, and F1, cyclophosphamide, melphalan, estramustine, maytansinol, rifamycin, streptovaricin, doxorubicin, daunorubicin, epirubicin, idarubicin, detorubicin, carininomyein, idarubicin, epirubicin, esorubicin, mitoxantrone, bleomyeins A, A2, and B, camptothecin, Irinotecan®, Topotecan®, 9-aminocamptothecin, 10,11-methylenedioxycamptothecin, 9-nitrocamptothecin, bortezomib, temozolomide, TAS103, NPI0052, combretastatin, combretastatin A-2, combretastatin A-4, calicheamicins, neocarcinostatins, epothilones A B, C, and semi-synthetic variants, Hereeptin®, Rituxan®, CD40 antibodies, asparaginase, interleukins, interferons, leuprolide, and pegaspargase, 5-fluorouracil, fluorodeoxyuridine, ptorafur, 5'-deoxyfluorouridine, UFT, MITC, S-1 capecitabine, diethylstilbestrol, tamoxifen, toremefine, tolmudex, thymitaq, flutamide, fluoxymesterone, bicalutamide, finasteride, estradiol, trioxifene, dexamethasone, leuproelin acetate, estramustine, droloxifene, medroxyprogesterone, megesterol acetate, aminoglutethimide, testolactone, testosterone, diethylstilbestrol, hydroxyprogesterone, mitomycins A, B and C, porfiromycin, cisplatin, carboplatin, oxaliplatin, tetraplatin, platinum-DACH, ormaplatin, thalidomide, lenalidomide, CI-973, telomestatin, CHIR258, Rad 001, SAHA, Tubacin, 17-AAG, sorafenib, IM-216, podophyllotoxin, epipodophyllotoxin, etoposide, teniposide, Tarceva®, Iressa®, Imatinib®, Miltefosine®, Perifosine®, aminopterin, methotrexate, methopterin, dichloro-methotrexate, 6-mercaptopurine, thioguanine, azattuoprine, allopurinol, cladribine, fludarabine, pentostatin, 2-chloroadenosine, deoxycytidine, cytosine arabinoside, cytarabine, azacitidine, 5-azacytosine, gencitabine, 5-azacytosine-arabinoside, vincristine, vinblastine, vinorelbine, leurosine, leurosidine and vindesine, paclitaxel, taxotere and docetaxel.

For the treatment of inflammatory diseases or pain, compounds and pharmaceutically acceptable salts of the compounds according to the present invention may be administered with an agent selected from the group comprising: corticosteroids, non-steroidal anti-inflammatories, muscle relaxants and combinations thereof with other agents, anaesthetics and combinations thereof with other agents, expectorants and combinations thereof with other agents, antidepressants, anticonvulsants and combinations thereof; antihypertensives, opioids, topical cannabinoids, capsaicin, betamethasone dipropionate (augmented and non-augemnted), betamethasone valerate, clobetasol propionate, prednisone, methyl prednisolone, diflorasone diacetate, halobetasol propionate, amcinonide, dexamethasone, dexosimethasone, fluocinolone acetononide, fluocinonide, halocinonide, clocortalone pivalate, dexosimetasone, flurandrenalide, salicylates, ibuprofen, ketoprofen, etodolac, diclofenac, meclofenamate sodium, naproxen, piroxicam, celecoxib, cyclobenzaprine, baclofen, cyclobenzaprine/lidocaine, baclofen/cyclobenzaprine, cyclobenzaprine/lidocaine/ketoprofen, lidocaine, lidocaine/deoxy-D-glucose, prilocalne, EMLA Cream (Eutectic Mixture of Local Anesthetics (lidocaine 2.5% and prilocalne 2.5%), guaifenesin, guaifenesin/ketoprofen/cyclobenzaprine, amitryptiline, doxepin, desipramine, imipramine, amoxapine, clomipramine, nortriptyline, protriptyline, duloxetine, mirtazepine, nisoxetine, maprotiline, reboxetine, fluoxetine, fluvoxamine, carbamazepine, felbamate, lamotrigine, topiramate, tiagabine, oxcarbazepine, carbamezipine, zonisamide, mexiletine, gabapentin/clonidine, gabapentin/carbarnazepine, carbamazepine/cyclobenzaprine, antihypertensives including clonidine, codeine, loperamide, tramadol, morphine, fentanyl, oxycodone, hydrocodone, levorphanol, butorphanol, menthol, oil of wintergreen, camphor, eucalyptus oil, turpentine oil; CBUCB2 ligands, acetaminophen, infliximab, nitric oxide synthase inhibitors, particularly inhibitors of inducible nitric oxide synthase, PDE4 inhibitors—similar mechanism to Ibudilast (AV-411), CDC-801, JNK inhibitors—CC-401, Combination TNF/PDE4 inhibitors—CDC-998, IL1 antagonists e.g. Anakinra-Kineret, AMG 108, (mAb) that targets IL-1, SHIP activators—AQX-MN100, C5 antagonists, C5a inhibitors, Pexelizumab, Pyrimidine synthesis inhibitors, lymphokine inhibitors, cytokine inhibitors, IKK inhibitors, P38MAPK inhibitors, ARRY-797, FISP90 inhibitors, multlikinase inhibitors, bisphosphanates, PPAR agonists, Cox1 and cox 2 inhibitors, Anti-CD4 therapy, B-cell inhibitors, COX/LOX dual inhibitors, Immunosuppressive agents, iNOS inhibitors, NSAIDs, sPLA2 inhibitors, Colchicine, allopurinol, oxypurinol, Gold, Ridaura—Auranofin, febuxostat, Puricase, PEG-uricase formulations, Benzbromarone, Long-acting beta-2 agonists (LABAs), salmeterol (Serevent Diskus) and formoterol (Foradil), Leukotriene modifiers include montelukast (Singulair) and zafirlukast (Accolate). Inhaled cromolyn (Intal) or nedocromil (Tilade), Theophylline. Short-acting beta-2 agonists, Ipratropium (Atrovent), Immunotherapy-(Allergy-desensitization shots), Anti-IgE monoclonal antibodies —Xolair, Common DMARDs include hydroxychloroquine (Plaquenil), the gold compound auranofin (Ridaura), sulfasalazine (Azulfidine), minocycline (Dynacin, Minocin) and methotrexate (Rheumatrex), leflunomide (Arava), azathioprine (Imuran), cyclosporine (Neoral, Sandimmune) and cyclophosphamide (Cytoxan), Antibiotics, CD80 antagonists, costimulatory factor antagonists, Humax-CD20 (ofatumumab); CD20 antagonists, MEK inhibitors, NF kappa B inhibitors, anti B-cell antibodies, denosumab, mAb that specifically targets the receptor activator of nuclear factor kappa B ligand (RANKL). IL17 inactivating anti-bodies, IL-17 receptor antagonists/inhibitors, CTLA inhibitors, CD20 inhibitors, soluble VEGFR-1 receptors, anti-VEGFR-1 receptor antibodies, anti-VEGF antibodies, integrin receptor antagonist, Selectin inhibitors, P-selectin and E-selectin inhibitors, Phospholipase A2 Inhibitors, Lipoxygenase Inhibitors, RANKL and RANK antagonists/antibodies, Osteoprotegerin antagonists, Lymphotoxin inhibitors, B-lymphocyte stimulator, MCP-1 inhibitors, MIF inhibitors, inhibitors of: CD2, CD3, CD4, CD25, CD40 and CD40 Ligand CD152 (CTLA4), Macrolide immunosuppressants, Selective inhibitors of nucleotide metabolism, Inhibitors of chemotaxis, CXC receptor and CXC ligand inhibitors, Chemokine Antagonists, leukocyte chemotaxis inhibitors Adhesion Molecule blockers, Selectins Lymphocyte Function Antigen-1 (LFA-1, CD11a) antagonists, Very Late Antigen-4 (VLA-4) antagonists, Matrix Metalloprotease Inhibitors, Elastase Inhibitors, Cathepsin Inhibitors.

For the treatment of ophthalmologic disorders and diseases of the eye, compounds and pharmaceutically acceptable salts of the compounds according to the present invention may be administered with an agent selected from the group comprising: beta-blockers, carbonic anhydrase inhibitors, .alpha.- and .beta.-adrenergic antagonists including a1-adrenergic antagonists, .alpha.2 agonists, miotics, prostaglandin analogs, corticosteroids, and immunosuppressant agents.

For the treatment of ophthalmologic disorders and diseases of the eye, compounds pharmaceutically acceptable salts of the compounds according to the present invention may be administered with an agent selected from the group comprising: timolol, betaxolol, levobetaxolol, carteolol, levobunolol, propranolol, brinzolamide, dorzolamide, nipradilol, iopidine, brimonidine, pilocarpine, epinephrine, latanoprost, travoprost, bimatoprost, unoprostone, dexamethasone, prednisone, methylprednisolone, azathioprine, cyclosporine, and immunoglobulins.

For the treatment of autoimmune disorders, compounds pharmaceutically acceptable salts of the compounds according to the present invention may be administered with an agent selected from the group comprising: corticosteroids, immunosuppressants, prostaglandin analogs and antimetabolites.

For the treatment of autoimmune disorders, compounds according to the present invention may be administered with an agent selected from the group comprising: dexamethasome, prednisone, methylprednisolone, azathioprine, cyclosporine, immunoglobulins, latanoprost, travoprost, bimatoprost, unoprostone, infliximab, rutuximab, methotrexate, non-steroidal anti-inflammatories, muscle relaxants and combinations thereof with other agents, anaesthetics and combinations thereof with other agents, expectorants and combinations thereof with other agents, antidepressants, anti-convulsants and combinations thereof; antihypertensives, opioids, topical cannabinoids, and other agents, such as capsaicin, betamethasone dipropionate (augmented and nonaugmented), betamethasone valerate, clobetasol propionate, prednisone, methyl prednisolone, diflorasone diacetate, halobetasol propionate, amcinonide, dexamethasone, dexosimethasone, fluocinolone acetononide, fluocinonide, halocinonide, clocortalone pivalate, dexosimetasone, flurandrenalide, salicylates, ibuprofen, ketoprofen, etodolac, diclofenac, meclofenamate sodium, naproxen, piroxicam, celecoxib, cyclobenzaprine, baclofen, cyclobenzaprine/lidocaine, baclofen/cyclobenzaprine, cyclobenzaprine/lidocaine/ketoprofen, lidocaine, lidocaine/deoxy-D-glucose, prilocalne, EMLA Cream (Eutectic Mixture of Local Anesthetics (lidocaine 2.5% and prilocalne 2.5%), guaifenesin, guaifenesin/ketoprofen/cyclobenzaprine, amitryptiline, doxepin, desipramine, imipramine, amoxapine, clomipramine, nortriptyline, protriptyline, duloxetine, mirtazepine, nisoxetine, maprotiline, reboxetine, fluoxetine, fluvoxamine, carbamazepine, felbamate, lamotrigine, topiramate, tiagabine, oxcarbazepine, carbamezipine, zonisamide, mexiletine, gabapentin/clonidine, gabapentin/carbamazepine, carbamazepine/cyclobenzaprine, antihypertensives including clonidine, codeine, loperamide, tramadol, morphine, fentanyl, oxycodone, hydrocodone, levorphanol, butorphanol, menthol, oil of wintergreen, camphor, eucalyptus oil, turpentine oil; CB1/CB2 ligands, acetaminophen, infliximab; nitric oxide synthase inhibitors, particularly inhibitors of inducible nitric oxide synthase; and other agents, such as capsaicin. PDE4 inhibitors—similar mechanism to Ibudilast (AV-411), CDC-801, JNK inhibitors —CC-401, Combination TNF/PDE4 inhibitors —CDC-998, IL1 antagonists e.g. Anakinra-Kineret, AMG 108, (mAb) that targets IL-1, SHIP activators—AQX-MN100, C5 antagonists, C5a inhibitors, Pexelizumab, Pyrimidine synthesis inhibitors, lymphokine inhibitors, cytokine inhibitors, IKK inhibitors, P38MAPK inhibitors, ARR-797, HSP90 inhibitors, multlikinase inhibitors, bisphosphanates, PPAR agonists, Cox1 and cox 2 inhibitors, Anti-CD4 therapy, B-cell inhibitors, COX/LOX dual inhibitors, Immunosuppressive agents, iNOS inhibitors, NSAIDs, sPLA2 inhibitors, Colchicine, allopurinol, oxypurinol, Gold, Ridaura Auranofin, febuxostat, Puricase, PEG-uricase formulations, Benzbromarone, Long-acting beta-2 agonists (LABAs), salmeterol (Serevent Diskus) and formoterol (Foradil), Leukotriene modifiers include montelukast (Singulair) and zafirlukast (Accolate). Inhaled cromolyn (Intal) or nedocromil (Tilade), Theophylline. Short-acting beta-2 agonists, Ipratropium (Atrovent), Immunotherapy-(Allergy-desensitization shots), Anti-IgE monoclonal antibodies—Xolair, Common DMARDs include hydroxychloroquine (Plaquenil), the gold compound auranofin (Ridaura), sulfasalazine (Azulfidine), minocycline (Dynacin, Minocin) and methotrexate (Rheumatrex), leflunomide (Arava), azathioprine (Imuran), cyclosporine (Neoral, Sandimmune) and cyclophosphamide (Cytoxan), Antibiotics, CD80 antagonists, costimulatory factor antagonists, Humax-CD20 (ofatumumab); CD20 antagonists, MEK inhibitors, NF kappa B inhibitors, anti B-cell antibodies, denosumab, mAb that specifically targets the receptor activator of nuclear factor kappa B ligand (RANKL). IL17 inactivating anti-bodies, IL-17 receptor antagonists/inhibitors, CTLA inhibitors, CD20 inhibitors, soluble VEGFR-1 receptors, anti-VEGFR-1 receptor antibodies, anti-VEGF antibodies, integrin receptor antagonist, Selectin inhibitors, P-selectin and E-selectin inhibitors, Phospholipase A2 Inhibitors, Lipoxygenase Inhibitors, RANKL and RANK antagonists/antibodies, Osteoprotegerin antagonists, Lymphotoxin inhibitors, B-lymphocyte stimulator, MCP-1 inhibitors, MIF inhibitors, inhibitors of: CD2, CD3, CD4, CD25, CD40 and CD40 Ligand CD152 (CTLA4), Macrolide immunosuppressants, Selective inhibitors of nucleotide metabolism, Inhibitors of chemotaxis, CXC receptor and CXC ligand inhibitors, Chemokine Antagonists, leukocyte chemotaxis inhibitors Adhesion Molecule blockers, Selectins Lymphocyte Function Antigen-1 (LFA-1, CD 11a) antagonists, Very Late Antigen-4 (VLA-4) antagonists, Matrix Metalloprotease Inhibitors, Elastase Inhibitors, Cathepsin Inhibitors.

For the treatment of metabolic disorders, compounds and pharmaceutically acceptable salts of the compounds according to the present invention may be administered with an agent selected from the group comprising: insulin, insulin derivatives and mimetics, insulin secretagogues, insulin sensitizers, biguanide agents, alpha-glucosidase inhibitors, insulinotropic sulfonylurea receptor ligands, protein tyrosine phosphatase-1B (PTP-1B) inhibitors, GSK3 (glycogen synthase kinase-3) inhibitors, GLP-1 (glucagon like peptide-1), GLP-1 analogs, DPPIV (dipeptidyl peptidase IV) inhibitors, RXR ligands sodium-dependent glucose co-transporter inhibitors, glycogen phosphorylase A inhibitors, an AGE breaker, PPAR modulators, LXR and FXR modulators, non-glitazone type PPARS agonist, selective glucocorticoid antagonists, metformin, Glipizide, glyburide, Amaryl, meglitinides, nateglinide, repaglinide, PT-112, SB-517955, SB4195052, SB-216763, NN-57-05441, NN-57-05445, GW-0791, AGN-.sup.194.sup.204, T-1095, BAY R3401, acarbose Exendin-4, DPP728, LAF237, vildagliptin, MK-0431, saxagliptin, GSK23A, pioglitazone, rosiglitazone, (R)-1-{4-[5-methyl-2-(4-trifluoromethyl-phenyl)-oxazol-4-ylmethoxy]-benze-nesulfonyl}2,3-dihydro-1H-indole-2-carboxylic acid described in the patent application WO 03/043985, as compound 19 of Example 4, and GI-262570.

Diseases

Described herein are methods of treating a disease in an individual suffering from said disease comprising administering to said individual an effective amount of a MEK protein kinase and Raf protein kinase inhibitor or a pharmaceutically acceptable salt, solvate, polymorph, ester, amide, tautomer, prodrug, hydrate, or derivative thereof.

In certain aspects of the invention, the disease is a hyperproliferative condition of the human or animal body, including, but not limited to cancer, hyperplasias, restenosis, inflammation, immune disorders, cardiac hypertrophy, atherosclerosis, pain, migraine, angiogenesis-related conditions or disorders, proliferation induced after medical conditions, including but not limited to surgery, angioplasty, or other conditions.

In further embodiments, said hyperproliferative condition is selected from the group consisting of hematologic and nonhematologic cancers. In yet further embodiments, said hematologic cancer is selected from the group consisting of multiple myeloma, leukemias, and lymphomas. In yet further embodiments, said leukemia is selected from the group consisting of acute and chronic leukemias. In yet further embodiments, said acute leukemia is selected from the group consisting of acute lymphocytic leukemia (ALL) and acute nonlymphocytic leukemia (ANLL). In yet further embodiments, said chronic leukemia is selected from the group consisting of chronic lymphocytic leukemia (CLL) and chronic myelogenous leukemia (CML). In further embodiments, said lymphoma is selected from the group consisting of Hodgkin's lymphoma and non-Hodgkin's lymphoma. In further embodiments, said hematologic cancer is multiple myeloma. In other embodiments, said hematologic cancer is of low, intermediate, or high grade. In other embodiments, said nonhematologic cancer is selected from the group consisting of: brain cancer, cancers of the head and neck, lung cancer, breast cancer, cancers of the reproductive system, cancers of the digestive system, pancreatic cancer, stomach cancer, and cancers of the urinary system. In further embodiments, said cancer of the digestive system is a cancer of the upper digestive tract or colorectal cancer. In further embodiments, said cancer of the urinary system is bladder cancer or renal cell carcinoma. In further embodiments, said cancer of the reproductive system is prostate cancer.

Additional types of cancers which may be treated using the compounds and methods described herein include: cancers of oral cavity and pharynx, cancers of the respiratory system, cancers of bones and joints, cancers of soft tissue, skin cancers, cancers of the genital system, cancers of the eye and orbit, cancers of the nervous system, cancers of the lymphatic system, and cancers of the endocrine system. In certain embodiments, these cancer s may be selected from the group consisting of: cancer of the tongue, mouth, pharynx, or other oral cavity; esophageal cancer, stomach cancer, or cancer of the small intestine; colon cancer or rectal, anal, or anorectal cancer; cancer of the liver, intrahepatic bile duct, gallbladder, pancreas, or other biliary or digestive organs; laryngeal, bronchial, and other cancers of the respiratory organs; heart cancer, melanoma, basal cell carcinoma, squamous cell carcinoma, other non-epithelial skin cancer; uterine or cervical cancer; uterine corpus cancer; ovarian, vulvar, vaginal, or other female genital cancer; prostate, testicular, penile or other male genital cancer; urinary bladder cancer; cancer of the kidney; renal, pelvic, or urethral cancer or other cancer of the genito-urinary organs; thyroid cancer or other endocrine cancer; chronic lymphocytic leukemia; and cutaneous T-cell lymphoma, both granulocytic and monocytic.

Yet other types of cancers which may be treated using the compounds and methods described herein include: adenocarcinoma, angiosarcoma, astrocytoma, acoustic neuroma, anaplastic astrocytoma, basal cell carcinoma, blastoglioma, chondrosarcoma, choriocarcinoma, chordoma, craniopharyngioma, cutaneous melanoma, cystadenocarcinoma, endotheliosarcoma, embryonal carcinoma, ependymoma, Ewing's tumor, epithelial carcinoma, fibrosarcoma, gastric cancer, genitourinary tract cancers, glioblastoma multiforme, hemangioblastoma, hepatocellular carcinoma, hepatoma, Kaposi's sarcoma, large cell carcinoma, leiomyosarcoma, liposarcoma, lymphangiosarcoma, lymphangioendotheliosarcoma, medullary thyroid carcinoma, medulloblastoma, meningioma mesothelioma, myelomas, myxosarcoma neuroblastoma, neurofibrosarcoma, oligodendroglioma, osteogenic sarcoma, epithelial ovarian cancer, papillary carcinoma, papillary adenocarcinomas, parathyroid tumors, pheochromocytoma, pinealoma, plasmacytomas, retinoblastoma, rhabdomyosarcoma, sebaceous gland carcinoma, seminoma, skin cancers, melanoma, small cell lung carcinoma, squamous cell carcinoma, sweat gland carcinoma, synovioma, thyroid cancer, uveal melanoma, and Wilds tumor.

Also described are methods for the treatment of a hyperproliferative disorder in a mammal that comprise administering to said mammal a therapeutically effective amount of a MEK protein kinase and Raf protein kinase inhibitor, or a pharmaceutically acceptable salt, solvate, polymorph, ester, amide, tautomer, prodrug, hydrate, or derivative thereof, in combination with an anti-tumor agent. In some embodiments, the anti-tumor agent is selected from the group consisting of mitotic inhibitors, alkylating agents, anti-metabolites, intercalating antibiotics, growth factor inhibitors, cell cycle inhibitors, enzyme inhibitors, topoisomerase inhibitors, biological response modifiers, anti-hormones, angiogenesis inhibitors, anti-androgens, SHIP activators—AQX-MN100, Humax-CD20 (ofatumumab), CD20 antagonists, IL2-diptheria toxin fusions.

The disease to be treated using the compounds, compositions and methods described herein may be a hematologic disorder. In certain embodiments, said hematologic disorder is selected from the group consisting of sickle cell anemia, myelodysplastic disorders (MDS), and myeloproliferative disorders. In further embodiments, said myeloproliferative disorder is selected from the group consisting of polycythemia vera, myelofibrosis and essential thrombocythemia.

Further, the disease to be treated by the compounds, compositions and methods described herein may cancer such as acute myeloid leukemia, thymus, brain, lung, squamous cell, skin, eye, retinoblastoma, intraocular melanoma, oral cavity and oropharyngeal, bladder, gastric, stomach, pancreatic, stomach, bladder, breast, cervical, head, neck, renal, kidney, liver, ovarian, prostate, colorectal, esophageal, testicular, gynecological, thyroid, CNS, PNS, AIDS related AIDS-Related (e.g. Lymphoma and Kaposi's Sarcoma) or Viral-Induced cancer. In some embodiments, the compounds and compositions are for the treatment of a non-cancerous hyperproliferative disorder such as benign hyperplasia of the skin (e.g., psoriasis), restenosis, or prostate (e.g., benign prostatic hypertrophy (BPH)).

Further, the disease to be treated by the compounds, compositions and methods described herein may pancreatitis, kidney disease (including proliferative glomerulonephritis and diabetes-induced renal disease), pain, a disease related to vasculogenesis or angiogenesis, tumor angiogenesis, chronic inflammatory disease such as rheumatoid arthritis, inflammatory bowel disease, atherosclerosis, skin diseases such as psoriasis, eczema, and scleroderma, diabetes, diabetic retinopathy, retinopathy of prematurity, age-related macular degeneration, hemangioma, tendonitis, bursitis, sciatica, glioma, melanoma, Kaposi's sarcoma and ovarian, breast, lung, pancreatic, stomach cancer, prostate, colon and epidermoid cancer in a mammal.

Further, the disease to be treated by the compounds, compositions and methods described herein may the prevention of blastocyte implantation in a mammal.

Patients that can be treated with the combinations described herein include, for example, patients that have been diagnosed as having breast cancer such as a ductal carcinoma in duct tissue in a mammary gland, medullary carcinomas, colloid carcinomas, tubular carcinomas, and inflammatory breast cancer; ovarian cancer, including epithelial ovarian tumors such as adenocarcinoma in the ovary and an adenocarcinoma that has migrated from the ovary into the abdominal cavity; uterine cancer; cervical cancer such as adenocarcinoma in the cervix epithelial including squamous cell carcinoma and adenocarcinomas; prostate cancer, such as a prostate cancer selected from the following: an adenocarcinoma or an adenocarinoma that has migrated to the bone; pancreatic cancer such as epitheliod carcinoma in the pancreatic duct tissue and an adenocarcinoma in a pancreatic duct; stomach cancer; bladder cancer such as a transitional cell carcinoma in urinary bladder, urothelial carcinomas (transitional cell carcinomas), tumors in the urothelial cells that line the bladder, squamous cell carcinomas, adenocarcinomas, and small cell cancers; leukemia such as acute myeloid leukemia (AML), acute lymphocytic leukemia, chronic lymphocytic leukemia, chronic myeloid leukemia, hairy cell leukemia, myelodysplasia, and myeloproliferative disorders; bone cancer; lung cancer such as non-small cell lung cancer (NSCLC), which is divided into squamous cell carcinomas, adenocarcinomas, and large cell undifferentiated carcinomas, and small cell lung cancer; skin cancer such as basal cell carcinoma, melanoma, squamous cell carcinoma and actinic keratosis, which is a skin condition that sometimes develops into squamous cell carcinoma; eye retinoblastoma; cutaneous or intraocular (eye) melanoma; primary liver cancer (cancer that begins in the liver); kidney cancer; thyroid cancer such as papillary, follicular, medullary and anaplastic; AIDS-related lymphoma such as diffuse large B-cell lymphoma, B-cell immunoblastic lymphoma and small non-cleaved cell lymphoma; Kaposi's Sarcoma; viral-induced cancers including hepatitis B virus (HBV), hepatitis C virus (HCV), and hepatocellular carcinoma; human lymphotropic virus-type 1 (HTLV-1) and adult T-cell leukemia/lymphoma; and human papilloma virus (HPV) and cervical cancer; central nervous system cancers (CNS) such as primary brain tumor, which includes gliomas (astrocytoma, anaplastic astrocytoma, or glioblastoma multiforme), Oligodendroglioma, Ependymoma, Meningioma, Lymphoma, Schwannoma, and Medulloblastoma; peripheral nervous system (PNS) cancers such as acoustic neuromas and malignant peripheral nerve sheath tumor (MPNST) including neurofibromas and schwannomas, malignant fibrous cytoma, malignant fibrous histiocytoma, malignant meningioma, malignant mesothelioma, and malignant mixed Müllerian tumor; oral cavity and oropharyngeal cancer such as, hypopharyngeal cancer, laryngeal cancer, nasopharyngeal cancer, and oropharyngeal cancer; stomach cancer such as lymphomas, gastric stromal tumors, and carcinoid tumors; testicular cancer such as germ cell tumors (GCTs), which include seminomas and nonseminomas, and gonadal stromal tumors, which include Leydig cell tumors and Sertoli cell tumors; thymus cancer such as to thymomas, thymic carcinomas, Hodgkin disease, non-Hodgkin lymphomas carcinoids or carcinoid tumors; rectal cancer; and colon cancer.

Kits

The present application concerns kits for use with the compounds described herein. In some embodiments, the invention provides a kit including an MEK protein kinase inhibitor and/or Raf protein kinase inhibitor in a dosage form, particularly a dosage form for oral administration. In some embodiments, the kit further includes a MEK protein kinase inhibitor and/or Raf protein kinase inhibitor in a dosage form. In specific embodiments, the MEK protein kinase inhibitor and/or Raf protein kinase inhibitor are in separate dosage forms. In other embodiments, the MEK protein kinase inhibitor and/or Raf protein kinase inhibitor are in the same dosage form. In some embodiments, the kit includes one or more doses of a MEK protein kinase inhibitor and/or Raf protein kinase inhibitor in tablets for oral administration. In other embodiments, however, the dose or doses of MEK protein kinase inhibitor and/or Raf protein kinase inhibitor may be present in a variety of dosage forms, such as capsules, caplets, gel caps, powders for suspension, etc. In some embodiments, the kit includes one or more doses of an MEK protein kinase inhibitor and/or Raf protein kinase inhibitor for oral administration. In other embodiments, however, the dose or doses of an MEK protein kinase inhibitor and/or Raf protein kinase inhibitor may be present in a variety of dosage forms, such as capsules, caplets, gel caps, powders for suspension, etc.

The container means of the kits will generally include at least one vial, test tube, flask, bottle, syringe and/or other container means, into which the at least one polypeptide can be placed, and/or preferably, suitably aliquoted. The kits can include a means for containing at least one fusion protein, detectable moiety, reporter molecule, and/or any other reagent containers in close confinement for commercial sale. Such containers may include injection and/or blow-molded plastic containers in which the desired vials are stored. Kits can also include printed material for use of the materials in the kit.

Packages and kits can additionally include a buffering agent, a preservative and/or a stabilizing agent in a pharmaceutical formulation. Each component of the kit can be enclosed within an individual container and all of the various containers can be within a single package. Invention kits can be designed for cold storage or room temperature storage.

Additionally, the preparations can contain stabilizers (such as bovine serum albumin (BSA)) to increase the shelf-life of the kits. Where the compositions are lyophilized, the kit can contain further preparations of solutions to reconstitute the lyophilized preparations. Acceptable reconstitution solutions are well known in the art and include, for example, pharmaceutically acceptable phosphate buffered saline (PBS).

Additionally, the packages or kits provided herein can further include any of the other moieties provided herein such as, for example, one or more reporter molecules and/or one or more detectable moieties/agents.

Packages and kits can further include one or more components for an assay, such as, for example, an ELISA assay, cytotoxicity assay, ADP-Ribosyltransferase activity assay, etc. Samples to be tested in this application include, for example, blood, plasma, and tissue sections and secretions, urine, lymph, and products thereof. Packages and kits can further include one or more components for collection of a sample (e.g., a syringe, a cup, a swab, etc.).

Packages and kits can further include a label specifying, for example, a product description, mode of administration and/or indication of treatment. Packages provided herein can include any of the compositions as described herein for treatment of any of the indications described herein.

The term "packaging material" refers to a physical structure housing the components of the kit. The packaging material can maintain the components sterilely, and can be made of material commonly used for such purposes (e.g., paper, corrugated fiber, glass, plastic, foil, ampules, etc.). The label or packaging insert can include appropriate written instructions. Kits, therefore, can additionally include labels or instructions for using the kit components in any method of the invention. A kit can include a compound in a pack, or dispenser together with instructions for administering the compound in a method described herein.

In some embodiments, a kit includes at least three dosage forms, one comprising an MEK protein kinase inhibitor, one comprising a Raf protein kinase inhibitor and the other comprising at least a third active pharmaceutical ingredient, other than the MEK protein kinase inhibitor or Raf protein kinase inhibitor. In some embodiments, the third active pharmaceutical ingredient is a second MEK protein kinase inhibitor. In other embodiments, the third active pharmaceutical ingredient is a second Raf protein kinase inhibitor. In some embodiments, the kit includes sufficient doses for a period of time. In particular embodiments, the kit includes a sufficient dose of each active pharmaceutical ingredient for a day, a week, 14 days, 28 days, 30 days, 90 days, 180 days, a year, etc. It is considered that the most convenient periods of time for which such kits are designed would be from 1 to 13 weeks, especially 1 week, 2 weeks, 1 month, 3 months, etc. In some specific embodiments, the each dose is physically separated into a compartment, in which each dose is segregated from the others.

In some embodiments, the kit includes at least two dosage forms one comprising a MEK protein kinase inhibitor and one comprising a Raf protein kinase inhibitor. In some embodiments, the kit includes sufficient doses for a period of time. In particular embodiments, the kit includes a sufficient dose of each active pharmaceutical ingredient for a day, a week, 14 days, 28 days, 30 days, 90 days, 180 days, a year, etc. In some specific embodiments, the each dose is physically separated into a compartment, in which each dose is segregated from the others.

In particular embodiments, the kit may advantageously be a blister pack. Blister packs are known in the art, and generally include a clear side having compartments (blisters or bubbles), which separately hold the various doses, and a backing, such as a paper, foil, paper-foil or other backing, which is easily removed so that each dose may be separately extracted from the blister pack without disturbing the other doses. In some embodiments, the kit may be a blister pack in which each dose of the MEK protein kinase inhibitor, the Raf protein kinase inhibitor and, optionally, a third active pharmaceutical ingredient are segregated from the other doses in separate blisters or bubbles. In some such embodiments, the blister pack may have perforations, which allow each daily dose to be separated from the others by tearing it away from the rest of the blister pack. The separate dosage forms may be contained within separate blisters. Segregation of the active pharmaceutical ingredients into separate blisters can be advantageous in that it prevents separate dosage forms (e.g., tablet and capsule) from contacting and damaging one another during shipping and handling. Additionally, the separate dosage forms can be accessed and/or labeled for administration to the patient at different times.

In some embodiments, the kit may be a blister pack in which each separate dose the MEK protein kinase inhibitor, the Raf protein kinase inhibitor, and, optionally, a third active pharmaceutical ingredient is segregated from the other doses in separate blisters or bubbles. In some such embodiments, the blister pack may have perforations, which allow each daily dose to be separated from the others by tearing it away from the rest of the blister pack. The separate dosage forms may be contained within separate blisters.

In some embodiments, the third active pharmaceutical ingredient may be in the form of a liquid or a reconstitutable powder, which may be separately sealed (e.g., in a vial or ampoule) and then packaged along with a blister pack containing separate dosages of the MEK protein kinase inhibitor and the Raf protein kinase inhibitor. In some embodiments, the MEK protein kinase inhibitor is in the form of a liquid or reconstitutable powder that is separately sealed (e.g., in a vial or ampoule) and then packaged along with a blister pack containing separate dosages of the MEK protein kinase inhibitor. These embodiments would be especially useful in a clinical setting where prescribed doses of the MEK protein kinase inhibitor, Raf protein kinase inhibitor, and, optionally, a third active pharmaceutically active agent would be used on a dosing schedule in which the MEK protein kinase inhibitor and Raf protein kinase inhibitor is each administered on certain days, the Raf protein kinase inhibitor is administered on the same or different days and the third active pharmaceutical ingredient is administered on the same or different days from either or both of the MEK protein kinase inhibitor and/or Raf protein kinase inhibitor within a weekly, bi-weekly, 2×weekly or other dosing schedule. Such a combination of blister pack containing a MEK protein kinase inhibitor, a Raf protein kinase inhibitor and an optional third active pharmaceutical agent could also include instructions for administering each of the MEK protein kinase inhibitor, Raf protein kinase inhibitor, and the optional third active pharmaceutical agent on a dosing schedule adapted to provide the synergistic or sequelae-treating effect of the MEk protein kinase inhibitor and/or the third active pharmaceutical agent.

In other embodiments, the kit may be a container having separate compartments with separate lids adapted to be opened on a particular schedule. For example, a kit may comprise a box (or similar container) having seven compartments, each for a separate day of the week, and each compartment marked to indicate which day of the week it corresponds to. In some specific embodiments, each compartment is further subdivided to permit segregation of one active pharmaceutical ingredient from another. As stated above, such segregation is advantageous in that it prevents damage to the dosage forms and permits dosing at different times and labeling to that effect. Such a container could also include instructions for administering a MEK protein kinase inhibitor, a Raf protein kinase inhibitor and the optional third active pharmaceutical ingredient on a dosing schedule adapted to provide the synergistic or sequelae-treating effect of the MEk protein kinase inhibitor and/or the third active pharmaceutical ingredient.

The kits may also include instructions teaching the use of the kit according to the various methods and approaches described herein. Such kits optionally include information, such as scientific literature references, package insert materials, clinical trial results, and/or summaries of these and the like, which indicate or establish the activities and/or advantages of the composition, and/or which describe dosing, administration, side effects, drug interactions, disease state for which the composition is to be administered, or other information useful to the health care provider. Such information may be based on the results of various studies, for example, studies using experimental animals involving in vivo models and studies based on human clinical trials. In various embodiments, the kits described herein can be provided, marketed and/or promoted to health providers, including physicians, nurses, pharmacists, formulary officials, and the like. Kits may, in some embodiments, be marketed directly to the consumer. In certain embodiments, the packaging material further comprises a container for housing the composition and optionally a label affixed to the container. The kit optionally comprises additional components, such as but not limited to syringes for administration of the composition.

Instructions can include instructions for practicing any of the methods described herein including treatment methods. Instructions can additionally include indications of a satisfactory clinical endpoint or any adverse symptoms that may occur, or additional information required by regulatory agencies such as the Food and Drug Administration for use on a human subject.

The instructions may be on "printed matter," e.g., on paper or cardboard within or affixed to the kit, or on a label affixed to the kit or packaging material, or attached to a vial or tube containing a component of the kit. Instructions may additionally be included on a computer readable medium, such as a disk (floppy diskette or hard disk), optical CD such as CD- or DVD-ROM/RAM, magnetic tape, electrical storage media such as RAM and ROM, IC tip and hybrids of these such as magnetic/optical storage media.

In some embodiments, the kit comprises a MEK protein kinase inhibitor that is visibly different from the Raf protein kinase inhibitor. In certain embodiments, each of the MEK protein kinase inhibitor dosage form and the Raf protein kinase inhibitor dosage form are visibly different from a third pharmaceutical agent dosage form. The visible differences may be for example shape, size, color, state (e.g., liquid/solid), physical markings (e.g., letters, numbers) and the like. In certain embodiments, the kit comprises a MEK protein kinase inhibitor (e.g. compound A or compound B) dosage form that is a first color, a Raf protein kinase inhibitor (e.g. sorafenib) dosage form that is a second color, and an optional third pharmaceutical composition that is a third color. In embodiments wherein the first, second and third colors are different, the different colors of the first, second and third pharmaceutical compositions is used, e.g., to distinguish between the first, second and third pharmaceutical compositions.

In some embodiments, wherein the packaging material further comprises a container for housing the pharmaceutical composition, the kit comprises a MEK protein kinase inhibitor composition that is in a different physical location within the kit from a Raf protein kinase inhibitor composition. In further embodiments, the kit comprises a third pharmaceutical agent that is in a separate physical location from either the Mek protein kinase inhibitor composition or the Raf protein kinase inhibitor composition. In some embodiments, the different physical locations of MEK protein kinase inhibitor composition and the Raf protein kinase inhibitor composition comprise separately sealed individual compartments. In certain embodiments, the kit comprises a MEK protein kinase inhibitor composition that is in a first separately sealed individual compartment and a Raf protein kinase inhibitor composition that is in a second separately sealed individual compartment. In embodiments wherein the MEK protein kinase inhibitor and Raf protein kinase inhibitor composition compartments are separate, the different locations are used, e.g., to distinguish between the MEK protein kinase inhibitor composition and Raf protein kinase inhibitor compositions. In further embodiments, a third pharmaceutical composition is in a third physical location within the kit.

The compounds described herein can be utilized for diagnostics and as research reagents. For example, the compounds described herein, either alone or in combination with other compounds, can be used as tools in differential and/or combinatorial analyses to elucidate expression patterns of genes expressed within cells and tissues. As one non-limiting example, expression patterns within cells or tissues treated with one or more compounds are compared to control cells or tissues not treated with compounds and the patterns produced are analyzed for differential levels of gene expression as they pertain, for example, to disease association, signaling pathway, cellular localization, expression level, size, structure or function of the genes examined. These analyses can be performed on stimulated or unstimulated cells and in the presence or absence of other compounds which affect expression patterns.

Besides being useful for human treatment, the compounds and formulations of the present invention are also useful for veterinary treatment of companion animals (e.g. dogs, cats), exotic animals and farm animals (e.g. horses), including mammals, rodents, and the like.

The examples and preparations provided below further illustrate and exemplify the compounds of the present invention and methods of preparing such compounds. It is to be understood that the scope of the present invention is not limited in any way by the scope of the following examples and preparations.

EXAMPLES

Synthesis of Compounds

Example 1

N-(3,4-difluoro-2-(2-fluoro-4-iodophenylamino)phenyl)-1-(2,3-dihydroxypropyl)cyclopropane-1-sulfonamide Step A: Butyl cyclopropanesulfonate

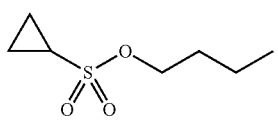

Cyclopropanesulfonyl chloride (5 g, 35 mmol, 1 eq) was dissolved in an excess BuOH (20 ml), the reaction mixture was cooled at −10° C. and pyridine (5.8 mL, 70 mmol, 2 eq) was slowly added dropwise. The mixture was slowly warmed at room temperature and stirred overnight. The solvent was removed under reduced pressure and the resulting white solid was dissolved in CHCl$_3$. The organic phase was washed with water, brine and dried (MgSO4) and concentrated to give an oil (4.8 g, 24.9 mmol, 71%). $^1$H NMR (300 MHz, CDCl$_3$): δ 4.25 (t, 2H), 2.46 (m, 1H), 1.74 (m, 2H), 1.45 (m, 2H), 1.25 (dd, 2H), 1.09 (dd, 2H), 0.93 (t, 3H).

Step B: Butyl. 1-allylcyclopropane-1-sulfonate

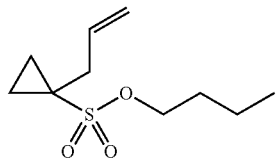

To a solution of 1-butyl cyclopropanesulfonate (4.8 g, 24.9 mmol) in THF at −78° C. was added simultaneously butyllithium solution (15.6 ml, 24.9 mmol, 1.6M, THF) and allyl iodide (24.9 mmol) under nitrogen atmosphere. The reaction mixture was stirred 2 hours at −78° C. and 3 hours at room temperature. The volatiles were evaporated under reduced pressure and the residue extracted with CH$_2$Cl$_2$ (100 ml). The extract was washed with water, dried (MgSO$_4$) and evaporated. The residue was purified over silica gel chromatography (eluants: hexane/CH$_2$Cl$_2$) to obtain the titled product (3.75 g, 69.0%) as a colorless oil. $^1$H NMR (300 MHz, CDCl$_3$): δ 5.6 (m, 1H), 5.13-5.08 (t, 2H), 4.21 (t, 2H), 2.65 (d, 2H), 1.7 (m, 2H), 1.4 (m, 4H), 0.93 (m, 5H).

Step C: Potassium 1-allylcyclopropane-1-sulfonate

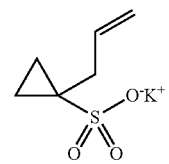

A mixture of 1-butyl 1-methyl-cyclopropanesulfonate (3.75 g, 17.2 mmol) and potassium thiocyanate (1.7 g, 17.2 mmol) in DME (20 ml) and water (20 ml) was refluxed for 16 h. The volatiles were evaporated to obtain the crude sulfonate (3.44 g, quantitative) which was dried under vacuum at 50° C. for 16 h. The crude product was used in the next reaction without further purification. $^1$H NMR (CDCl$_3$): δ 5.6 (m, 1H), 4.91-4.85 (dd, 2H), 2.471-2.397 (d, 2H), 0.756 (m, 2H), 0.322 (m, 2H).

Step D: 1-allylcyclopropane-1-sulfonyl chloride

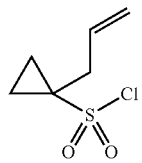

A solution of potassium 1-allylcyclopropane-1-sulfonate (3.44 g, 17.2 mmol), thionyl chloride (10 ml) and DMF (5 drops) was refluxed at 60° C. for 16 h. The volatiles evaporated under reduced pressure and the residue extracted with $CH_2Cl_2$ (50 ml). The extract was washed with water, dried ($MgSO_4$) and evaporated to obtain the crude product as yellow gummy oil which was washed with hexane and used in the next reaction without further purification (2.7 g, 15 mmol, 87%). $^1$HNMR (300 MHz, $CDCl_3$): δ 5.728 (m, 1H), 5.191 (t, 2H), 2.9 (d, 2H), 0.756 (m, 2H), 0.322 (m, 2H).

Step E: 1-allyl-N-(3,4-difluoro-2-(2-fluoro-4-iodophenylamino)phenyl)cyclopropane-1-sulfonamide

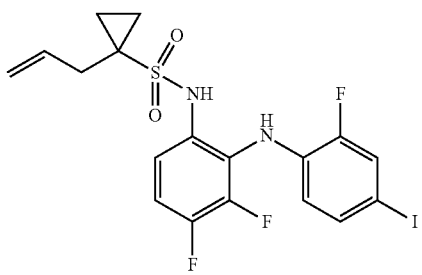 [SMILES: C=CCC1(S(=O)(=O)Nc2ccc(F)c(F)c2Nc2ccc(I)cc2F)CC1]

According to the general procedure B, 5,6-difluoro-N1-(2-fluoro-4-iodophenyl)benzene-1,2-diamine was reacted with 1-allylcyclopropane-1-sulfonyl chloride to obtain the desired product. m/z=507 [M−1]$^-$.

Step F: N-(3,4-difluoro-2-(2-fluoro-4-iodophenylamino)phenyl)-1-(2,3-dihydroxypropyl)cyclopropane-1-sulfonamide

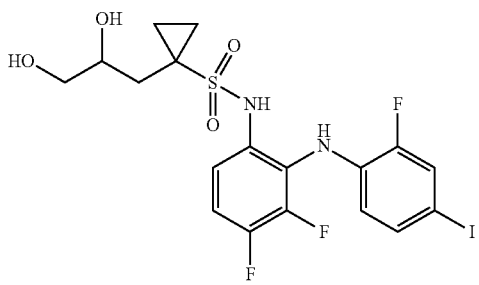 [SMILES: O=S(=O)(Nc1ccc(F)c(F)c1Nc1ccc(I)cc1F)C1(CC(O)CO)CC1]

1-Allyl-N-(3,4-difluoro-2-(2-fluoro-4-iodophenylamino)phenyl)cyclopropane-1-sulfonamide (0.77 g, 1.52 mmol) and 4-methylmorpholine N-oxide (0.18 g, 1.52 mmol) were dissolved in THF (50 mL). Osmium tetroxide was added at room temperature (0.152 mmol, 0.965 mL, 4% in $H_2O$) and the reaction mixture was stirred at room temperature for 16 hours. EtOAc was added, the organic phase was washed with water, dried ($MgSO_4$) and concentrated under reduced pressure. The residue was purified over silica gel chromatography (eluants: EtOAc/MeOH) to obtain the titled product (0.65 g, 79%). $^1$H NMR (300 MHz, $CDCl_3+D_2O$): δ 7.38 (dd, J=1.8 & 10.5 Hz, 1H), 7.36 (ddd, J=2.4, 5.1 & 9.3 Hz, 1H), 725 (d, J=8.7 Hz, 1H), 7.02 (dd, J=9.0 & 17.7 Hz, 1H), 6.27 (dt, J=3.0, 8.7 & 17.4 Hz, 1H), 3.92 (m, 1H), 3.54 (dd, J=3.9 & 11.1 Hz, 1H), 3.39 (dd, J=6.6 & 11.1 Hz, 1H), 2.16 (dd, J=9.6 & 15.9 Hz, 1H), 1.59 (d, J=14.1 Hz, 1H), 1.41 (m, 1H), 1.26 (m, 1H), 0.83 (m, 2H); m/z=542 [M−1]$^-$.

Example 1A (S)—N-(3,4-difluoro-2-(2-fluoro-4-iodophenylamino)phenyl)-1-(2,3-dihydroxypropyl)cyclopropane-1-sulfonamide

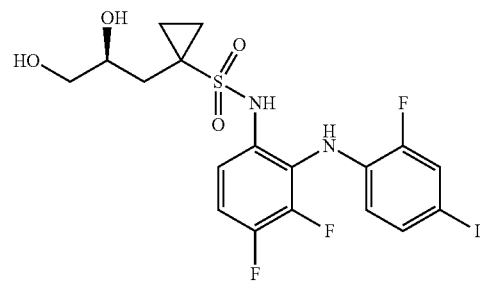 [SMILES: O=S(=O)(Nc1ccc(F)c(F)c1Nc1ccc(I)cc1F)C1(C[C@H](O)CO)CC1]

The pure S isomer was obtained by chiral HPLC separation of the racemic mixture (example 13). $^1$H NMR (300 MHz, $CDCl_3+D_2O$): δ 7.38 (dd, J=1.8 & 10.5 Hz, 1H), 7.36 (ddd, J=2.4, 5.1 & 9.3 Hz, 1H), 7.25 (d, J=8.7 Hz, 1H), 7.02 (dd, J=9.0 & 17.7 Hz, 1H), 6.27 (dt, J=3.0, 8.7 & 17.4 Hz, 1H), 3.92 (m, 1H), 3.54 (dd, J=3.9 & 11.1 Hz, 1H), 3.39 (dd, J=6.6 & 11.1 Hz, 1H), 2.16 (dd, J=9.6 & 15.9 Hz, 1H), 1.59 (d, J=14.1 Hz, 1H), 1.41 (m, 1H), 1.26 (m, 1H), 0.83 (m, 2H); m/z=542 [M−1]$^-$.

Example 1B

Example 1A (R)—N-(3,4-difluoro-2-(2-fluoro-4-iodophenylamino)phenyl)-1-(2,3-dihydroxypropyl)cyclopropane-1-sulfonamide

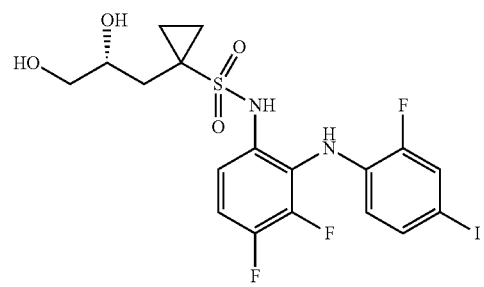 [SMILES: O=S(=O)(Nc1ccc(F)c(F)c1Nc1ccc(I)cc1F)C1(C[C@@H](O)CO)CC1]

The pure R isomer was obtained by chiral HPLC separation of the racemic mixture (example 13). $^1$H NMR (300 MHz, $CDCl_3+D_2O$): δ 7.38 (dd, J=1.8 & 10.5 Hz, 1H), 7.36 (ddd, J=2.4, 5.1 & 9.3 Hz, 1H), 7.25 (d, J=8.7 Hz, 1H), 7.02 (dd, J=9.0 & 17.7 Hz, 1H), 6.27 (dt, J=3.0, 8.7 & 17.4 Hz, 1H), 3.92 (m, 1H), 3.54 (dd, J=3.9 & 11.1 Hz, 1H), 3.39 (dd, J=6.6 & 11.1 Hz, 1H), 2.16 (dd, J=9.6 & 15.9 Hz, 1H), 1.59 (d, J=14.1 Hz, 1H), 1.41 (m, 1H), 1.26 (m, 1H), 0.83 (m, 2H); m/z=542 [M−1]$^-$.

Example 2

1-(2,3-Dihydroxy-propyl)-cyclopropanesulfonic acid [3,4,6-trifluoro-2-(4-fluoro-2-iodo-phenylamino)-phenyl]-amide

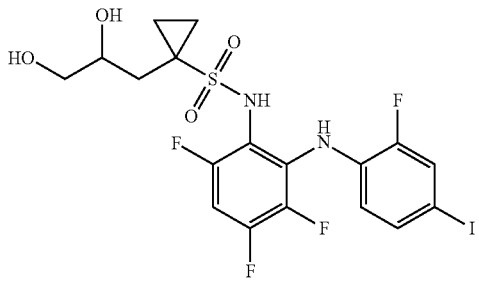 [SMILES: O=S(=O)(Nc1c(F)cc(F)c(F)c1Nc1ccc(I)cc1F)C1(CC(O)CO)CC1]

Step A: 1-Allyl-cyclopropanesulfonic acid [3,4,6-trifluoro-2-(2-fluoro-4-iodo-phenylamino)phenyl]-amide

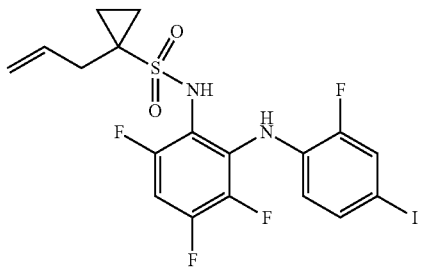 [SMILES: C=CCC1(S(=O)(=O)Nc2c(F)cc(F)c(F)c2Nc2ccc(I)cc2F)CC1]

To a stirred solution of the amine, i.e., 3,5,6-trifluoro-$N^1$-(2-fluoro-4-iodophenyl)benzene-1,2-diamine, (1 eq) in anhydrous pyridine (5 ml/mmole) was added the sulfonyl chloride, i.e., 1-allyl-cyclopropanesulfonyl chloride, (1-5 eq). The reaction mixture was stirred at 40° C. for 48 hours. The reaction mixture was partitioned with water and EtOAc. The organic layer was washed with brine, dried (MGSO$_4$) and concentrated under reduced pressure. The residue was purified by flash column chromatography on silica. $^1$H NMR (CDCl$_3$, 300 MHz): δ 7.41 (dd, 1H), 7.38 (dd, 1H), 7.09 (s, 1H), 6.78 (m, 1H), 6.49 (m, 1H), 5.96 (s, 1H), 5.86 (m, 1H), 5.18 (d, 2H), 2.76 (d, 2H), 1.23 (m, 2H), 0.872 (m, 2H).

Step B: 1-(2,3-Dihydroxypropyl)-N-(3,4,6-trifluoro-2-(2-fluoro-4-iodophenylamino)phenyl)cyclopropane-1-sulfonamide

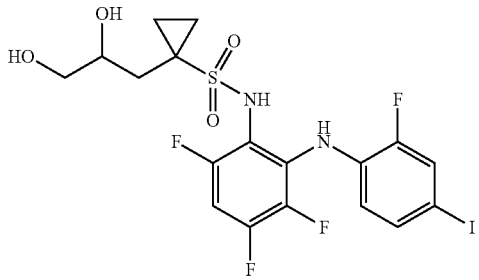 [SMILES: O=S(=O)(Nc1c(F)cc(F)c(F)c1Nc1ccc(I)cc1F)C1(CC(O)CO)CC1]

1-Allyl-cyclopropanesulfonic acid [3,4,6-trifluoro-2-(2-fluoro-4-iodo-phenyl amino)-phenyl]-amide (110 mg, 0.21 mmol) and 4-methylmorpholine N-oxide (24.6 mg, 0.21 mmol) was dissolved in THF (8 mL). Osmium tetroxide was added at room temperature (0.021 mmol, 0.153 mL, 4% in H$_2$O) and the reaction mixture was stirred at room temperature for 16 hours. EtOAc was added, the organic phase was washed with water, dried (MgSO$_4$) and concentrated under reduced pressure. The residue was purified over silica gel chromatography (eluants: EtOAc/MeOH) to obtain the titled product (0.89 g, 75%). $^1$H NMR (CDCl$_3$, 300 MHz): δ 7.39 (dd, J=1.5 & 10.6 Hz, 1H), 7.29 (d, J=8.8 Hz, 1H), 7.28 (s, 1H), 6.97 (s, 1H), 6.76 (m, 1H), 6.49 (m, 1H), 4.13 (m, 1H), 3.66 (dd, J=3.7 & 11.4 Hz, 1H), 3.53 (dd. J=6.7 & 11.2 Hz, 1H), 2.50 (dd, J=10.0 & 16.1 Hz, 1H), 1.6 (m, 1H), 1.46 (m, 1H), 1.28 (m, 1H), 1.20 (m, 2H), 0.92 (m, 2H); m/z=559 [M−1]$^-$.

Example 2A (S)-1-(2,3-dihydroxypropyl)-N-(3,4,6-trifluoro-2-(2-fluoro-4-iodophenylamino)phenyl)cyclopropane-1-sulfonamide

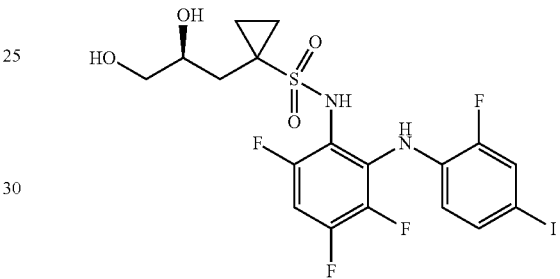

The pure S isomer was obtained by chiral HPLC separation of the racemic mixture (example 52). $^1$H NMR (CDCl$_3$, 300 MHz): δ 7.39 (dd, J=1.5 & 10.6 Hz$_5$ 1H), 7.29 (d, J=8.8 Hz, 1H), 7.28 (s, 1H), 6.97 (s, 1H), 6.76 (m, 1H), 6.49 (m, 1H), 4.13 (m, 1H), 3.66 (dd, J=3.7 & 11.4 Hz$_5$ 1H), 3.53 (dd, J=6.7 & 11.2 Hz, 1H), 2.50 (dd, J=10.0 & 16.1 Hz, 1H), 1.6 (m, 1H), 1.46 (m, 1H), 1.28 (m, 1H), 1.20 (m, 2H), 0.92 (m, 2H); m/z=559 [M−1]$^-$.

Example 2B (R)-1-(2,3-dihydroxypropyl)-N-(3,4,6-trifluoro-2-(2-fluoro-4-iodophenylamino)phenyl)cyclopropane-1-sulfonamide

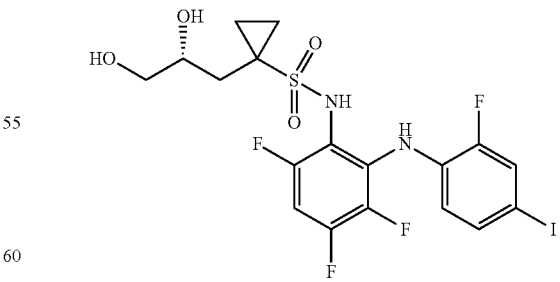

The pure R isomer was obtained by chiral HPLC separation of the racemic mixture (example 52). $^1$H NMR (CDCl$_3$, 300 MHz): δ 7.39 (dd, J=1.5 & 10.6 Hz, 1H), 7.29 (d, J=8.8 Hz, 1H), 7.28 (s, 1H), 6.97 (s, 1H), 6.76 (m, 1H), 6.49 (m, 1H), 4.13 (m, 1H), 3.66 (dd, J=3.7 & 11.4 Hz, 1H), 3.53 (dd, J=6.7

& 11.2 Hz, 1H), 2.50 (dd, J=10.0 & 16.1 Hz, 1H), 1.6 (m, 1H), 1.46 (m, 1H), 1.28 (m, 1H), 1.20 (m, 2H), 0.92 (m, 2H); m/z=559 [M–1]⁻¹.

Example 3

Synthesis of N-(4-(2-fluoro-4-iodophenylamino)-1,5-dimethyl-6-oxo-1,6-dihydropyridin-3-yl)cyclopropanesulfonamide

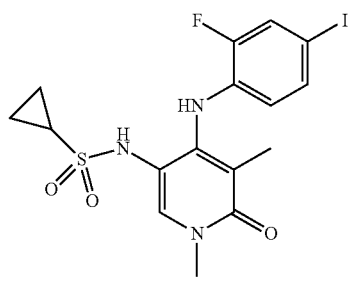 [SMILES: Cc1c(Nc2ccc(I)cc2F)c(NS(=O)(=O)C2CC2)cn(C)c1=O]

Step a: Diethyl 2-methyl-3-oxopentanedioate

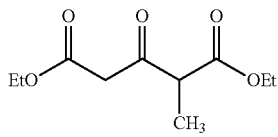

This compound was synthesized according to U.S. Pat. No. 6,833,471. To 20 mL of dry THF that had been purged with Ar(gas) was added diethyl 3-oxopentanedioate (5 mL, 27.54 mmol) and the solution was cooled to −15° C. prior to the dropwise addition of LDA (2M) (15 mL, 30 mmol). The reaction was maintained under Ar(gas) at −15° C., and MeI (3 mL, 48.2 mmol) was added slowly. The reaction was allowed to reach room temperature gradually over 3 hours, and the stirring was continued overnight. After 18 hours, the reaction mixture was poured into 140 mL of a 1:1 mixture of 0.5 N HCl (aq) and Et₂O. The organic layer was separated, and the aqueous layer was extracted twice with Et₂O (15 mL×2). The organic layers were combined, washed with brine, dried (MgSO₄) and concentrated to give an yellow oil, which was flash chromatography purified (SiO₂, Hexane:EtOAc=8:2 (v:v)) to afford a colorless/light yellow oil as the title compound. (1.37 g, 23% yield). MW m/z: 215.3 (MW−1, low intensity). ¹H NMR (CDCl₃, 300 Hz) δ ppm 4.20 (q, 4H), 3.68 (q, 1H), 3.60 (dd, 2H), 1.37 (d, 3H), 1.26 (t, 6H).

Step b: Ethyl 4-hydroxy-1,5-dimethyl-6-oxo-1,6-dihydropyridine-3-carboxylate

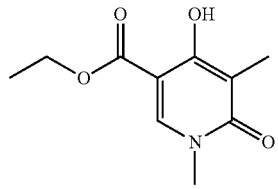

Triethyl orthoformate (1.25 mL, 7.51 mmol) and Ac₂O (2 mL) were added to diethyl 2-methyl-3-oxopentanedioate (1.37 g, 6.34 mmol) and heated to 135° C. After 1.5 hours, the reaction mixture was cooled to room temperature and concentrated under the reduced pressure. The resulting residue was cooled to 0° C. under an ice-water bath, and MeNH₂ (40% in water) (3 mL) was added. The resulting mixture was stirred at room temperature for 16 hours. Aqueous HCl (1N) was added until pH ~7. The solution was extracted with EtOAc (30 mL×2). The combined organic layers were washed with brine, dried (MgSO₄) and concentrated to give a solid, which was purified by flash chromatograph (SiO₂, EtOAc:DCM=1:1 (v:v), Rf~0.4) to afford an off-white solid as the title compound. (314 mg, 23% yield). MW m/z: 212.2 (MW+1), 234.2 (MW+Na); 210.2 (MW−1). ¹H NMR (DMSO-d6, 300 Hz): δ ppm 10.71 (s, br, 1H), 8.46 (s, 1H), 4.32 (q, J=7.2 Hz, 2H), 3.45 (s, 3H), 1.83 (s, 3H), 1.30 (t, J=7.2 Hz, 3H).

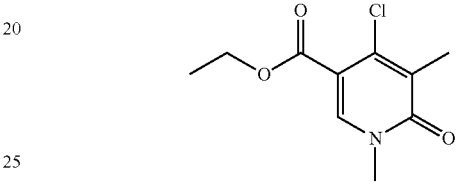

Step c: 4-Chloro-1,5-dimethyl-6-oxo-1,6-dihydropyridine-3-carboxylate

To the mixture of ethyl 4-hydroxy-1,5-dimethyl-6-oxo-1,6-dihydropyridine-3-carboxylate (310 mg, 1.47 mmol) dissolved in dry toluene (13 mL) was added POCl₃ (600 uL, 6.44 mmol). The resulted mixture was heated to 110° C. for 3 hours. After cooled to room temperature, the mixture was poured into ice-cold saturated aqueous NaHCO₃ (50 mL) to make it basic. The mixture was extracted with EtOAc (50 mL×2). The organic layers were combined, washed with brine, dried (MgSO₄) and concentrated to give a brown solid, which was purified by TLC (SiO₂, EtOAc:DCM=6:4 v:v; Rf~0.6) to afford an off-white solid as the title compound. (178 mg, 53% yield). MW m/z: 231.3 (MW+1); 227.8 (MW−1). ¹H NMR (DMSO-d6, 300 Hz): δ ppm 8.04 (s, 1H), 4.33 (q, J=7.2 Hz, 2H), 3.59 (s, 3H), 2.27 (s, 3H), 1.37 (t, J=7.2 Hz, 3H).

Step d: 4-Chloro-1,5-dimethyl-6-oxo-1,6-dihydropyridine-3-carboxylic acid

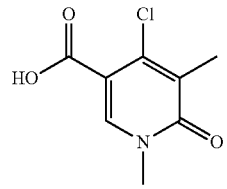

To a solution of ethyl 4-chloro-1,5-dimethyl-6-oxo-1,6-dihydropyridine-3-carboxylate (172 mg, 0.75 mmol) dissolved in a 4:1 mixture of THF:MeOH (5 mL) (v:v), was added a aqueous solution of LiOH (1.52 mmol, 1M). After stirring for 40 min, the reaction mixture was acidified to pH ~1 with HCl(1N, aq) and extracted with EtOAc (30 mL×3). The combined organic layers were washed with brine (30 mL), dried (MgSO₄), filtered and concentrated under the reduced pressure to give an off-white solid as the title compound. (163 mg, 100% yield). MW m/z: 202.3 (MW+1), 204.2 (MW+1+Cl pattern); 200.4 (MW−1), 202.4 (MW−1+Cl pattern). $^1$H NMR (DMSO-d6, 300 Hz): δ ppm 12.97 (s, 1H), 8.42 (s, 1H), 3.48 (s, 3H), 2.10 (s, 3H).

Step e: 4-(2-Fluoro-4-iodophenylamino)-1,5-dimethyl-6-oxo-1,6-dihydropyridine-3-carboxylic acid

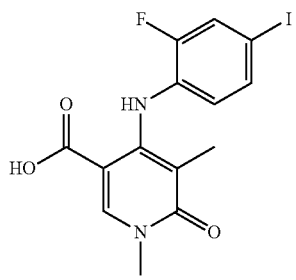 [SMILES: Cc1c(Nc2ccc(I)cc2F)c(C(=O)O)cn(C)c1=O]

To the stirred solution of 2-fluoro-4-iodoaniline (470 mg, 1.94 mmol) in dry THF (4 mL) cooled to −78° C., was added LDA (2M in THF) (1.35 mL, 2.70 mmol). After vigorous stirring for 10 minutes at this temperature, a solution of 4-chloro-1,5-dimethyl-6-oxo-1,6-dihydropyridine-3-carboxylic acid (160 mg, 0.792 mmol) dissolved in dry THF (8 mL) was added dropwise through a syringe. The dry-ice bath was removed after 1 hour, and the reaction was stirred for 16 hours at room temperature At this time, LC/MS indicated 23% of the title product and 33% of unreacted chloride in the reaction mixture. The same reaction mixture was continued to stir at room temperature for additional 24 hours. The mixture was then re-cooled to −78° C. under a dry-ice/acetone bath. Additional LDA (1.35 mL, 2.70 mmol) (2M in THF) was added to the reaction mixture and slowly warmed to room temperature in 16 hours until LC/MS showed the consumption of chloride material. The mixture was cooled to −5° C., and aqueous HCl (1N) (15 mL) was added. The solution was extracted with EtOAc (15 mL×3). The combined organic layers was dried (MgSO₄) and concentrated to give a residue which was triturated with DCM to give a solid. The title compound was used for the next reaction without further purification. (165 mg, 52% yield). MW m/z: 403.13 (MW+1), 401.18 (MW−1). $^1$H NMR (DMSO-d6, 300 Hz): δ ppm 13.26 (s, br, 1H), 9.08 (s, 1H), 8.48 (s, 1H), 7.62 (d, J=10.8 Hz, 1H), 7.39 (d, J=8.1 Hz, 1H), 6.49 (t, J=8.7 Hz, 1H), 3.48 (s, 3H), 1.58 (s, 3H)

Step f: 1-(2-Fluoro-4-iodophenyl)-5,7-dimethyl-1H-imidazo[4,5-e]pyridine-2,6(3H,5H)-dione

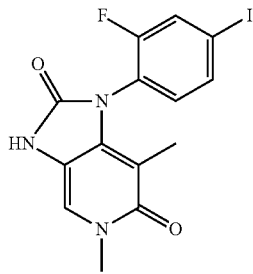 [SMILES: Cc1c(=O)n(C)cc2[nH]c(=O)n(-c3ccc(I)cc3F)c12]

To the suspension of 4-(2-fluoro-4-iodophenylamino)-1,5-dimethyl-6-oxo-1,6-dihydropyridine-3-carboxylic acid (148 mg, 0.368 mmol) in dry toluene (15 mL), was added DPPA (95 uL, 0.439 mmol) and followed by TEA (56 uL, 0.40 mmol). The solution became clear pink and was heated to 100° C. under Argon for 4 hours, at which time LC/MS indicated the complete disappearance of starting material. Aqueous HCl (1N) (25 mL) was added, and the solution was extracted with EtOAc (15 mL×3). The combined organic layers was washed with brine, dried (MgSO₄), and concentrated to give an oil residue, which was purified via flash chromatography (SiO₂, EtOAc:MeOH=9:1, Rf~0.25) to give an off-white solid as the title compound. (139 mg, 95% yield). MW m/z: 400.1 (MW+1), 398.2 (MW−1). $^1$H NMR (DMSO-d6, 300 Hz): δ ppm 10.95 (s, 1H), 7.90 (dd, J=9.6 Hz, 1H), 7.73 (d, J=8.4 Hz, 1H), 7.36 (t, J=8.4 Hz, 1H), 7.35 (s, 1H), 3.40 (s, 3H), 1.47 (s, 3H)

Step g: N-(4-(2-fluoro-4-iodophenylamino)-1,5-dimethyl-6-oxo-1,6-dihydropyridin-3-yl)cyclopropanesulfonamide

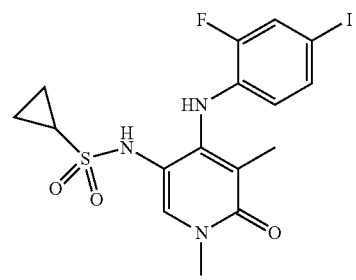 [SMILES: Cc1c(Nc2ccc(I)cc2F)c(NS(=O)(=O)C2CC2)cn(C)c1=O]

To the solution of 1-(2-fluoro-4-iodophenyl)-5,7-dimethyl-1H-imidazo[4,5-c]pyridine-2,6(3H,5H)-dione (23 mg, 0.0576) dissolved in dry DMF (2 mL) cooled to below 0° C. under an ice-bath, was added NaH (60% in mineral oil) (5.0 mg, 0.125 mmol). The cooling bath was removed after addition and the solution was allowed to stir at room temperature for 1 hour. The same solution was re-cooled to −5° C. in a dry-ice/acetone bath, and added cyclopropanesulfonyl chloride (28 mg, 0.20 mmol) dissolved in dry THF (0.5 mL) slowly. The mixture was allowed to warm to room temperature and stirred was and additional 16 hours. The reaction mixture was cooled to 0° C., additional NaH (60% in oil) (5.0 mg, 0.125 mmol), followed by cyclopropanesulfonyl chloride (15 mg, 0.11 mmol) were added. The solution was stirred at room temperature for additional 5 hours. To the same reaction mixture was added aqueous NaOH (1N) (5 mL). The mixture was heated to 65° C. for 40 minutes. After cooled to room temperature, aqueous HCl (1N) (25 mL) was added to acidify the solution, which was extracted with EtOAc (15 mL×3). The combined organic layers was washed with brine, dried (MgSO₄), and concentrated under the reduced pressure to give a residue, which was HPLC purified. (9.6 mg, 35% yield). MW m/z: 478.08 (MW+1), 476.10 (MW−1). $^1$H NMR (DMSO-d₆, 300 Hz): δ ppm 8.89 (s, 7.65 (s, 1H), 7.56 (dd, J=10.8, 1.5 Hz, 1H), 7.42 (s, 1H), 7.0 (d, J=8.7 Hz, 1H), 6.34 (t, J=8.7 Hz, 1H), 3.43 (s, 3H), 2.43 (m, 2H), 1.65 (s, 3H), 0.69-0.79 (m, 4H)

Biology

Example 1

Generation of MEK IC50 Data

Materials and preparation of reagents: Human GST-MEK1 and the constitutively active allele GST-MEK1$^{CA}$ (harboring the mutations Ser218Asp and Ser222Asp) are subcloned into the yeast expression vector pGEM4Z (Promega, Madison, Wis.) from the wild type human MEK1 cDNA. GST-MEK1$^{CA}$ was expressed in *Escherichia coli* and partially purified using Glutathione Sepharose 4B affinity resin (Amersham Pharmacia Biotech, Piscataway, N.J.). The ERK2 allele was subcloned from MAPK2/Erk2 cDNA (wild type) in pUSEamp (Upstate Biotechnology, Inc., Waltham, Mass.) into the vector pET21a (Novagen, Madison, Wis.) resulting in an N-terminal histidine-tagged mouse ERK2 allele. ERK2 was expressed and purified to homogeneity [Zhang, 1993 #33]. Myelin basic protein (MBP) is purchased from Gibco BRL (Rockville, Md.). EasyTides adenosine 5'-triphosphate (ATP) ([γ-$^{33}$P]) (NEN Perkin Elmer, Wellesley, Mass.) is the source of radiolabel for all kinase reactions. Activated Raf-1 (truncated) and activated MAPKinase 2/ERK2 are purchased from Upstate, Inc. (Lake Placid, N.Y.). 4-20% Criterion Pre-cast gels are purchased from Bio-Rad (Hercules, Calif.).

Determination of enzymatic activity: Compounds are diluted from dimethylsulfoxide (DMSO) stocks into 1×HMNDE (20 mM HEPES pH 7.2, 1 mM MgCl$_2$, 100 mM NaCl, 1.25 mM DTT, 0.2 mM EDTA). A typical 25-microliter assay contained 0.002 nanomoles MEK1$^{CA}$, 0.02 nanomoles ERK2, 0.25 nanomoles MBP, 0.25 nanomoles unlabeled ATP, and 0.1 μCi [γ$^{33}$P] ATP. The screening assay essentially comprised four additions. Five μl of diluted compound are dispensed to 96-well assay plates. Ten μl of 2.5× enzyme cocktail (MEK1$^{CA}$ and ERK2 only) are then added to each well followed by a pre-incubation for 30 minutes at ambient temperature. Ten μl of 2.5× substrate cocktail (labeled and unlabeled ATP plus MBP) are then added, followed by incubation for 60 minutes at ambient temperature. Finally, 100 μl of 10% trichloroacetic acid (TCA) were added and incubated for 30 minutes at room temperature to halt the reaction and precipitate radiolabeled protein products. Reaction products are harvested on glass fiber 96 well filter plates prewetted with water and 1% pyrophosphate. The filter plate is then washed 5 times with water. Water is displaced by absolute ethanol and the plate was allowed to air dry for 30 minutes at room temperature. A back seal is applied manually and 40 μl of scintillation cocktail are dispensed to each well. A top seal is applied and the plate is counted in the TopCount for two seconds per well. For certain experiments a truncated version of MEK that requires activation by Raf kinase are used.

Example 2

Generation of MEK EC50 Data

Effects of compounds in the cell are determined by Western blotting for phosphorylated ERK. MDA-MB-231 breast cancer cells were plated in a 48 well plate at 20,000 cells per well and grown in a 37° humidified CO$_2$ incubator. The following day, the growth media (DMEM+10% fetal bovine serum) is removed and replaced with starve media (DMEM+0.1% fetal bovine serum). Cells are incubated in the starve media for sixteen hours and then treated with a range of compound concentrations for thirty minutes. After incubation with compound, cells are stimulated with 100 ng/ml EGF for five minutes. The cells are then lysed and analyzed by Western blot using a monoclonal antibody raised to phosphorylated ERK. The signal is amplified using a secondary antibody conjugated to a near—IR dye and detected on a Licor Odyssey scanner. The intensity of signal is quantitated and this data is used to generate dose response curves and EC50 calculations.

Example 3

Generation of Raf IC50 Data

A method for determining IC50 values for a Raf protein kinase inhibitor, e.g. sorafenib, in human cancerous cell lines is described in U.S. application Ser. No. 10/488,576, filed on Mar. 4, 2004, entitled "Pyridylfurans and pyrroles as Raf kinase inhibitors," and is hereby incorporated by reference in its entirety. Human diploid foreskin fibroblasts (HFF) or human colon carcinoma (Colo 201) cells are grown in Dulbecco's modified Eagle's medium (DMEM) (Invitrogen/Life Technologies) containing 10% fetal bovine serum (FBS) and the antibiotics penicillin (100 Units/ml) and streotomycin (100 micrograms/ml) (Invitrogen/Life Technologies). Growth is maintained at 37° C. in humidified 5% CO2 incubators in 75 cm 2 plastic flasks. Cells are harvested using 0.25% trypsin/1 mM ethylenediaminetetraacetic acid (EDTA), resuspended in growth medium, and counted using a hemocytometer. Flat-bottomed 96-well plates are seeded with 2×10 3 cells/well in a volume of 200 ul from trypsinized exponentially growing cultures. To "blank" wells, growth medium is added with no additions. Cells will be incubated overnight to permit attachment.

Twenty-four hours later, medium from wells that contained cells is replaced with 180 microliters of fresh medium. Appropriate dilutions of test compounds are added to the wells from stock solutions of Raf protein kinase compound dissolved in dimethyl sulfoxide (DMSO); final DMSO concentration in all wells was 0.2%. Cells plus compound are incubated for an additional 72 hr at 37° C. under normal growth conditions. Cells are then assayed for viability using standard XTT/PMS. Fifty microliters of XTT/PMS solution is added to each well and plates are incubated for 90 minutes at 37° C. Absorbance at 450 nM is then determined using a 96-well UV plate reader (Molecular Devices). Under these conditions, absorbance of untreated control cells at 450 nm is at least 1.0 optical density unit/ml. Percent viability of cells in each well is calculated from these data (having been corrected for background absorbance) which will be equal to 100× (A450 test well/A450 untreated control well), wherein the A450s being averages of triplicate determinations. IC50 will be determined based on that concentration of Raf kinase inhibitor compound that reduced cell viability to 50% of control (untreated) viability, as determined from plots of concentration vs percent viability.

Example 4

In Vitro Apoptosis Assay: Detection of Cell Death by Trypan Blue

Several cell lines were contacted in vitro with a combination of compound A and sorafenib and/or a combination of compound B and sorafenib in various cell lines to determine effect on apoptosis of the cell lines. In particular, HUH7, HepG2, D 37, Hs766T, L35, NSCLC MV522, NSCLC H727 cell lines were treated with sorafenib and compound A or sorafenib and compound B. After drug treatment, the cell lines were harvested by trypsinization with trypsin/EDTA for 10 min at 37° C. As some apoptotic cells detached from the culture substratum into the medium, these cells were also collected by centrifugation of the medium at 1,200 rpm for 5 min. The pooled cell pellets were resuspended and mixed with trypan blue dye. At the completion of the Trypan blue stain, cells were counted by using a light microscope and a hemocytometer. Blue dye-incorporating cells were scored as being dead. Five hundred cells from randomly chosen fields were counted, and the number of dead cells were counted and expressed as a percentage of the total number of cells counted. This assay for the detection of apoptosis levels by trypan blue is also referred to herein as an "in vitro apoptosis method." Some of the results using this assay are depicted in FIGS. 1, 2, 4, and 5, and subfigures therein.

Example 5

In Vivo Apoptosis Assay

MEK inhibitor, e.g., Compound A or Compound B, in combination with Raf inhibitor, e.g., sorafenib are examined in vivo to determine their effect on apoptosis of cancer cells. 40 patients are voluntarily enrolled in the study, all of which are suffering from pancreatic cancer at a similar stage of cancerous development. 10 patients are administered a combination of MEK inhibitor and sorafenib. 10 patients are administered only MEK inhibitor. Another 10 patients are administered only sorafenib. The final 10 patients are administered placebo. Each patient is administered a daily dose for 14 days.

After 14 days, each patient will consume a detectable lipopolysaccharide binding protein (LBP) reagent coupled to a label. In accordance with WO/2006/054068, which is hereby incorporated by reference in its entirety, each patient is then placed in the field of a scanning apparatus whereby the scaring apparatus detects the consumed reagent bound to dead cells. The number of dead cells can be correlated to a level apoptosis of each patient. The apoptosis levels in patients administered the combinations and those administered the single entity agents can be compared against each others, as well as with respect to the cohort group administered placebo. An identical study as that described in the Example is also conducted in parallel which includes patients suffering from stomach cancer. The assays utilized for the detection of apoptosis levels using a lipopolysaccharide binding protein and scanning apparatus is referred to as the herein as an "in vivo apoptosis method."

Example 6A

In Vitro Cell Proliferation Assay of Hep3B Cell Line

The effect of compound A in combination with sorafenib was examined in a cell line derived from a human hepatocellular carcinoma in a cell proliferation assay.

Cell culture/Growth Inhibition Assay: Human hepatocelluar carcinoma Hep3B cells were obtained from ATCC (Manassas, Va.). Hep3B cells were maintained in EMEM supplemented with 10% fetal bovine serum, penicillin (100 U/ml), and streptomycin (100 µg/ml). Cells were maintained at 37° C., 5% CO2, and 100% humidity. For cell proliferation experiments, cells were plated in white 96-well plates with clear bases at either 3000 cells/100 µl/well, 2000 cells/100 µl/well or 1000 cells/100 µl/well and treated as follows for 3 days, 4 days, or 6 days respectively. After 24 hr, cell media was removed and replaced with media containing combinations of compound A of formula I and sorafenib. Following incubation for the indicated time at 37° C., ATP levels were determined using CellTiterGlo (Promega, Madison, Wis.) and reading luminescence values using a LJL Biosystems Analyst FIT (Sunnyvale, Calif.). The ATP level for each dose combination was determined in triplicate using independent wells, and the experiment was performed several times. For synergy experiments, either compound A of formula I or sorafenib was dosed at a fixed, subefficacious dose, while the second agent (sorafenib or compound A of formula I respectively) was added across a range of doses. For comparison, the dose response for each single agent was also determined. The relative cell proliferation number was determined with the following formula:

$$\text{Relative cell number} = \frac{(\text{mean } RLU \ (621119 \text{ and sorafenib treated}))}{(\text{mean } RLU \text{ Vehicle Only control})}.$$

This growth inhibition assay is also referred to herein as an "in vitro cell proliferation assay." Some of the results of this assay are depicted in FIGS. 8A, 8B and 8C.

Example 6B

In Vitro Cell Proliferation Assay of Hep3B Cell Line

The effect of compound A in combination with (1) Sunitinib, (2) Perifosine, (3) Gefinitib, (4) Imatinib, (5) Temozolomide, (6) Lapatinib, (7) Gemcitabine, and (8) Vorinostat, were each examined in a cell line derived from a human hepatocellular carcinoma in a cell proliferation assay.

Cell culture/Growth Inhibition Assay: Human hepatocelluar carcinoma Hep3B cells were obtained from ATCC (Manassas, Va.). Hep3B cells were maintained in EMEM supplemented with 10% fetal bovine serum, penicillin (100 U/ml), and streptomycin (100 µg/ml). Cells were maintained at 37° C., 5% CO2, and 100% humidity. For cell proliferation experiments, cells were plated in white 96-well plates with clear bases at either 3000 cells/100 µl/well, 2000 cells/100 µl/well or 1000 cells/100 µl/well and treated as follows for 3 days, 4 days, or 6 days respectively. After 24 hr, cell media was removed and replaced with media containing combinations of compound A of formula I and sorafenib. Following incubation for the indicated time at 37° C., ATP levels were determined using CellTiterGlo (Promega, Madison, Wis.) and reading luminescence values using a Lit Biosystems Analyst HT (Sunnyvale, Calif.). The ATP level for each dose combination was determined in triplicate using independent wells, and the experiment was performed several times. For synergy experiments, either compound A of formula I or sorafenib was dosed at a fixed, subefficacious dose, while the second agent (sorafenib or compound A of formula I respectively) was added across a range of doses. For comparison, the dose response for each single agent was also determined. The relative cell proliferation number was determined with the following formula:

$$\text{Relative cell number} = \frac{(\text{mean } RLU \ (621119 \text{ and sorafenib treated}))}{(\text{mean } RLU \text{ Vehicle Only control})}.$$

The results for each of these experiments showed no synergy between compound A and (1) Sunitinib, (2) Perifosine, (3)

Gefinitib, (4) Imatinib, (5) Temozolomide, (6) Lapatinib, (7) Gemcitabine, or (8) Vorinostat.

Example 7

In Vivo Cell Proliferation Assay

A method for determining cell proliferation counts in cancerous cells treated with a MEK protein kinase inhibitor or a Raf protein kinase inhibitor, or both, is understood in the art and is described in Kenny, L. M. et al., Positron Emission Tomography (PET) Imaging of Cell Proliferation in Oncology, Clinical Oncology, 16:176-185 (2004), which is hereby incorporated by reference in its entirety. A MEK protein kinase inhibitor (e.g. Compound A or Compound B) in combination with a Raf protein kinase inhibitor (e.g. sorafenib) is examined in vivo to determine their effect on proliferation of cancerous cells. 75 patients are voluntarily enrolled in the study, all of which are suffering from pancreatic cancer at a similar stage of cancerous development. 15 patients are administered a combination of compound A and sorafenib. 15 patients are administered a combination of compound B and sorafenib. 15 patients are administered only compound A. An additional 15 patients are administered only sorafenib. The final 15 patients are administered placebo. Each patient is administered a daily dose for 14 days with a radio labeled tracer, e.g. labeled fluoro-2-deoxy-DF-glucose (FDG).

After 14 days of treatment, a trained physician using a non-invasive positron emission tomography (PET) imaging apparatus detects tumor cell proliferation. Moreover, the trained physician will determine cell proliferation counts of both tumor and normal cell tissue for patients treated with Compound A, Compound B, sorafenib, combinations thereof, and placebo. The results will indicate a synergistic decrease in cell proliferation counts between the MEK protein kinase inhibitor (e.g. Compound A or Compound B) when administered in combination with the Raf protein kinase inhibitor sorafenib. An identical study as that described in the Example is also conducted in parallel which includes patients suffering from stomach cancer. The assays utilized for the determining cell proliferation counts using labeled tracers and PET imaging is referred to herein as an "in vivo cell proliferation method." Other in vivo cell proliferation methods are known in the art.

Example 8

In Vitro Cell Proliferative Activity of AGS Cell Line

The effect of compound A in combination with sorafenib was examined in a cell line derived from a human gastric adenocarcinoma, in a cell proliferation assay.

Figure 9A:
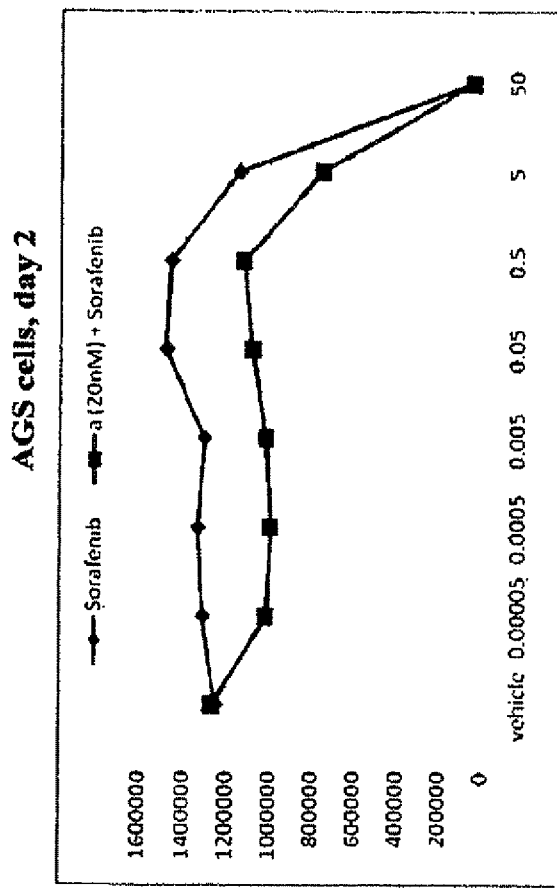
FIG. 9A shows a graph of relative cell number vs increasing concentration of Sorafenib either alone or in the presence of 20 nM compound A, and demonstrates that sorafenib shows little activity in inhibiting proliferation of AGS cells after 48 hours at doses of 5 uM and lower, whereas the addition of a subefficacious dose (20 nM) of compound A greatly increases the inhibition of cell proliferation by sorafenib at 5 uM.
Figure 9B:
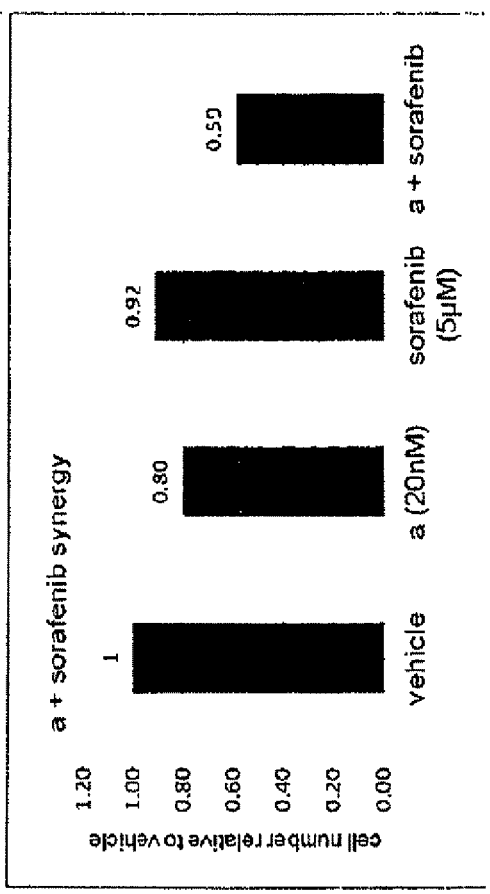
FIG. 9B shows a bar graph of the cell number (relative to vehicle) for vehicle, sorafenib alone (5 uM), compound A alone (20 nM) and a combination of sorafenib+compound A. The figure shows that sorafenib at 5 uM shows little activity in inhibiting proliferation of AGS cells after 48 hours; however the addition of a subefficacious dose of 20 nM compound A synergistically increases the inhibition of cell proliferation by sorafenib alone at 5 uM.
Figure 11A:
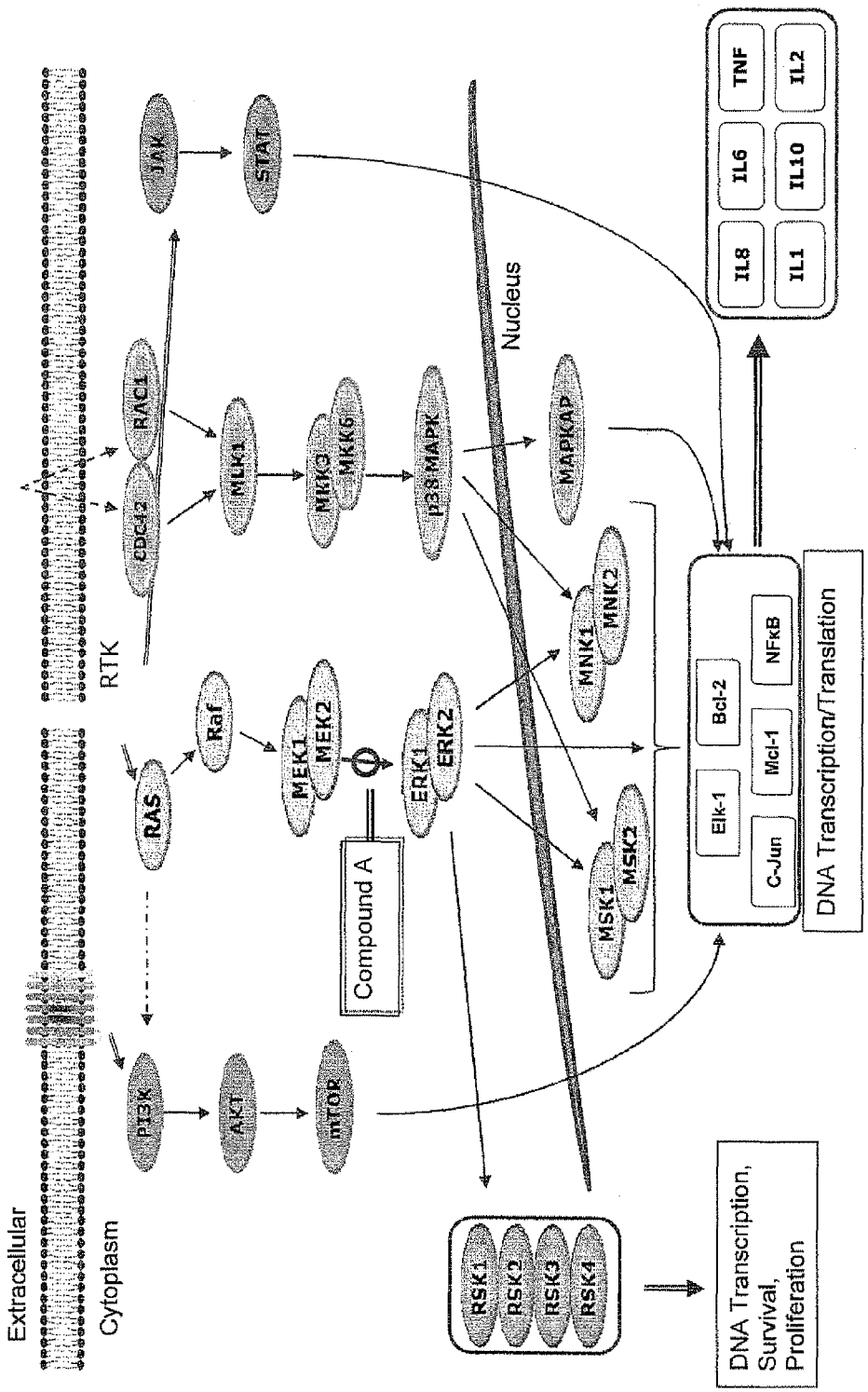
FIGS. 11A and 11B depict a relevant portion of the MAP kinase cascade.
Figure 11B:
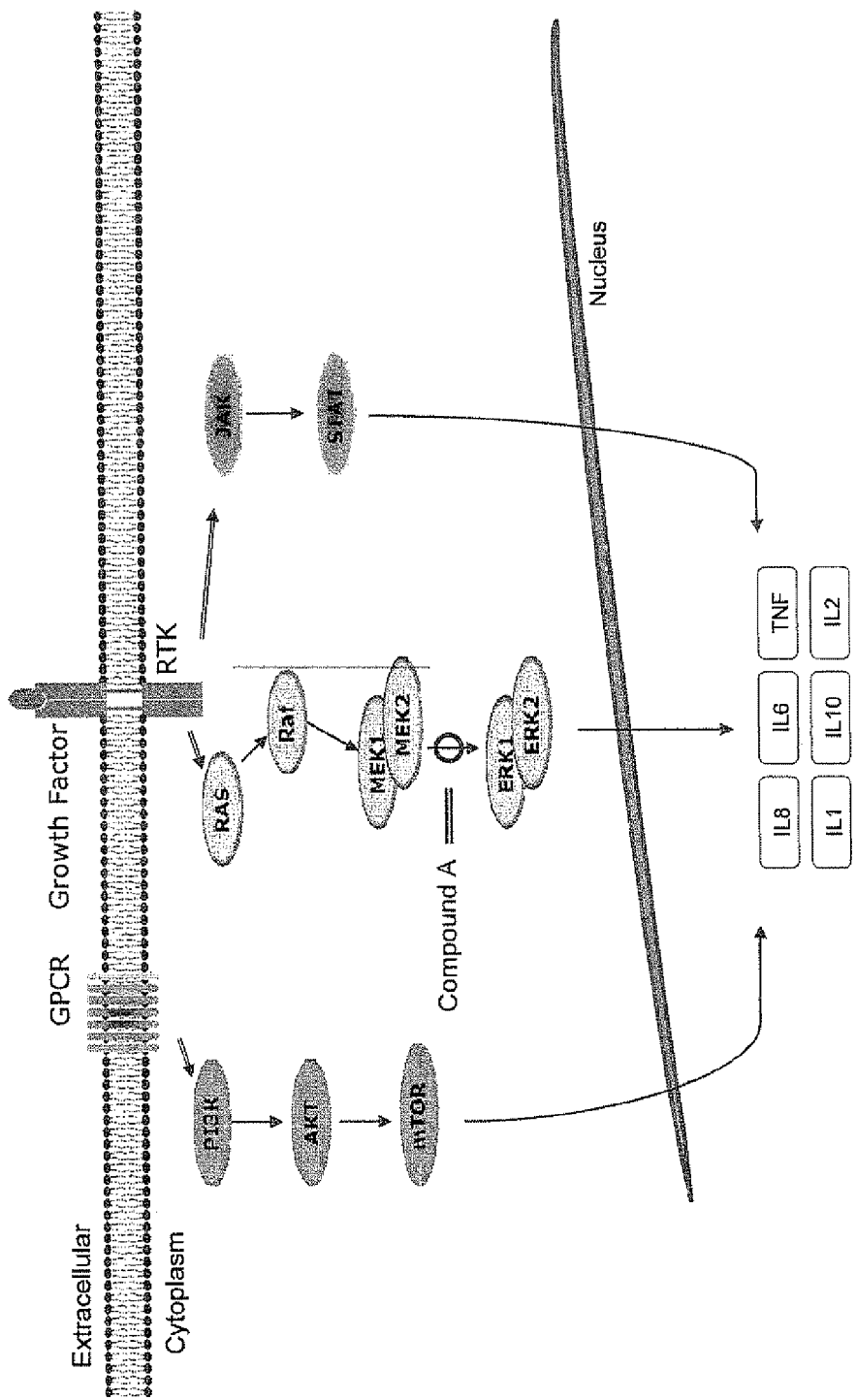
Figure 12:
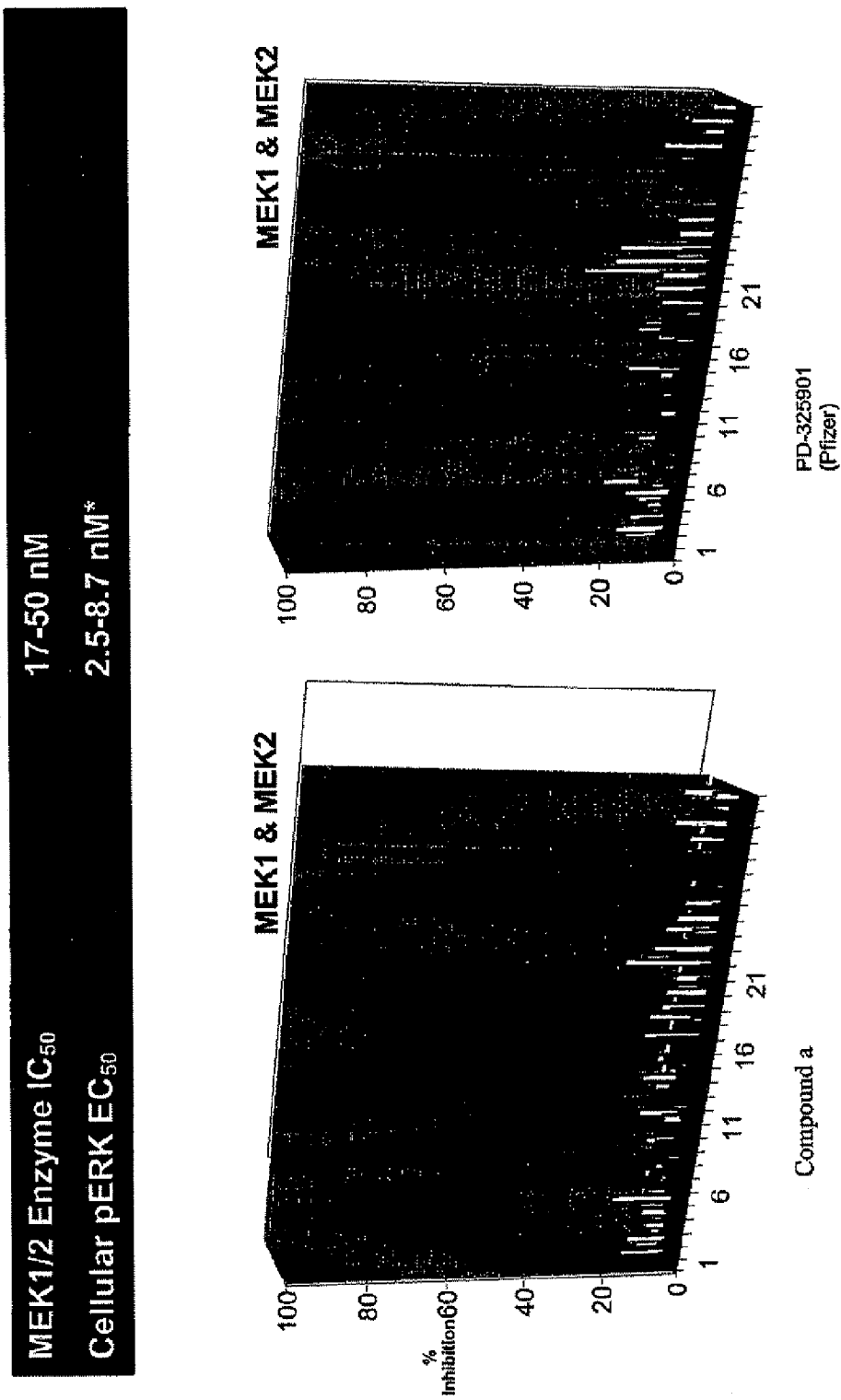
FIG. 12 is a bar graph depicting the selectivity of compound A for MEK1 and MEK2 enzymes.

Cell culture/Growth Inhibition Assay: The human gastric adenocarcinoma cell line AGS was obtained from ATCC (Manassas, Va.). AGS cells were maintained in DMEM/F12 supplemented with 10% fetal bovine serum, penicillin (100 U/ml), and streptomycin (100 µg/ml). Cells were maintained at 37° C., 5% CO2, and 100% humidity. For cell proliferation experiments, cells were plated in white 96-well plates with clear bases at 3000 cells/100 µl/well. After 24 hr, cell media was removed and replaced with media containing combinations of 621119 and sorafenib. Following incubation for 48 hours at 37° C., ATP levels were determined using CellTiter-Glo (Promega, Madison, Wis.) and reading luminescence values using a LJL Biosystems Analyst HT (Sunnyvale, Calif.). The ATP level for each dose combination was determined in triplicate using independent wells, and the experiment was performed several times. For synergy experiments, either 621119 or sorafenib was dosed at a fixed, subefficacious dose, while the second agent (sorafenib or 621119 respectively) was added across a range of doses. For comparison, the dose response for each single agent was also determined. See FIGS. 9A and 9B. The relative cell proliferation number was determined with the following formula:

$$\text{Relative cell number} = \frac{(\text{mean } RLU \text{ (Compound A and Sorafenib Treated)})}{(\text{mean } RLU \text{ Vehicle Only control})}.$$

Example 9

IC50 Determination and Preparation of Isobalogram Curve

A fluorometric assay was prepared to determine cell viability by measuring the ability of cells in culture to catalyse the reduction of resazurin to resorufin. The assay procedure involved the addition of a single reagent (CellTiter-Blue® Reagant) directly to cells cultured in 96 multiwell plates, incubation at 37° C., and measurement of fluorescence. The signal produced by conversion of resazurin to resorfurin is directly proportional to viable cell number.

IC50 data was determined using a 10-point half dilution series starting at 2.5 µM. The small molecules tested included compound A and sorafenib. The cell lines included A549, NCI-460 and NCI-H596, and HUH-7. The A549, NCI-460 and NCI-H596 cell lines were seeded in one 96-well plate. With respect to the HUH-7 cell line, two plates were prepared. Seeding concentrations included 3,000 cells/well for A549, 4,000 cells/well for NCI-460, 4,000 cells/well for NCI-H596, and 4,000 cells/well for HUH-7. The A549, NCI-460 and NCI-H596 cell lines and one plate of the HUH-7 cell line were analyzed 48 hours after addition of compound A and sorafenib. The remaining HUH-7 cell line was analyzed 72 hours after addition of compound A and sorafenib.

Figure 7A:
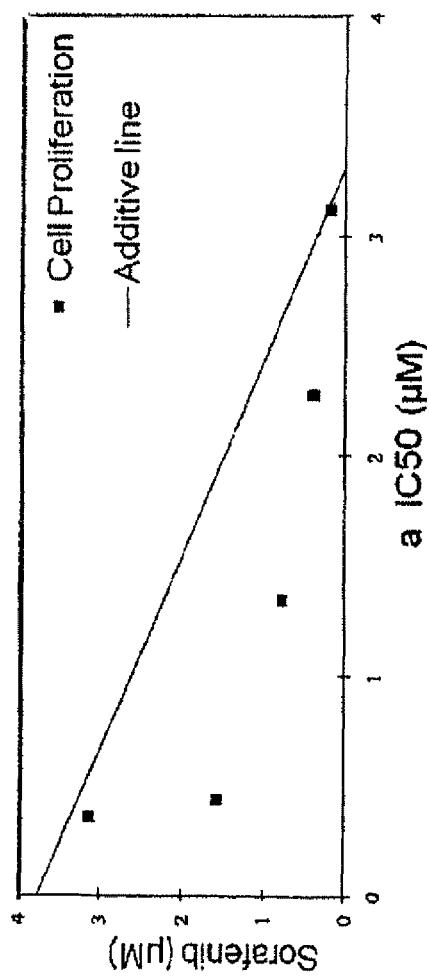
FIG. 7A shows a line graph of the synergistic decrease in cell proliferation level of Hep3B Hepatoma cells with varying concentrations of compound A in combination with varying concentrations of sorafenib. Experimental and additive points that are on the isobolographic line demonstrate additive effects of the two compounds, data points that are below are synergistic, and data above the line are antagonistic.
Figure 7B:
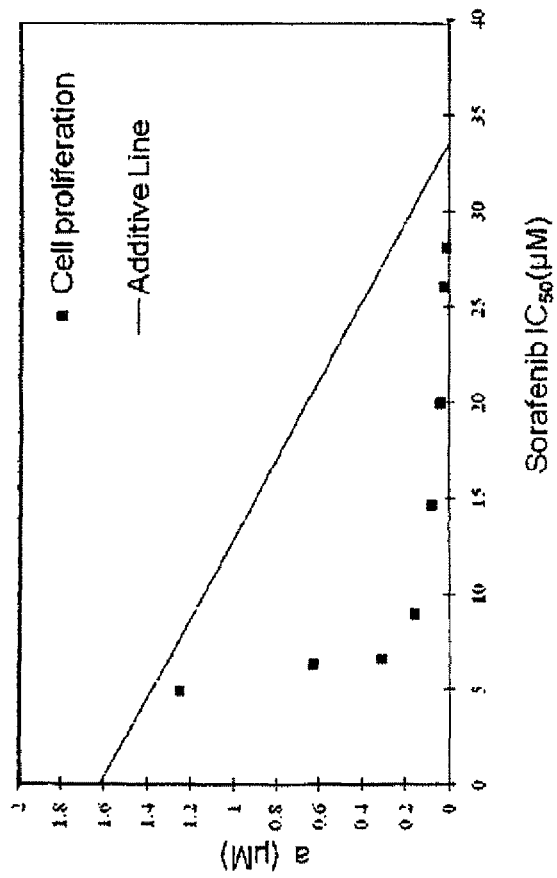
FIG. 7B shows a line graph of the decrease in cell proliferation level of Pancreatic cells with varying concentrations of compound A in combination with varying concentrations of sorafenib. Experimental and additive points that are on the isobolographic line demonstrate additive effects of the two compounds, data points that are below are synergistic, and data points above the line are antagonistic.

The isobologram curve was prepared using the duplicate 96-well plate based on an isobologram template in which a 8-point half dilution series was used for sorafenib and a 9-point half dilution series was used for compound A. See, e.g., FIGS. 7A and 7B.

Example 10

In Vivo Biological Activity

The compounds and compositions described herein are useful for the treatment or prophylaxis of one or more diseases including but not limited to cancer. The compounds and compositions described herein are also useful for the once- or twice-daily oral treatment or prophylaxis of one or more diseases including but not limited to cancer.

In vivo tests of compound A in combination with sorafenib and tests of compound B in combination with sorafenib are described in this example. Human tumors are implanted in nu/nu mice. Compound A and sorafenib are administered orally for 14 days once tumors are approximately 100 mm3 in size. Tumor growth inhibition (TGI) is determined after 14 days of treatment as the reduction in the size of tumors in treated groups versus vehicle controls. The time to endpoint (TTE) is calculated as the time for the tumor to reach the specified endpoint volume or the last day of the study, which-ever comes first. Treatment outcome is determined from percent tumor growth delay (% TGD), defined as the percent increase in median TTE of treated versus vehicle-treated control mice. Animals are also monitored for regression responses. Levels of pERK in tumors and brain are determined by Western blots and correlated with plasma levels of sorafenib and compound A and/or compound B for the pharmacodynamic/pharmacokinetic study. A number of tumor models are evaluated with different doses and dosing regimens. Treatment with 5, 10, 15, 20, 25 or 50 mg/kg once daily (QD) of each agent will show statistically significant % TGD in L35 pancreatic tumors, A375 melanoma tumors, Colo205 colon cancer tumors, and A431 epidermoid tumors. Statistically significant TGI is observed for oral dosing at 5, 10, 15, 20 or 25 mg/kg QD of each agent for these tumor models as well as in HT29 colon cancer tumors. The effect of different dosing regimens is evaluated in A375 xenografts. A pharmacodynamic/pharmacokinetic study in L35 xenografts will show inhibition of pERK formation in tumors while minimal inhibition was observed in brain suggesting potent anti-tumor activity with limited CNS penetration. An identical study as that described in the Example is also conducted in parallel which includes patients suffering from stomach cancer.

Example 11

Human Clinical Trial

A randomized, Double-blind, open label, historical control, single group assignment, safety/efficacy human phase I clinical trial with compound A and sorafenib versus compound A and placebo in Patients with chemo-naive advanced or metastatic pancreatic cancer will be performed.

The primary purpose of the study is to evaluate the safety and tolerability of the combined treatment of sorafenib with compound A. A secondary outcome will be to evaluate the response rate, clinical benefit, and tumor shrinkage after treatment with sorafenib with compound A. Further, the study will be designed to evaluate time to disease progression and overall survival of patients with the pancreatic cancer. In addition, pharmacodynamic changes in tumor vascular parameters will be evaluated (including, e.g. blood flow, blood volume, time to peak ROC-receiver operator characteristics curve) by DCE-MRI.

Moreover, the biologic markers such as VEGF, eNOS and HIF1-alpha, MEK, Raf, VEGF-R2 genetic plymorphisms and serum proteomics will be used to correlate outcomes. This will also permit the respectability rates of tumors after treatment to be determined, as well as the MTD for sorafenib and compound A to be evaluated. During the study, sorafenib will be administered in varying doses of about 50 mg, about 100 mg, about 150 mg, about 200 mg, about 250 mg, about 300 mg, about 350 mg, about 400 mg, about 450 mg, and/or about 500 mg. Compound A will be administered in varying does of about 1 mg, about 1.5 mg, about 2 mg, about 2.5 mg, about 3 mg, about 3.5 mg, about 4.0 mg, about 4.5 mg, about 5 mg, about 5.5 mg, about 6 mg, about 6.5 mg, about 7 mg, about 7.5 mg, about 8 mg, about 8.5 mg, about 9 mg, about 9.5 mg, about 10 mg, about 10.5 mg, about 11 mg, about 11.5 mg, about 12 mg, about 12.5 mg, about 13 mg, about 13.5 mg, about 14 mg, about 14.5, or about 15 mg.

Inclusion criteria for the study will be based on the following factors:

Histologically/pathologically confirmed locally advanced unrespectable or borderline unrespectable pancreatic cancer, and no evidence of metastatic disease.

Diagnosis of locally advanced unrespectable pancreatic cancer based on assessment by dual-phase CT scan and/or endoscopic ultrasound (BUS) (EUS described in Appendix F).

Measurable disease according to RECIST and obtained by dual-phase CT scan within 14 days prior to being registered for protocol therapy.

Tumor size greater than or equal to 2 cm on dual-phase computed tomography scan.

Adequate organ function documented within 14 days of registration as evidenced by: absolute neutrophil count>1500/mm3; platelet count; 100,000/mm3; hemoglobin$^3$ 9 gm/dL without transfusion requirement in the prior 4 weeks; total bilirubin≤1.5 times upper limit of normal (ULN); transaminases (AST and/or ALT)≤2.5× ULN; PT (or INR)≤1.5×ULN and aPTT within normal limits (patients who receive anticoagulation treatment with an agent such as warfarin or heparin will be allowed to participate; for patients on warfarin, close monitoring of at least weekly evaluations will be performed until INR is stable based on a measurement at predose, as defined by the local standard of care; Creatinine clearance of >60 ml/min calculated using the Cockcroft-Gault formula.

Exclusion Criteria will include: prior treatment with compound A within 6 months prior to registration; prior treatment with sorafenib or other Ras or VEGF pathway inhibitors ever; clinical evidence of duodenal mucosal invasion by tumor (as documented by endoscopy or endoscopic ultrasound); minor surgical procedure (e.g. fine needle aspiration or needle biopsy) within 14 days of study registration; major surgical procedure, significant traumatic injury, or serious non-healing wound, ulcer or bone fracture within 21 days of study registration; any of the following within 6 months prior to study drug administration: severe/unstable angina (anginal symptoms at rest), new onset angina (began within the last 3 months) or myocardial infarction, congestive heart failure, cardiac ventricular arrhythmias requiring anti-arrhythmic therapy; history of thrombotic or embolic events such as cerebrovascular accident or transient ischemic attack within the past 6 months; history of aneurysm or arteriovenous malformation; known human immunodeficiency virus (HIV) infection or chronic Hepatitis B or C; active clinically serious infection greater than CTCAE grade 2; receipt of any investigational agent within 4 weeks of study registration; uncontrolled hypertension defined as systolic blood pressure greater than 150 mmHg or diastolic pressure greater than 90 mmHg, despite optimal medical management; pulmonary hemorrhage/bleeding event greater than CTCAE Grade 2 within 4 weeks of study registration; any other hemorrhage/bleeding event greater than CTCAE Grade 3 within 4 weeks of study registration; evidence or history of bleeding diathesis or coagulopathy; chronic, daily treatment with aspirin or other nonsteroidal anti-inflammatory medications; use of St. John's Wort, rifampin (rifampicin), ketoconazole, itraconazole, ritonavir, or grapefruit juice; known or suspected allergy to sorafenib or compound A; any condition that impairs patient's ability to swallow whole pill; any malabsorption problem; other severe, acute or chronic medical or psychiatric condition, or laboratory abnormality that may increase the risk associated with study participation or study drug administration, or may interfere with the interpretation of study results, and in the judgment of the investigator would make the patient inappropriate for entry into this study; history of collagen vascular disease; any contraindication to undergo magnetic resonance imaging.

Example 12

Human Clinical Trial

A randomized, Double-blind, open label, historical control, single group assignment, safety/efficacy human phase I clinical trial with compound B and sorafenib versus compound B and placebo in Patients with chemo-naive advanced or metastatic pancreatic cancer will be performed in a similar manner as that prescribed in Example 11. The primary purpose again will be to evaluate the safety and tolerability of the active ingredients studied, specifically sorafenib and compound B. The secondary purpose of the study will be to evaluate the efficacy of the active of the drugs administered to the patients enrolled in the study.

Example 13

Human Clinical Trial

A randomized, Double-blind, open label, historical control, single group assignment, safety/efficacy human phase I clinical trial with compound A and sorafenib versus compound A and placebo in Patients with chemo-naive advanced or metastatic stomach cancer will be performed in the same manner as that prescribed in Example 11, except the enrolled patients with be diagnosed either lymphoma, gastric stromal tumors, or carcinoid tumors of the stomach.

Example 14

Human Clinical Trial

A randomized, Double-blind, open label, historical control, single group assignment, safety/efficacy human phase I clinical trial with compound B and sorafenib versus compound B and placebo in Patients with chemo-naive advanced or metastatic stomach cancer will be performed in the same manner as that prescribed in Example 12, except the enrolled patients with be diagnosed either lymphoma, gastric stromal tumors, or carcinoid tumors of the stomach.

What is claimed is:

1. A pharmaceutical combination comprising an effective amount of (a) at least one MEK protein kinase inhibitor; and (b) at least one Raf protein kinase inhibitor, wherein (a) and (b) are in separate dosage forms or in the same dosage form, wherein:
   (a) the MEK protein kinase inhibitor is a compound selected from the group consisting of:

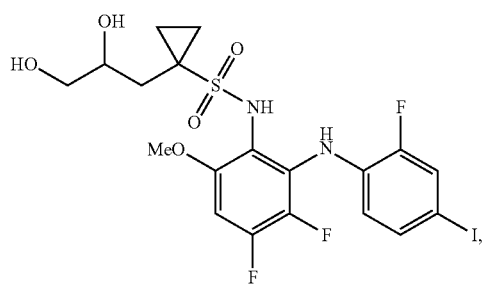

Formula 1

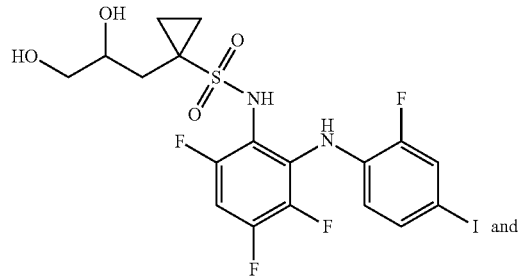

Formula 2

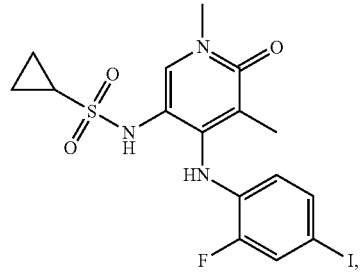

Formula 3 or a pharmaceutically acceptable salt, solvate, polymorph, ester, or tautomer thereof and is present in an amount of 0.1 mg to 200 mg; and
   (b) the Raf protein kinase inhibitor is sorafenib and is present in an amount of 10 mg to 1,000 mg.

2. The pharmaceutical combination of claim 1, wherein the MEK protein kinase inhibitor is present in an amount of 0.5 mg to 100 mg, and
   the Raf protein kinase inhibitor is present in an amount of 50 mg to 700 mg.

3. The pharmaceutical combination of claim 1, wherein the MEK protein kinase inhibitor is present in an amount of 2 mg to 20 mg, and
   the Raf protein kinase inhibitor is present in an amount of 100 mg to 600 mg.

4. The pharmaceutical combination of claim 1, wherein the MEK protein kinase inhibitor is present in an amount of 2 mg to 3 mg, and
   the Raf protein kinase inhibitor is present in an amount of 100 mg.

5. The pharmaceutical combination of claim 1, wherein the MEK protein kinase inhibitor is present in an amount of 4 mg to 6 mg, and
   the Raf protein kinase inhibitor is present in an amount of 200 mg.

6. The pharmaceutical combination of claim 1, wherein the MEK protein kinase inhibitor is present in an amount of 7 mg to 10 mg, and
   the Raf protein kinase inhibitor is present in an amount of 300 mg.

7. The pharmaceutical combination of claim 1, wherein the MEK protein kinase inhibitor is present in an amount of 10 mg to 12 mg, and
   the Raf protein kinase inhibitor is present in an amount of 400 mg.

8. The pharmaceutical combination of claim 1, wherein the MEK protein kinase inhibitor is present in an amount of 13 mg to 16 mg, and
   the Raf protein kinase inhibitor is present in an amount of 500 mg.

9. The pharmaceutical combination of claim 1, wherein the MEK protein kinase inhibitor is present in an amount of 16 mg to 20 mg, and the Raf protein kinase inhibitor is present in an amount of 600 mg.

10. The pharmaceutical combination of claim 1, wherein the MEK protein kinase inhibitor is a compound of formula 1 wherein the 2-OH carbon on the compound is in the S configuration.

11. The pharmaceutical combination of claim 10 wherein the compound MEK protein kinase inhibitor is present in amount 50 mg; and wherein the Raf protein kinase inhibitor is sorafenib and is present in an amount of 400 mg.

12. The pharmaceutical combination of claim 10 wherein the compound MEK protein kinase inhibitor is present in amount 50 mg; and wherein the Raf protein kinase inhibitor is sorafenib and is present in an amount of 200 mg.

13. The pharmaceutical combination of claim 1 wherein the MEK protein kinase inhibitor and Raf protein kinase inhibitor comprise a fixed combination.

14. The pharmaceutical combination of claim 1 wherein the MEK protein kinase inhibitor and Raf protein kinase inhibitor comprise a non-fixed combination.

* * * * *